United States Patent
Haydon et al.

(10) Patent No.: US 9,511,073 B2
(45) Date of Patent: Dec. 6, 2016

(54) AROMATIC AMIDES AND USES THEREOF

(75) Inventors: David John Haydon, Oxfordshire (GB); Lloyd George Czaplewski, Oxfordshire (GB); Neil Robert Stokes, Oxfordshire (GB); David Davies, Oxfordshire (GB); Ian Collins, Oxfordshire (GB); James T. Palmer, Victoria (AU); Jeffrey Peter Mitchell, Victoria (AU); Gary Robert William Pitt, Victoria (AU); Daniel Offermann, Victoria (AU)

(73) Assignee: TAXIS Pharmaceuticals, Inc., North Brunswick, NJ (US)

( * ) Notice: Subject to any disclaimer, the term of this patent is extended or adjusted under 35 U.S.C. 154(b) by 0 days.

(21) Appl. No.: 14/112,735

(22) PCT Filed: Apr. 20, 2012

(86) PCT No.: PCT/AU2012/000416
§ 371 (c)(1),
(2), (4) Date: Feb. 4, 2014

(87) PCT Pub. No.: WO2012/142671
PCT Pub. Date: Oct. 26, 2012

(65) Prior Publication Data
US 2014/0135332 A1    May 15, 2014

Related U.S. Application Data

(60) Provisional application No. 61/477,197, filed on Apr. 20, 2011.

(51) Int. Cl.
| | |
|---|---|
| *C07D 263/32* | (2006.01) |
| *C07D 417/06* | (2006.01) |
| *C07D 413/06* | (2006.01) |
| *C07D 277/24* | (2006.01) |
| *C07D 417/12* | (2006.01) |
| *C07D 413/12* | (2006.01) |
| *C07D 285/08* | (2006.01) |
| *C07D 513/04* | (2006.01) |
| *C07D 413/10* | (2006.01) |
| *C07D 271/06* | (2006.01) |
| *A61K 31/5377* | (2006.01) |
| *A61K 31/166* | (2006.01) |
| *A61K 31/4245* | (2006.01) |
| *A61K 31/421* | (2006.01) |
| *A61K 31/426* | (2006.01) |
| *A61K 31/427* | (2006.01) |
| *A61K 31/433* | (2006.01) |
| *A61K 31/437* | (2006.01) |

(Continued)

(52) U.S. Cl.
CPC ......... *A61K 31/5377* (2013.01); *A61K 31/166* (2013.01); *A61K 31/421* (2013.01); *A61K 31/426* (2013.01); *A61K 31/427* (2013.01); *A61K 31/4245* (2013.01); *A61K 31/433* (2013.01); *A61K 31/437* (2013.01); *A61K 31/4439* (2013.01); *A61K 31/496* (2013.01); *A61K 31/506* (2013.01); *C07D 263/32* (2013.01); *C07D 271/06* (2013.01); *C07D 277/24* (2013.01); *C07D 277/30* (2013.01); *C07D 285/08* (2013.01); *C07D 413/06* (2013.01); *C07D 413/10* (2013.01); *C07D 413/12* (2013.01); *C07D 417/06* (2013.01); *C07D 417/12* (2013.01); *C07D 513/04* (2013.01)

(58) Field of Classification Search
CPC ... C07D 263/32; C07D 417/06; C07D 413/06; C07D 277/24; C07D 417/12; C07D 413/12; C07D 285/08; C07D 513/04; C07D 413/10; C07D 271/06
See application file for complete search history.

(56) References Cited

U.S. PATENT DOCUMENTS 7,273,867 B2 * 9/2007 Dorsch ................ A61K 31/165
                                                     514/239.5
8,865,736 B2 * 10/2014 Brown et al. ................ 514/301

FOREIGN PATENT DOCUMENTS

| WO | 0071510 A2 | 11/2000 |
|---|---|---|
| WO | 02057236 A1 | 7/2002 |

(Continued)

OTHER PUBLICATIONS

Merriam-Webster Online Defintion for Derivative, Obtained from http://www.merriam-webster.com/dictionary/derivative on Aug. 5, 2014.*

(Continued)

*Primary Examiner* — Matthew Coughlin
(74) *Attorney, Agent, or Firm* — Viksnins Harris & Padys PLLP

(57) ABSTRACT

The present invention provides compounds of Formula (I): and salts, racemates, isomers, diastereoisomers, enantiomers, hydrates, solvates, N-oxides, pharmaceutically acceptable derivatives or prodrugs thereof. Also provided the use of these compounds as antibacterials, compositions comprising them and processes for their manufacture.

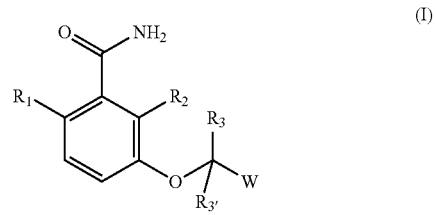

(I)

30 Claims, 1 Drawing Sheet

(51) Int. Cl.
*A61K 31/4439* (2006.01)
*A61K 31/496* (2006.01)
*A61K 31/506* (2006.01)
*C07D 277/30* (2006.01)

(56) References Cited

FOREIGN PATENT DOCUMENTS

| WO | WO 2007107758 A1 * | 9/2007 | |
|---|---|---|---|
| WO | WO 2009037485 A1 * | 3/2009 | ........... C07D 285/08 |
| WO | 2009041904 A1 | 4/2009 | |
| WO | WO 2009041904 A1 * | 4/2009 | |
| WO | 2007107758 A1 | 9/2009 | |

OTHER PUBLICATIONS

Merriam-Webster Online Defintion for Isomer, Obtained from http://www.merriam-webster.com/dictionary/isomer on Aug. 5, 2014.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
CAS Registry No. 1016783-18-8, which entered STN on Apr. 23, 2008.*
Patani et al. Chem. Rev. 1996, 96, 3147-3176.*
Haydon et al. J. Med. Chem. 2010, 53, 3927-3936.*
International Search Report based on PCT/AU2012/000416, mailed on Jul. 30, 2012.

* cited by examiner

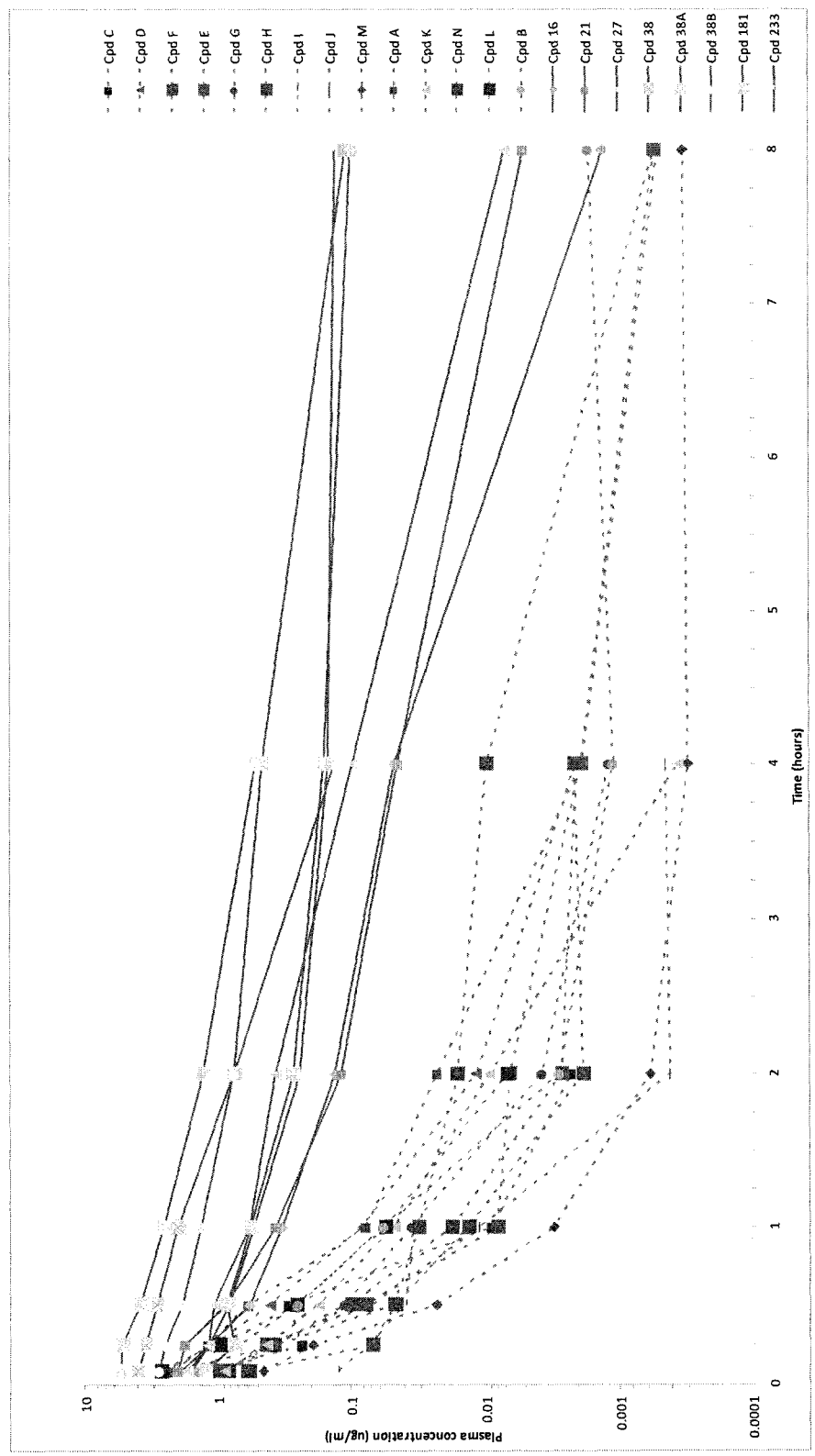

AROMATIC AMIDES AND USES THEREOF

TECHNICAL FIELD

This invention relates to novel aromatic amides, their use as antibacterial agents and to pharmaceutical compositions comprising them.

BACKGROUND

FtsZ is a well-conserved protein that is essential for the viability of a wide range of bacteria. During cell division, FtsZ undergoes guanosine 5'-triphosphate (GTP)-dependent polymerization to form the Z ring at the mid-cell. FtsZ recruits other proteins that together drive cell division and the formation of new cell poles.

FtsZ is a distant structural and functional homologue of mammalian β-tubulin, the target of the taxane class of anticancer drugs.

International Publication Nos. WO 2007/107758, WO2009/037485 and WO2009/040507 disclose classes of Applicant's compounds that demonstrate antibacterial activity. Without being bound by theory, the present inventors believe that the antibacterial activity of the compounds in those classes is a consequence of binding to FtsZ.

The present inventors have now identified a novel class of compounds with antibacterial activity and further which demonstrate one or more advantageous properties as pharmaceuticals for use in the treatment of bacterial infections such as staphylococcal infections, for example, bacterial infections caused by drug sensitive or resistant staphylococci including but not limited to S. aureus, S. epidermidis, S. haemolyticus, S. hominis, S. lugdunensis, S. saprophyticus and S. warneri. The compounds also include a core modification with demonstrated improved pharmacokinetic properties and which also allows for the introduction of, for example, solubilising moieties, prodrug moieties and the like in addition to a chiral centre and accordingly, enantiomeric R and S forms or a mixture thereof. In addition, the class also includes compounds which have improved activities against spontaneous first step mutations.

SUMMARY

The present invention provides a compound of Formula (I):

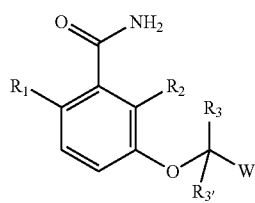

(I)

or a salt, racemate, isomer, diastereoisomer, enantiomer, hydrate, solvate, N-oxide, pharmaceutically acceptable derivative or prodrug thereof
wherein
W is an optionally substituted $C_{6-10}$-membered monocyclic or fused bicyclic aryl group or an optionally substituted 5-10-membered monocyclic or fused bicyclic heteroaryl group preferably a 5-6-membered monocyclic heteroaryl or 9-10-membered fused bicyclic heteroaryl group, more preferably a 5-6-membered monocyclic heteroaryl with optionally substituted 5-membered heteroaryls being particularly preferred;

$R_1$ and $R_2$ are each independently selected from halo or H;

$R_3$ is selected from the group consisting of $C_t$alkyl-$R_4$, $C_{1-6}$alkyl, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more, preferably one or two $R_4$ groups;

t is an integer selected from 0, 1, 2 and 3;

$R_{3'}$ is H;

$R_4$ is selected from the group consisting of $R_5$, $OR_6$, (C=O)$R_6$, O(C=O)$R_6$, C(=O)O$R_6$, N($R_6$)$_2$, $NR_6$C(=O)$R_5$, C(=O)N($R_6$)$_2$, $NR_6$C(=O)O$R_5$, OC(=O)N($R_6$)$_2$, C(=O)N—NC(=O)$R_5$, NHC(=O)NH$C_{1-6}$alkyl, NHS(O)$_x$$R_5$, S(O)$_x$$R_5$, OS(O)$_x$$R_5$, OP(=O)(O$R_6$)$_2$ and P(=O)(O$R_6$)$_2$;

$R_5$ is optionally substituted and is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H or optionally substituted $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

wherein each $R_5$ and $R_6$ independently may be further optionally substituted with one or more, preferably one or two optional substituents independently selected from the group consisting of $C_{1-3}$alkyl, $C_{2-3}$alkenyl, $C_{1-3}$alkoxyl, $OR_7$, oxo, (C=O)$R_7$, O(C=O)$R_7$, C(=O)O$R_7$, N($R_7$)$_2$, $NR_7$C(=O)$R_7$, C(=O)N($R_7$)$_2$, $NR_7$C(=O)O$R_7$, OC(=O)N($R_7$)$_2$, C(=O)N—NC(=O)$R_7$, S(O)$_x$$R_7$, OS(O)$_x$$R_7$, OP(=O)(O$R_7$)$_2$ and P(=O)(O$R_7$)$_2$ wherein each $R_7$ is independently selected from H, $C_{1-3}$alkyl and $C_{2-3}$alkenyl preferably H or $C_{1-3}$alkyl;
and x is 0 or an integer from 1 to 2;

provided that the compound is not 3[1-(5-chlorobenzothiazol-2-yl)-ethoxy]-2,6-difluoro-benzamide or 3-{1-[3-(4-chloro-phenyl)-[1,2,4]oxadiazol-5-yl]-ethoxy}-2,6-difluoro-benzamide.

In one embodiment, W is substituted with one or two substituents.

In a preferred embodiment, W is a heteroaryl of the general formula:

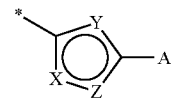

wherein
* represents the point of attachment to the $R_3$/$R_{3'}$ carbon atom;

X and Y are each independently a heteroatom selected from O, N and S or a carbon atom having an optional substituent;

Z is a heteroatom selected from O, N and S or is C—B;

A is selected from H, halo, optionally substituted $C_{6-10}$aryl, optionally substituted 4-10 membered heterocyclyl or A together with B and the carbon atoms to which they are respectively attached join to form an optionally substituted 6-membered fused ring system;

B is selected from H, halo, optionally substituted $C_{1-6}$alkyl, optionally substituted $C_{2-6}$alkenyl, optionally substituted $C_{2-6}$alkynyl or B together with A and the carbon atoms to which they are respectively attached join to form an optionally substituted 6-membered fused ring system.

The present invention also provides a method of treating a bacterial infection in a subject comprising administering an effective amount of a compound of Formula (I) or a pharmaceutically acceptable salt, racemate, isomer, diastereoisomer, enantiomer, hydrate, solvate, N-oxide, pharmaceutically acceptable derivative or prodrug thereof to the subject.

The present invention further provides a compound of Formula (I) or a pharmaceutically acceptable salt, racemate, isomer, diastereoisomer, enantiomer, hydrate, solvate, N-oxide, pharmaceutically acceptable derivative or prodrug thereof for treating a bacterial infection.

The present invention also provides the use of a compound of Formula (I) or a pharmaceutically acceptable salt, racemate, isomer, diastereoisomer, enantiomer, hydrate, solvate, N-oxide, pharmaceutically acceptable derivative or prodrug thereof in the preparation of a medicament for the treatment of a bacterial infection in a subject. In addition, the present invention provides a composition comprising a compound of Formula (I) or a salt, racemate, isomer, diastereoisomer, enantiomer, hydrate, solvate, N-oxide, pharmaceutically acceptable derivative or prodrug thereof. Preferably the composition is a pharmaceutical composition and the salt is a pharmaceutically acceptable salt.

A further aspect of the present invention is a method of disinfecting a living or non-living substrate which is the subject of a bacterial infestation, the method comprising applying a compound of Formula (I) or a salt, racemate, isomer, diastereoisomer, enantiomer, hydrate, solvate, or N-oxide thereof to the substrate.

According to a another aspect there is provided a process for preparing a compound of Formula (I) or a salt, racemate, isomer, diastereoisomer, enantiomer, hydrate, solvate, N-oxide, pharmaceutically acceptable derivative or prodrug thereof comprising the step of coupling a compound of Formula (III) with a compound of general formula LG-C($R_3$)($R_{3'}$)—W where W and $R_{3'}$ are as previously defined and more particularly is a compound of Formula (IV) as follows:

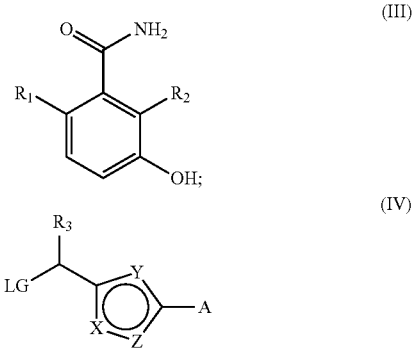

wherein A, X, Y, Z $R_1$, $R_2$ and $R_3$ are as previously defined and LG is a leaving group.

BRIEF DESCRIPTION OF THE FIGURES

FIG. 1: Illustrates the comparative pharmacokinetic (PK) profiles for selected comparator compounds A-N against selected compounds of Formula (I) in accordance with the present invention following 3 mg/kg intravenous administration in mice.

DETAILED DESCRIPTION

The inventors have found a class of novel aromatic amides with particular usefulness as antibacterial agents.

Compounds

In one embodiment there is provided a compound of Formula (I) wherein W is an optionally substituted 5-6-membered monocyclic heteroaryl or a 9-10-membered fused bicyclic heteroaryl group. Optionally substituted 5-membered monocyclic heteroaryl rings are particularly preferred and include pyrrolyl, pyrazolyl, imidazolyl, triazolyl, tetrazolyl, furanyl, oxazolyl, isoxazolyl, oxadiazolyl, thiphenyl, thiazolyl, isothiazolyl and thiadiazolyl ring systems and any of those fused together with an optionally substituted phenyl or 6-membered heteroaryl group containing nitrogen such as a pyridyl ring to form a 9-membered fused bicyclic heteroaryl group, such as for example, benzothiazolyl and thiazolylpyridinyl ring systems.

In one embodiment W is optionally substituted with one or two substituents.

In a particularly preferred embodiment the compound of Formula (I) is a compound of Formula (Ia):

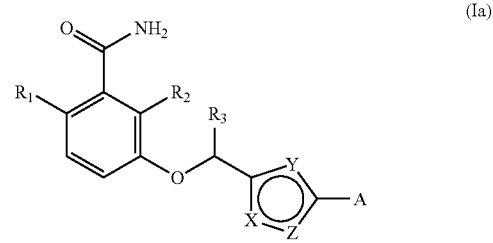

or a salt, racemate, isomer, diastereoisomer, enantiomer, hydrate, solvate, N-oxide, pharmaceutically acceptable derivative or prodrug thereof
wherein
X and Y are each independently a heteroatom selected from O, N and S or a carbon atom having an optional substituent;
Z is a heteroatom selected from O, N and S or is C—B;
A is selected from H, halo, optionally substituted $C_{6-10}$aryl, optionally substituted 4-10 membered heterocyclyl or A together with B and the carbon atoms to which they are respectively attached join to form an optionally substituted 6-membered fused ring system;
B is selected from H, halo, optionally substituted $C_{1-6}$alkyl, optionally substituted $C_{2-6}$alkenyl, optionally substituted $C_{2-6}$alkynyl or B together with A and the carbon atoms to which they are respectively attached join to form an optionally substituted 6-membered fused ring system;
$R_1$ and $R_2$ are each independently selected from halo or H;
$R_3$ is selected from the group consisting of $C_t$alkyl-$R_4$, $C_{1-6}$alkyl, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more, preferably one or two $R_4$ groups;
t is an integer selected from 0, 1, 2 or 3;
$R_4$ is selected from the group consisting of $R_5$, $OR_6$, (C=O)$R_6$, O(C=O)$R_6$, C(=O)O$R_6$, N($R_6$)$_2$, N$R_6$C(=O)$R_5$, C(=O)N($R_6$)$_2$, N$R_6$C(=O)O$R_5$, OC(=O)N($R_6$)$_2$, C(=O)N—NC(=O)$R_5$, NHC(=O)NH$C_{1-6}$alkyl, NHS(O)$_x$$R_5$, S(O)$_x$$R_5$, OS(O)$_x$$R_5$, OP(=O)(O$R_6$)$_2$, P(=O)(O$R_6$)$_2$ and prodrugs thereof;

$R_5$ is optionally substituted and is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H or is optionally substituted $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

wherein each $R_5$ and $R_6$ independently may be further optionally substituted with one or more, preferably one or two optional substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)N-NC(=O)R_7$, $S(O)_xR_7$, $OS(O)_xR_7$, $OP(=O)(OR_7)_2$ and $P(=O)(OR_7)_2$ wherein each $R_7$ is independently selected from H and $C_{1-3}$alkyl;

and x is 0 or an integer from 1 to 2;

provided that the compound is not 3[1-(5-chlorobenzothiazol-2-yl)-ethoxy]-2,6-difluoro-benzamide or 3-{1-[3-(4-chloro-phenyl)-[1,2,4]oxadiazol-5-yl]-ethoxy}-2,6-difluoro-benzamide.

In one embodiment, $R_1$ is halo and $R_2$ is hydrogen.
In one embodiment, $R_2$ is halo and $R_1$ is hydrogen.
In one embodiment, $R_1$ and $R_2$ are each halo.
In one embodiment, each of $R_1$ and $R_2$ is hydrogen.
In one embodiment, the halo of $R_1$ and/or $R_2$ is fluoro.

In one embodiment, A is an optionally substituted $C_6$aryl or an optionally substituted 5-6 membered hetoaryl containing one, two, three or four heteroatoms independently selected from O, N and S as previously defined. Optionally substituted 5-membered monocyclic heteroaryl rings are previously defined and include pyrrolyl, pyrazolyl, imidazolyl, triazolyl, tetrazolyl, furanyl, oxazoles, isoxazoles, oxadiazolyls, thiphenyl, thiazolyl, isothiazolyl and thiadiazolyl ring systems. Optionally substituted 6-membered monocyclic heteroaryl rings include pyridyl, pyrimidinyl, pyrazinyl and pyridazinyl rings and also N-oxides thereof and oxo substituted forms, such as pyridione. Optionally substituted phenyl is particularly preferred.

In one embodiment ring A may be substituted with 1, 2, or 3 optional substituents, preferably 1 or 2 optional substituents, each independently selected from substituents including but not limited to OH, CN, halo (particularly Cl, Br and F), $C_{1-3}$alkyl particularly methyl, $C_{1-3}$alkoxyl including optionally substituted $C_{1-3}$alkoxyl such as $OCH_2CH_2OCH_3$ with methoxy being particularly preferred, halo$C_{1-3}$alkyl, halo$C_{1-3}$alkoxyl, $CO_2H$, $CO_2C_{1-3}$alkyl particularly $CO_2CH_3$ or $CO_2CH_2CH_3$, $SO_2C_{1-3}$alkyl particularly $SO_2CH_3$, $NH_2$, $NHC_{1-3}$alkyl particularly $NHCH_3$, $N(C_{1-3}alkyl)_2$ particularly $N(CH_3)_2$, $CONH_2$, $CONHC_{1-3}$alkyl particularly $CONHCH_3$, $CON(C_{1-3}alkyl)_2$ particularly $CON(CH_3)_2$, CO—N-morpholinyl and 5-membered heterocyclylic groups such as pyrrolidinyl and oxadiazolyl optionally substituted with methyl. Halo, halo$C_{1-3}$alkyl halo$C_{1-3}$alkoxyl are particularly preferred with F, $CHF_2$, $CF_3$, $OCHF_2$ and $OCF_3$ being particularly preferred.

In a further embodiment ring A is a para-substituted phenyl and may be additionally substituted with one or two optional substituents as previously defined.

In one embodiment, Z is C—B where B is selected from H, halo, optionally substituted $C_{1-6}$alkyl, $C_{2-6}$alkenyl and $SC_{1-3}$alkyl. In a particularly preferred embodiment B is halo most preferably Br.

The inventors have surprisingly discovered that the introduction of the $R_3$ group offers potential advantages in improving the metabolic stability of the compounds. This particular pharmacokinetic property of compounds for use in the treatment of staphylococcal infections is particularly important due to the site(s) of bacterial proliferation and mode of delivery required. That is, staphylococcal infections are generally skin and tissue infections. Accordingly, treatment requires delivery of an antibacterial agent with good pharmacokinetic parameters. The inventors have demonstrated comparative improvement in the metabolic stability of a compound with an $R_3$ substituent against its analogue in which the $R_3$ substituent is absent. Without wishing to be bound by theory, it is considered that substitution of the compounds of Formula (I) with an $R_3$ moiety blocks metabolism resulting in competitive pharmacokinetic profiles.

Furthermore, the $R_3$ moiety allows for the introduction of, for example, solubilising e.g. polar groups and prodrug moieties e.g. ester moieties such as succinate.

In one embodiment, $R_3$ is selected from $C_t$alkyl-$R_4$, $C_{1-6}$alkyl and $C_{2-6}$alkenyl where each alkyl and alkenyl group may be optionally substituted with one or more $R_4$ groups and t is an integer selected from 0, 1, 2 and 3. In a further embodiment $R_3$ is $C_t$alkyl-$R_4$, unsubstituted $C_{2-4}$alkenyl or optionally substituted $C_{1-3}$alkyl including methyl and ethyl optionally substituted with OH. In one embodiment when t is 0, $R_4$ is selected from $C(=O)OR_6$ and $C(=O)N(R_6)_2$ where each $R_6$ is independently selected from H or $C_{1-3}$alkyl. In a particularly preferred embodiment $R_3$ is $C_t$alkyl-$R_4$ and t is 1, 2 or 3, more preferably $C_{1-2}$alkyl-$R_4$ and most preferably $CH_2$—$R_4$.

In one embodiment $R_4$ is selected from $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$, $OC(=O)N(R_6)_2$, $C(=O)N—NC(=O)R_5$, $NHC(=O)NHC_{1-6}$alkyl, $NHS(O)_xR_5$, $S(O)_xR_5$, $OS(O)_xR_5$, $OP(=O)(OR_6)_2$ and $P(=O)(OR_6)_2$ where $R_5$ and $R_6$ are as previously defined. In a further embodiment $R_4$ is selected from $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$ and $OC(=O)N(R_6)_2$ and prodrugs thereof.

Optionally substituted phenyl and benzyl are particularly preferred $C_{6-10}$aryl and $C_{1-6}$alkylaryl groups for $R_5$ and $R_6$.

Optionally substituted 5-6-membered heterocyclyl (preferably heteroaryl) and $C_{1-3}$alkyl-5-6-membered heterocyclyl (preferably heteroaryl) groups containing 1, 2, 3 or 4 heteroatoms independently selected from O, N and S as previously defined are particularly preferred 4-10-membered heterocyclyl and $C_{1-6}$alkylheterocyclyl groups for $R_5$ and $R_6$. Preferred non-aromatic 5-6-membered heterocyclyl groups include optionally substituted pyrrolidinyl, piperidinyl, piperazinyl and morpholinyl, In a particularly preferred embodiment $R_4$ is $OR_6$ or $O(C=O)R_6$ and prodrugs thereof wherein $R_6$ is H or optionally substituted $C_{1-6}$alkyl, preferably methyl, ethyl and propyl and most preferably is H or methyl.

When $R_3$ is an alkyl, alkenyl, alkynyl, cycloalkyl, aryl or heterocyclyl optionally substituted with one or more $R_4$ groups then preferably there are one, two, three or four $R_4$ groups or a range between any two of these integers.

The introduction of the $R_3$ group also advantageously provides a chiral centre and accordingly, enantiomeric forms of the compounds of Formula (I). A preferred enantiomeric form of the compounds of Formula (I) is provided according to general Formula (II):

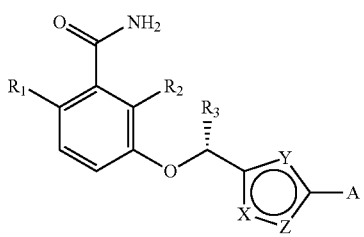

(II)

In one embodiment there is provided an R-enantiomer of a compound of Formula (I) or a salt, hydrate, solvate, N-oxide, pharmaceutically acceptable derivative or prodrug thereof.

In another embodiment there is provided an S-enantiomer of a compound of Formula (I) or a salt, hydrate, solvate, N-oxide, pharmaceutically acceptable derivative or prodrug thereof.

In still another embodiment there is provided a mixture of R- and S-enantiomers of a compound of Formula (I) or a salt, hydrate, solvate, N-oxide, pharmaceutically acceptable derivative or prodrug thereof.

Remarkably, the present inventors have also found that the ring comprising atoms X, Y and Z is an important factor in determining activity against otherwise resistant strains of bacteria.

Accordingly, in one embodiment, Y is a heteroatom selected from N, S or O, preferably N.

In another embodiment, X is a heteroatom selected from N, S or O, preferably O or S, more preferably O.

In one embodiment, Z is C—B.

In one embodiment B is halo, preferably bromo.

The inventors have discovered that a particular sub-class of compounds of the present invention in which this ring is a bromo-substituted oxazole have been shown to have clinically useful activity against bacteria having the FtsZ G196A mutation. The inventors have demonstrated this particular advantage by comparing the activity of an oxazole (or thiazole or bromo-substituted thiazole) and bromo-substituted oxazole analogue against the S. aureus FtsZ G196A mutant strain. The potential benefits) of activity against spontaneous first step mutations being lower mutant prevention concentrations (MPCs) and/or lower resistance frequencies.

Accordingly, in a preferred form of compounds of Formula (I), Y is N and Z is O and B is halo, preferably bromo and A is as previously defined.

In one embodiment, there is provided a compound selected from the group consisting of the compounds in Table 1, or a salt, racemate, isomer, diastereoisomer, enantiomer, hydrate, solvate, N-oxide, pharmaceutically acceptable derivative or prodrug thereof.

DEFINITIONS

As used herein, the term "halo" or "halogen" refers to fluorine (fluoro), chlorine (chloro), bromine (bromo) or iodine (iodo).

As used herein, the term "alkyl" either used alone or in compound terms such as NH(alkyl) or N(alkyl)$_2$, refers to monovalent straight chain or branched hydrocarbon groups, having 1 to 3, or 1 to 6 carbons as appropriate. Each $C_{1-6}$alkyl group is preferably $C_1$, $C_2$ or $C_3$ alkyl, ie $C_{1-3}$alkyl. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl or 2-, 3-, 4- or 5-methylpentyl.

The term "haloalkyl" refers to an alkyl group which has one or more halo substituents. One, two or three halo substituents are particularly preferred. For instance, $CF_3$ is a haloalkyl group as is $CHF_2$.

As used herein, the term "alkenyl" refers to a straight chain or branched hydrocarbon groups having one or more double bonds between carbon atoms. Suitable alkenyl groups include, but are not limited to, ethenyl, allyl, propenyl, iso-propenyl, butenyl, pentenyl and hexenyl. Each $C_{2-6}$alkynyl group is preferably $C_2$ or $C_3$ alkynyl, ie $C_{2-3}$alkynyl.

As used herein, the term "alkynyl" refers to a straight chain or branched hydrocarbon groups having one or more triple bonds between carbon atoms. Each $C_{2-6}$alkenyl group is preferably $C_2$ or $C_3$ alkyl, ie $C_{2-3}$alkyl.

The terms "cycloalkyl", "carbocyclic" and "carbocyclyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "alkylaryl" includes, for example, benzyl.

The terms "heterocycle", "heterocyclic" and "heterocyclyl" when used alone or in compound words includes monocyclic, polycyclic, fused or conjugated hydrocarbon residues wherein one or more carbon atoms (and where appropriate, hydrogen atoms attached thereto) are replaced by a heteroatom so as to provide a non-aromatic residue. The bonds between atoms may be saturated or unsaturated. Suitable heteroatoms include O, N and S. Where two or more carbon atoms are replaced, this may be by two or more of the same heteroatom or by different heteroatoms. Suitable examples of heterocyclic groups may include azetidine, pyrrolidinyl, piperidyl, piperazinyl, azepane, morpholino, quinolinyl, isoquinolinyl, thiomorpholino, dioxanyl, 2,2'-dimethyl-[1,3]-dioxolanyl, tetrahydrofuranyl, tetrahydropyranyl, tetrahydropyrrolyl, cyclic sulfonamides such as sultams etc. The term heterocyclyl will be understood to encompass heteroaromatic/heteroaryl ring systems.

The term "heteroaromatic" or "heteroaryl" may be used interchangeably and includes but is not limited to a 5- or 6-membered heteroaromatic ring containing one or more heteroatoms selected from O, N and S. Suitable examples of heteroaryl groups include 5-membered heteroaryls such as furanyl, thiophenyl, tetrazolyl, 1,2,3-triazolyl, 1,2,4-triazolyl, imidazolyl, pyrrolyl, pyrazolyl, pyridinyl, pyrimidinyl, pyrazinyl, pyridazinyl, oxazolyl, isoxazolyl, oxadiazolyl, thioazolyl, isothiazolyl, thiodiazolyl, etc and 6-membered heteroaryls such as pyridinyl, pyrimidinyl, pyrazinyl, pyridazinyl, etc. The heteroaromatic ring may be fused to a 5- or 6-membered aromatic or heteroaromatic ring to form an 8-10 membered bicyclic aromatic ring system eg benzofuran, pyrrolopyrimidine, furopyridine, benzothiazole, benzisothiazole, benzoxazole, benzisoxazole, benzimidazole, benztriazole, benzothiophene, oxazolopyridine, imidazopyridine, thiazolopyridine, quinoline, isoquinoline, indazole, indole, isoindole, etc.

The term "leaving group" will be understood by the skilled person and means a molecular fragment which is capable of being displaced as a stable species taking it with it the bonding electrons. Leaving groups are used in organic chemistry to facilitate covalent bonding between two moieties. The term "leaving group" includes but is not limited to, halo groups (such as iodo, bromo, and chloro) or sulfonate ester groups such as mesylate, tosylate, osylate, nosylate, or besylate.

Unless otherwise stated, each alkyl, cycloalkyl, alkylaryl, aryl, heterocyclyl, or heteroaryl group may be optionally substituted with, for example, $(C_1-C_6)$alkyl, $(C_2-C_6)$alkenyl, $(C_2-C_6)$alkynyl, $(C_1-C_6)$alkoxy, hydroxy, hydroxy$(C_1-C_6)$alkyl, $(C_1-C_3)$alkoxy$(C_1-C_3)$alkyl, mercapto, mercapto$(C_1-C_6)$alkyl, $(C_1-C_6)$alkylthio, halo (including fluoro, bromo and chloro), fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile (—CN), oxo (═O), thiols, alkylthiols, trialkylsilyl, diarylalkylsilyl, trialkylsilyloxy, diarylalkylsilyloxy, dialkylphosphonyl, dialkoxyphosphonyl, diarylphosphonyl, diaryloxyphosphonyl, alkylphosphinyl, arylphosphinyl, alkoxyphosphinyl, aryloxyphosphinyl, dialkyoxyphosphoryl, diaryloxyphosphoryl, phosphoryl, phosphinyl, phenyl, phenyl$(C_1-C_3)$alkyl-, phenoxy, monocyclic heteroaryl, heteroaryl$(C_1-C_3)$alkyl-, or heteroaryloxy with 5 or 6 ring atoms, cycloalkyl having 3 to 6 ring carbon atoms, —COOR$^A$, —COR$^A$, —OCOR$^A$, SO$_2$R$^A$, —CONR$^A$R$^B$, —CONHNH$_2$, —SO$_2$NR$^A$R$^B$, —NR$^A$R$^B$, —NHNH$_2$, —OCONR$^A$R$^B$, —NR$^B$COR$^A$, —NR$^B$COOR$^A$, —NR$^B$SO$_2$OR$^A$ or —NR$^A$-CONR$^A$R$^B$ wherein R$^A$ and R$^B$ are independently hydrogen or a $(C_1-C_6)$alkyl, hydroxy$(C_1-C_6)$alkyl, or $(C_1-C_3)$alkoxy$(C_1-C_3)$alkyl group or, in the case where R$^A$ and R$^B$ are linked to the same N atom, R$^A$ and R$^B$ taken together with that nitrogen may form a cyclic amino ring such as morpholinyl, piperidinyl. piperazinyl, or 4-$(C_1-C_6)$alkyl-piperizinyl such as 4-methyl-piperazinyl. In a preferred form, each alkyl, cycloalkyl, alkylaryl, aryl, heterocyclyl, or heteroaryl group may be optionally substituted with one or more of $C_1-C_3$alkyl, $C_3-C_6$cycloalkyl, $C_6$aryl, heterocyclyl, heteroaryl, $C_1-C_3$alkylOH, alkylaryl, OH, OC$_1-C_3$alkyl, halo, CN, NO$_2$, CO$_2$H, CO$_2$C$_1-C_3$alkyl, CONH$_2$, CONH$(C_1-C_3$alkyl), C(O)N(C$_1-C_3$alkyl)$_2$, haloC$_{1-3}$alkyl such as CF$_3$ and CHF$_2$, haloC$_{1-3}$alkoxy such as OCHCF$_2$ and OCF$_3$, ═O, C(O)C$_{1-3}$alkyl, C(O)haloC$_{1-3}$alkyl, NH$_2$, NH(C$_1$-C$_3$alkyl) or N(C$_1$-C$_3$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Each optional alkyl, cycloalkyl, alkylaryl, aryl, heterocyclyl, or heteroaryl substituent may also be optionally substituted.

In a preferred form, where a group is substituted by an optional substituent, there are 1 to 4 optional substituents, 1 to 3 optional substitutents, 1 to 2 optional substituents or 1 optional substituent.

Examples of optional substituents also include suitable oxygen and nitrogen protecting groups (see "Greene's Protective Groups in Organic Synthesis" Peter G. M. Wuts and Theodora W. Greene, Fourth Edition, Wiley, 2006).

The salts of the compounds are preferably pharmaceutically acceptable, but it will be appreciated that non-pharmaceutically acceptable salts also fall within the scope of the present invention, since these are useful as intermediates in the preparation of pharmaceutically acceptable salts.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1$^{st}$ edition, 2002, Wiley-VCH.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

Hydroxyl groups may be esterified with groups including lower alkyl carboxylic acids, such as acetic acid and 2,2-dimethylpropionic acid, or sulfonated with groups including alkyl sulfonic acids, such as methyl sulfonic acid.

It will be recognised that the compounds of Formula I are likely to possess asymmetric centres (particularly about the carbon of which R$_3$ is a substituent) and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

This invention also encompasses prodrugs of the compounds. Compounds having free amino, amido, hydroxy or carboxylic groups can be converted into prodrugs.

Prodrugs include compounds wherein an amino acid residue, or a polypeptide chain of two or more (eg, two, three or four) amino acid residues which are covalently joined to free amino, hydroxy and carboxylic acid groups of the compounds. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of the compounds through hydroxyl, amine or carbonyl functionalities. Prodrugs also include phosphate derivatives of the compounds (such as acids, salts of acids, or esters) joined through a phosphorus-oxygen bond to a free hydroxyl of the compounds.

Other prodrugs include esters or peptides formed respectively between hydroxyl groups or amine groups of the compounds with acids such as succinic acid, malonic acid, glutaric acid and the like.

Methods of Treatment

The present invention also provides a method of treating a bacterial infection in a subject comprising administering an effective amount of a compound of Formula (I) to the subject.

The present invention further provides a compound of Formula (I) for treating a bacterial infection.

The present invention also provides the use of a compound of Formula (I) in the preparation of a medicament for the treatment of a bacterial infection in a subject.

The compounds have shown particular efficacy against bacterial infections caused by drug sensitive or resistant staphylococci including but not limited to *S. aureus, S. epidermidis, S. haemolyticus, S. hominis, S. lugdunensis, S. saprophyticus* and *S. warneri*. Accordingly, in one embodiment the bacterial infection to treat is a staphylococcal infection. In a preferred embodiment the staphylococcal infection is a *S. aureus* infection.

In other embodiments, the bacterial infection is a strain resistant to other antibiotics such as methicillin (MRSA, MRSE), vancomycin or is multi-drug resistant (MDRSA). Staphylococcal infections include clinical manifestations in the form of skin and skin-structure infections, tissue infections such as lung infections and heart infections, infections of the blood, bone and bone marrow, joints, gastro-intestinal tract and genitourinary tract. Conditions to treat include, for example, cuts, wounds, stitched wounds, impetigo, styes, boils, carbuncles, scalded skin syndrome, paronychia, dermatitis, eczema, decolonisation of skin, nose or gut to remove staphylococci prior to, during or post-invasive treatment, community-acquired and hospital-acquired (nosocominal) pneumonia including necrotising pneumonia, complications in cystic fibrosis, bacteremia, sepsis, bloodstream infections, osteomyelitis, septic arthritis, endocarditis, toxic shock syndrome, gastroenteritis and genitourinary tract infection. A further aspect of the present invention is a method of disinfecting a living or non-living substrate which is the subject of a bacterial infestation, the method comprising applying a compound of Formula (I) to the substrate.

Living substrates include exterior or interior portions of the body such as nasal passages, skin, scalp and intestines. For instance, compounds of the present invention might be used in nasal or intestinal decolonisation of MRSA prior to elective surgery. Non-living substrates include hospital surfaces and equipment but may also include any surface subject to bacterial infestation or fouling.

Compositions

The compounds of the present invention may be administered by any suitable means, for example, orally, parenterally, such as by subcutaneous, intravenous, intramuscular, or intracisternal injection or infusion techniques (e.g., as sterile injectable aqueous or non-aqueous solutions or suspensions).

In a preferred embodiment the administration is intravenous administration, oral administration or a combination thereof.

There is also provided a composition comprising a compound of Formula (I). Preferably, the composition further comprises a pharmaceutically acceptable carrier, diluent or excipient.

The compositions of the present invention may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use. In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female. The term "effective amount" means the amount of the subject composition that will elicit the biological or medical response of a tissue, system, animal or human that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The term "composition" as used herein is intended to encompass a product comprising the specified ingredients in the specified amounts, as well as any product which results, directly or indirectly, from combination of the specified ingredients in the specified amounts.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In the treatment or prevention of bacterial infections, an appropriate dosage level will generally be about 0.01 to 500 mg per kg patient body weight per day which can be administered in single or multiple doses. For oral administration, the compositions are preferably provided in the form of tablets containing 1.0 to 1000 milligrams of the active ingredient for the symptomatic adjustment of the dosage to the patient to be treated. The compounds may be administered on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The pharmaceutical compositions and methods of the present invention may further comprise other therapeutically active compounds which are usually applied in the treatment of bacterial infections. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects. Accordingly, in one aspect of the present invention, there is provided a pharmaceutical composition comprising a compound of Formula (I) and a further antibacterial agent.

In another aspect of the present invention, there is provided a method of treating a bacterial infection comprising administering a compound of Formula (I) together with a further antibacterial agent wherein said compound of Formula (I) and said antibacterial agent are administered in either order and can be administered simultaneously or sequentially.

Said further antibacterial agent may be selected from the group consisting of those indicated for the treatment of Stapylococci infections, including but not limited to for example, oxazolidinones such as linezolid, glycopeptides such as vancomycin and telavancin, fluoroquinolones such as levofloxacin, beta-lactams such as the cephalosporin ceftobiprole, cyclic lipopeptides such as daptomycin and macrolides such as azithromycin, etc.

When other therapeutic agents are employed in combination with the compounds of the present invention they may be used for example in amounts as noted in the Physician Desk Reference (PDR) or as otherwise determined by one of ordinary skill in the art.

Methods of Preparation

Compounds of Formula (I) may generally be prepared by coupling a compound of Formula (III) with a compound of general formula LG-C($R_3$)($R_3'$)—W where W and $R_3'$ are as previously defined and more particularly, for the preparation of compounds of Formula (Ia) is a compound of Formula (IV) under the following conditions

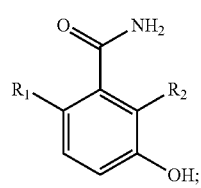

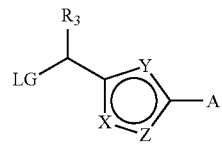

wherein A, X, Y, Z $R_1$, $R_2$ and $R_3$ are as previously defined and LG is a leaving group. To a solution of (IV) (approximately 1.0 eq) in an organic solvent such as DMF is added a base such as $K_2CO_3$ (approximately 2.0 eq) followed by (III) (approximately 1.0 eq). The resulting reaction mixture is stirred under a $N_2$ atmosphere at room temperature. After completion of the reaction the product is extracted into an organic solvent such as EtOAc and purified by silica gel chromatography. Alternatively, where LG is OH, triphenylphosphine (approximately 1.2 eq) is dissolved in a suitable solvent such as THF and treated with diethylazodicarboxylate (approximately 1.2 eq) at 0° C. After stirring for a short time a solution of (III) (1 eq), (IV) (1 eq) and TEA (1.1 mL, 1 eq) in the same solvent is added to the initial mixture and allowed to warm to room temperature. After completion of the reaction, the mixture may be concentrated and purified by silica chromatography.

It will be understood by those skilled in the art that a considerable diversity of compounds of Formula (I) may be accessed by variation of an α-halo ketone building block. Accordingly, the succeeding methods which are generally described for the synthesis of compounds of Formula (I) utilise an α-halo ketone as a starting material or precursor intermediate. An extensive selection of α-bromo and α-chloro ketones is available from commercial suppliers. Alternatively, a further diversity of α-bromo ketones may be prepared according to one or more the following standard methods.

One Pot Conversion of a Substituted Carboxylic Acid to an α-Bromo Ketone

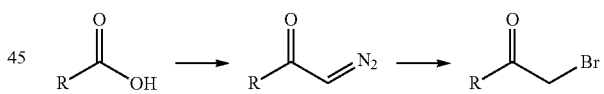

To an ice-cold solution of a substituted carboxylic acid (1.0 eq) in an inert solvent (such as dichloromethane) is added oxalyl chloride (5.0 eq) and DMF (catalytic amount). The resulting reaction mixture is stirred at room temperature. When the reaction is complete, the mixture is concentrated under inert atmosphere to obtain the crude product, which is then dissolved in diethyl ether, cooled to 0° C. and treated with TMS-diazomethane (1.50 eq). The resulting solution is stirred at 0° C. for 30 minutes, followed by addition of HBr (47% aq solution). After completion of reaction, water is added to the mixture and the product extracted into EtOAc (3 times). The combined organics are washed with brine, dried over anhydrous $Na_2SO_4$, filtered and concentrated in vacuo. The crude residue may be purified by silica chromatography (typically eluted with EtOAc/hexane) to obtain the purified α-bromo ketone, typically in low yield.

Conversion of a Carboxylic Acid to an α-Bromo Ketone Via a Stille Coupling

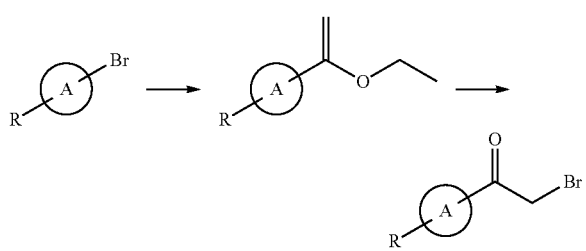

A solution of optionally substituted heteroaryl bromide (1.0 eq) and ethoxyvinyl tri-n-butyltin (1.50 eq) in DMF is purged with nitrogen for 15 minutes followed by addition of tetrakis(triphenylphosphine)palladium (0.10 eq). The resulting solution is again purged with nitrogen for 15 minutes and then heated to approximately 110° C. for 2 h. After the completion of reaction, ice-cold water is added to the reaction mixture, which is then washed with EtOAc (3 times). The combined organics are washed with brine, dried over anhydrous $Na_2SO_4$, filtered and concentrated in vacuo. The crude residue may be purified by silica chromatography (typically eluted with EtOAc/hexane) to obtain the pure enol ether, typically in good yields. If this product hydrolyses spontaneously to a methyl ketone, it may be converted to the desired α-methyl ketone by one of the methods described below. In all other cases, an ice-cold solution of the enol ether (1.0 eq) in THF-$H_2O$ (3:1) is treated with NBS (1.0 eq) and stirred at room temperature for 30 minutes. After the completion of reaction water is added to the mixture, which is then washed with EtOAc (3 times). The combined organics are washed with brine, dried ($Na_2SO_4$), filtered and concentrated under reduced pressure. The crude residue may be purified by silica chromatography (typically eluted with EtOAc/hexane) to obtain the purified α-bromo ketone.

Preparation of an α-Bromo Ketone by Bromination of a Methyl Ketone

Approach i):

To a solution of a substituted methyl ketone (1.0 eq) in THF is added tetrabutylammonium tribromide (1.0 eq) and the resulting reaction mixture heated at reflux for 2 h. After completion of reaction, water is added to the mixture and the product extracted into EtOAc (3 times). The combined organics are washed with brine, dried ($Na_2SO_4$), filtered and concentrated under reduced pressure. The crude residue may be purified by silica chromatography (typically eluted with EtOAc/hexane) to obtain the purified α-bromo ketone, typically in good yield.

Approach ii):

A solution of substituted methyl ketone (1.0 eq) in glacial acetic acid is cooled to 0° C. and treated drop-wise with bromine (1.0 eq). A catalytic amount of HBr in acetic acid is added to the reaction mixture and allowed to stir at room temperature typically for 10-20 h. After the completion of reaction, the mixture is cooled to 0° C. and quenched with ice-cold water, followed by extraction with EtOAc (3 times). The combined organics are washed with brine, dried over anhydrous $Na_2SO_4$, filtered and concentrated in vacuo. The crude residue may be purified by silica chromatography (typically eluted with EtOAc/hexane) to obtain the purified α-bromo ketone, typically in 20-40% yield.

Approach iii):

A solution of substituted methyl ketone (1.0 eq) in THF and 5,5-dibromobarbituric acid (0.90 eq) is heated at reflux, typically for 10-20 h. After completion of the reaction, water is added to the mixture, which is then washed with EtOAc (3 times). The combined organics are washed with brine, dried over anhydrous $Na_2SO_4$, filtered and concentrated in vacuo. The crude residue may be purified by silica chromatography (typically eluted with EtOAc/hexane) to obtain the purified α-bromo ketone, typically in good yield.

Many methyl ketones are available commercially and are suitable for bromination according to the foregoing methods. In addition to commercially-sourced materials, further methyl ketones may be prepared by the following method.

Conversion of a Carboxylic Acid to a Methyl Ketone Via a Weinreb Amide

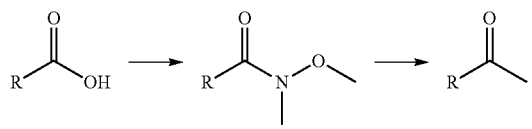

To a solution of substituted carboxylic acid (1.0 eq) in DMF is added N,O-dimethylhydroxylamine hydrochloride (1.10 eq), 1-(3-dimethylaminopropyl)-3-ethylcarbodiimide hydrochloride (1.50 eq), 1-hydroxybenzotriazole (1.0 eq), 4-dimethylaminopyridine (1.0 eq) and a catalytic amount of triethylamine. The resulting reaction mixture is stirred at room temperature. After the completion of reaction (TLC monitoring), ice-cold water is added to the reaction mixture, which is then extracted with EtOAc (3 times). The combined organics are washed with ice-cold water and brine, dried over anhydrous $Na_2SO_4$, filtered and concentrated in vacuo. If required, the crude product may be purified by silica chromatography (typically eluted with EtOAc/hexane). A solution of the above Weinreb amide (1.0 eq) in THF is cooled to 0° C. and treated with methylmagnesium bromide (2.0 eq). The resulting reaction mixture is stirred at 0° C. for approximately 45 minutes. At the completion of reaction (TLC monitoring), saturated ammonium chloride solution is added to the reaction mixture, followed by extraction with EtOAc (3 times). The combined organics are washed with brine, dried over anhydrous $Na_2SO_4$, filtered and concentrated in vacuo. The crude residue may be purified by silica chromatography (typically eluted with EtOAc/hexane) to obtain the pure methyl ketone.

General Method A

One general method for the preparation of compounds of Formula (I) is described in Scheme 1.

Scheme 1: General Method A, for preparation of compounds of Formula (I) where R is one or more optional substituents, A ring is an optionally substituted phenyl, heteroaryl or heterocyclyl, Y is N and X is O or S.

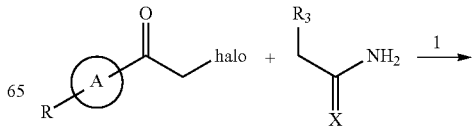

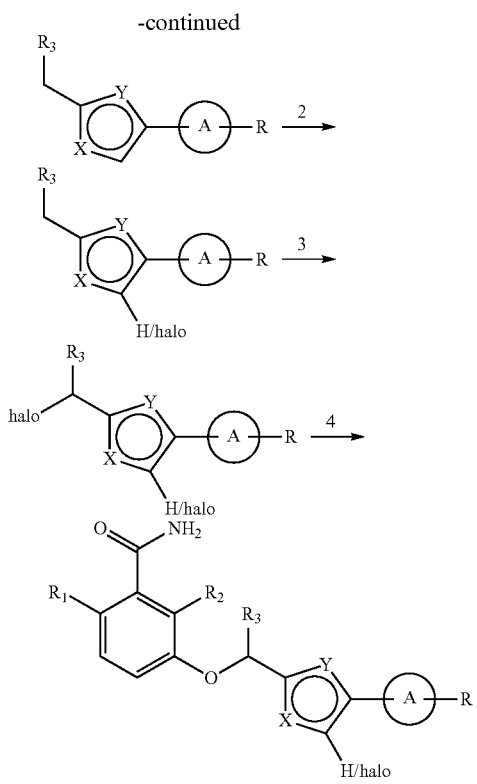

Step 1: Formation of Oxazole/Thiazole Ring; Coupling of Halomethyl Ketones with Amide/Thioamide Derivatives:

A mixture of α-halo ketone R-A-C(O)—CH$_2$-halo (1.0 eq) and amide/thioamide derivative R$^3$—CH$_2$—C(X)NH$_2$ (2.50 eq) is heated at 120-130° C. for 2-3 h. After completion of reaction, water is added to the reaction mass and washed with EtOAc. The combined organics are collected, washed sequentially with water and brine, dried over anhydrous Na$_2$SO$_4$, filtered and concentrated in vacuo. The crude residue may be purified by silica chromatography (EtOAc/hexane) to obtain the desired products, typically in moderate to good yields.

Step 2: Optional Ring Halogenation (Bromo/Chloro):

Approach i):

To a solution of the 5-H oxazolyl or thiazolyl substrate (1.0 eq) in acetic acid (~5 mL/mmol) is added NBS or NCS (1.0 eq) and the resulting reaction mixture is stirred at room temperature for 30-45 minutes. After the completion of reaction (TLC monitoring), the reaction mass is diluted with water, basified with saturated sodium bicarbonate solution and extracted with EtOAc. The combined organics are washed with brine, dried, filtered and concentrated. The residue may be purified over silica gel to obtain the desired products, typically in moderate yields.

Approach ii):

To an ice-cold solution of a 5-H oxazole derivative (1.0 eq) in DCM (~10 mL/mmol) is added a stock solution of 1M bromine in DCM (1.0 eq) and the resulting solution is stirred at room temperature for 5-6 h while constantly monitoring the progress of the reaction by TLC/MS. After the majority of the starting material is converted to product, the reaction is quenched by addition of saturated aqueous NaHCO$_3$ solution followed by extraction with EtOAc (3 times). The combined organics are washed with brine, dried over anhydrous Na$_2$SO$_4$, filtered and concentrated under reduced pressure. The crude material may be purified by flash chromatography (EtOAc-hexane) to obtain the desired product, typically in good yield.

Step 3: Halogenation of the Side Chain on the Heteroaryl Ring:

To a solution of the starting material (1.0 eq) in CCl$_4$ is added NBS (1.0 eq) and AIBN (0.10 eq). The resulting reaction mixture is stirred at 80° C. for 5-6 h. After the completion of reaction (TLC monitoring), the reaction mixture is filtered and concentrated. The crude residue may be purified over silica gel to obtain the pure alkyl halide, typically in moderate yield.

Step 4: Coupling of the Head Group (2,6-Difluoro-3-Hydroxybenzamide) by Nucleophilic Substitution of an Alkyl Halide:

To a solution of the appropriate alkyl halide (1.0 eq) in DMF is added K$_2$CO$_3$ (2.0 eq) followed by 2,6-difluoro-3-hydroxybenzamide (1.0 eq). The resulting reaction mixture is stirred under N$_2$ atmosphere at room temperature for 2 h. After the reaction is complete (TLC monitoring), ice-cold water is added to the reaction mixture and extracted with EtOAc (3 times). The combined organics are washed with 1M NaOH solution, water and brine, dried (Na$_2$SO$_4$), filtered and concentrated. The crude residue may be purified by silica chromatography to obtain the desired product, typically in moderate to good yields.

General Method B

One general method for the preparation of compounds of Formula (I) where R$_3$ is a hydroxyl or hydroxyalkyl moiety is described in Scheme 2.

Scheme 2: General method of preparation of compounds of Formula (I) where R is one or more optional substituents and A ring is an optionally substituted phenyl, heterocyclyl or heteroaryl.

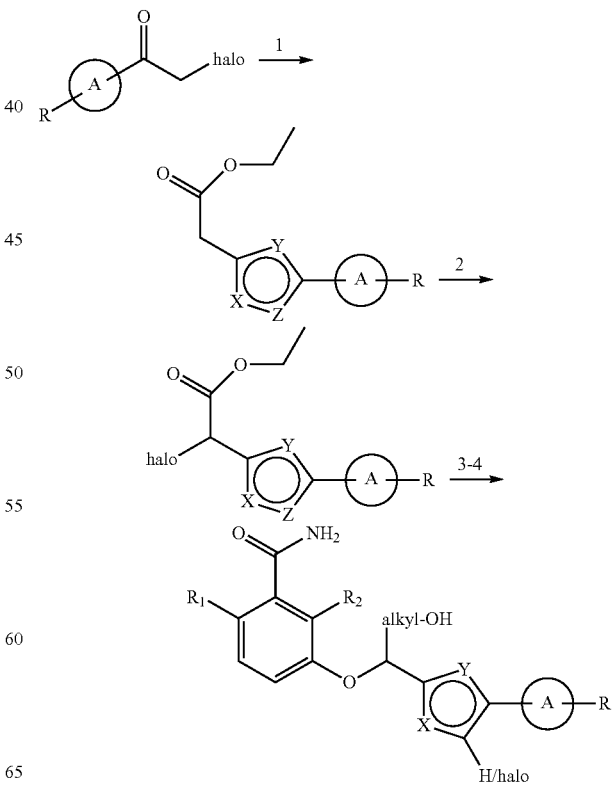

Step 1:
  Ring formation as per step 1 General Method A.
Step 2:
  Halogenation as per step 3 General Method A.
Step 3:
  Coupling as per step 4 General Method A.
Step 4: Reduction of the Ester/Keto Group:
  To an ice cold solution of the corresponding ester derivative (1.0 eq) in MeOH is added $NaBH_4$ (3.0 eq) portion wise and the resulting reaction mixture is refluxed for 2 h. After the completion of reaction (TLC monitoring), water is added to the mixture and extracted with EtOAc (3 times). The combined organics are washed with water, brine, dried ($Na_2SO_4$), filtered and concentrated to obtain the desired product (in good to excellent yields), typically without need for further purification.
  In an alternative method the carboxylate produced following step 1 may be converted to a hydroxyl then protected as an acetate during functional group interconversions of substituents on the heteroaryl or A ring then deprotected to the hydroxyl following coupling to the benzamide head group.
General Method C
  One general method for the preparation of compounds of Formula (I) wherein $R_3$ is a carboxylate moiety, e.g. carboxylic acid, esters, acetates, is described in Scheme 3.

Scheme 3: General method of preparation of compounds of Formula (I) where R is one or more optional substituents and A ring is an optionally substituted phenyl, heterocyclyl or heteroaryl.

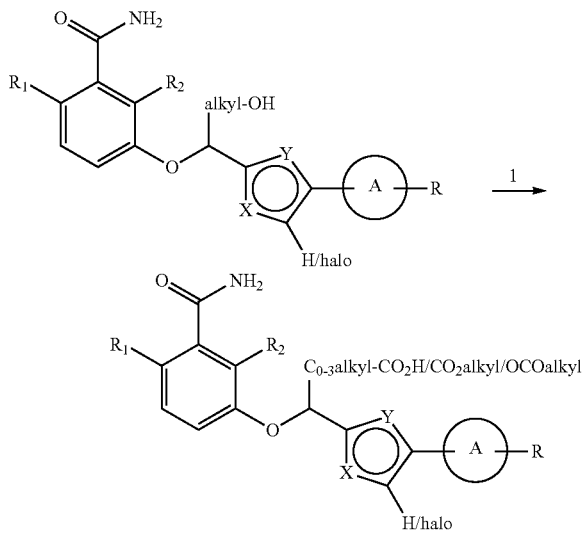

Step 1: Carboxyl Formation:
  To a solution of the starting material having the primary hydroxyl group in DCM is added a suitable base such as imidazole (1.20 eq) and an acylating agent, such as an activated ester, an alkyl halide or an anhydride (1.20 eq). The resulting reaction mixture is stirred at room temperature. After the completion of reaction (TLC monitoring), water is added followed by extraction with EtOAc (3 times). The combined organics are washed with brine, dried ($Na_2SO_4$), filtered and concentrated under reduced pressure. The residue may be purified by chromatography to obtain the desired product.
  Alternatively oxidation conditions such as $CrO_3$, $H_2SO_4$, acetone (Jones Reagent) may be employed to form carboxylates from starting materials having the primary hydroxyl group. Other suitable acylating or oxidizing reagents and conditions will be familiar to the skilled person.
Functional Group Interconversions
  The skilled person will appreciate that a wide diversity of compounds may be provided by functional group interconversions of hydroxyls and carboxylates including but not limited to halogens, ethers, ketones, carboxylic acids, esters, carbonates, amines, amides, ureas, carbamates, sulfates, sulfonamides, phosphates, heterocycles, heteroaryls, optionally substituted alkyl chain extensions and so on. Suitable reaction conditions for these functional group interconversions will be familiar to those in the art.
  Those skilled in the art will appreciate that the invention described herein is susceptible to variations and modifications other than those specifically described. The invention will now be described without limitation by reference to the examples which follow.

EXAMPLES $^1H$ NMR spectra were recorded on a Bruker Ultrashield™ 400 spectrometer. Spectra were recorded in $CDCl_3$, $d_6$-acetone, $CD_3CN$, $CD_3OD$ or $d_6$-DMSO using the residual solvent peak as a reference. Chemical shifts are reported on the δ scale in parts per million (ppm) using the following conventions to assign the multiplicity: s (singlet), d (doublet), t (triplet), q (quartet), m (multiplet) and the prefix br (broad). Mass spectra (ESI) were typically recorded on a Thermo Finnigan LCQ Advantage or LCQ Deca mass spectrometer coupled with a Thermo Finnigan Surveyor HPLC system. The HPLC was performed using Waters Acquity UPLC BEH or Phenomenex C8(2) or C18(2) columns. Water containing 0.1% formic acid (solvent A) and acetonitrile containing 0.1% formic acid (solvent B) were used for separations at acidic pH. Ammonium acetate (5 mM, solvent A) and methanol or acetonitrile (solvent B) were used for separations at neutral pH. Flash chromatography was performed on 40-63 μm or 125-250 μm silica gel or using a Biotage SP4 with GraceResolv™ silica cartridge.
Compounds
  Compounds of Formula (I) are prepared according to the General Methods or Schemes previously described herein and/or by reference to the Representative Examples which follow.

Representative Example 1

Synthesis of 3-(1-(5-bromo-4-(4-chlorophenyl)oxazol-2-yl)propoxy)-2,6-difluorobenzamide

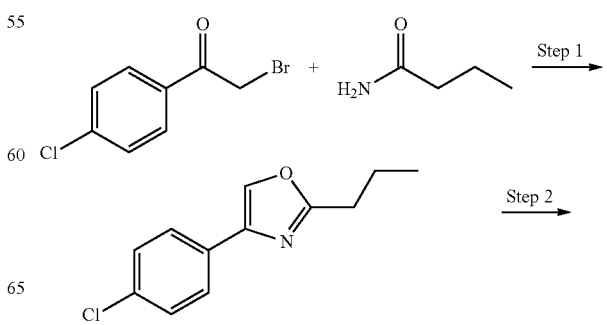

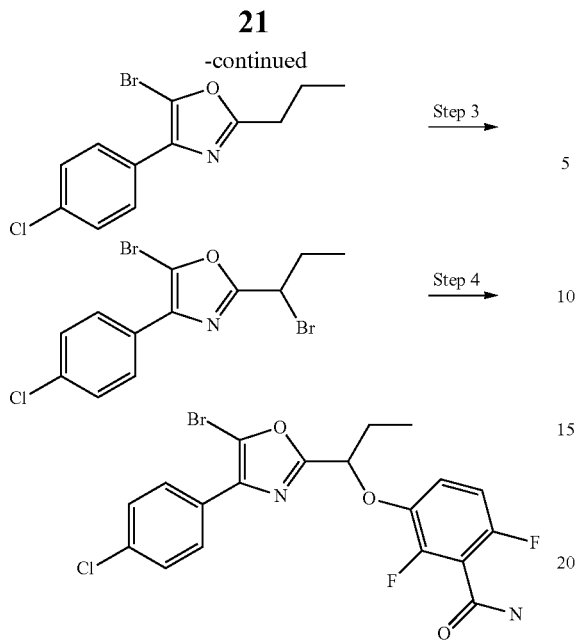

EtOAc/hexane) to yield 3-(1-(5-bromo-4-(4-chlorophenyl)oxazol-2-yl)propoxy)-2,6-difluorobenzamide (0.33 g, 54%).

Representative Example 2

Synthesis of 3-(1-(5-bromo-4-(4-(trifluoromethyl)phenyl)oxazol-2-yl)-2-hydroxyethoxy)-2,6-difluorobenzamide

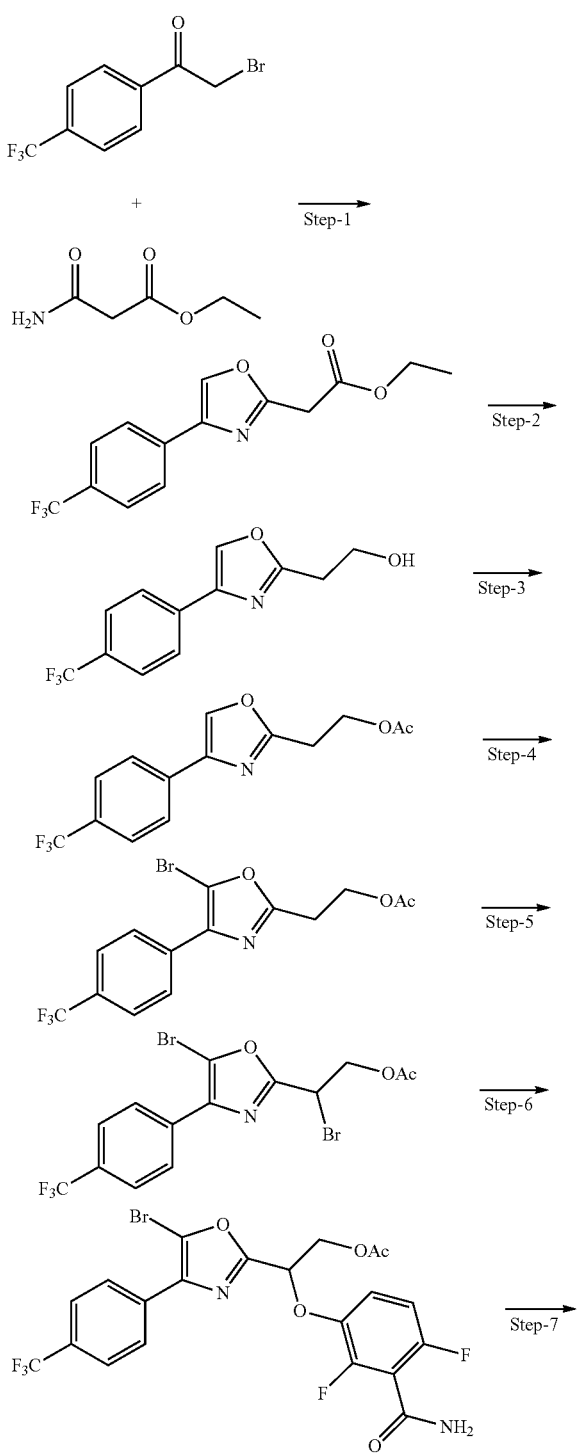

Step 1:

A mixture of 4-chlorophenacyl bromide (1.0 g, 4.28 mmol) and butyramide (0.75 g, 8.56 mmol) was heated to 110° C. for 3 h. When the reaction was complete (TLC), water was added and the mixture was washed with EtOAc (3×100 mL). The combined organic layers were washed with water and brine, dried using $Na_2SO_4$, filtered and concentrated. The crude residue was purified by flash chromatography (using hexane as the eluent) to afford 4-(4-chlorophenyl)-2-propyloxazole (0.70 g, 74%).

Step 2:

To a solution of 4-(4-chlorophenyl)-2-propyloxazole (0.40 g, 1.80 mmol) in AcOH (5 mL) was added NBS (0.32 g, 1.80 mmol) and the resulting solution was stirred at room temperature for 2 h. At the completion of reaction (TLC monitoring), the mixture was poured onto the crushed ice and the product extracted into EtOAc (3×150 mL). The combined organic layers were washed with saturated sodium bicarbonate solution and brine, dried over $Na_2SO_4$, filtered and concentrated. The residue was purified over by flash chromatography (using hexane as the eluent) to afford 5-bromo-4-(4-chlorophenyl)-2-propyloxazole (0.30 g, 55%).

Step 3:

To a solution of 5-bromo-4-(4-chlorophenyl)-2-propyloxazole (0.50 g, 1.68 mmol) in $CCl_4$ (10 mL) was added NBS (0.30 g, 1.68 mmol) and AIBN (0.028 g, 0.17 mmol). The resulting reaction mixture was then heated to 80° C. for 3 h. The mixture was filtered, concentrated in vacuo and purified by flash chromatography (hexane) to obtain 5-bromo-2-(1-bromopropyl)-4-(4-chlorophenyl)oxazole (0.48 g, 76%).

Step 4:

To a solution of 5-bromo-2-(1-bromopropyl)-4-(4-chlorophenyl)oxazole (0.50 g, 1.31 mmol) in DMF (10 mL) was added $K_2CO_3$ (0.55 g, 3.95 mmol) followed by 2,6-difluoro-3-hydroxybenzamide (0.25 g, 1.45 mmol). The resulting reaction mixture was stirred under a nitrogen atmosphere at room temperature for 3 h. After this time, ice-cold water was added and the mixture was washed with EtOAc (3×100 mL). The combined organic phases were washed with water and brine, dried over $Na_2SO_4$, filtered and concentrated. The crude residue was purified by flash chromatography (1:3

-continued

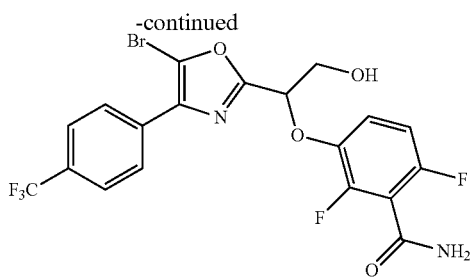

Step 1:

A mixture of 4'-(trifluoromethyl)phenacyl bromide (1.50 g, 5.62 mmol) and ethylmalonate monoamide (1.84 g, 14.05 mmol) was heated at 130° C. for 2 h. Water was added and the mixture was washed with EtOAc (3×100 mL). The combined organic layers were washed with water and brine, dried over $Na_2SO_4$, filtered and concentrated in vacuo. The crude residue was purified by silica chromatography (2% EtOAc/hexane) to afford ethyl 2-(4-(4-(trifluoromethyl)phenyl)oxazol-2-yl)acetate (0.73 g, 43%).

Step 2:

To an ice cold solution of ethyl 2-(4-(4-(trifluoromethyl)phenyl)oxazol-2-yl)acetate (0.57 g, 1.90 mmol) in MeOH (10 mL) was added $NaBH_4$ (0.216 g, 5.75 mmol) portionwise and the resulting mixture was stirred at reflux for 2 h. When the reaction was complete, water was added and the mixture washed with EtOAc (3×50 mL). The combined organic layers were washed with water and brine, dried over $Na_2SO_4$, filtered and concentrated to give 2-(4-(4-(trifluoromethyl)phenyl)oxazol-2-yl)ethanol (0.43 g, 88%), which was carried forward without further purification.

Step 3:

An ice cold solution of 2-(4-(4-(trifluoromethyl)phenyl)oxazol-2-yl)ethanol (0.527 g, 2.05 mmol) and $Et_3N$ (430 µL, 3.08 mmol) in DCM (10 mL) was stirred for 5-10 minutes followed by drop-wise addition of acetyl chloride (175 µl, 2.46 mmol). After stirring at room temperature for 0.5 h, water was added and the product extracted into EtOAc (3×50 mL). The combined organic phases were washed with water and brine, dried over $Na_2SO_4$, filtered and concentrated to yield 2-(4-(4-(trifluoromethyl)phenyl)oxazol-2-yl) ethyl acetate, which was carried forward to the next step without further purification.

Step 4:

To a solution of 2-(4-(4-(trifluoromethyl)phenyl)oxazol-2-yl)ethyl acetate (0.66 g, 2.21 mmol) in acetic acid (10 mL) was added NBS (0.393 g, 2.21 mmol) and the resulting reaction mixture was stirred at room temperature for 30-45 minutes. At the completion of reaction, the reaction mixture was diluted with water, basified with saturated sodium bicarbonate solution and the product extracted into EtOAc (3×50 mL). The combined organic phases were washed with brine, dried over $Na_2SO_4$, filtered and concentrated. The residue was purified by silica chromatography (0.50% EtOAc/hexane) to afford 2-(5-bromo-4-(4-(trifluoromethyl)phenyl)oxazol-2-yl)ethyl acetate (0.328 g, 39%).

Step 5:

To a solution of 2-(5-bromo-4-(4-(trifluoromethyl)phenyl)oxazol-2-yl)ethyl acetate (0.325 g, 0.86 mmol), in $CCl_4$ (15 mL) was added NBS (0.153 g, 0.86 mmol) and AIBN (0.015 g, 0.09 mmol). The resulting reaction mixture was stirred at 80° C. for 5-6 h. After the completion of reaction, the mixture was filtered and the filtrate concentrated in vacuo. The residue was purified by flash chromatography (1.0% EtOAc/hexane) to yield 2-bromo-2-(5-bromo-4-(4-(trifluoromethyl)phenyl)oxazol-2-yl)ethyl acetate (0.155 g, 39%).

Step 6:

To a solution of 2-bromo-2-(5-bromo-4-(4-(trifluoromethyl)phenyl)oxazol-2-yl)ethyl acetate (0.155 g, 0.34 mmol) in DMF (10 mL) was added $K_2CO_3$ (0.094 g, 0.68 mmol) and 2,6-difluoro-3-hydroxybenzamide (0.059 g, 0.34 mmol). The resulting reaction mixture was stirred under $N_2$ atmosphere at room temperature for 2 h. After this time, the mixture was diluted with ice-cold water and washed with EtOAc (3×50 mL). The combined organic layers were washed sequentially with 1 M NaOH (aq), water and brine, then dried over $Na_2SO_4$, filtered and concentrated. The residue was purified by silica chromatography (40% EtOAc/hexane) to afford 2-(5-bromo-4-(4-(trifluoromethyl)phenyl)oxazol-2-yl)-2-(3-carbamoyl-2,4-difluorophenoxy)ethyl acetate (0.051 g, 27%).

Step 7:

To a solution of 2-(5-bromo-4-(4-(trifluoromethyl)phenyl)oxazol-2-yl)-2-(3-carbamoyl-2,4-difluorophenoxy)ethyl acetate (0.05 g, 0.09 mmol) in MeOH (5 mL) was added $K_2CO_3$ (0.019 g, 0.14 mmol) and the resulting reaction mixture was stirred at room temperature for 1 h. The reaction mixture was diluted with water and extracted with EtOAc (4×25 mL). The combined organic layers were washed with brine, dried over $Na_2SO_4$, filtered and concentrated. The residue was purified by preparative TLC to afford 3-(1-(5-bromo-4-(4-(trifluoromethyl)phenyl)oxazol-2-yl)-2-hydroxyethoxy)-2,6-difluorobenzamide (0.041 g, 90%).

Prepared by an analogous procedure (starting from ethylmalonate monoamide and 1-bromopentan-2-one) were, for example, 2-(5-bromo-4-(1-(3-carbamoyl-2,4-difluorophenoxy)propyl)oxazol-2-yl)ethyl acetate and 3-(1-(5-bromo-2-(2-hydroxyethyl)oxazol-4-yl)propoxy)-2,6-difluorobenzamide.

Also similarly prepared was, for example, 3-(1-(5-ethyl-2-(4-methoxyphenyl)oxazol-4-yl)-2-hydroxyethoxy)-2,6-difluorobenzamide in which case a tert-butyldiphenylsilyl (TBDPS) function was used instead of acetate as the alcohol protection group. Methodology for TBDPS protection/deprotection is well known in the art.

Representative Example 3

Synthesis of 3-(1-(4-(4-chlorophenyl)thiazol-2-yl)-2-hydroxyethoxy)-2,6-difluorobenzamide

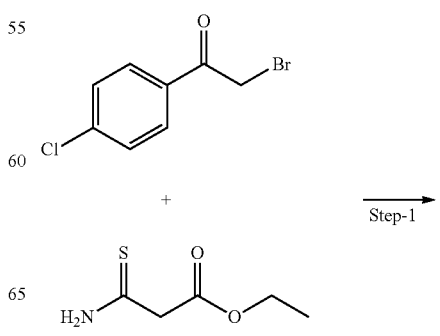

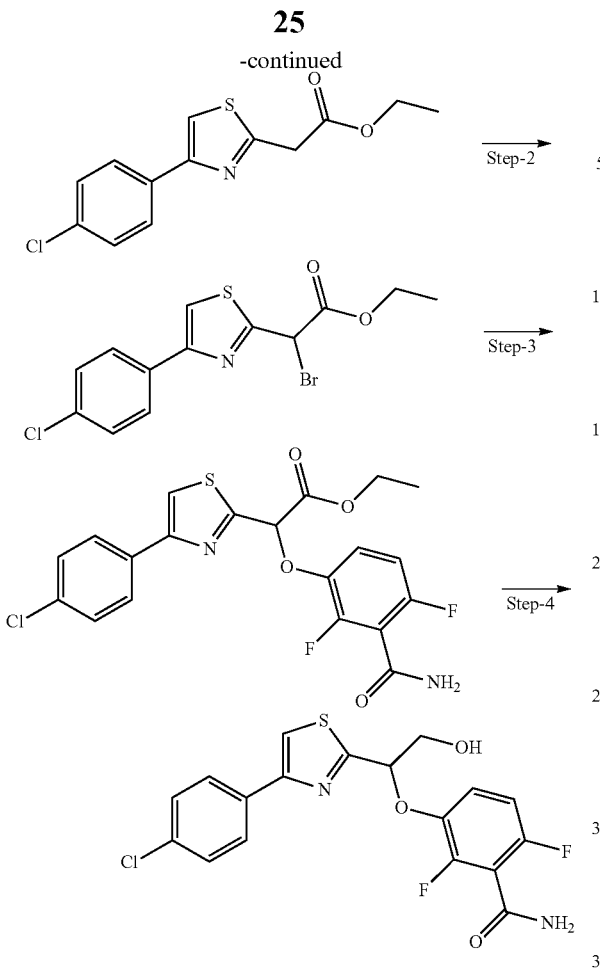

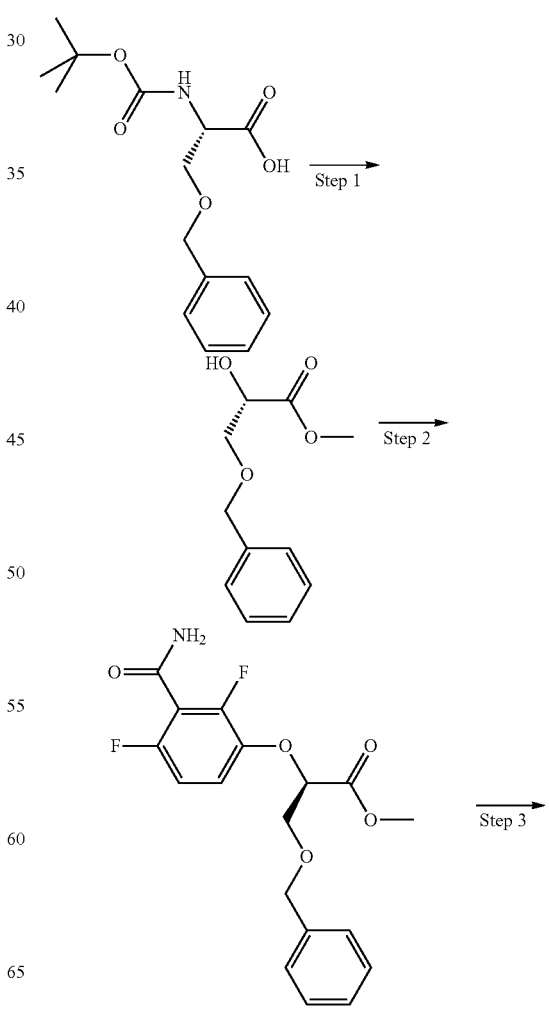

monitoring), ice-cold water was added to the mixture before extracting the product into EtOAc (3×50 mL). The combined organic layers were washed with water and brine, dried over Na$_2$SO$_4$, filtered and concentrated. The crude residue was purified by flash chromatography (30% EtOAc/hexane) to provide ethyl 2-(3-carbamoyl-2,4-difluorophenoxy)-2-(4-(4-chlorophenyl)thiazol-2-yl)acetate (0.045 g, 24%).

Step 4:

To an ice-cold solution of ethyl 2-(3-carbamoyl-2,4-difluorophenoxy)-2-(4-(4-chlorophenyl)thiazol-2-yl)acetate (0.20 g, 0.44 mmol) in MeOH (10 mL) was added NaBH$_4$ (0.17 g, 4.40 mmol) portion-wise. The mixture was allowed to stir at room temperature for 30 minutes. After this time, the MeOH was removed in vacuo, 1M HCl (aq) was added and the mixture was washed with EtOAc (3×50 mL). The combined organic layers were washed with water and brine, dried over Na$_2$SO$_4$, filtered and concentrated. The residue was purified by flash chromatography (40% EtOAc/hexane) to give 3-(1-(4-(4-chlorophenyl)thiazol-2-yl)-2-hydroxyethoxy)-2,6-difluorobenzamide (0.90 g, 50%).

Representative Example 4

Synthesis of (R)-3-(1-(5-bromo-4-(4-(trifluoromethyl)phenyl)oxazol-2-yl)-2-hydroxyethoxy)-2,6-difluorobenzamide Step 1:

A solution of 4-chlorophenacyl bromide (0.79 g, 3.38 mmol) and ethyl-3-amino-3-thioxopropanoate (0.50 g, 3.38 mmol) in EtOH (10 mL) was heated to 75° C. for 2 h under an atmosphere of N$_2$. At the completion of the reaction the EtOH was evaporated, water was added and the mixture was washed with EtOAc (3×50 mL). The combined organic phases were washed with water and brine, dried over Na$_2$SO$_4$, filtered and concentrated. The crude residue was purified by silica chromatography (5% EtOAc/hexane) to afford ethyl 2-(4-(4-chlorophenyl)thiazol-2-yl)acetate (0.67 g, 70%).

Step 2:

To a solution of ethyl 2-(4-(4-chlorophenyl)thiazol-2-yl) acetate (0.66 g, 2.34 mmol) in CCl$_4$ (10 mL) was added NBS (0.42 g, 2.34 mmol) and AIBN (0.038 g, 0.23 mmol) at room temperature. The resulting reaction mixture was then heated at 80° C. for 2 h. After the completion of reaction, the mixture was filtered and the filtrate concentrated in vacuo to yield ethyl 2-bromo-2-(4-(4-chlorophenyl)thiazol-2-yl)acetate (0.80 g, 67%) together with some of the corresponding dibromination product. The crude material was sufficiently pure to carry forward to the next step without further purification at this stage.

Step 3:

To a solution of ethyl 2-bromo-2-(4-(4-chlorophenyl) thiazol-2-yl)acetate (0.15 g, 0.41 mmol) in DMF (5 mL) was added K$_2$CO$_3$ (0.20 g, 1.45 mmol) followed by 2,6-difluoro-3-hydroxybenzamide (0.071 g, 0.41 mmol). The resulting reaction mixture was stirred under N$_2$ atmosphere at room temperature for 2 h. At the completion of reaction (TLC -continued

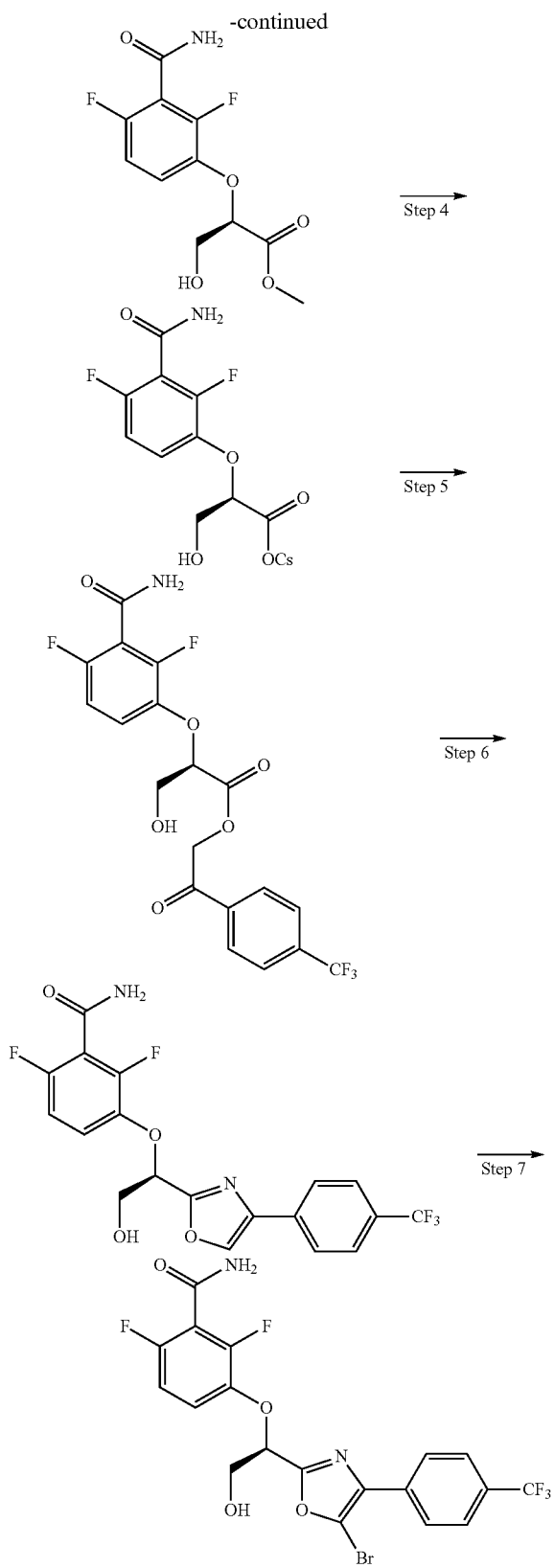

Step 1:

Boc-L-Ser-OH (5.9 g, 20 mmol) was dissolved in TFA (~8 mL, 100 mmol) and the solution was allowed to stand at room temperature for 45 minutes. Water (25 mL) and acetone (5 mL) were added. The solution was cooled to <5° C. and sodium acetate was added carefully to raise the pH to 4 (approximately 8 g). Acetone was then added to ensure re-dissolution of the precipitated solids before sodium nitrite (0.8 g) was introduced as an aqueous solution while maintaining the temperature below 5° C. The solution was warmed to ambient temperature and stirred for 4 hours. Additional sodium nitrite (1.6 g) was added while cooling to <10° C. The solution was then allowed to warm to ambient temperature and stirred for a further 16 h before concentrating in vacuo to yield crude (S)-3-benzyloxy-2-hydroxy-propionic acid as a thick syrup. This was dissolved in methanol (100 mL), treated with sulfuric acid (6 mL) and trimethyl orthoformate (10 mL) and stirred at reflux for 16 h. When esterification was complete (LC-MS) and the mixture was cooled and filtered. The filtrate was concentrated, suspended in a small volume of water and neutralised with half-saturated sodium bicarbonate. The product was extracted into EtOAc (3×50 mL) and the combined organic extracts were dried (MgSO$_4$) and concentrated to yield an orange liquid that was purified by flash chromatography (20-30% EtOAc in hexanes) to give (S)-3-benzyloxy-2-hydroxy-propionic acid methyl ester (2.6 g, 62%) as a clear oil.

Step 2:

Triphenylphosphine (2.54 g, 9.7 mmol, 1.2 eq) was dissolved in THF (10 mL) and treated with diethylazodicarboxylate (1.51 mL, 1.2 eq) at 0° C. After stirring for 5 minutes a solution of 2,6-difluoro-3-hydroxybenzamide (1.4 g, 8.1 mmol), (S)-3-benzyloxy-2-hydroxypropionic acid methyl ester (1.7 g, 8.1 mmol) and TEA (1.1 mL, 1 eq) in THF (10 mL) was added. The reaction mixture was allowed to warm to room temperature. After 40 minutes, an additional amount of triphenylphosphine (0.6 eq) was dissolved in THF (3 mL), chilled in ice/water, treated with diethylazodicarboxylate (0.6 eq) and then added to the main reaction solution at 0° C. After stirring for a further 48 h, the reaction mixture was concentrated and purified by flash chromatography (5-100% EtOAc in hexanes) to yield (R)-3-benzyloxy-2-(3-carbamoyl-2,4-difluoro-phenoxy)-propionic acid methyl ester as a clear oil (1.58 g, 53%).

Step 3:

(R)-3-Benzyloxy-2-(3-carbamoyl-2,4-difluoro-phenoxy)-propionic acid methyl ester (236 mg, 0.65 mmol) was dissolved in THF (20 mL), treated with 20% Pd(OH)$_2$ on carbon, evacuated of air and placed under an atmosphere of hydrogen at 1 atm. The mixture was stirred at ambient temperature for 1 h, then filtered and concentrated to yield (R)-2-(3-carbamoyl-2,4-difluorophenoxy)-3-hydroxypropionic acid methyl ester as a clear oil (178 mg, 100%).

Step 4:

(R)-2-(3-Carbamoyl-2,4-difluorophenoxy)-3-hydroxypropionic acid methyl ester (175 mg) and cesium carbonate (105 mg, 0.5 eq) were dissolved in water (4 mL) and acetonitrile (4 mL). The solution was heated to 55° C. for 3.5 hours. The solution was freeze-dried to yield cesium (R)-2-(3-carbamoyl-2,4-difluorophenoxy)-3-hydroxypropionate as a yellow foamy solid (230 mg, 92%).

Step 5:

Cesium (R)-2-(3-carbamoyl-2,4-difluorophenoxy)-3-hydroxypropionate (115 mg) was suspended in DMF (1 mL) and treated with 2-bromo-1-(4-trifluoromethylphenyl)ethanone (82 mg, 1.05 eq). The mixture was stirred at room temperature for 1 h and concentrated. The residue was purified by flash chromatography (20-100% EtOAc/hexanes) to yield (R)-2-(3-carbamoyl-2,4-difluorophenoxy)-3-hydroxypropionic acid 2-oxo-2-(4-trifluoromethyl-phenyl)-ethyl ester as a clear glass (95 mg, 73%).

Step 6:

(R)-2-(3-Carbamoyl-2,4-difluorophenoxy)-3-hydroxy-propionic acid 2-oxo-2-(4-trifluoromethylphenyl)-ethyl ester (95 mg) and acetamide (63 mg, 5 eq) were dissolved in xylenes (4 mL). Boron trifluoride diethyletherate (15 μL, 0.5 eq) was added and the mixture was stirred at reflux. After 2 h the reaction mixture was concentrated and partitioned between water (2 mL) and dichloromethane (3 mL). The aqueous layer was further extracted with EtOAc (1 mL) and the combined organic extracts were filtered through cotton wool and concentrated. The residue was purified by flash chromatography (20-100% EtOAc in hexanes) to yield 2,6-difluoro-3-{(R)-2-hydroxy-1-[4-(4-trifluoromethylphe-nyl)-oxazol-2-yl]-ethoxy}-benzamide as an off-white solid (19 mg, 21%).

Step 7: 2,6-Difluoro-3-{(R)-2-hydroxy-1-[4-(4-trifluorom-ethylphenyl)-oxazol-2-yl]-ethoxy}-benzamide (12 mg, 0.028 mmol) was dissolved in dichloromethane (250 μL), treated with a solution of bromine (7.3 μL, 0.14 mmol) in dichloromethane (1.4 mL) and allowed to stand for 16 h. The solution was washed with 5% sodium bicarbonate (1 mL) and brine (1 mL). The organic layer was filtered through a plug of cotton wool and purified by flash chromatography (0-5% MeOH in CH$_2$Cl$_2$) to yield (R)-3-(1-(5-bromo-4-(4-(trifluoromethyl)phenyl)oxazol-2-yl)-2-hydroxyethoxy)-2,6-difluorobenzamide as a white solid (9 mg, 63%).

Representative Example 5

Synthesis of (R)-3-(1-(5-bromo-4-(4-(trifluorom-ethyl)phenyl)oxazol-2-yl)ethoxy)-2,6-difluorobenz-amide

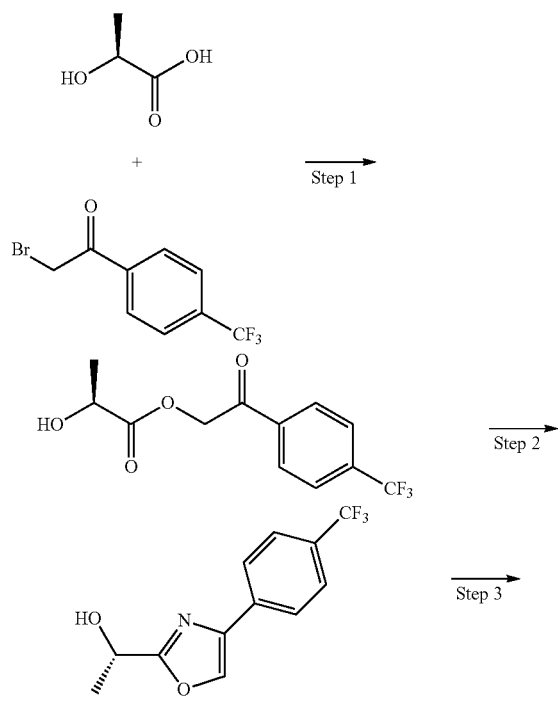

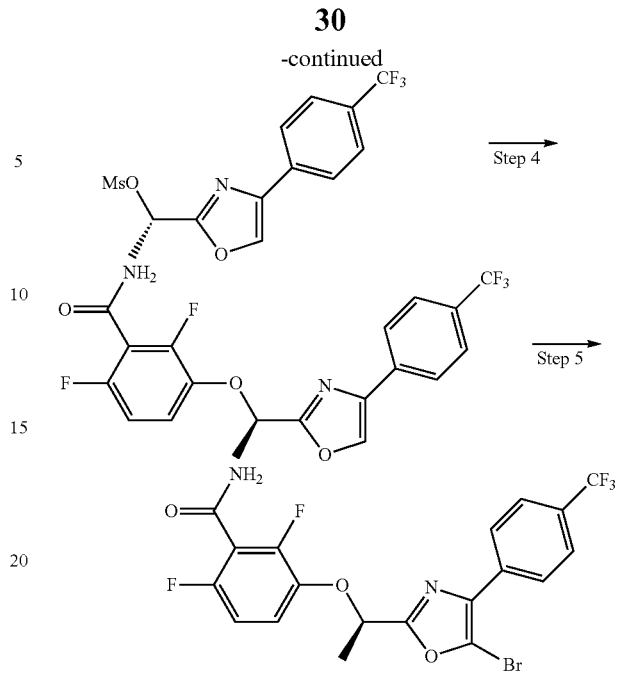

Step 1:

L-Lactic acid (0.50 g, 5.55 mmol) was taken up in water (1.0 mL) and then titrated to pH 7 with an aqueous solution of Cs$_2$CO$_3$. The resulting solution was then concentrated to obtain a clear oil, which was then diluted and reconcentrated with DMF (5 mL). The residue was again suspended in DMF (10 mL) and treated with 4-trifluoromethyl phenacyl bro-mide (1.63 g, 6.11 mmol) at room temperature. After stirring for 16 h the reaction mixture was concentrated under reduced pressure. The residue was suspended in water and washed with EtOAc (3×50 mL). The combined organic layers were washed with brine, dried over Na$_2$SO$_4$, filtered and concentrated under reduced pressure. The residue was purified by flash chromatography (50% EtOAc/hexane) to afford (S)-2-oxo-2-(4-(trifluoromethyl)phenyl)ethyl 2-hy-droxypropanoate (0.735 g, 48%).

Step 2:

To a solution of (S)-2-oxo-2-(4-(trifluoromethyl)phenyl) ethyl 2-hydroxypropanoate (0.835 g, 3.02 mmol) in glacial acetic acid (5-7 mL) was added NH$_4$OAc (1.17 g, 15.12 mmol) and the resulting reaction mixture was stirred at 120° C. for 30 minutes. At the completion of reaction (TLC), the mixture was diluted with ice-cold water and the product extracted into EtOAc (3×100 mL). The combined organic layers were washed with brine, dried over Na$_2$SO$_4$, filtered and concentrated under reduced pressure. The residue was purified by silica chromatography (10% EtOAc/hexane) to afford (S)-1-(4-(4-(trifluoromethyl)phenyl)oxazol-2-yl) ethanol (0.165 g, 21%).

Step 3:

To an ice-cold solution of (S)-1-(4-(4-(trifluoromethyl) phenyl)oxazol-2-yl)ethanol (0.165 g, 0.64 mmol) in DCM (10.0 mL) was added triethylamine (0.097 g, 0.96 mmol) and methanesulfonyl chloride (0.088 g, 0.77 mmol). The resulting reaction mixture was stirred at room temperature for 1 h. When reaction was complete (TLC) water was added and the mixture was washed with EtOAc (3×50 mL). The combined organic extracts were washed with brine, dried over Na$_2$SO$_4$, filtered and concentrated to yield (S)-1-(4-(4-(trifluoromethyl)phenyl)oxazol-2-yl)ethyl methanesulfonate (0.196 g, 91%), which was carried forward to the next step without further purification.

Step 4:

To a solution of (S)-1-(4-(4-(trifluoromethyl)phenyl)oxazol-2-yl)ethyl methanesulfonate (0.196 g, 0.58 mmol) in DMF (5.0 mL) was added K$_2$CO$_3$ (0.324 g, 2.34 mmol) and 2,6-difluoro-3-hydroxybenzamide (0.102 g, 0.58 mmol). The resulting reaction mixture was stirred under N$_2$ atmosphere at room temperature for 10-12 h. At the completion of reaction (TLC), ice-cold water was added and the mixture washed with EtOAc (3×75 mL). The combined organic layers were washed with brine, dried over Na$_2$SO$_4$, filtered and concentrated. The residue was purified by flash chromatography (35% EtOAc/hexane) to afford (R)-2,6-difluoro-3-(1-(4-(4-(trifluoromethyl)phenyl)oxazol-2-yl)ethoxy)benzamide (0.12 g, 50%). Chiral HPLC indicated 93.72% ee.

Step 5:

To a solution of (R)-2,6-difluoro-3-(1-(4-(4-(trifluoromethyl)phenyl)oxazol-2-yl)ethoxy)benzamide (0.05 g, 0.12 mmol) in DCM (2.0 mL) was added 1M bromine solution in DCM (130 µl, 0.13 mmol). The resulting solution was stirred at room temperature for 2 h. The majority of the starting material remained unconsumed at this time, so a further 1 eq of bromine solution was added over the course of 4 h. The resulting reaction mixture was left to stir overnight at room temperature before diluting with water and washing with EtOAc (3×20 mL). The combined organic extracts were washed with brine, dried over Na$_2$SO$_4$, filtered and concentrated under reduced pressure. The residue was purified by flash chromatography (30% EtOAc/hexane) to yield (R)-3-(1-(5-bromo-4-(4-(trifluoromethyl)phenyl)oxazol-2-yl)ethoxy)-2,6-difluorobenzamide (0.02 g, 34%).

Representative Example 6

Synthesis of (S)-2,6-difluoro-3-(1-(4-(4-methoxyphenyl)oxazol-2-yl)ethoxy)benzamide

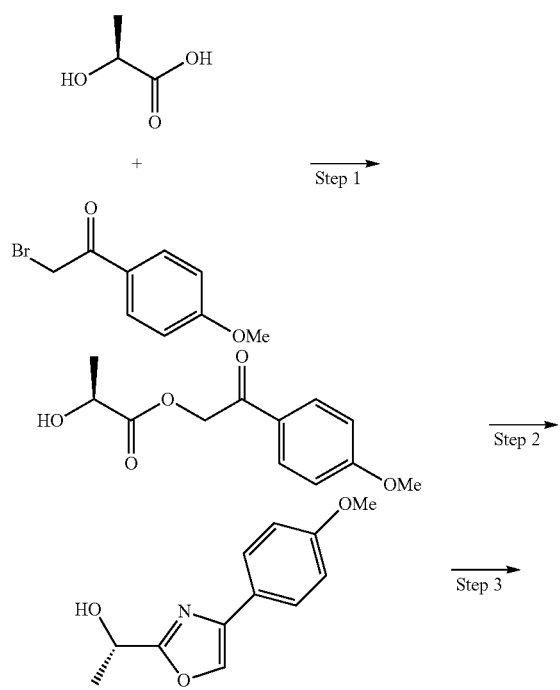

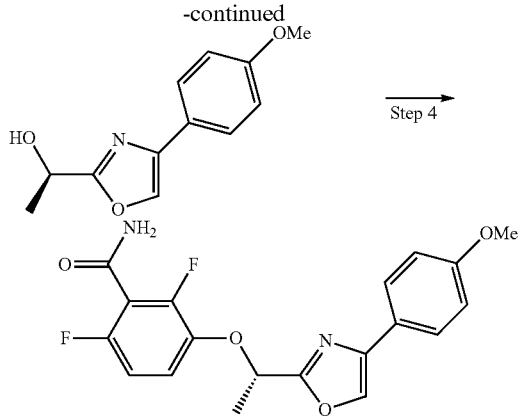

Step 1:

L-(+)-Lactic acid (Aldrich, 1.0 g, 11.1 mmol) was dissolved in water (2 mL) and titrated with an aqueous solution of cesium carbonate (1.98 g in 8 mL) to pH 7. The solution was concentrated to give a clear oil, which was twice reconcentrated from DMF. The residue was suspended in DMF (10 mL), treated with 2-bromo-1-(4-methoxyphenyl)ethanone (2.8 g, 1.1 eq) and allowed to stand at room temperature. Complete conversion was observed (LCMS) after 5 minutes. The DMF was removed in vacuo and the residue suspended in water. The product was extracted into EtOAc (3×50 mL) and the combined organic extracts were dried (MgSO$_4$) and concentrated. The residue was purified by flash chromatography (10-100% EtOAc/Hexane gradient) to yield (S)-2-hydroxypropionic acid 2-(4-methoxyphenyl)-2-oxo-ethyl ester as a white solid (2.2 g, 83%).

Step 2:

(S)-2-Hydroxy-propionic acid 2-(4-methoxyphenyl)-2-oxo-ethyl ester (1.5 g) and ammonium acetate (4 g) were suspended in acetic acid (15 mL). The mixture was stirred and heated at reflux for 2 h. The reaction mixture was neutralised with saturated Na$_2$CO$_3$ and washed with EtOAc (4×50 mL). The organic extracts were dried (MgSO$_4$) and concentrated and the residue purified by flash chromatography (5-25% EtOAc in hexanes) to provide the target, (S)-1-[4-(4-methoxyphenyl)-oxazol-2-3/1]-ethanol, as a yellow solid (157 mg, 11%).

Step 3:

The reaction vessel was charged with (S)-1-[4-(4-methoxyphenyl)-oxazol-2-yl]-ethanol (60 mg), 4-nitrobenzoic acid (92 mg, 2 eq), triphenylphosphine (144 mg, 2 eq) and THF (1.5 mL). Diethyl azodicarboxylate (85 µL) was added at 0° C. and the mixture was allowed to warm to room temperature. Formation of the product was evident after 1 h (LCMS). The mixture was concentrated and purified by silica chromatography (5 to 15% EtOAc in hexanes) to yield 4-nitrobenzoic acid (R)-1-[4-(4-methoxyphenyl)-oxazol-2-yl]-ethyl ester. The yellow solid was suspended in acetonitrile/methanol (1:1, 6 mL). A solution of NaOH (135 mg) in methanol (4 mL) was added and the suspension was allowed to stand at room temperature for 1 h before concentrating in vacuo. The residue was taken up in saturated NaHCO$_3$ (10 mL) and EtOAc (10 mL). The aqueous layer was washed with EtOAc (3×10 mL) and the combined organic extracts were dried (MgSO$_4$) and concentrated. The residue was purified by flash chromatography (5-30% EtOAc in hexanes) to yield (R)-1-[4-(4-methoxyphenyl)-oxazol-2-yl]-ethanol as a waxy solid (26 mg, 43%).

Step 4:

Triphenylphosphine (34 mg, 1.1 eq) was dissolved in dry THF (0.5 mL) and treated with diethylazodicarboxylate (21 µL, 1.1 mmol) at 0° C. After stirring for 5 minutes, a solution of 2,6-difluoro-3-hydroxybenzamide (21.6 mg, 1.05 mmol), (R)-1-[4-(4-methoxyphenyl)-oxazol-2-yl]-ethanol (26 mg, 0.12 mmol) and TEA (16.5 µL, 1 eq) in THF (1 mL) was added. The solution was warmed to room temperature. After 30 minutes no product was evident (LCMS). An additional quantity of triphenylphosphine (68 mg, 2.2 eq) was dissolved in THF (0.5 mL) and treated with diethylazodicarboxylate (44 µL, 2.4 mmol) at 0° C. The fresh betaine was added to the reaction solution at 0° C. and then the mixture was stirred at room temperature for 16 h. The mixture was concentrated and twice washed through silica using diethyl ether. The partially purified residue was subjected to flash chromatography (30-60% EtOAc in hexanes) to yield 2,6-difluoro-3-{(S)-1-[4-(4-methoxyphenyl)-oxazol-2-yl]-ethoxy}-benzamide as a white powder (26 mg, 59%).

Similarly prepared, starting from 3-(benzyloxycarbonylamino)-2-hydroxypropanoic acid, was, for example, benzyl (2-(3-carbamoyl-2,4-difluorophenoxy)-2-(4-(4-(trifluoromethyl)phenyl)oxazol-2-yl)ethyl)carbamate.

Representative Example 7

Synthesis of 3-(1-(4-(4-chlorophenyl)thiazol-2-yl)-2-(dimethylamino)-2-oxoethoxy)-2,6-difluorobenzamide

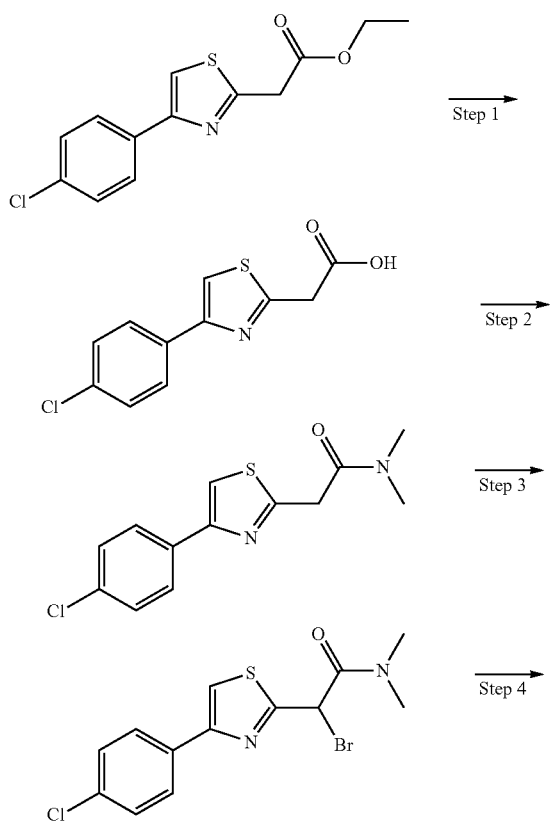

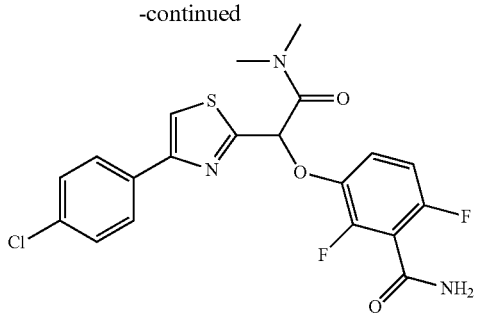

Step 1:

To a solution of ethyl 2-(4-(4-chlorophenyl)thiazol-2-yl) acetate (0.50 g, 1.77 mmol, prepared as described in Representative Example 3 in EtOH (15 mL) was added a solution of KOH (0.45 g, 8.0 mmol) in H$_2$O (2 mL) and the resulting reaction mixture was heated to 80° C. for 2 h. When the reaction was complete (TLC), water was added and the mixture was washed with EtOAc (2×50 mL). The organic layer was discarded and the pH of the aqueous layer was adjusted to 4-5 by addition of 6 M HCl. The product was extracted into EtOAc (3×50 mL) and the combined organic phases were washed with brine, dried over Na$_2$SO$_4$, filtered and concentrated to give 2-(4-(4-chlorophenyl)thiazol-2-yl) acetic acid (0.40 g, 89%).

Step 2:

To a solution of 2-(4-(4-chlorophenyl)thiazol-2-yl)acetic acid (0.20 g, 0.79 mmol) in DCM (20 mL) was added dimethylamine hydrochloride (0.097 g, 1.18 mmol), EDCI·HCl (0.38 g, 1.97 mmol), HOBt (0.30 g, 1.97 mmol) and DMAP (0.48 g, 3.95 mmol) sequentially. The resulting reaction mixture was stirred at room temperature for 4 h. At the completion of the reaction (TLC), water was added and the product extracted into EtOAc (3×50 mL). The combined organic layers were washed with water and brine, dried over Na$_2$SO$_4$, filtered and concentrated. The residue was purified by flash chromatography (30% EtOAc/hexane) to afford 2-(4-(4-chlorophenyl)thiazol-2-yl)-N,N-dimethylacetamide (0.14 g, 63%) as an off-white crystalline solid.

Step 3:

To a solution of 2-(4-(4-chlorophenyl)thiazol-2-yl)-N,N-dimethylacetamide (0.14 g, 0.49 mmol) in CCl$_4$ (10 mL) was added NBS (0.090 g, 0.49 mmol) and AIBN (0.008 g, 0.05 mmol) at room temperature. The resulting reaction mixture was then heated at 80° C. for 30 minutes. At the completion of the reaction (TLC), the solution was filtered and concentrated. The residue was subjected to flash chromatography (9% EtOAc/hexane) to yield 2-bromo-2-(4-(4-chlorophenyl)thiazol-2-yl)-N,N-dimethylacetamide (0.10 g, 56%).

Step 4:

To a solution of 2-bromo-2-(4-(4-chlorophenyl)thiazol-2-yl)-N,N-dimethylacetamide (0.10 g, 0.27 mmol) in DMF (5 mL) was added K$_2$CO$_3$ (0.115 g, 0.81 mmol) followed by 2,6-difluoro-3-hydroxybenzamide (0.047 g, 0.27 mmol). The resulting reaction mixture was stirred under N$_2$ atmosphere at room temperature for 3 h. After the completion of reaction (TLC), ice-cold water was added and the product extracted with EtOAc (3×50 mL). The combined organic layers were washed with water and brine, dried over Na$_2$SO$_4$, filtered and concentrated. The residue thus obtained was washed with ether to give 3-(1-(4-(4-chlorophenyl)thiazol-2-yl)-2-(dimethylamino)-2-oxoethoxy)-2,6-difluorobenzamide (0.07 g, 57%).

Representative Example 8

Synthesis of 3-(1-(3-(4-chlorophenyl)-1,2,4-thiadiazol-5-yl)ethoxy)-2,6-difluorobenzamide

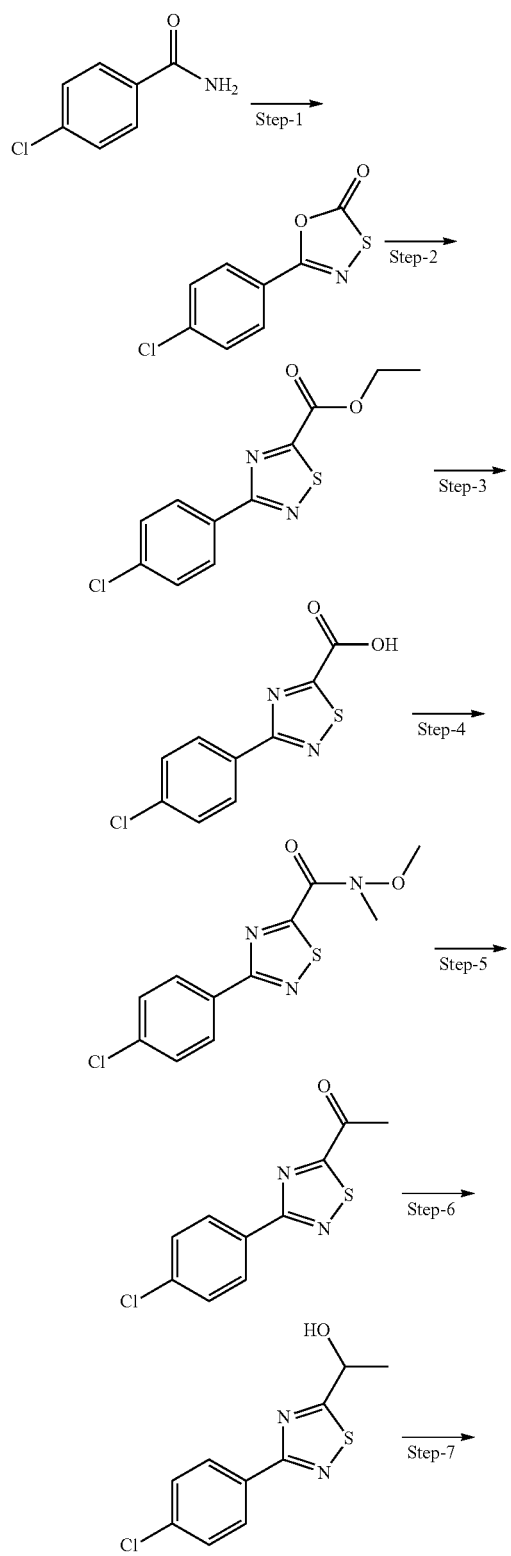

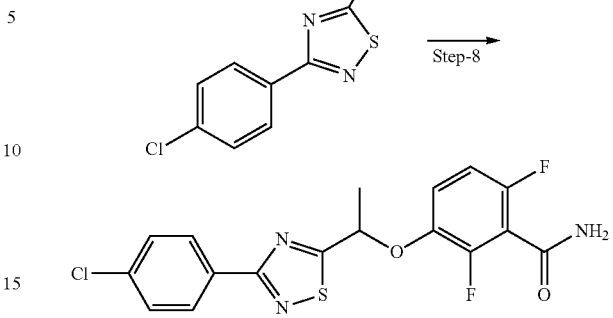

Step 1:
To a solution of 4-chlorobenzamide (0.25 g, 1.60 mmol) in toluene (10 ml) was added chlorocarbonylsulfenyl chloride (0.70 ml, 8.03 mmol). The resulting reaction mixture was heated to 80° C. for 3 h. After the completion of the reaction (TLC monitoring) the mixture was concentrated, resuspended in diethyl ether and washed twice with water, twice with 5% NaHCO$_3$, again with water, was dried over Na$_2$SO$_4$ and concentrated under vacuum to give the crude product (crude yield 0.520 g) which was carried forward to the next step without further purification.

Step 2:
To a solution of 5-(4-chlorophenyl)-[1,3,4]oxathiazol-2-one (0.60 g, 2.80 mmol) in n-dodecane (0.80 ml) was added ethyl cyanoformate (1.10 ml, 11.20 mmol). The resulting reaction mixture was refluxed for 20 h at 150° C. After the completion of the reaction (TLC monitoring), ice-cold water was added and the mixture washed with ethyl acetate (3×75 ml). The combined organic layers were dried over Na$_2$SO$_4$, filtered and concentrated under vacuum. The crude residue was purified by flash chromatography (20% EtOAc-Hexane) to afford the desired product (0.23 g, 30%).

Step 3:
To a solution of ethyl 3-(4-chlorophenyl)-1,2,4-thiadiazole-5-carboxylate (1.0 eq) in EtOH was added an aqueous solution of NaOH (3.0 eq) and the resulting solution was heated to reflux for 1 h. After the completion of reaction, the solvent was evaporated, water was added and the mixture washed with EtOAc (3 times). The organic layer was discarded and the aqueous fraction was carefully acidified to pH 5 with 6N HCl before washing with EtOAc (3 times). The combined organic layers were washed with brine, dried over Na$_2$SO$_4$, filtered and concentrated under reduced pressure to give the desired product.

Step 4:
To a solution of 3-(4-chlorophenyl)-1,2,4-thiadiazole-5-carboxylic acid (1.0 eq) in DMF was added N,O-dimethylhydroxylamine hydrochloride (1.10 eq), 1-(3-dimethylaminopropyl)-3-ethylcarbodiimide hydrochloride (1.50 eq), 1-hydroxybenzotriazole (1.0 eq), 4-(dimethylamino)pyridine (1.0 eq) and a catalytic amount of triethylamine. The resulting reaction mixture was stirred at room temperature for 16 h. After this time, the mixture was diluted with ice-cold water and washed with EtOAc three times. The combined organic layers were washed with cold water and brine, dried over anhydrous Na$_2$SO$_4$, filtered and concentrated in vacuo. The crude residue was purified by flash chromatography (30-50% EtOAc/hexane) to afford the desired product.

Step 5:

A solution of the Weinreb amide (1.0 eq) in THF was cooled to 0° C. and treated with methylmagnesium bromide (2.0 eq). The resulting reaction mixture was stirred at 0° C. for 45 minutes. After the completion of reaction (TLC monitoring), saturated ammonium chloride solution was added, followed by extraction with EtOAc (3 times). The combined organic layers were washed with brine, dried over anhydrous $Na_2SO_4$, filtered and concentrated in vacuo. The crude residue was purified by flash chromatography (10-20% EtOAc-Hexane) to afford the desired product Step 6:

1-[3-(4-chlorophenyl)-1,2,4-thiadiazol-5-yl]ethanone was reduced to the corresponding alcohol using the method described for Step 2, Representative example 2.

Step 7:

To a solution of 1-[3-(4-chlorophenyl)-1,2,4-thiadiazol-5-yl]ethanol (1.0 eq) in toluene was added $PBr_3$ (1.50 eq) and the resulting reaction mixture was heated at reflux for 30 minutes. At the completion of the reaction, the solvent was evaporated and the residue resuspended in water and washed with EtOAc (3 times). The combined organic layers were washed with a saturated solution of $NaHCO_3$, dried over $Na_2SO_4$, filtered and concentrated under reduced pressure to give 5-(1-bromoethyl)-3-(4-chlorophenyl)-1,2,4-thiadiazole.

Step 8:

2,6-difluoro-3-hydroxybenzamide was alkylated with 5-(1-bromoethyl)-3-(4-chlorophenyl)-1,2,4-thiadiazole according to the method described for Step 4, Representative Example 1.

Similarly prepared was, for example, 3-(1-(4-bromothiazol-2-yl)ethoxy)-2,6-difluorobenzamide (via Steps 6-8 from 4-bromothiazole-2-carbaldehyde, which was in turn prepared from commercially available 2,4-dibromothiazole and DMF via n-butyllithium-mediated lithium/halogen exchange).

Representative Example 9

Synthesis of (R)-3-(1-(6-chlorothiazolo[5,4-b]pyridin-2-yl)-2-hydroxyethoxy)-2,6-difluorobenzamide

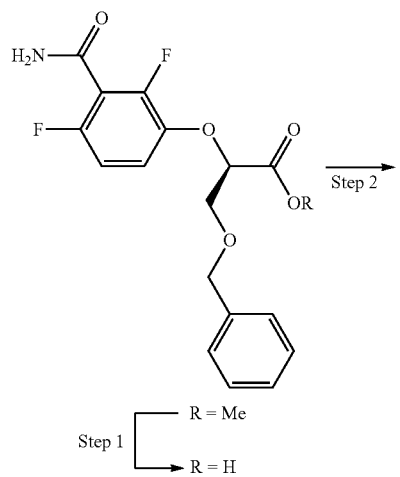

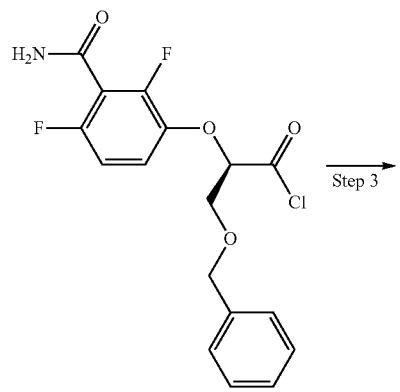

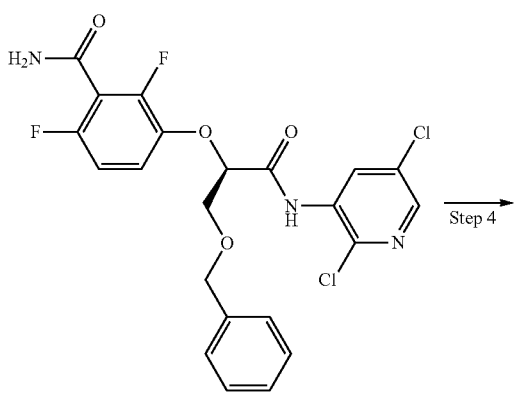

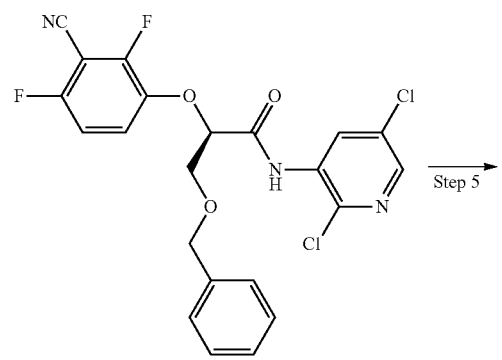

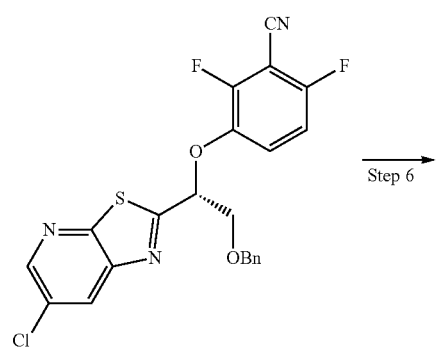

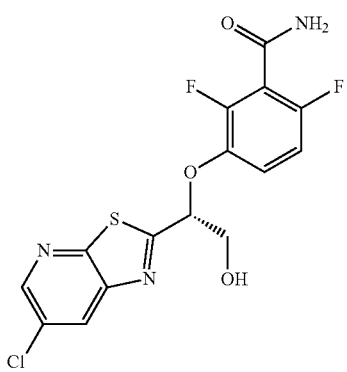

Step 1:

To a solution of (R)-methyl 3-(benzyloxy)-2-(3-carbamoyl-2,4-difluoro-phenoxy)propanoate (1.0 g, 2.73 mmol, prepared as described in Representative Example 4) in THF (10.0 mL) was added an aqueous solution of lithium hydroxide (0.57 g, 13.68 mmol). The resulting reaction mixture was stirred at room temperature for 3 h. When the reaction was complete (TLC), water (50 mL) was added and the mixture was washed with EtOAc (2×50 mL). The organic layer was discarded and the aqueous layer was adjusted to pH 4 using 2 M HCl. The product was extracted into EtOAc (3×50 mL) and the combined organic layers were washed with brine, dried over anhydrous $Na_2SO_4$, filtered and concentrated in vacuo. The residue was triturated with n-pentane/ether to give (R)-3-(benzyloxy)-2-(3-carbamoyl-2,4-difluorophenoxy)-propanoic acid (0.95 g, 98%).

Step 2:

To an ice-cold solution of (R)-3-(benzyloxy)-2-(3-carbamoyl-2,4-difluoro-phenoxy)propanoic acid (1.0 g, 2.84 mmol) in DCM was added oxalyl chloride (1.2 mL, 14.23 mmol). The reaction mixture was allowed to warm to room temperature and a catalytic amount of DMF was added. When the reaction was complete (TLC, with addition of methanol), the mixture was concentrated under nitrogen at reduced pressure to afford crude (R)-3-(benzyloxy)-2-(3-carbamoyl-2,4-difluorophenoxy)propanoyl chloride (1.0 g), suitable for use in the next step without further purification.

Step 3:

To an ice-cold solution of (R)-3-(benzyloxy)-2-(3-carbamoyl-2,4-difluoro-phenoxy)propanoyl chloride in DCM was added 3-amino-2,5-dichloropyridine (0.42 g, 2.55 mmol) and triethylamine (1.97 mL, 14.23 mmol). The resulting reaction mixture was stirred at room temperature for 1 h. After the completion of reaction (TLC), water was added and the product extracted into EtOAc (3×50 mL). The combined organic layers were washed with brine, dried over anhydrous $Na_2SO_4$, filtered and concentrated in vacuo. The crude residue was purified by silica chromatography (30% EtOAc/hexane) to afford (R)-3-(3-(benzyloxy)-1-(2,5-dichloropyridin-3-ylamino)-1-oxopropan-2-yloxy)-2,6-difluorobenzamide (0.50 g, 36%).

Step 4:

To an ice-cold solution of acetonitrile (10.0 mL) and DMF (5.0 mL) was added oxalyl chloride (0.47 mL, 5.03 mmol). The resulting mixture was stirred at that temperature for 10 minutes, followed by addition of a solution of (R)-3-(3-(benzyloxy)-1-(2,5-dichloropyridin-3-ylamino)-1-oxopropan-2-yloxy)-2,6-difluorobenzamide (0.50 g, 1.0 mmol) in acetonitrile (10.0 mL). The reaction mixture was stirred at room temperature for 30 minutes. After this time, water was added and the product was extracted with EtOAc (3×50 mL). The combined organic layers were washed with brine, dried over anhydrous $Na_2SO_4$, filtered and concentrated in vacuo. The crude residue was purified by silica chromatography (10% EtOAc/hexane) to yield (R)-3-(benzyloxy)-2-(3-cyano-2,4-difluorophenoxy)-N-(2,5-dichloropyridin-3-yl)propanamide (0.40 g, 83%).

Step 5:

To a solution of (R)-3-(benzyloxy)-2-(3-cyano-2,4-difluorophenoxy)-N-(2,5-dichloropyridin-3-yl)propanamide (0.70 g, 1.46 mmol) in toluene (50 mL) was added $P_2S_5$ (1.29 g, 2.92 mmol). The resulting reaction mixture was heated at reflux for 1 h. After the completion of reaction (TLC monitoring), toluene was evaporated under reduced pressure and water was added. The product was extracted into EtOAc (3×50 mL). The combined organic layers were washed with brine, dried over anhydrous $Na_2SO_4$, filtered and concentrated in vacuo. The crude residue was purified by flash chromatography (50% EtOAc/hexane) to afford (R)-3-(2-(benzyloxy)-1-(6-chlorothiazolo[5,4-b]pyridin-2-yl)ethoxy)-2,6-difluorobenzonitrile. (0.24 g, 36%).

Step 6:

A solution of (R)-3-(2-(benzyloxy)-1-(6-chlorothiazolo[5,4-b]pyridin-2-yl)ethoxy)-2,6-difluorobenzonitrile (0.24 g, 0.52 mmol) in sulfuric acid (1.5 mL) was heated at 60° C. After 30 minutes, the reaction was quenched with crushed ice, neutralized with 1.0 M NaOH (aq) and the product was extracted into EtOAc (3×25 mL). The combined organic layers were washed with brine, dried over anhydrous $Na_2SO_4$, filtered and concentrated in vacuo. The crude residue was purified by flash chromatography (70% EtOAc/hexane) and then by preparative TLC to yield (R)-3-(1-(6-chlorothiazolo[5,4-b]pyridin-2-yl)-2-hydroxyethoxy)-2,6-difluorobenzamide (0.03 g, 15%).

Representative Example 10

Synthesis of 3-(1-(5-bromo-4-(4-(trifluoromethyl)phenyl)oxazol-2-yl)-2,3-dihydroxypropoxy)-2,6-difluorobenzamide

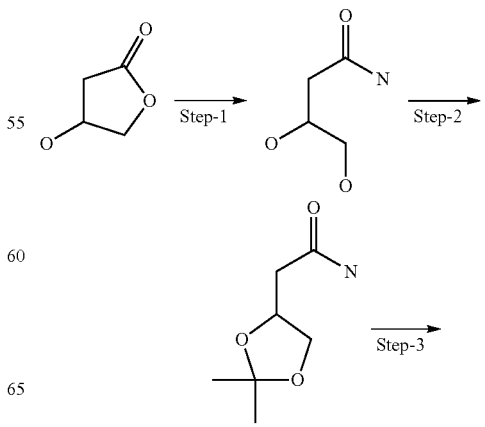

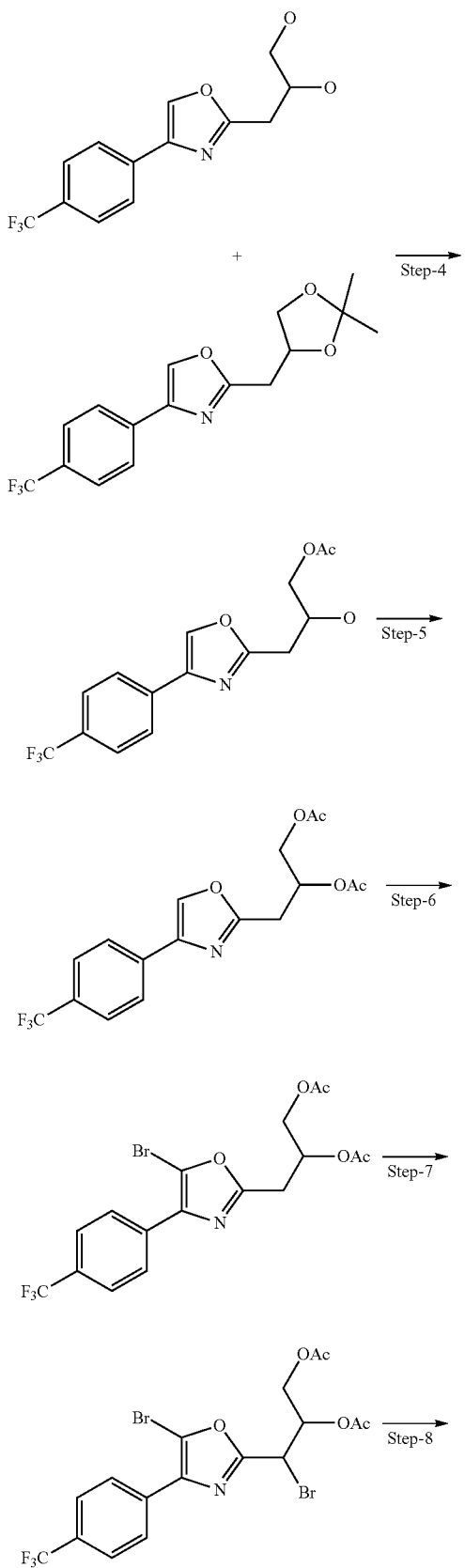

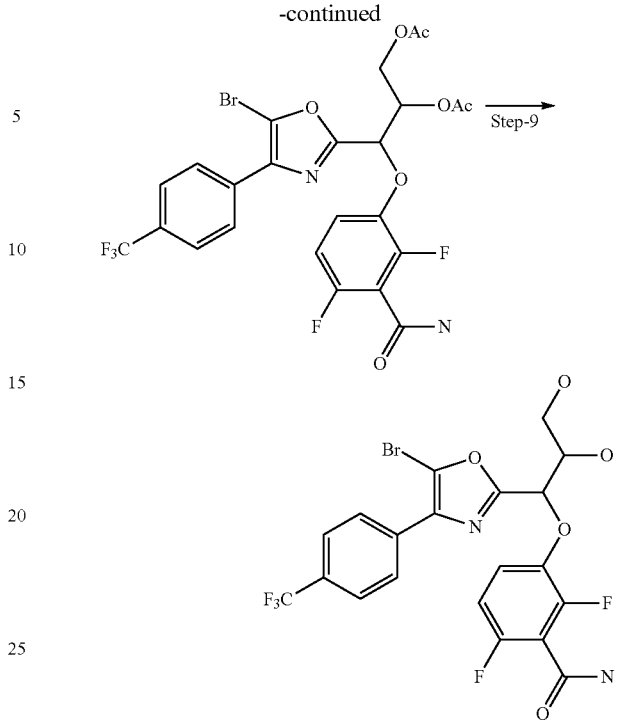

Step 1:
A solution of 2-hydroxy-γ-butyrolactone (10.0 g, 97.95 mmol) in 25% aqueous ammonia (25 mL) was stirred at room temperature for 16 h in a sealed tube. After completion of the reaction, the mixture was concentrated under reduced pressure. The viscous product was triturated with dichloromethane to obtain 3,4-dihydroxybutanamide as an off white solid (12.0 g, 95%).

Step 2:
To a solution of 3,4-dihydroxybutanamide (0.50 g, 4.19 mmol) in acetone (10 mL) was added 2,2-dimethoxypropane (1.0 mL, 8.38 mmol) and p-toluenesulfonic acid (0.036 g, 0.20 mmol). The resulting reaction mixture was heated at reflux for 30 minutes and then allowed to stir at room temperature for 16 h. After this time sodium carbonate was added (1.0 g, 9.40 mmol) and the mixture was again stirred for 1 h. Methanol (5 mL) was added, the mixture was filtered and the filter cake was washed with methanol. The combined filtrate was concentrated under reduced pressure to yield 2-(2,2-dimethyl-1,3-dioxolan-4-yl)acetamide as an off-white solid (0.50 g, 38%).

Step 3:
A mixture of 4'-(trifluoromethyl)phenacyl bromide (8.06 g, 30.18 mmol) and 2-(2,2-dimethyl-1,3-dioxolan-4-yl)acetamide (12.0 g, 75.45 mmol) was heated at 130° C. for 2.5 h. After completion of the reaction the mixture was cooled, diluted with water (200 mL) and washed with ethyl acetate (3×100 mL). The combined organic layers were dried over anhydrous sodium sulfate, filtered and concentrated. The crude residue was purified by flash chromatography (10% EtOAc/hexane) to obtain 2-[(2,2-dimethyl-1,3-dioxolan-4-yl)methyl]-4-[4-(trifluoromethyl)phenyl]oxazole (1.50 g, 15%). Further elution of the silica (50% EtOAc/hexane) afforded the target 3-(4-(4-(trifluoromethyl)phenyl)oxazol-2-yl)propane-1,2-diol (2.40 g, 28%)

Step 4:
An ice cold solution of 3-(4-(4-(trifluoromethyl)phenyl)oxazol-2-yl)propane-1,2-diol (0.50 g, 1.74 mmol) and Et₃N (0.29 mL, 2.08 mmol) in DCM (15 mL) was stirred for 5-10 minutes and then treated drop-wise with acetyl chloride (0.18 mL, 2.61 mmol). The reaction mixture was then stirred at room temperature for 30-45 minutes. After the completion of reaction (TLC), water was added and the reaction mixture was washed with EtOAc (3×50 mL). The combined organic layers were washed with water and brine, dried over $Na_2SO_4$, filtered and concentrated. The residue was purified by flash chromatography (30% EtOAc/hexane) to afford 2-hydroxy-3-(4-(4-(trifluoromethyl)phenyl)oxazol-2-yl) propyl acetate (0.25 g, 44%).

Step 5:

An ice cold solution of 2-hydroxy-3-(4-(4-(trifluoromethyl)phenyl)oxazol-2-yl)propyl acetate (0.25 g, 0.75 mmol) and $Et_3N$ (0.08 mL, 1.12 mmol) in DCM (10 mL) was stirred for 5-10 minutes followed by drop-wise addition of acetyl chloride (0.21 mL, 1.51 mmol). The reaction mixture was the stirred at room temperature for 30-45 minutes. After the completion of reaction (TLC), water was added and the reaction mixture was washed with EtOAc (3×50 mL). The combined organic layers were washed with water and brine, dried over $Na_2SO_4$, filtered and concentrated. The residue was purified by flash chromatography (10% EtOAc/hexane) to afford 3-(4-(4-(trifluoromethyl)phenyl)oxazol-2-yl)propane-1,2-diyl diacetate (0.18 g, 64%).

Step 6:

To a solution of 3-(4-(4-(trifluoromethyl)phenyl)oxazol-2-yl)propane-1,2-diyl diacetate (0.18 g, 0.48 mmol) in acetic acid (5 mL) was added NBS (0.08 g, 0.48 mmol) and the resulting reaction mixture was stirred at room temperature for 30 minutes. After the completion of reaction (TLC) the mixture was diluted with water, basified with saturated sodium bicarbonate solution and washed with EtOAc (3×50 mL). The combined organic layers were washed with brine, dried over $Na_2SO_4$, filtered and concentrated. The residue was purified by flash chromatography (8% EtOAc/hexane) to yield 3-(5-bromo-4-(4-(trifluoromethyl)phenyl)oxazol-2-yl)propane-1,2-diyl diacetate (0.13 g, 59%).

Step 7:

To a solution of 3-(5-bromo-4-(4-(trifluoromethyl)phenyl)oxazol-2-yl)propane-1,2-diyl diacetate (0.17 g, 0.37 mmol) in $CCl_4$ (5.0 mL) was added NBS (0.07 g, 0.37 mmol) and AIBN (0.006 g, 0.03 mmol). The reaction mixture was stirred at 80° C. for 8 h. After this time the mixture was filtered and the filtrate was concentrated in vacuo.

The residue was purified by flash chromatography (5% EtOAc/hexane) to afford 3-bromo-3-(5-bromo-4-(4-(trifluoromethyl)phenyl)oxazol-2-yl)propane-1,2-diyl diacetate (0.06 g, 32%).

Step 8:

To a solution of 3-bromo-3-(5-bromo-4-(4-(trifluoromethyl)phenyl)oxazol-2-yl)propane-1,2-diyl diacetate (0.40 g, 0.75 mmol) in DMF (5 mL) was added $K_2CO_3$ (0.31 g, 2.25 mmol) followed by 2,6-difluoro-3-hydroxybenzamide (0.13 g, 0.75 mmol). The resulting reaction mixture was stirred under $N_2$ atmosphere at room temperature for 4 h. After this time, the reaction mixture was washed with ice-cold water and EtOAc (3×50 mL). The combined organic layers were washed with brine, dried over $Na_2SO_4$, filtered and concentrated. The residue was purified by flash chromatography (30% EtOAc/hexane) to afford 3-(5-bromo-4-(4-(trifluoromethyl)-phenyl)oxazol-2-yl)-3-(3-carbamoyl-2,4-difluorophenoxy)propane-1,2-diyl diacetate (0.09 g, 19%).

Step 9:

To a solution of 3-(5-bromo-4-(4-(trifluoromethyl)phenyl)oxazol-2-yl)-3-(3-carbamoyl-2,4-difluorophenoxy)propane-1,2-diyl diacetate (0.09 g, 0.14 mmol) in MeOH (5 mL) was added $K_2CO_3$ (0.060 g, 0.43 mmol) and the resulting reaction mixture was stirred at room temperature for 1 h. At the completion of reaction (TLC monitoring), the mixture was diluted with water and washed with EtOAc (3×25 mL). The combined organic layers were washed with brine, dried over $Na_2SO_4$, filtered and concentrated. The residue was purified by preparative TLC to yield 3-(1-(5-bromo-4-(4-(trifluoromethyl)phenyl)oxazol-2-yl)-2,3-dihydroxypropoxy)-2,6-difluorobenzamide (0.013 g, 17%).

Representative Example 11

Synthesis of 3-(1-(5-bromo-4-(4-(trifluoromethyl) phenyl)oxazol-2-yl-3,4-dihydroxybutoxy)-2,6-difluorobenzamide

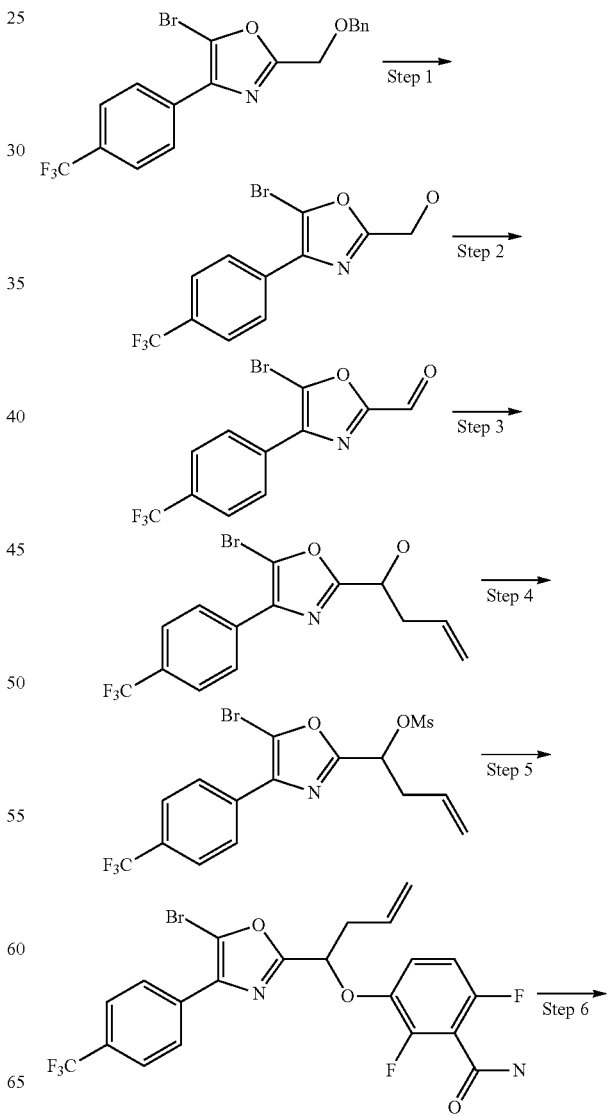

-continued

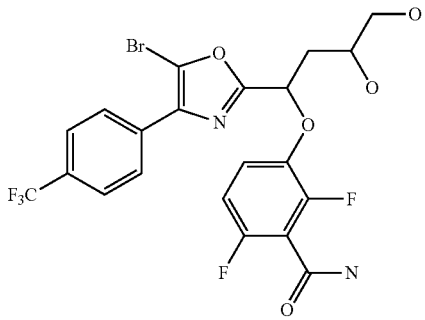

Step 1:

An ice cold solution of 2-(benzyloxymethyl)-5-bromo-4-(4-(trifluoromethyl)-phenyl)oxazole (1.5 g, 3.63 mmol, prepared from 2-bromo-1-[4-(trifluoromethyl)-phenyl]ethanone and 2-benzyloxyacetamide in the analogous manner as described for Steps 1 and 2 of General Method A) in DCM (20 mL) was added methanesulfonic acid (4.7 mL, 72.78 mmol). The resulting reaction mixture was stirred at room temperature for 1 h. Water was added and the mixture was washed with EtOAc (3×100 mL). The combined organic layers were washed with saturated sodium bicarbonate and brine, dried over $Na_2SO_4$, filtered and concentrated. The residue was purified by flash chromatography (10% EtOAc/hexane) to afford (5-bromo-4-(4-(trifluoromethyl)phenyl)oxazol-2-yl)methanol (0.80 g, 68%).

Step 2:

To a solution of (5-bromo-4-(4-(trifluoromethyl)phenyl)oxazol-2-yl)methanol (0.80 g, 2.48 mmol) in DCM (20.0 mL) was added pyridinium chlorochromate (1.33 g, 6.20 mmol). The resulting mixture was stirred at room temperature for 6 h and then concentrated. The residue was resuspended in water and washed with EtOAc (3×100 mL). The combined organic layers were washed with brine, dried over anhydrous $Na_2SO_4$, filtered and concentrated in vacuo. The crude material was purified by flash chromatography (6% EtOAc/hexane) to provide 5-bromo-4-(4-(trifluoromethyl)-phenyl)oxazole-2-carbaldehyde (0.60 g, 76%).

Step 3:

To a solution of 5-bromo-4-(4-(trifluoromethyl)phenyl)oxazole-2-carbaldehyde (0.10 g, 0.31 mmol) in de-mineralized water (5.0 mL) was added allyl bromide (0.076 g, 0.62 mmol) and indium (0.072 g, 0.62 mmol) and the resulting reaction mixture was stirred at the room temperature for 2 h. After the completion of reaction (TLC monitoring), the mixture was acidified with 1N HCl to pH~1-2 and then the product was extracted into EtOAc (3×50 mL). The combined organic layers were washed with brine, dried over $Na_2SO_4$, filtered and concentrated to afford 1-(5-bromo-4-(4-(trifluoromethyl)phenyl)oxazol-2-yl)but-3-en-1-ol (0.10 g). The crude product was used directly in the next step without further purification.

Step 4:

Methanesulfonyl chloride (0.042 mL, 0.55 mmol) and triethylamine (0.19 mL, 1.38 mmol) were added to an ice-cold solution of 1-(5-bromo-4-(4-(trifluoromethyl)-phenyl)oxazol-2-yl)but-3-en-1-ol (0.10 g, 0.27 mmol) in DCM and stirred for 30 minutes. When the reaction was complete (TLC monitoring) water was added and the mixture was washed with EtOAc (3×50 mL). The combined organic layers were washed with brine, dried over $Na_2SO_4$, filtered and concentrated to give 1-(5-bromo-4-(4-(trifluoromethyl) phenyl)oxazol-2-yl)but-3-enyl methanesulfonate (0.10 g). The crude product was used directly in the next step without further purification.

Step 5:

To a solution of 1-(5-bromo-4-(4-(trifluoromethyl)phenyl)oxazol-2-yl)but-3-enyl methanesulfonate (0.10 g, 0.22 mmol) in DMF (5.0 mL) was added $K_2CO_3$ (0.094 g, 0.68 mmol) followed by 2,6-difluoro-3-hydroxybenzamide (0.039 g, 0.22 mmol).

The resulting reaction mixture was stirred under $N_2$ at room temperature for 6 h. At the completion of reaction (TLC monitoring), ice-cold water was added and the reaction mixture was washed with EtOAc (3×50 mL). The combined organic layers were washed with 1M NaOH solution, water and brine, dried over $Na_2SO_4$, filtered and concentrated. The residue was purified by flash chromatography (20% EtOAc/hexane) to provide 3-(1-(5-bromo-4-(4-(trifluoromethyl)phenyl)oxazol-2-yl)but-3-enyloxy)-2,6-difluorobenzamide (0.060 g, 52%).

Step 6:

To a solution of 3-(1-(5-bromo-4-(4-(trifluoromethyl)phenyl)oxazol-2-yl)but-3-enyloxy)-2,6-difluorobenzamide (0.025 g, 0.04 mmol) in acetone (10.0 mL) was added N-methylmorpholine N-oxide (0.028 g, 0.24 mmol), osmium tetraoxide (0.90 mL, 0.08 mmol) and water (1 mL). The resulting reaction mixture was stirred at room temperature for 2 h. When the reaction was complete (TLC monitoring), the mixture was diluted with ice-cold water and the product extracted into EtOAc (3×50 mL). The combined organic layers were washed with brine, dried over $Na_2SO_4$, filtered and concentrated. The residue was purified by preparative TLC to yield 3-(1-(5-bromo-4-(4-(trifluoromethyl) phenyl)oxazol-2-yl)-3,4-dihydroxybutoxy)-2,6-difluorobenzamide as a mixture of two diastereomeric pairs of enantiomers (0.013 g, 49%). The two racemates, viz. (R,S)/(S,R)-3-(1-(5-bromo-4-(4-(trifluoromethyl)phenyl)oxazol-2-yl)-3,4-dihydroxybutoxy)-2,6-difluorobenzamide and (S,S)/(R,R)-3-(1-(5-bromo-4-(4-(trifluoromethyl)phenyl) oxazol-2-yl)-3,4-dihydroxybutoxy)-2,6-difluorobenzamide, were isolated from each other by reverse-phase HPLC (C18). Three of the four individual enantiomers were also successfully isolated from the original mixture by means of preparative chiral HPLC. The chiral HPLC conditions utilised were as described in the subsequent example for separation of 3-(1-(5-bromo-4-(4-(trifluoromethyl)phenyl) oxazol-2-yl)-2-hydroxyethoxy)-2,6-difluorobenzamide.

Similarly prepared were, for example, 3-((5-bromo-4-(4-chlorophenyl)oxazol-2-yl)(pyridin-3-yl)methoxy)-2,6-difluorobenzamide, 3-((1-(5-bromo-4-(4-(trifluoromethyl)phenyl)oxazol-2-yl)allyl)oxy)-2,6-difluorobenzamide, 3-((1-(5-bromo-4-(4-(trifluoromethyl)phenyl)oxazol-2-yl)pent-4-en-1-yl)oxy)-2,6-difluorobenzamide and 3-((1-(5-bromo-4-(4-(trifluoromethyl)phenyl)oxazol-2-yl)-4,5-dihydroxypentyl) oxy)-2,6-difluorobenzamide (as a mixture of two diastereomeric pairs of enantiomers). These compounds were prepared using the corresponding Grignard reagent in THF at Step 3 in place of aqueous allyl bromide and indium.

Representative Example 12

Synthesis of 3-(1-(5-bromo-4-(4-(trifluoromethyl)phenyl)oxazol-2-yl)-4-hydroxy-3-(hydroxymethyl)butoxy)-2,6-difluorobenzamide

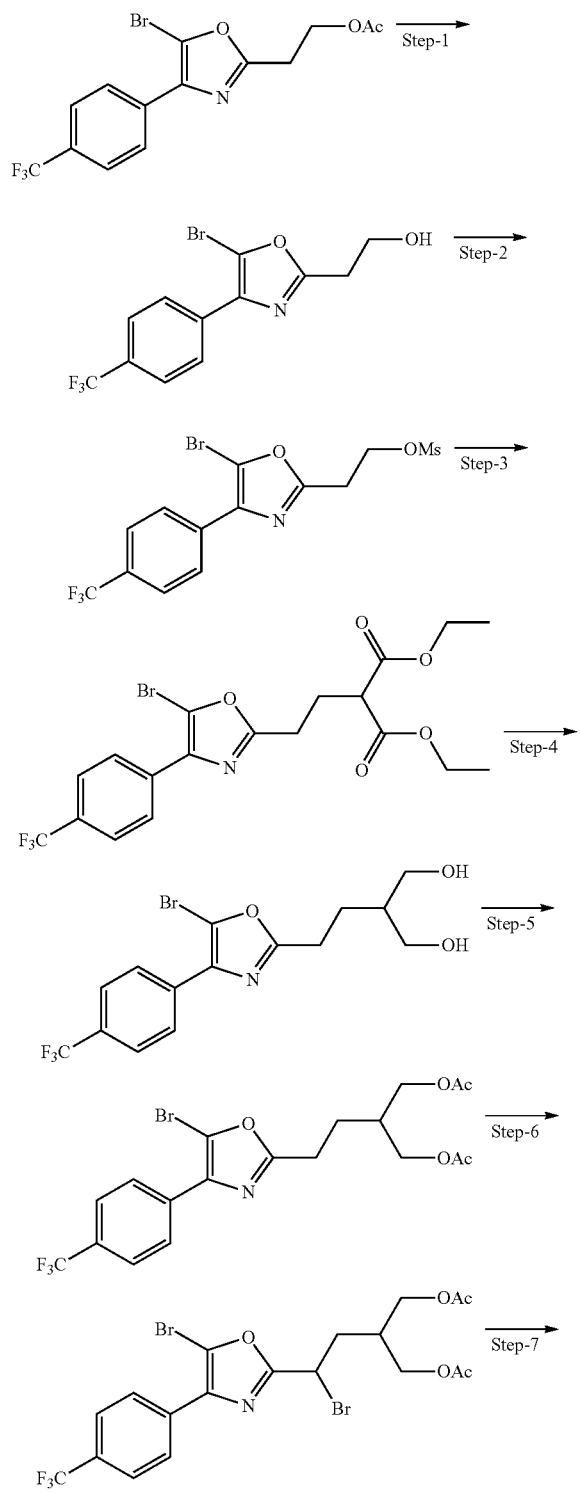

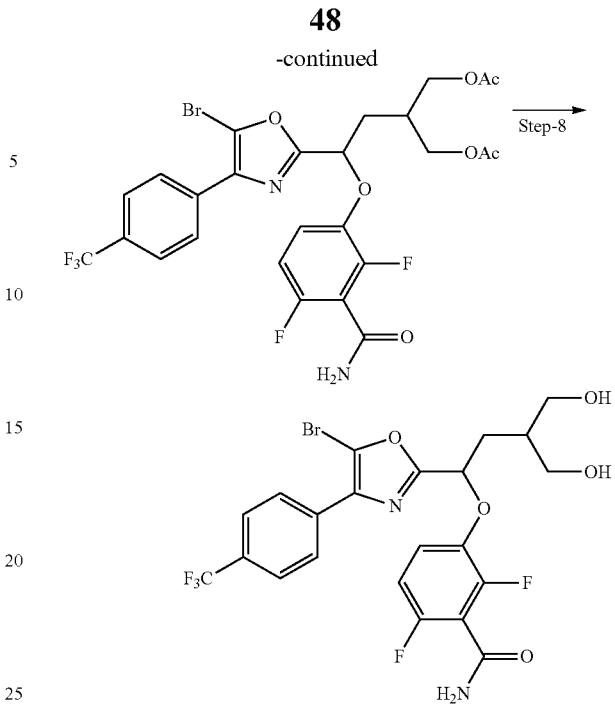

Step 1:

To a solution of 2-(5-bromo-4-(4-(trifluoromethyl)phenyl)oxazol-2-yl)ethyl acetate (1.0 g, 2.64 mmol, prepared as described in Representative Example 2 in MeOH (15 mL) was added $K_2CO_3$ (1.1 g, 7.93 mmol) and the resulting reaction mixture was stirred at room temperature for 1 h. The reaction mixture was diluted with water and washed with EtOAc (4×25 mL). The combined organic layers were washed with brine, dried over $Na_2SO_4$, filtered and concentrated under reduced pressure to afford 2-(5-bromo-4-(4-(trifluoromethyl)phenyl)oxazol-2-yl)ethanol (0.80 g, 90%).

Step 2:

To a solution of 2-(5-bromo-4-(4-(trifluoromethyl)phenyl)oxazol-2-yl)ethanol (0.80 g, 2.38 mmol) in DCM (10.0 mL) was added triethylamine (0.66 mL, 4.76 mmol) and methanesulfonyl chloride (0.28 mL, 3.57 mmol). After stirring for 1 h water was added and the mixture was washed EtOAc (3×50 mL). The combined organic layers were washed with brine, dried over $Na_2SO_4$, filtered and concentrated. The residue was purified by flash chromatography (10% EtOAc/hexane) to afford 2-(5-bromo-4-(4-(trifluoromethyl)phenyl)oxazol-2-yl)ethyl methanesulfonate (0.90 g, 92%).

Step 3:

To an ice-cold solution of 2-(5-bromo-4-(4-(trifluoromethyl)phenyl)oxazol-2-yl)ethyl methanesulfonate (0.90 g, 2.17 mmol) in THF (10.0 mL) was added sodium hydride (60% in mineral oil, 0.22 g, 5.43 mmol) portion-wise. The resulting mixture was stirred at room temperature for 30 minutes, followed by addition of a solution of diethyl malonate (0.83 mL, 5.43 mmol) in THF (5.0 mL). The reaction mixture was heated at 65° C. for 4 h. Water was added and the product extracted into EtOAc (3×50 mL). The combined organic layers were washed with brine, dried over $Na_2SO_4$, filtered and concentrated. The residue was purified by flash chromatography (6% EtOAc/hexane) to obtain diethyl 2-(2-(5-bromo-4-(4-(trifluoromethyl)phenyl)oxazol-2-yl)ethyl)malonate (0.75 g, 75%).

Step 4:
To an ice cold solution of diethyl 2-(2-(5-bromo-4-(4-(trifluoromethyl)phenyl)oxazol-2-yl)ethyl)malonate (1.3 g, 2.71 mmol) in methanol (25.0 mL) was added sodium borohydride (1.02 g, 27.18 mmol) portion-wise. The resulting reaction mixture was heated at 65° C. for 3 h. After the completion of reaction (TLC monitoring), the mixture was diluted with ice cold water and washed with EtOAc (3×100 mL). The combined organic layers were washed with brine, dried over $Na_2SO_4$, filtered and concentrated under reduced pressure to afford 2-(2-(5-bromo-4-(4-(trifluoromethyl)phenyl)oxazol-2-yl)ethyl)propane-1,3-diol (0.80 g, 80%).

Step 5:
To an ice cold solution of 2-(2-(5-bromo-4-(4-(trifluoromethyl)phenyl)oxazol-2-yl)ethyl)propane-1,3-diol (0.80 g, 2.02 mmol) in DCM (15.0 mL) was added triethylamine (0.56 mL, 4.05 mmol) and acetyl chloride (0.22 mL, 3.03 mmol). The resulting reaction mixture was stirred at room temperature for 1 h. The mixture was diluted with water and washed with EtOAc (3×100 mL). The combined organic layers were washed with brine, dried over $Na_2SO_4$, filtered and concentrated. The residue was purified by flash chromatography (15% EtOAc/hexane) to afford 2-(2-(5-bromo-4-(4-(trifluoromethyl)phenyl)oxazol-2-yl)ethyl)propane-1,3-diyl diacetate (0.65 g, 67%).

Step 6:
To a solution of 2-(2-(5-bromo-4-(4-(trifluoromethyl)phenyl)oxazol-2-yl)ethyl)propane-1,3-diyl diacetate (0.65 g, 1.36 mmol) in carbon tetrachloride (15.0 mL) was added NBS (0.24 g, 1.36 mmol) and AIBN (0.022 g, 0.13 mmol). The mixture was heated at reflux for 16 h. When the reaction was complete (TLC), water was added and the product extracted into EtOAc (3×100 mL). The combined organic layers were washed with brine, dried over $Na_2SO_4$, filtered and concentrated under reduced pressure to afford 2-(2-bromo-2-(5-bromo-4-(4-(trifluoromethyl)phenyl)oxazol-2-yl)-ethyl)propane-1,3-diyl diacetate (0.75 g).

Step 7:
To a solution of 2-(2-bromo-2-(5-bromo-4-(4-(trifluoromethyl)phenyl)oxazol-2-yl)ethyl)propane-1,3-diyl diacetate (0.80 g, 1.43 mmol) in DMF (10 mL) was added $K_2CO_3$ (0.40 g, 2.86 mmol) followed by 2,6-difluoro-3-hydroxybenzamide (0.25 g, 1.43 mmol). The resulting reaction mixture was stirred under $N_2$ at room temperature for 4 h. After the completion of reaction (TLC monitoring), ice-cold water was added and the product was extracted with EtOAc (3×50 mL). The combined organic phases were washed with brine, dried over $Na_2SO_4$, filtered and concentrated. The residue was purified by flash chromatography (40% EtOAc/hexane) to afford 2-(2-(5-bromo-4-(4-(trifluoromethyl)phenyl)oxazol-2-yl)-2-(3-carbamoyl-2,4-difluorophenoxy)ethyl)-propane-1,3-diyl diacetate (0.55 g, 59%).

Step 8:
To a solution of 2-(2-(5-bromo-4-(4-(trifluoromethyl)phenyl)oxazol-2-yl)-2-(3-carbamoyl-2,4-difluorophenoxy)ethyl)propane-1,3-diyl diacetate (0.11 g, 0.16 mmol) in MeOH (5 mL) was added $K_2CO_3$ (0.58 g, 0.42 mmol) and the resulting reaction mixture was stirred at room temperature for 1 h. After the completion of reaction (TLC), the mixture was diluted with water and the product extracted with EtOAc (3×50 mL). The combined organic layers were washed with brine, dried over $Na_2SO_4$, filtered and concentrated. The residue was purified by preparative TLC to afford 3-(1-(5-bromo-4-(4-(trifluoromethyl)phenyl)oxazol-2-yl)-4-hydroxy-3-(hydroxymethyl)-butoxy)-2,6-difluorobenzamide (0.020 g, 21%).

Representative Examples of Alcohol Transformations

Starting from the corresponding analogue where $R_3$ is a hydroxyalkyl moiety the following transformations were performed.

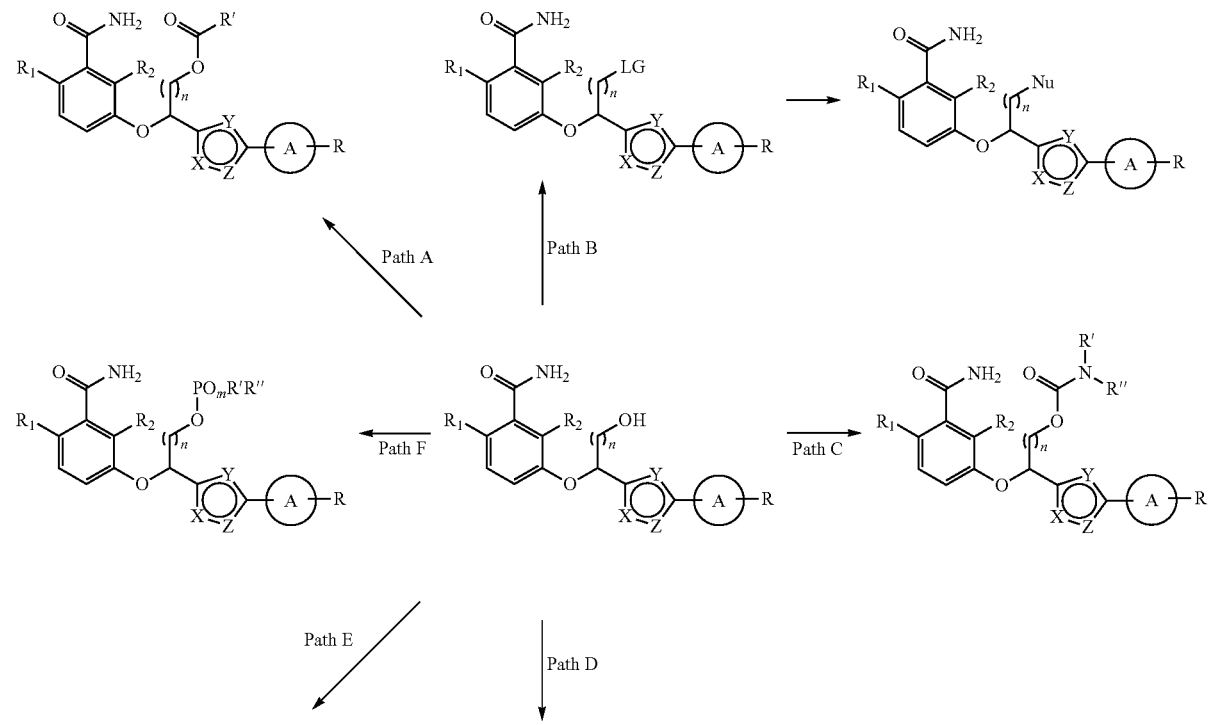

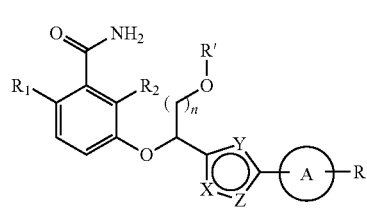
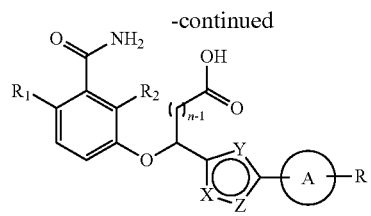

Path A: Example of Esterification of an Alkyl-OH

Synthesis of 2-(3-carbamoyl-2,4-difluorophenoxy)-2-(5-chloro-4-(4-(trifluoromethyl)phenyl)oxazol-2-yl)ethyl ethyl succinate

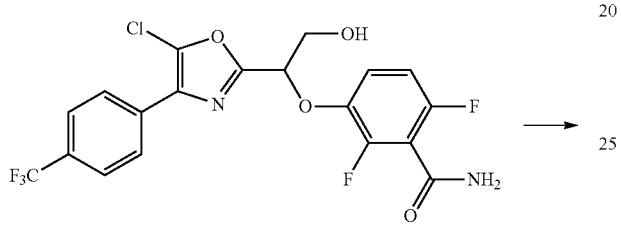
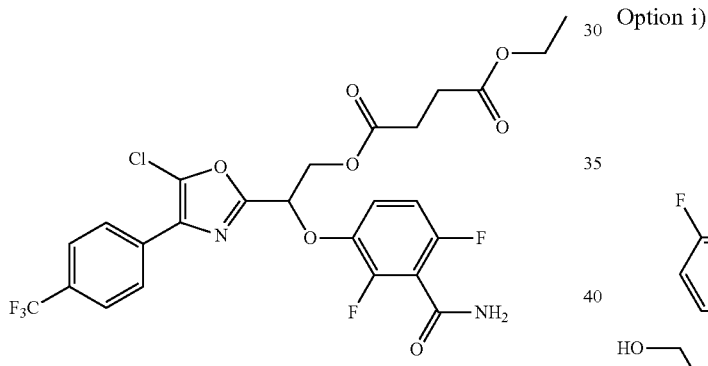

To an ice cold solution of 3-(1-(5-chloro-4-(4-(trifluoromethyl)phenyl)oxazol-2-yl)-2-hydroxyethoxy)-2,6-difluorobenzamide (0.02 g, 0.043 mmol) in DCM (10 mL) was added triethylamine (0.07 g, 0.06 mmol) followed by ethylsuccinyl chloride (0.011 g, 0.06 mmol). The resulting reaction mixture was allowed to stir at room temperature. When the reaction was complete (TLC monitoring), water was added and the product was extracted into EtOAc (3×25 mL). The combined organic layers were washed with brine, dried over Na$_2$SO$_4$, filtered and concentrated. The residue was purified by preparative TLC to afford 2-(3-carbamoyl-2,4-difluorophenoxy)-2-(5-chloro-4-(4-(trifluoromethyl)phenyl)oxazol-2-yl)ethyl ethyl succinate (0.015 g, 59%). Similarly prepared were, for example, 2-(5-bromo-4-(4-(trifluoromethyl)phenyl)oxazol-2-yl)-2-(3-carbamoyl-2,4-difluorophenoxy)ethyl 2-(dimethylamino)acetate, and 2-(3-carbamoyl-2,4-difluorophenoxy)-2-(5-chloro-4-(4-chlorophenyl)oxazol-2-yl)ethyl 2-(methylamino)acetate (from its Boc-protected analogue by treatment with HCl-dioxane solution), 2-(5-bromo-4-(4-(trifluoromethyl)phenyl)oxazol-2-yl)-2-(3-carbamoyl-2,4-difluorophenoxy)ethyl 2-((tert-butoxycarbonyl)(methyl)amino)acetate and 2-(5-bromo-4-(4-(trifluoromethyl)phenyl)oxazol-2-yl)-2-(3-carbamoyl-2,4-difluorophenoxy)ethyl 2-(methylamino)acetate (from its Boc-protected analogue by treatment with HCl-dioxane solution), 2-(5-bromo-4-(4-(trifluoromethyl)phenyl)oxazol-2-yl)-2-(3-carbamoyl-2,4-difluorophenoxy)ethyl 2-(1H-pyrrol-1-yl)acetate, and 2-(5-bromo-4-(4-(trifluoromethyl)phenyl)oxazol-2-yl)-2-(3-carbamoyl-2,4-difluorophenoxy)ethyl 4-(1,3-dioxoisoindolin-2-yl)butanoate. In some cases, imidazole was used in place of triethylamine and the products were variously purified by silica chromatography or preparative HPLC.

Path B

Examples of Sulfonation/Halogenation of an Alkyl-OH and Optional Nucleophilic Substitution Option i)

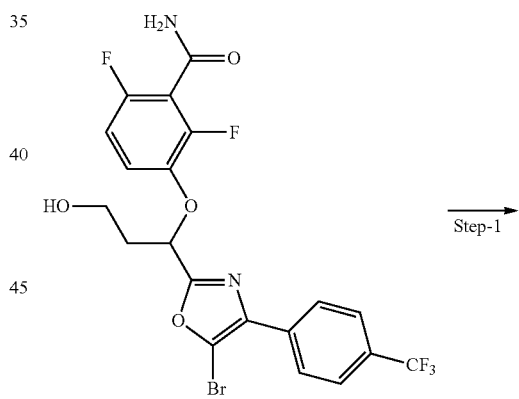

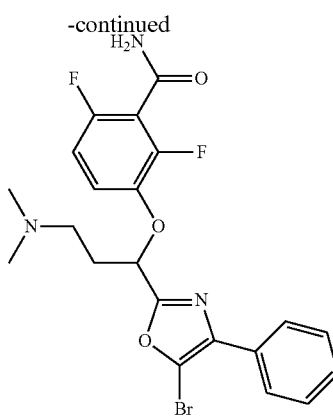

Step 1:
To a solution of 3-[1-[5-bromo-4-[4-(trifluoromethyl)phenyl]oxazol-2-yl]-3-hydroxy-propoxy]-2,6-difluoro-benzamide (1.0 eq) in toluene was added PBr₃ (1.50 eq) and the resulting reaction mixture was heated at reflux for 30 minutes. Upon completion of the reaction, the solvent was evaporated, water was added and the product was extracted into EtOAc (×3). The combined organic layers were washed with saturated NaHCO₃, dried over Na₂SO₄, filtered and concentrated under reduced pressure to give 3-(3-bromo-1-(5-bromo-4-(4-(trifluoromethyl)phenyl)oxazol-2-yl)propoxy)-2,6-difluorobenzamide, suitable for use in the next step.

Step 2:
To an ice-cold solution of 3-(3-bromo-1-(5-bromo-4-(4-(trifluoromethyl)-phenyl)oxazol-2-yl)propoxy)-2,6-difluorobenzamide (0.10 g, 0.17 mmol) in THF (10.0 mL) was added dimethylamine (2M in THF, 0.17 mL, 0.34 mmol). The resulting solution was stirred at room temperature overnight. After the completion of reaction (TLC monitoring) the solvent was evaporated. Water was added and the product was extracted into EtOAc (3×100 mL). The combined organic layers were washed with brine, dried over Na₂SO₄, filtered and concentrated under reduced pressure. The residue was precipitated with diethyl ether to afford 3-(1-(5-bromo-4-(4-(trifluoromethyl)phenyl)oxazol-2-yl)-3-(dimethylamino)propoxy)-2,6-difluoro-benzamide (30 mg, 32%).

Option ii)

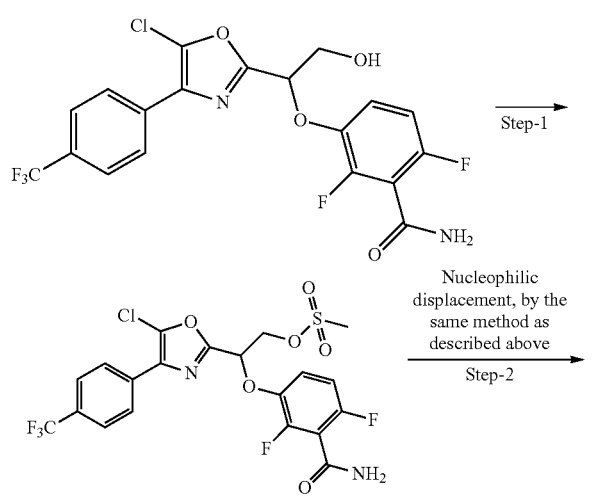

Step 1:
To an ice-cold solution of 3-(1-(5-chloro-4-(4-(trifluoromethyl)phenyl)oxazol-2-yl)-2-hydroxyethoxy)-2,6-difluorobenzamide (0.06 g, 0.13 mmol) in DCM (10 mL) was added Et3N (0.04 mL, 0.26 mmol) followed by methanesulfonyl chloride (0.015 mL, 0.20 mmol) and the resulting reaction mixture was stirred for 30 minutes. After the completion of reaction (TLC), water was added and the product was extracted with EtOAc (3×20 mL). The combined organic layers were washed with water and brine, dried over Na₂SO₄, filtered and concentrated. The residue was precipitated with n-pentane to afford 2-(3-carbamoyl-2,4-difluorophenoxy)-2-(5-chloro-4-(4-(trifluoro-methyl)phenyl)oxazol-2-yl)ethyl methanesulfonate (0.064 g, 91%), m.p. 163° C.

Step 2:
General procedure as described above for Path B(i).

Path C

Examples of Carbamate Formation from an Alkyl-OH

Option i)

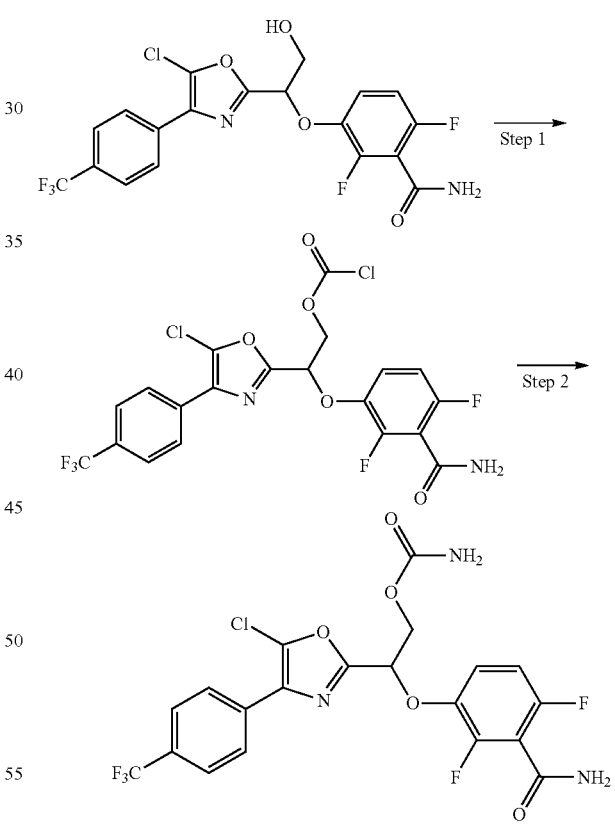

To a solution of 3-(1-(5-chloro-4-(4-(trifluoromethyl)phenyl)oxazol-2-yl)-2-hydroxyethoxy)-2,6-difluorobenzamide (0.02 g, 0.043 mmol) in acetonitrile (10 mL) at 0° C. was added trichloromethylchloroformate (0.013 g, 0.066). The resulting reaction mixture was allowed to stir at room temperature for 6 h. After the completion of reaction (TLC monitoring by adding MeOH), the solvent was evaporated and the residue was taken up in THF (5 mL). The resulting solution was treated with NH₃ (g) for 5 minutes and then allowed to stir at room temperature for 16 h. When the reaction was complete (TLC), the solvent was evaporated, water added and product extracted into EtOAc (3×25 mL). The combined organic layers were washed with brine, dried over Na₂SO₄, filtered and concentrated. The residue was purified by preparative TLC to afford 2-(3-carbamoyl-2,4-difluorophenoxy)-2-(5-chloro-4-(4-(trifluoromethyl)-phenyl)oxazol-2-yl)ethyl carbamate (0.05 g, 23%).

Similarly prepared was, for example, 2-(5-bromo-4-(4-(trifluoromethyl)phenyl)oxazol-2-yl)-2-(3-carbamoyl-2,4-difluorophenoxy)ethyl dimethylcarbamate and 2-(5-bromo-4-(4-(trifluoromethyl)phenyl)oxazol-2-yl)-2-(3-carbamoyl-2,4-difluorophenoxy)ethyl methylcarbamate using 1.2 eq of the respective amines Option ii)

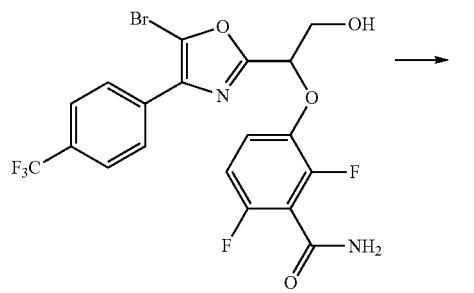

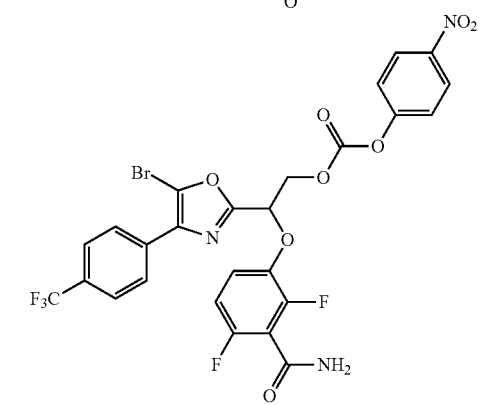

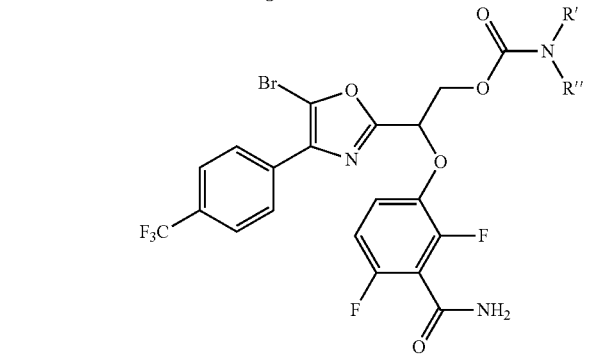

To a solution of 3-(1-(5-bromo-4-(4-(trifluoromethyl)phenyl)oxazol-2-yl)-2-hydroxyethoxy)-2,6-difluorobenzamide (1.50 g, 2.95 mmol) in DCM (15 mL) was added 4-nitrophenyl chloroformate (0.713 g, 3.54 mmol), followed by a solution of pyridine (0.35 mL, 4.42 mmol) in DCM (5 mL). The resulting solution was stirred at room temperature for 2 h. After the completion of reaction (TLC monitoring), water (75 mL) was added to the mixture and the product extracted with EtOAc (3×100 mL). The combined organic layers were washed with brine, dried over Na₂SO₄, filtered and concentrated under reduced pressure. The crude residue was purified by flash chromatography (30% EtOAc/hexane) to give 2-(5-bromo-4-(4-(trifluoromethyl)phenyl)oxazol-2-yl)-2-(3-carbamoyl-2,4-difluorophenoxy)ethyl 4-nitrophenyl carbonate (1.10 g).

To a solution of the above carbonate (1.0 eq) in DMF was added DIPEA (1.50 eq) or NMM (1.50 eq), followed by the appropriate amine (1.20 eq). The resulting reaction mixture was allowed to stir to room temperature until reaction was complete (TLC; typically 2 h). Ice-cold water was then added and the mixture washed with EtOAc (3 times). The combined organic layers were washed with 1N NaOH and brine, dried over Na₂SO₄, filtered and concentrated under reduced pressure. The residue was purified by flash chromatography to yield the desired carbamate. In this manner were prepared for example, 2-(5-bromo-4-(4-(trifluoromethyl)phenyl)oxazol-2-yl)-2-(3-carbamoyl-2,4-difluorophenoxy)ethyl pyridin-4-ylcarbamate, 2-(5-bromo-4-(4-(trifluoromethyl)phenyl)oxazol-2-yl)-2-(3-carbamoyl-2,4-difluorophenoxy)ethyl (2-(3-methyl-1,2,4-oxadiazol-5-yl)ethyl)carbamate, 2-(5-bromo-4-(4-(trifluoromethyl)phenyl)oxazol-2-yl)-2-(3-carbamoyl-2,4-difluorophenoxy)ethyl((5-methyl-1,3,4-oxadiazol-2-yl)methyl)carbamate, 2-(5-bromo-4-(4-(trifluoromethyl)phenyl)oxazol-2-yl)-2-(3-carbamoyl-2,4-difluorophenoxy)ethyl((3-methyl-1,2,4-oxadiazol-5-yl)methyl)carbamate.

Option iii)

Examples 2-(5-bromo-4-(4-(trifluoromethyl)phenyl)oxazol-2-yl)-2-(3-carbamoyl-2,4-difluorophenoxy)ethyl 3-(methylsulfonyl)-2-oxoimidazolidine-1-carboxylate and 2-(5-bromo-4-(4-(trifluoromethyl)phenyl)oxazol-2-yl)-2-(3-carbamoyl-2,4-difluorophenoxy)ethyl morpholine-4-carboxylate were prepared directly from the alcohol using the relevant commercially-available carbamoyl chlorides.

Path D

Example of Oxidation of an Alkyl-OH and Optional Amide Formation

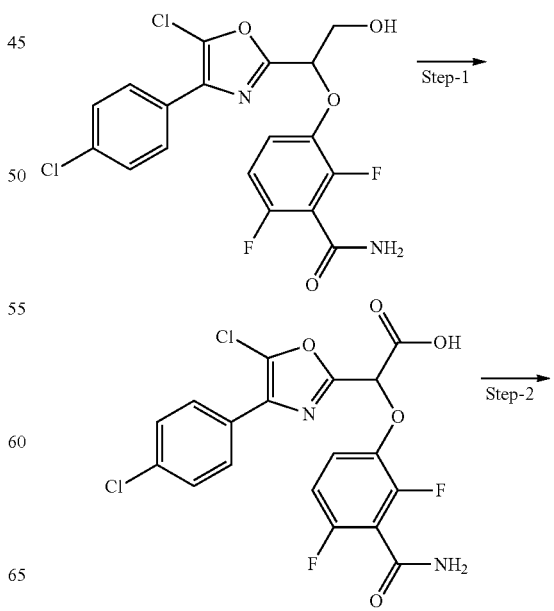

-continued

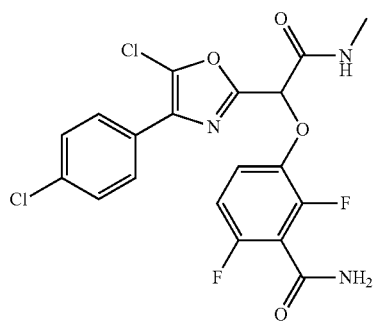

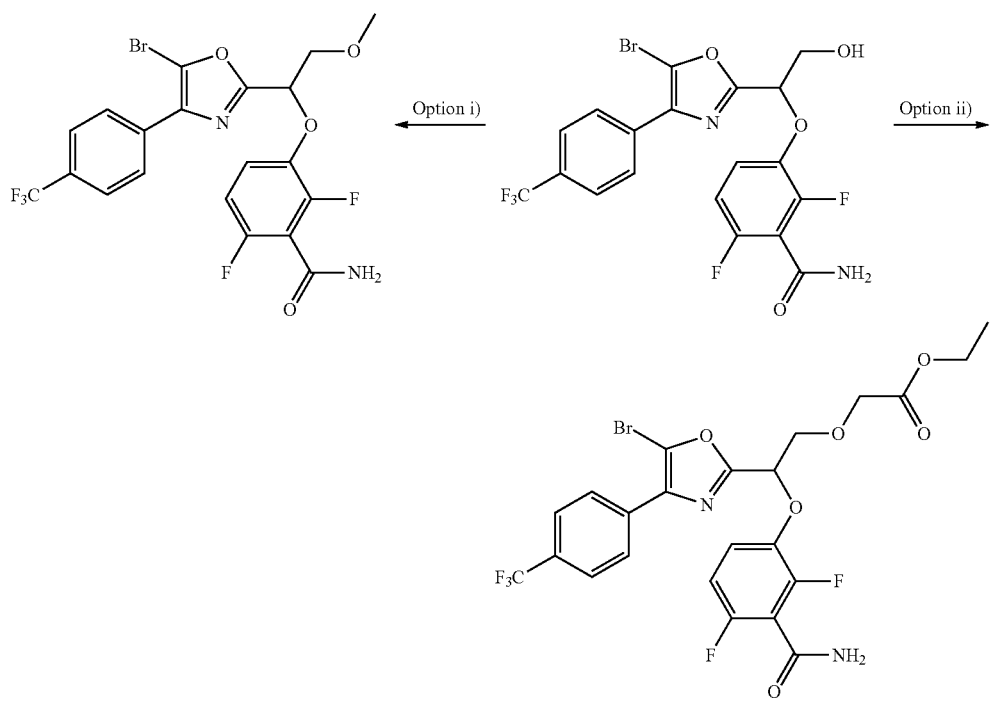

Path E

Examples of Alkylation of an Alkyl-OH

Step 1:
To an ice cold solution of 3-(1-(5-chloro-4-(4-chlorophenyl)oxazol-2-yl)-2-hydroxyethoxy)-2,6-difluorobenzamide (0.10 g, 0.23 mmol) in acetone (5 mL) was added Jones Reagent (0.30 mL) and the mixture was stirred at 0° C. for 5 minutes and at room temperature for 16 h. [Jones Reagent was prepared by taking up $CrO_3$ (0.50 g) in $H_2O$ (0.80 mL), cooling the solution to 0° C., adding $H_2SO_4$ (0.40 mL) drop-wise and making up the resulting mixture to 1.60 mL by addition of water.] After the completion of reaction (TLC monitoring) the solvent was evaporated, water was added and the product was extracted into EtOAC (3×50 mL). The combined organic layers were dried over $Na_2SO_4$, filtered and concentrated. The residue was purified by preparative TLC to afford the desired carboxylic acid product (0.002 g, 2%).

Step 2:
To a solution of crude 2-(3-carbamoyl-2,4-difluorophenoxy)-2-(5-chloro-4-(4-chlorophenyl)oxazol-2-yl)acetic acid (0.15 g) in DCM (10 mL) was added methylamine hydrochloride (0.05 g, 0.68 mmol), EDCI.HCl (0.13 g 0.68 mmol), HOBt (0.10 g, 0.68 mmol) and DMAP (0.13, 1.01 mmol). The resulting reaction mixture was stirred at room temperature for 16 h. After the completion of reaction (TLC monitoring), water was added and the reaction mixture was washed with EtOAc (3×100 mL). The combined organic layers were washed with water and brine, dried over $Na_2SO_4$, filtered and concentrated. The residue was purified by flash chromatography (45% EtOAc/hexane) to afford 3-(1-(5-chloro-4-(4-chlorophenyl)oxazol-2-yl)-2-(methylamino)-2-oxoethoxy)-2,6-difluorobenzamide (0.011 g, 8%). Similarly prepared was, for example, 3-(1-(5-chloro-4-(4-(trifluoromethyl)phenyl)oxazol-2-yl)-2-(methylamino)-2-oxoethoxy)-2,6-difluorobenzamide.

Option i): Alkylation with an Alkyl Halide
To a solution of 3-(1-(5-bromo-4-(4-(trifluoromethyl)phenyl)oxazol-2-yl)-2-(2-hydroxyethoxy)ethoxy)-2,6-difluorobenzamide (0.035 g, 0.06 mmol) in acetonitrile (5.0 mL) was added $Ag_2O$ (0.074 g, 0.31 mmol) and MeI (68 µl, 1.08 mmol). The resulting solution was stirred at room temperature overnight. After the completion of reaction (TLC monitoring), the mixture was filtered and diluted with water. The mixture was washed with EtOAc (3×50 mL) and the combined organic layers were dried over anhydrous $Na_2SO_4$, filtered and concentrated under reduced pressure. The residue was purified by preparative TLC to afford the desired ether (0.009 g, 26%) as a white solid.

Similarly prepared was, for example, 3-(1-(5-bromo-4-(4-(trifluoromethyl)phenyl)oxazol-2-yl)-2-methoxyethoxy)-2,6-difluorobenzamide.

Option ii): Alkylation with a Diazo Derivative
To an ice-cold solution of the alcohol (0.10 g, 0.19 mmol) in DCM (10 mL) was added ethyl diazoacetate (0.067 g, 0.59 mmol) and $BF_3.OEt_2$ (48 µL, 0.38 mmol). The resulting reaction mixture was allowed to stir at room temperature for 4 h. After this time, water was added and the mixture was washed with EtOAc (3×50 mL). The combined organic layers were washed with brine, dried over Na$_2$SO$_4$, filtered and concentrated under reduced pressure. The residue was purified by flash chromatography (30% EtOAc-hexane) to afford the desired ether, ethyl 2-(2-(5-bromo-4-(4-(trifluoromethyl)phenyl)oxazol-2-yl)-2-(3-carbamoyl-2,4-difluorophenoxy)ethoxy)acetate (0.04 g, 34%).

Additional examples were prepared from the above by means of known functional group transformations. For example, 3-(1-(5-bromo-4-(4-(trifluoromethyl)phenyl)oxazol-2-yl)-2-(2-hydroxyethoxy)ethoxy)-2,6-difluorobenzamide was prepared by reduction of the ester to the alcohol using sodium borohydride. In turn, the resulting alcohol may itself be alkylated to afford an ether of the type exemplified by 3-(1-(5-bromo-4-(4-(trifluoromethyl)phenyl)oxazol-2-yl)-2-(2-methoxyethoxy)ethoxy)-2,6-difluorobenzamide. Alternatively, the alcohol moiety may be converted to a leaving group by sulfonation and displaced with an amine nucleophile to give amine derivatives such as 3-(1-(5-bromo-4-(4-(trifluoromethyl)phenyl)oxazol-2-yl)-2-(2-morpholinoethoxy)ethoxy)-2,6-difluorobenzamide.

Path F

Example Synthesis of Phosphor Derivatives from an Alkyl-OH

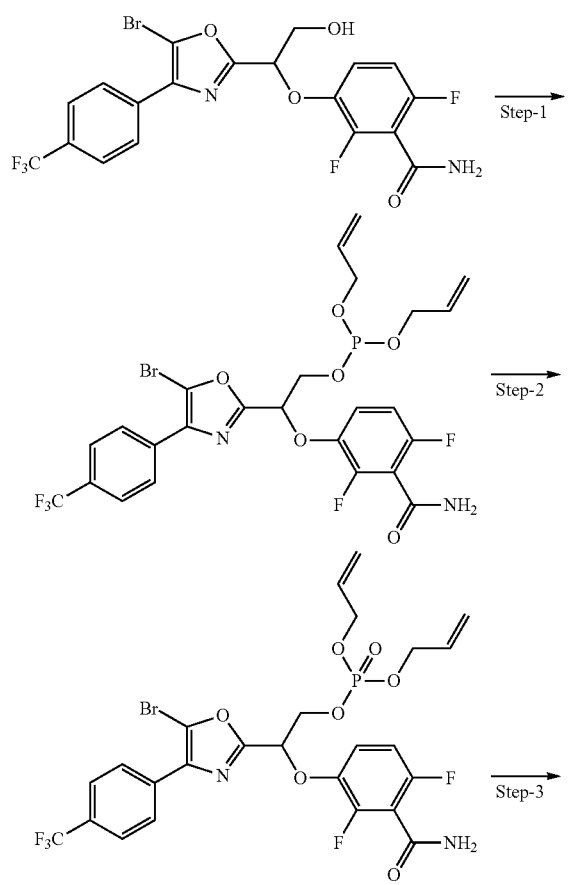

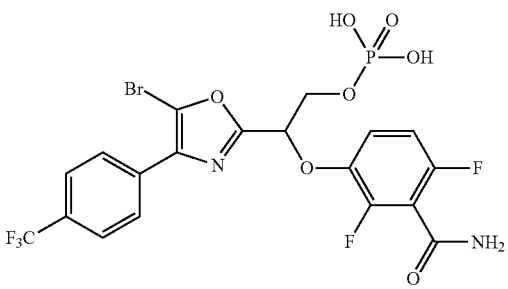

Step 1:

To a solution of 3-(1-(5-bromo-4-(4-(trifluoromethyl)phenyl)oxazol-2-yl)-2-hydroxyethoxy)-2,6-difluorobenzamide (0.10 g, 0.19 mmol) in DCM (10 mL) was added tetrazole (0.208 mL, 2.36 mmol) and diallyl N,N-diisopropylphosphoramidite (0.175 mL, 0.66 mmol) and the resulting reaction mixture was stirred at room temperature for 16 h. After this time the resulting solution of diallyl 2-(5-bromo-4-(4-(trifluoromethyl)phenyl)oxazol-2-yl)-2-(3-carbamoyl-2,4-difluorophenoxy)ethyl phosphite was carried forward to the next step without further purification.

Step 2:

A solution of diallyl 2-(5-bromo-4-(4-(trifluoromethyl)phenyl)oxazol-2-yl)-2-(3-carbamoyl-2,4-difluorophenoxy)ethyl phosphite in DCM was cooled to 0° C., treated with t-butyl peroxide (6M solution, 0.060 mL, 0.38 mmol) and then stirred for 16 h. After this time the reaction mixture was concentrated, resuspended in water and washed with EtOAc (3×50 mL). The combined organic layers were washed with water and brine, dried over anhydrous Na$_2$SO$_4$, filtered and concentrated in vacuo. The crude residue was purified by HPLC to afford diallyl 2-(5-bromo-4-(4-(trifluoromethyl)phenyl)oxazol-2-yl)-2-(3-carbamoyl-2,4-difluorophenoxy)ethyl phosphate (0.040 g, 34%).

Step 3:

To a cold solution of diallyl 2-(5-bromo-4-(4-(trifluoromethyl)phenyl)oxazol-2-yl)-2-(3-carbamoyl-2,4-difluorophenoxy)ethyl phosphate (0.092 g, 0.13 mmol) in DCM (15.0 mL) was added n-tributyltin hydride (0.037 mL, 0.13 mmol) and bis(triphenylphosphine)palladium(II)dichloride (0.005 g, 0.006 mmol). The resulting mixture was stirred at room temperature for 2 h. After this time water was added and the reaction mixture washed with EtOAc (3×50 mL). The combined organic layers were washed with water and brine, dried over anhydrous Na$_2$SO$_4$, filtered and concentrated in vacuo. The crude residue was purified by HPLC to give [2-[5-bromo-4-[4-(trifluoromethyl)phenyl]oxazol-2-yl]-2-(3-carbamoyl-2,4-difluoro-phenoxy)ethyl]dihydrogen phosphate (0.006 g, 7%).

Representative Examples of Ester Transformations

Starting from the corresponding analogue where R$_3$ is a carboxylate moiety, e.g. ester, the following transformations were performed.

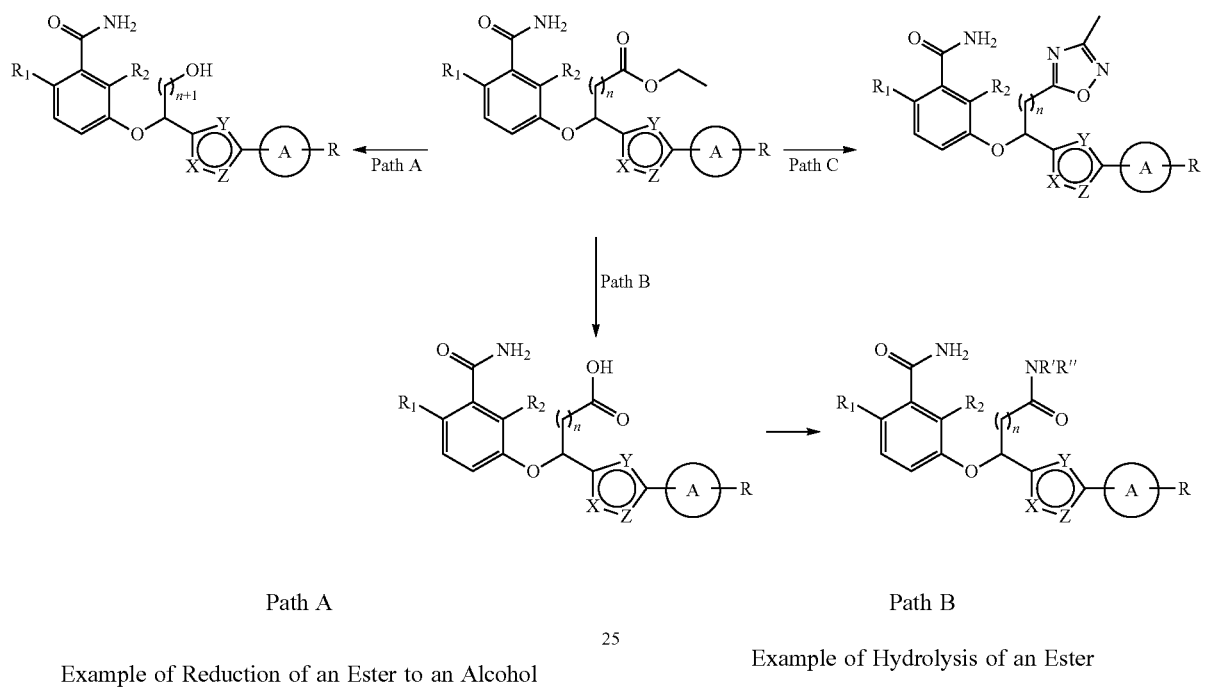

Path A

Example of Reduction of an Ester to an Alcohol

Path B

Example of Hydrolysis of an Ester

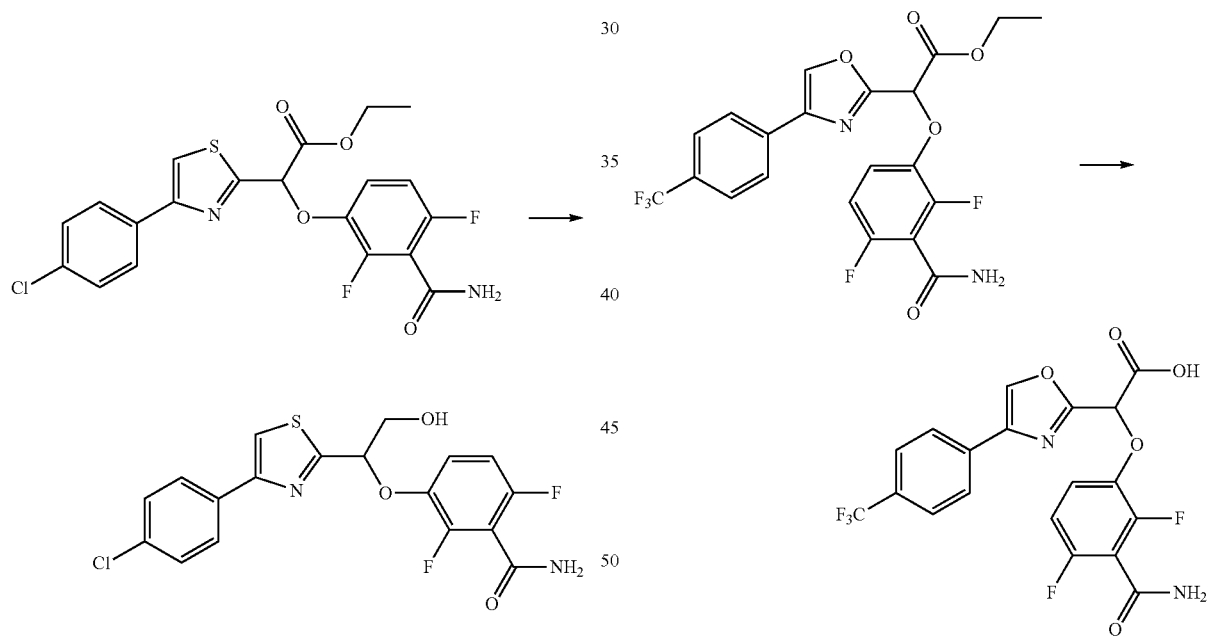

To an ice-cold solution of ethyl 2-(3-carbamoyl-2,4-difluorophenoxy)-2-(4-(4-chlorophenyl)thiazol-2-yl)acetate (0.20 g, 0.44 mmol) in MeOH (10 mL) was added NaBH$_4$ (0.17 g, 4.40 mmol) in portions. The reaction mixture was allowed to stir at room temperature for 30 minutes. After this time the MeOH was removed in vacuo and the residue resuspended in 1M HCl. The product was extracted into EtOAc (3×50 mL) and the combined organic layers were washed with water and brine, dried over Na$_2$SO$_4$, filtered and concentrated. The residue was purified by flash chromatography (40% EtOAc/hexane) to afford 3-(1-(4-(4-chlorophenyl)thiazol-2-yl)-2-hydroxyethoxy)-2,6-difluorobenzamide (0.90 g, 50%).

To a solution of ethyl 2-(3-carbamoyl-2,4-difluorophenoxy)-2-[4-[4-(trifluoromethyl)-phenyl]oxazol-2-yl]acetate in THF was added an aqueous solution of NaOH (3.0 eq). The resulting reaction mixture was stirred at room temperature until complete (as monitored by TLC or HPLC). The solvent was then evaporated and the residue taken up in water and washed with EtOAc (3 times). The aqueous layer was adjusted to pH 5 by addition of dilute HCl and then washed with EtOAc (3 times). The combined organic layers were washed with brine, dried (Na$_2$SO$_4$), filtered and concentrated under reduced pressure to afford 2-(3-carbamoyl-2,4-difluoro-phenoxy)-2-[4-[4-(trifluoromethyl)phenyl]oxazol-2-yl]acetic acid.

Similarly prepared, but without the acidification step, was, for example, ethyl 2-(3-carbamoyl-2,4-difluorophenoxy)-2-(4-(4-chlorophenyl)oxazol-2-yl)acetate.

It will be understood by a person skilled in the art that a carboxylic acid of this type may be condensed with a suitable amine, using the conditions already described, to effect amide formation.

Path C

Example of the Conversion of an Ester Substituent to an Aromatic Heterocycle (Heteroaryl)

To a solution of ethyl 2-(3-carbamoyl-2,4-difluorophenoxy)-2-(4-(4-(trifluoromethyl)-phenyl)oxazol-2-yl)acetate (1.0 eq) in toluene was added acetamidoxime (2.0 eq) and $K_2CO_3$ (5.0 eq) and the resulting reaction mixture was heated at reflux overnight. After the completion of reaction (TLC monitoring) water was added and the mixture was washed with EtOAc (3 times). The combined organic layers were washed with brine, dried over $Na_2SO_4$, filtered and concentrated under reduced pressure. The residue was purified by flash chromatography (EtOAc/hexane) to afford 2,6-difluoro-3-((3-methyl-1,2,4-oxadiazol-5-yl)(4-(4-(trifluoromethyl)phenyl)oxazol-2-yl)methoxy)benzamide.

Representative Examples of Amine Synthesis and Subsequent Transformations and treated with 10% Pd/C (15 mg). The mixture was degassed and then placed under an atmosphere of hydrogen. When the reaction was complete, the mixture was filtered through celite and concentrated. The residue was redissolved in EtOAc, washed with dilute 1M HCl (three times) and the aqueous layer was then adjusted to pH 9 by addition of NaOH. The product was extracted into EtOAc (three times) and concentrated in vacuo. The residue was washed with 2 M HCl and freeze-dried to afford 3-(2-amino-1-(4-(4-(trifluoromethyl)phenyl)oxazol-2-yl)ethoxy)-2,6-difluorobenzamide (38 mg, 61%) as a white hydrochloride salt.

Path B

Example of Urea Synthesis

Benzyl (2-(3-carbamoyl-2,4-difluorophenoxy)-2-(4-(4-(trifluoromethyl)phenyl)oxazol-2-yl)ethyl)carbamate (94 mg, 0.17 mmol) was hydrogenolysed as described above and filtered. To the filtrate was added triethylamine (40 µL, 0.29 mmol) and ethyl isocyanate (15 µL, 0.19 mmol). The reaction mixture was stirred under argon at room temperature for 2 h then diluted with EtOAc (50 mL), washed with 1M HCl and brine and separated. The organic phase was dried over $MgSO_4$ and concentrated under reduced pressure. Purification via flash column chromatography (25-100%

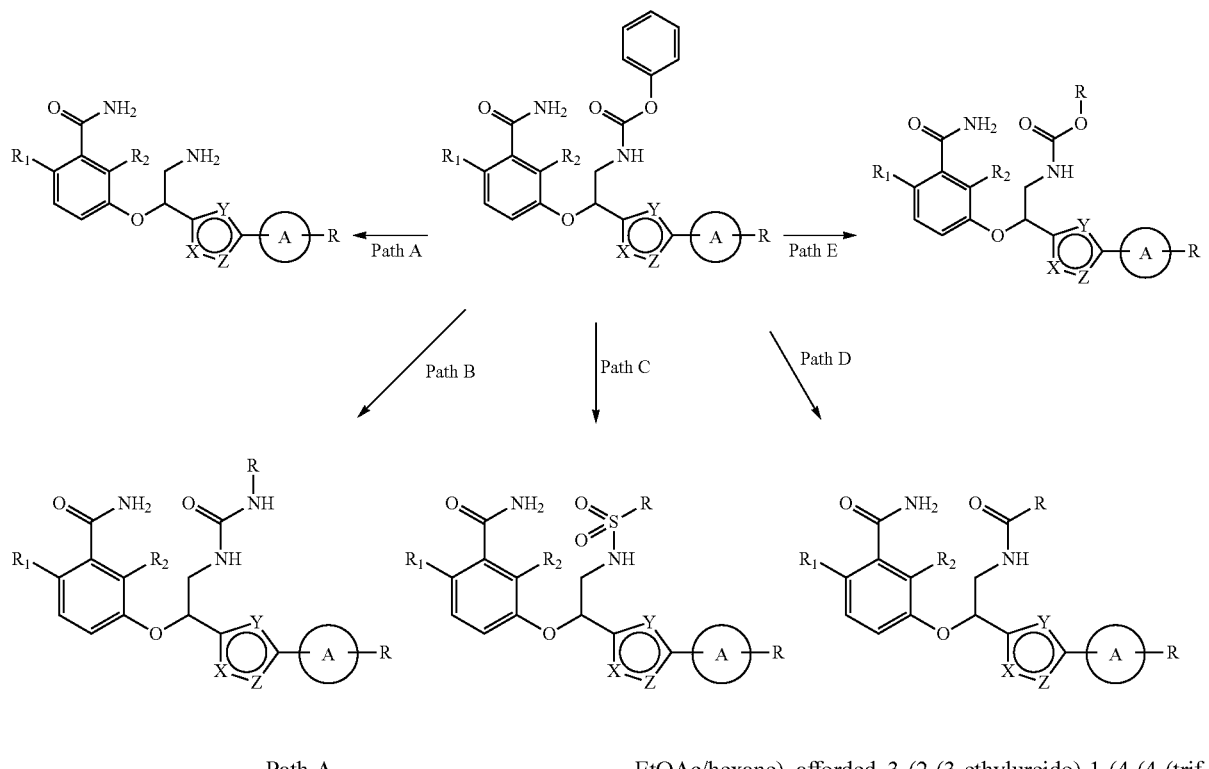

Path A

Example of Primary Amine Synthesis

Benzyl (2-(3-carbamoyl-2,4-difluorophenoxy)-2-(4-(4-(trifluoromethyl)phenyl)oxazol-2-yl)ethyl)carbamate (80 mg, 0.14 mmol, prepared by the procedure described in Representative Example 6) was dissolved in THF (15 mL)

EtOAc/hexane) afforded 3-(2-(3-ethylureido)-1-(4-(4-(trifluoromethyl)phenyl)oxazol-2-yl)ethoxy)-2,6-difluorobenzamide (56 mg, 77%) as a white solid. Similarly prepared, and using the bromination methodology described previously, was, for example, the bromooxazole/urea 3-(1-(5-bromo-4-(4-(trifluoromethyl)phenyl)oxazol-2-yl)-2-(3-ethylureido)ethoxy)-2,6-difluorobenzamide. For this type of compound it should be noted that the sequence of steps is important and that bromination of the oxazole must be performed prior to the urea formation.

Path C

Example of Sulfonamide Synthesis

Benzyl (2-(3-carbamoyl-2,4-difluorophenoxy)-2-(4-(4-(trifluoromethyl)phenyl)oxazol-2-yl)ethyl)carbamate (94 mg, 0.17 mmol) was hydrogenolysed as described above and filtered. To the filtrate was added triethylamine (50 μL, 0.36 mmol) and methanesulfonyl chloride (20 μL, 0.26 mmol). The reaction mixture was stirred under argon at room temperature for 2 h then diluted with EtOAc (50 mL), washed with 1M HCl and brine and separated. The organic phase was dried over MgSO$_4$ and concentrated under reduced pressure. Purification via flash column chromatography (50-100% EtOAc/hexane) afforded 2,6-difluoro-3-(2-(methylsulfonamido)-1-(4-(4-(trifluoromethyl)phenyl)oxazol-2-yl)ethoxy)benzamide (62 mg, 73%) as a white solid.

Path D

Example of Amide Synthesis

Benzyl (2-(3-carbamoyl-2,4-difluorophenoxy)-2-(4-(4-(trifluoromethyl)phenyl)oxazol-2-yl)ethyl)carbamate (103 mg, 0.18 mmol) was hydrogenolysed as described above and filtered. To the filtrate was added triethylamine (50 μL, 0.36 mmol) and acetic anhydride (20 μL, 0.21 mmol). The reaction mixture was stirred under argon at room temperature for 16 h and then diluted with EtOAc (50 mL), washed with 1M HCl and brine and separated. The organic phase was dried over MgSO$_4$ and concentrated under reduced pressure. Purification by flash column chromatography (50-100% EtOAc/hexane) afforded 3-(2-acetamido-1-(4-(4-(trifluoromethyl)phenyl)oxazol-2-yl)-ethoxy)-2,6-difluorobenzamide (55 mg, 64%) as a white solid.

Path E

Example of Carbamate Synthesis

Benzyl (2-(3-carbamoyl-2,4-difluorophenoxy)-2-(4-(4-(trifluoromethyl)phenyl)oxazol-2-yl)ethyl)carbamate (85 mg, 0.15 mmol) was hydrogenolysed as described above and filtered. To the filtrate was added triethylamine (40 μL, 0.29 mmol) and methyl chloroformate (15 μL, 0.19 mmol). The reaction mixture was stirred under argon at room temperature for 2 h then diluted with EtOAc (50 mL), washed with 1M HCl and brine and separated. The organic phase was dried over MgSO$_4$ and concentrated under reduced pressure. Purification via flash column chromatography (50-100% EtOAc/hexane) afforded methyl (2-(3-carbamoyl-2,4-difluorophenoxy)-2-(4-(4-(trifluoromethyl)phenyl)oxazol-2-yl)ethyl)carbamate (56 mg, 76%) as a white solid.

Representative Example of a Suzuki Coupling

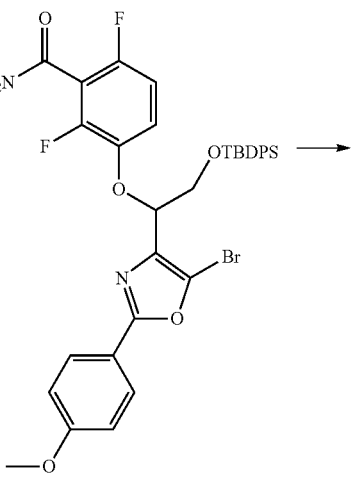

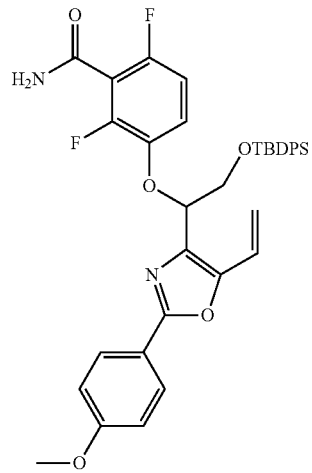

3-[1-[5-Bromo-2-(4-methoxyphenyl)oxazol-4-yl]-2-[tert-butyl(diphenyl)silyl]oxy-ethoxy]-2,6-difluoro-benzamide (1.09 g, 1.54 mmol, prepared using the procedure described in Representative Example 6,4,4,5,5-tetramethyl-2-vinyl-1,3,2-dioxaborolane (390 μL, 2.30 mmol) and Pd(dppf)Cl$_2$CH$_2$Cl$_2$ (60 mg, 0.08 mmol) were dissolved in 1,4-dioxane (15 mL). A solution of Cs$_2$CO$_3$ (1.51 g, 4.62 mmol) in water (5 mL) was added and the mixture was heated at 80° C. for 15 minutes. The reaction mixture was diluted with EtOAc (100 mL) and washed with water and brine. The organic fraction was dried over MgSO$_4$ and concentrated under reduced pressure. Purification by silica chromatography (10-60% EtOAc/hexane) afforded 3-[2-[tert-butyl(diphenyl)silyl]oxy-1-[2-(4-methoxyphenyl)-5-vinyl-oxazol-4-yl]ethoxy]-2,6-difluoro-benzamide (978 mg, 97%). 2,6-difluoro-3-(2-hydroxy-1-(2-(4-methoxyphenyl)-5-vinyloxazol-4-yl)ethoxy)benzamide was obtained after removal of the TBDPS group by known methods.

Representative Example of a Stille Coupling

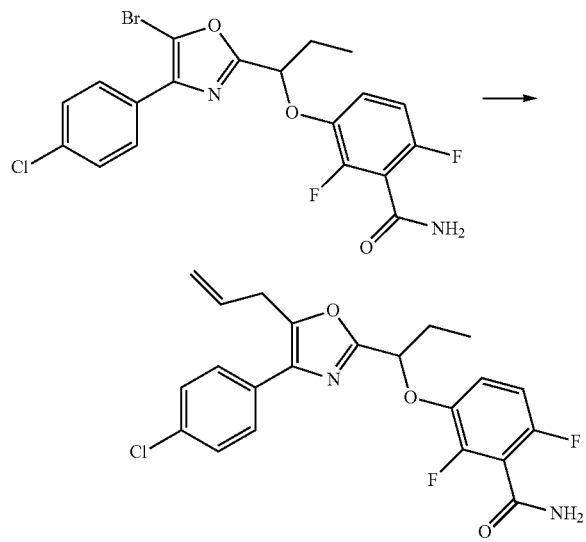

A solution of 3-(1-(5-bromo-4-(4-chlorophenyl)oxazol-2-yl)propoxy)-2,6-difluoro-benzamide (0.15 g, 0.32 mmol) and allyl tributyltin (0.16 g, 0.48 mmol) in DMF (3 mL) was purged with nitrogen for 10 minutes, followed by addition of tetrakis(triphenylphosphine)palladium(0) (0.037 g, 0.03 mmol). The resulting reaction mixture was heated to 100° C. in a microwave reactor (Biotage Sixty™) for 1 h before pouring into water and extracting the product with EtOAc (3×100 mL). The combined organic layers were washed with water and brine, dried over Na$_2$SO$_4$, filtered and concentrated. The residue was purified by flash chromatography (20% EtOAc/hexane) to afford 3-(1-(5-allyl-4-(4-chlorophenyl)oxazol-2-yl)propoxy)-2,6-difluorobenzamide (0.10 g, 72%).

Similarly prepared was, for example, 3-(1-(5-allyl-4-(4-(trifluoromethoxy)phenyl)oxazol-2-yl)ethoxy)-2,6-difluorobenzamide.

Representative Example of a Sonogashira Coupling

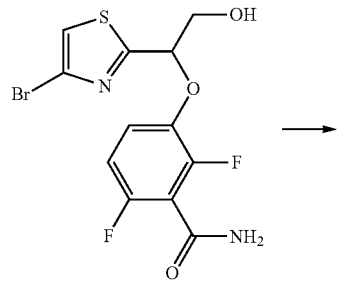

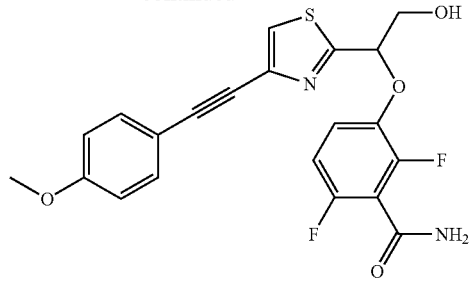

To a solution of 3-(1-(4-bromothiazol-2-yl)-2-hydroxyethoxy)-2,6-difluorobenzamide (0.25 g, 0.66 mmol) in THF (25 mL) was added 4-methoxyphenylacetylene (0.22 g, 1.65 mmol), CuI (0.020 g, 0.099 mmol) and Et$_3$N (0.78 mL, 5.60 mmol). The resulting reaction mixture was purged with nitrogen for 15 minutes, followed by addition of tetrakis(triphenylphosphine)palladium(0) (0.12 g, 0.099 mmol). The reaction mixture was purged with nitrogen for a further 10 minutes before heating at 60° C. for 16 h. After the completion of reaction, water was added and the product extracted into EtOAc (3×50 mL). The combined organic layers were washed with brine, dried over Na$_2$SO$_4$, filtered and concentrated under reduced pressure. The crude residue was purified by flash chromatography (80% EtOAc/hexane) to provide 2,6-difluoro-3-(2-hydroxy-1-(4-((4-methoxyphenyl)ethynyl)thiazol-2-yl)ethoxy)benzamide (0.17 g, 60%).

Representative Examples of Alkyne or Alkene Reduction

It will be clear to a person skilled in the art that the unsaturated products of the preceding examples may subsequently be reduced using known methodology to obtain the corresponding saturated analogues. Examples of this procedure are as follows.

i)

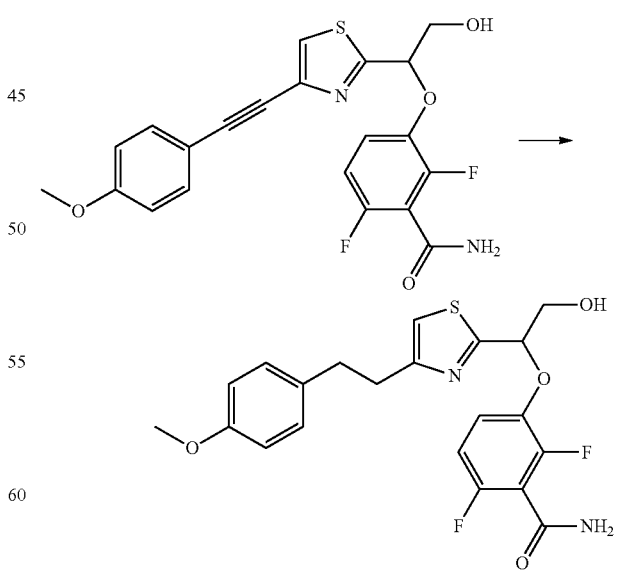

To a solution of 2,6-difluoro-3-(2-hydroxy-1-(4-((4-methoxyphenyl)ethynyl)thiazol-2-yl)ethoxy)benzamide (0.17 g, 0.39 mmol) in MeOH (20 mL) was added Pd on carbon (20% w/w, 34 mg). The resulting solution was stirred under a hydrogen atmosphere until the completion of reaction. The mixture was filtered through a celite bed, washing with EtOAc. The combined filtrate was concentrated under reduced pressure and the residue was purified by flash chromatography (70% EtOAc/hexane) to yield 2,6-difluoro-3-(2-hydroxy-1-(4-(4-methoxyphenethyl)thiazol-2-yl)ethoxy)benzamide (0.065 g, 38%).

ii)

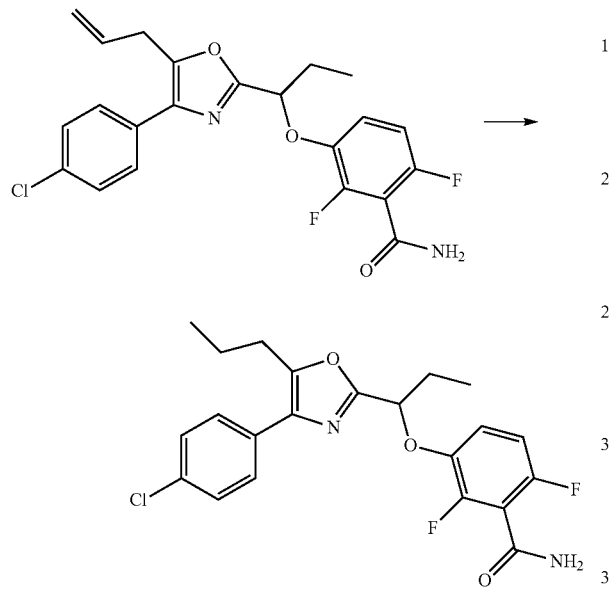

To a solution of 3-(1-(5-allyl-4-(4-chlorophenyl)oxazol-2-yl)propoxy)-2,6-difluorobenzamide (0.11 g, 0.25 mmol) in MeOH (7 mL) was added 20% Pd on carbon (10 mg, 0.1 eq) and the resulting solution was stirred under hydrogen (atmospheric pressure) at room temperature for 20 minutes. After the completion of reaction (TLC monitoring), the mixture was filtered through a celite bed and the filtrate was concentrated. The residue was purified by preparative HPLC to afford 3-(1-(4-(4-chlorophenyl)-5-propyloxazol-2-yl)propoxy)-2,6-difluorobenzamide (0.04 g, 36%). Similarly prepared was, for example, 2,6-difluoro-3-(1-(5-propyl-4-(4-(trifluoromethoxy)phenyl)oxazol-2-yl)ethoxy)benzamide.

Representative Example of the Conversion of an Oxazolyl Halide to a Thiol

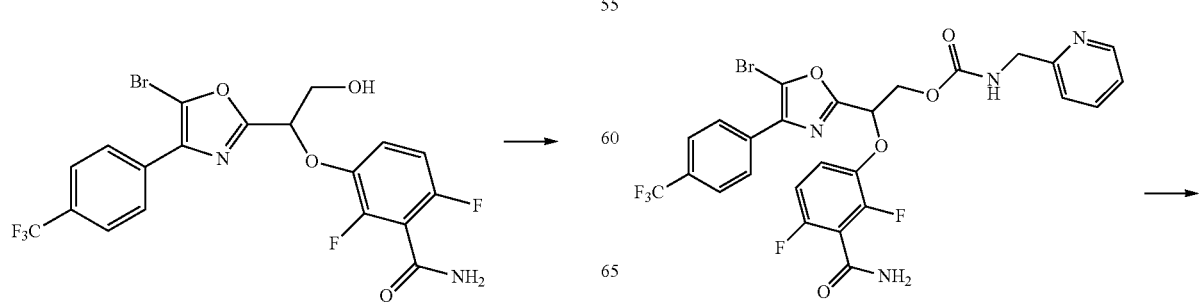

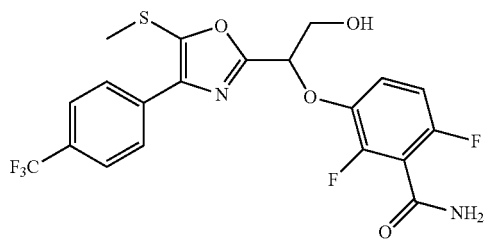

3-[1-[5-bromo-4-[4-(trifluoromethyl)phenyl]oxazol-2-yl]-2-hydroxy-ethoxy]-2,6-difluorobenzamide (20 mg, 0.039 mmol, prepared as previously described) and sodium thiomethoxide (2.6 mg, 0.037 mmol) were combined in DMF (1 mL) at 0° C. and stirred for 1 h. After this time the reaction mixture was diluted with EtOAc (5 mL) and brine (1 mL) and the organic layer was separated. The aqueous layer was further washed with EtOAc (2×5 mL). The combined organic layers were dried over $MgSO_4$, filtered and concentrated to give a colourless gum. The residue was purified by flash chromatography (30-60% EtOAc/hexane) to give 2,6-difluoro-3-(2-hydroxy-1-(5-(methylthio)-4-(4-(trifluoromethyl)phenyl)oxazol-2-yl)ethoxy)benzamide (14 mg, 75%) as a white solid.

Similarly prepared from the same substrate was 2-fluoro-3-(2-hydroxy-1-(5-(methylthio)-4-(4-(trifluoromethyl)phenyl)oxazol-2-yl)ethoxy)-6-(methylthio)benzamide by using an excess of sodium thiomethoxide at room temperature.

Representative Example of Thiazolopyridine Tynthesis

Compounds 3-(1-(5-bromo-6-ethoxythiazolo[5,4-b]pyridin-2-yl)ethoxy)-2,6-difluorobenzamide and 3-(1-(6-ethoxythiazolo[5,4-b]pyridin-2-yl)ethoxy)-2,6-difluorobenzamide were prepared analogously to the manner described in *J Med Chem* 2010, 53, 3927-3936 for the preparation of 3-[6-ethoxythiazolo[5,4-b]pyridin-2-yl)methoxy]-2,6-difluoro-benzamide, using propionyl chloride in place of acetyl chloride.

Representative Example of N-Oxide Preparation

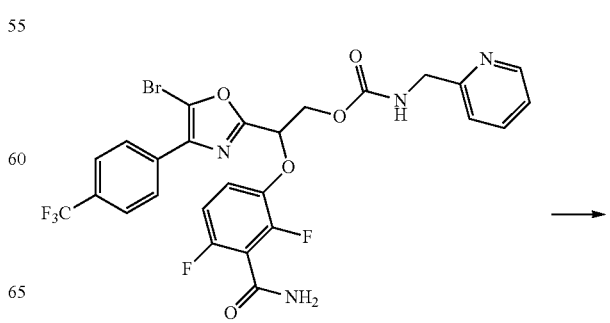

-continued

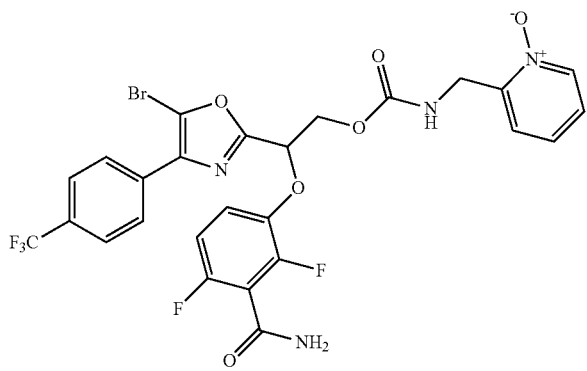

To a solution of 2-(5-bromo-4-(4-(trifluoromethyl)phenyl)oxazol-2-yl)-2-(3-carbamoyl-2,4-difluorophenoxy)ethyl pyridin-2-ylmethylcarbamate (0.055 g, 0.08 mmol) in DCM (10 mL) was added methyltrioxorhenium (catalytic) and $H_2O_2$ (aq, 30%, 5 mL). The resulting solution was stirred room temperature for 4 h. After this time $MnO_2$ was added and the solution stirred until the evolution of oxygen had ceased. The reaction mixture was filtered through celite. Water was added to the filtrate and the product extracted into EtOAc (3×50 mL). The combined organic layers were dried over anhydrous $Na_2SO_4$, filtered and concentrated under reduced pressure. The crude residue was further purified by preparative TLC to afford the target N-oxide, 2-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide (26 mg, 46%) as a white solid.

Representative Example of Prodrug Formation

Synthesis of (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid

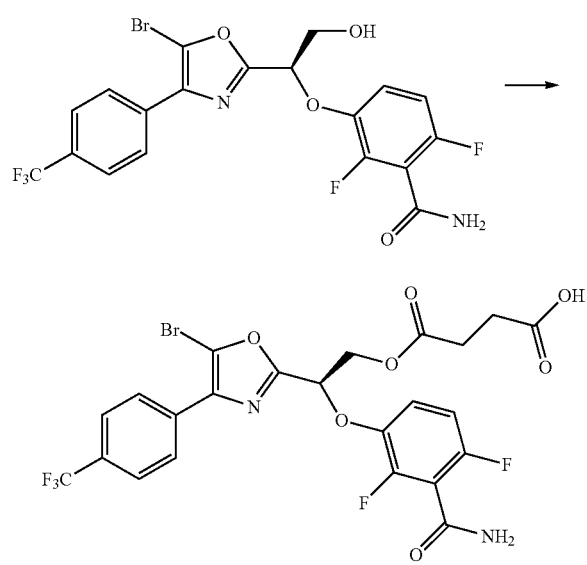

To a solution of (R)-3-(1-(5-bromo-4-(4-(trifluoromethyl)phenyl)oxazol-2-yl)-2-hydroxyethoxy)-2,6-difluorobenzamide (0.40 g, 0.79 mmol) in pyridine (10 mL) was added DMAP (catalytic) and succinic anhydride (0.08 g, 0.79 mmol). The resulting reaction mixture was allowed to stir at room temperature for 16 h. The reaction mixture was cooled to 0° C., adjusted to pH 4-5 by drop-wise addition of 6 M HCl and the product extracted into EtOAc (2×50 mL). The combined organic layers were dried over anhydrous $Na_2SO_4$, filtered and concentrated under reduced pressure to afford (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid (0.40 g, 84%).

Representative Example of Salt Formation

Synthesis of (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid arginine salt

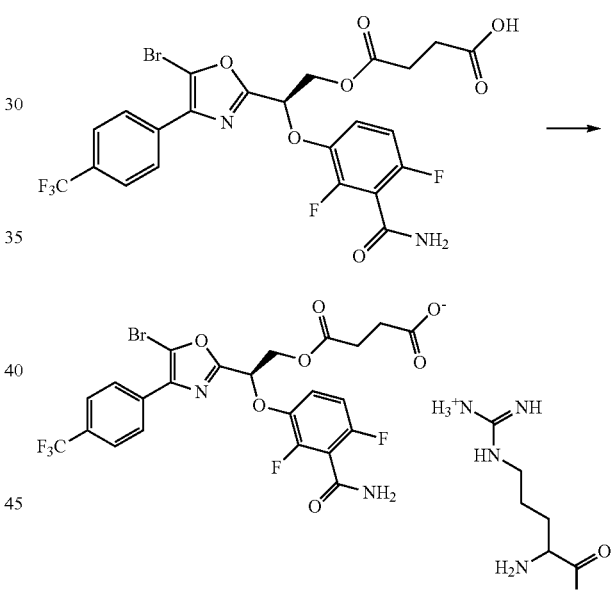

To a solution of (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid (0.30 g, 0.49 mmol) in methanol:DCM (1:1, 8 mL) was added L-arginine (0.086 g, 0.49 mmol). The resulting reaction mixture was stirred at room temperature for 1 h. After completion of the reaction (TLC monitoring) the mixture was concentrated under reduced pressure and the residue was triturated with diethyl ether to afford (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid L-arginine salt as an off white solid (0.30 g, 78%).

Similarly prepared was 4-(2-(5-bromo-4-(4-(trifluoromethyl)phenyl)oxazol-2-yl)-2-(3-carbamoyl-2,4-difluorophenoxy)ethoxy)-4-oxobutanoic acid L-arginine salt.

The compounds were characterised using a combination of LCMS and $^1$H NMR data as provided in Table 1.

TABLE 1

Characterisation of compounds by LCMS and ¹H NMR

| Cpd No | Name | LCMS m/z = [M + H]+ | ¹H NMR |
|---|---|---|---|
| 1 | 3-(1-(5-bromo-4-(4-chlorophenyl)oxazol-2-yl)ethoxy)-2,6-difluorobenzamide | 456.9 | ¹H NMR (DMSO-d6) δ 8.14 (br s, 1H), 7.90 (m, 2H), 7.87 (br, s, 1H), 7.58 (m, 2H), 7.36 (m, 1H), 7.10 (m, 1H), 5.68 (q, J = 6.40 Hz, 1H), 1.73 (d, J = 6.40 Hz, 3H) |
| 2 | 3-(1-(4-bromothiazol-2-yl)ethoxy)-2,6-difluorobenzamide | 362.94 | ¹H NMR (DMSO-d6) δ 7.85 (br s, 1H), 7.92 (br s, 2H), 7.35 (m, 1H), 7.08 (m, 1H), 5.85 (q, J = 6.0 Hz, 1H), 1.67 (d, J = 6.0 Hz, 3H) |
| 3 | 2,6-difluoro-3-(1-(2'-methoxy-[4,5'-bithiazol]-2-yl)ethoxy)benzamide | 397.94 | ¹H NMR (DMSO-d6) δ 8.23 (br s, 1H), 8.02 (s, 1H), 7.88 (br s, 1H), 7.66 (s, 1H), 7.32 (m, 1H), 7.07 (m, 1H), 5.89 (m, 1H), 4.04 (s, 3H), 1.70 (d, J = 6.0 Hz, 3H) |
| 4 | 3-(1-(4-(4-chlorophenyl)oxazol-2-yl)ethoxy)-2,6-difluorobenzamide | 379.02 | ¹H NMR (DMSO-d6) δ 8.69 (s, 1H), 8.13 (br, s, 1H), 7.85 (br, s, 1H), 7.77 (m, 2H), 7.49 (m, 2H), 7.33 (m, 1H), 7.08 (m, 1H), 5.70 (q, J = 6.40 Hz, 1H), 1.73 (d, J = 6.40 Hz, 3H) |
| 5 | 3-(1-(5-bromo-4-(4-methoxyphenyl)oxazol-2-yl)ethoxy)-2,6-difluorobenzamide | 452.98 | ¹H NMR (DMSO-d6) δ 8.15 (br s, 1H), 7.87 (br s, 1H), 7.81 (d, J = 8.80 Hz, 2H), 7.34 (m, 1H), 7.05-7.12 (m, 3H), 5.68 (q, J = 6.40 Hz, 1H), 3.79 (s, 3H), 1.72 (d, J = 6.40 Hz, 3H) |
| 5A | (S)-3-(1-(5-bromo-4-(4-methoxyphenyl)oxazol-2-yl)ethoxy)-2,6-difluorobenzamide | 453.0 | ¹H NMR (acetone-d6) δ 7.90 (d, J = 8.9 Hz, 2H), 7.44 (br s, 1H), 7.34 (td, J = 9.2, 5.2 Hz, 1H), 7.14 (br s, 1H), 7.04 (d, J = 8.9 Hz, 2H), 6.98 (td, J = 8.9, 1.9 Hz, 1H), 5.56 (q, J = 6.6 Hz, 1H), 3.85 (s, 3H), 1.81 (d, J = 6.6 Hz, 3H). |
| 5B | (R)-3-(1-(5-bromo-4-(4-methoxyphenyl)oxazol-2-yl)ethoxy)-2,6-difluorobenzamide | 452.9 | ¹H NMR (acetone-d6) δ 7.90 (d, J = 8.9 Hz, 2H), 7.44 (br s, 1H), 7.34 (td, J = 9.2, 5.3 Hz, 1H), 7.15 (br s, 1H), 7.04 (d, J = 8.9 Hz, 2H), 6.98 (td, J = 9.0, 1.9 Hz, 1H), 5.56 (q, J = 6.6 Hz, 1H), 3.84 (d, J = 9.4 Hz, 3H), 1.81 (d, J = 6.6 Hz, 3H). |
| 6 | ethyl 2-(3-carbamoyl-2,4-difluorophenoxy)-2-(4-(4-chlorophenyl)oxazol-2-yl)acetate | 436.96 | ¹H NMR (DMSO-d6) δ 8.82 (s, 1H), 8.17 (br s, 1H), 7.89 (br s, 1H), 7.81 (d, J = 8.40 Hz, 2H), 7.54 (d, J = 8.40 Hz, 2H), 7.36 (m, 1H), 7.12 (m, 1H), 6.54 (s, 1H), 4.25 (m, 2H), 1.19 (t, J = 6.80 Hz, 3H) |
| 7 | 3-(1-(5-allyl-4-(4-chlorophenyl)oxazol-2-yl)ethoxy)-2,6-difluorobenzamide | 418.97 | ¹H NMR (DMSO-d6) δ 8.13 (br s, 1H), 7.86 (br s, 1H), 7.64 (d, J = 8.80 Hz, 2H), 7.49 (d, J = 8.40 Hz, 2H), 7.33 (m, 1H), 7.08 (m, 1H), 5.95 (m, 1H), 5.64 (q, J = 6.4 Hz, 1H), 5.15 (m, 1H), 5.08 (d, J = 17.20 Hz, 1H), 3.69 (d, J = 5.60 Hz, 2H), 1.71 (d, J = 6.40 Hz, 3H) |
| 8 | 2,6-difluoro-3-(1-(4-phenyl-5-propyloxazol-2-yl)ethoxy)benzamide | 387.13 | ¹H NMR (DMSO-d6) δ 8.13 (br s, 1H), 7.85 (br s, 1H), 7.63 (m, 2H), 7.46 (m, 2H), 7.35 (m, 2H), 7.08 (m, 1H), 5.63 (m, 1H), 2.87 (d, J = 7.20 Hz, 2H), 1.72 (d, J = 6.40 Hz, 3H), 1.64 (m, 2H), 0.89 (t, J = 7.20 Hz, 3H) |
| 9 | 3-(1-(5-allyl-4-(4-methoxyphenyl)oxazol-2-yl)ethoxy)-2,6-difluorobenzamide | 415.10 | ¹H NMR (DMSO-d6) δ 8.13 (br s, 1H), 7.86 (br s, 1H), 7.54 (d, J = 8.40 Hz, 2H), 7.35 (m, 1H), 7.08 (m, 1H), 7.01 (d, J = 8.80 Hz, 2H), 5.95 (m, 1H), 5.62 (q, J = 6.40 Hz, 1H), 5.14 (dd, J = 1.20 and 10.0 Hz respectively, 1H), 5.07 (d, J = 16.0 Hz, 1H), 3.77 (s, 3H), 3.64 (m, 2H), 1.71 (d, J = 6.40 Hz, 3H) |

TABLE 1-continued

Characterisation of compounds by LCMS and $^1$H NMR

| Cpd No | Name | LCMS m/z = [M + H]+ | $^1$H NMR |
|---|---|---|---|
| 10 | 3-(1-(4-(4-chlorophenyl)oxazol-2-yl)-2-hydroxyethoxy)-2,6-difluorobenzamide | 395.11 | $^1$H NMR (DMSO-d6) δ 8.70 (s, 1H), 8.15 (br s, 1H), 7.86 (br s, 1H), 7.78 (d, J = 6.80 Hz, 2H), 7.51 (d, J = 6.80 Hz, 2H), 7.30 (m, 1H), 7.08 (m, 1H), 5.51 (t, J = 5.60 Hz, 1H), 5.40 (br s, 1H), 4.0 (br s, 2H) |
| 11 | ethyl 2-(3-carbamoyl-2,4-difluorophenoxy)-2-(4-(4-chlorophenyl)thiazol-2-yl)acetate | 452.94 | $^1$H NMR (DMSO-d6) δ 8.34 (s, 1H), 8.18 (br s, 1H), 7.98 (d, J = 8.40 Hz, 2H), 7.90 (br s, 1H), 7.54 (d, J = 8.40 Hz, 2H), 7.35 (m, 1H), 7.12 (m, 1H), 6.58 (s, 1H), 4.25 (m, 2H), 1.19 (t, J = 7.20 Hz, 3H) |
| 12 | 2-(3-carbamoyl-2,4-difluorophenoxy)-2-(4-(4-chlorophenyl)oxazol-2-yl)acetic acid | 409.08 | $^1$H NMR (DMSO-d6) δ 8.59 (s, 1H), 8.12 (br s, 1H), 7.79 (m, 3H), 7.50 (d, J = 8.40 Hz, 2H), 7.10 (m, 1H), 6.98 (m, 1H), 5.38 (s, 1H) |
| 13 | 3-(1-(4-(4-chlorophenyl)thiazol-2-yl)-2-hydroxyethoxy)-2,6-difluorobenzamide | 411.0 | $^1$H NMR (DMSO-d6) δ 8.20 (s, 1H), 8.15 (br s, 1H), 7.98 (d, J = 8.0 Hz, 2H), 7.87 (br s, 1H), 7.52 (d, J = 7.60 Hz, 2H), 7.34 (m, 1H), 7.04 (m, 1H), 5.74 (s, 1H), 5.42 (s, 1H), 3.99 (br s, 1H), 3.92 (t, J = 6.0 Hz, 1H) |
| 14 | 3-(1-(2'-ethoxy-[4,5'-bithiazol]-2-yl)ethoxy)-2,6-difluorobenzamide | 411.98 | $^1$H NMR (DMSO-d6) δ 8.15 (br s, 1H), 7.92 (s, 1H), 7.87 (br s, 1H), 7.62 (s, 1H), 7.36 (m, 1H), 7.09 (m, 1H), 5.89 (q, J = 6.40 Hz, 1H), 4.45 (q, J = 7.20 Hz, 2H), 1.70 (d, J = 6.40 Hz, 3H), 1.37 (t, J = 7.20 Hz, 3H) |
| 15 | 2,6-difluoro-3-(1-(4-(4-methoxyphenyl)-5-propyloxazol-2-yl)ethoxy)benzamide | 417.1 | $^1$H NMR (DMSO-d6) δ 8.13 (br s, 1H), 7.85 (br s, 1H), 7.52 (d, J = 8.40 Hz, 2H), 7.36 (m, 1H), 7.10 (m, 1H), 7.01 (d, J = 8.40 Hz, 2H), 5.61 (q, J = 6.40 Hz, 1H), 3.77 (s, 3H), 2.84 (t, J = 7.20 Hz, 2H), 1.71 (d, J = 6.40 Hz, 3H), 1.59-1.69 (m, 2H), 0.88 (t, J = 7.20 Hz, 3H) |
| 16 | 3-(1-(5-bromo-4-(4-(trifluoromethoxy)phenyl)oxazol-2-yl)ethoxy)-2,6-difluorobenzamide | 506.8 | $^1$H NMR (DMSO-d6) δ 8.14 (br s, 1H), 7.98 (d, J = 8.40 Hz, 2H), 7.86 (br s, 1H), 7.52 (d, J = 8.40 Hz, 2H), 7.37 (m, 1H), 7.10 (m, 1H), 5.70 (q, J = 6.80 Hz, 1H), 1.73 (d, J = 6.80 Hz, 3H) |
| 17 | 3-(1-(5-allyl-4-(4-(trifluoromethoxy)phenyl)oxazol-2-yl)ethoxy)-2,6-difluorobenzamide | 468.97 | $^1$H NMR (DMSO-d6) δ 8.13 (br s, 1H), 7.86 (br s, 1H), 7.75 (d, J = 8.0 Hz, 2H), 7.45 (d, J = 8.0 Hz, 2H), 7.35 (m, 1H), 7.08 (m, 1H), 5.94 (m, 1H), 5.64 (q, J = 5.20 Hz, 1H), 5.08-5.16 (m, 2H), 3.70 (d, J = 5.60 Hz, 2H), 1.72 (d, J = 5.60 Hz, 3H) |
| 18 | 3-(1-(5-bromo-4-(4-chlorophenyl)oxazol-2-yl)propoxy)-2,6-difluorobenzamide | 471.0 | $^1$H NMR (DMSO-d6) δ 8.13 (br s, 1H), 7.87 (m, 3H), 7.58 (d, J = 7.60 Hz, 2H), 7.32 (m, 1H), 7.10 (m, 1H), 5.50 (t, J = 6.80 Hz, 1H), 2.11 (m, 2H), 1.03 (t, J = 7.20 Hz, 3H) |
| 19 | 3-(1-(4-(4-chlorophenyl)-5-propyloxazol-2-yl)ethoxy)-2,6-difluorobenzamide | 420.94 | $^1$H NMR (DMSO-d6) δ 8.12 (br s, 1H), 7.84 (br s, 1H), 7.65 (d, J = 8.40 Hz, 2H), 7.51 (d, J = 8.40 Hz, 2H), 7.36 (m, 1H), 7.10 (m, 1H), 5.60 (q, J = 6.40 Hz, 1H), 2.88 (t, J = 7.20 Hz, 2H), 1.70 (d, J = 6.40 Hz, 3H), 1.61-1.67 (m, 2H), 0.88 (t, J = 7.20 Hz, 3H) |
| 20 | 2,6-difluoro-3-(1-(5-propyl-4-(4-(trifluoromethoxy)phenyl)oxazol-2-yl)ethoxy)benzamide | 471.02 | $^1$H NMR (DMSO-d6) δ 8.12 (br s, 1H), 7.84 (br s, 1H), 7.76 (d, J = 8.40 Hz, 2H), 7.44 (d, J = 8.40 Hz, 2H), 7.32 (m, 1H), 7.07 (m, 1H), 5.63 (m, 1H), 2.88 (t, J = 7.20 Hz, |

TABLE 1-continued

Characterisation of compounds by LCMS and ¹H NMR

| Cpd No | Name | LCMS m/z = [M + H]+ | ¹H NMR |
|---|---|---|---|
| | | | 2H), 1.70 (d, J = 6.40 Hz, 3H), 1.64 (m, 2H), 0.89 (t, J = 7.20 Hz, 3H) |
| 21 | 3-(1-(5-chloro-4-(4-(trifluoromethoxy)phenyl)oxazol-2-yl)ethoxy)-2,6-difluorobenzamide | 462.88 | ¹H NMR (DMSO-d6) δ 8.14 (br s, 1H), 7.87 (d, J = 8.40 Hz, 2H), 7.87 (br s, 1H), 7.50 (d, J = 8.40 Hz, 2H), 7.38 (m, 1H), 7.10 (m, 1H), 5.67 (q, J = 6.40 Hz, 1H), 1.73 (d, J = 6.40 Hz, 3H) |
| 22 | 3-(1-(5-allyl-4-(4-chlorophenyl)oxazol-2-yl)propoxy)-2,6-difluorobenzamide | 433.03 | ¹H NMR (DMSO-d6) δ 8.13 (br s, 1H), 7.85 (br s, 1H), 7.59 (d, J = 7.60 Hz, 2H), 7.51 (d, J = 7.60 Hz, 2H), 7.28 (m, 1H), 7.06 (m, 1H), 5.95 (m, 1H), 5.41 (t, J = 6.80 Hz, 1H), 5.15 (d, J = 10.0 Hz, 1H), 5.0 (d, J = 17.20 Hz, 1H), 3.67 (d, J = 5.20 Hz, 2H), 2.15 (m, 2H), 1.01 (t, J = 7.20 Hz, 3H) |
| 23 | 3-(1-(5-bromo-4-(4-chlorophenyl)oxazol-2-yl)butoxy)-2,6-difluorobenzamide | 485 | ¹H NMR (DMSO-d6) δ 8.14 (br s, 1H), 7.89 (m, 3H), 7.58 (d, J = 8.0 Hz, 2H), 7.32 (m, 1H), 7.08 (m, 1H), 5.54 (t, J = 6.40 Hz, 1H), 2.10 (m, 2H), 1.50 (m, 2H), 0.94 (t, J = 7.20 Hz, 3H) |
| 24 | 3-(1-(4-bromo-5-chlorothiazol-2-yl)ethoxy)-2,6-difluorobenzamide | 396.99 | ¹H NMR (DMSO-d6) δ 8.14 (br s, 1H), 7.88 (br s, 1H), 7.35 (m, 1H), 7.09 (m, 1H), 5.81 (q, J = 6.40 Hz, 1H), 1.65 (d, J = 6.40 Hz, 3H) |
| 25 | 3-(1-(5-bromo-6-ethoxythiazolo[5,4-b]pyridin-2-yl)ethoxy)-2,6-difluorobenzamide | 458 | ¹H NMR (DMSO-d6) δ 8.15 (m, 2H), 7.89 (br s, 1H), 7.35 (m, 1H), 7.10 (m, 1H), 5.95 (m, 1H), 4.26 (q, J = 7.20 Hz, 2H), 1.75 (d, J = 6.40 Hz, 3H), 1.41 (t, J = 7.20 Hz, 3H) |
| 26 | 3-(1-(4-(4-chlorophenyl)-5-propyloxazol-2-yl)propoxy)-2,6-difluorobenzamide | 435.03 | ¹H NMR (DMSO-d6) δ 8.34 (br s, 1H), 7.84 (br s, 1H), 7.63 (d, J = 8.0 Hz, 2H), 7.50 (d, J = 8.0 Hz, 2H), 7.29 (m, 1H), 7.06 (m, 1H), 5.40 (t, J = 6.40 Hz, 1H), 2.86 (t, J = 7.20 Hz, 2H), 2.15 (m, 2H), 1.66 (m, 2H), 1.01 (t, J = 7.60 Hz, 3H), 0.87 (t, J = 7.20 Hz, 3H) |
| 27 | 3-(1-(5-bromo-4-(4-(trifluoromethyl)phenyl)oxazol-2-yl)ethoxy)-2,6-difluorobenzamide | 490.85 | ¹H NMR (DMSO-d6) δ 8.12 (br s, 1H), 8.10 (d, J = 8.40 Hz, 2H), 7.87 (d, J = 8.40 Hz, 2H), 7.84 (br s, 1H), 7.36 (m, 1H), 7.10 (m, 1H), 5.71 (q, J = 6.40 Hz, 1H), 1.74 (d, J = 6.40 Hz, 3H) |
| 28 | 3-(1-(5-allyl-4-(4-chlorophenyl)oxazol-2-yl)butoxy)-2,6-difluorobenzamide | 446.97 | ¹H NMR (DMSO-d6) δ 8.12 (br s, 1H, D₂O exchangeable), 7.84 (br s, 1H, D₂O exchangeable), 7.61 (d, J = 8.40 Hz, 2H), 7.49 (d, J = 8.40 Hz, 2H), 7.26 (m, 1H), 7.03 (m, 1H), 5.89 (m, 1H), 5.41 (t, J = 7.20 Hz, 1H), 5.13 (d, J = 10.0 Hz, 1H), 5.0 (d, J = 17.20 Hz, 1H), 3.64 (m, 2H), 2.05 (m, 2H), 1.46 (m, 2H), 0.98 (t, J = 7.20 Hz, 3H) |
| 29 | 3-(1-(6-ethoxythiazolo[5,4-b]pyridin-2-yl)ethoxy)-2,6-difluorobenzamide | 380.01 | Characterised by LCMS |
| 30 | 3-(1-(4-(4-chlorophenyl)-5-propyloxazol-2-yl)butoxy)-2,6-difluorobenzamide | 449.08 | ¹H NMR (DMSO-d6) δ 8.12 (br s, 1H), 7.84 (br s, 1H), 7.64 (d, J = 8.0 Hz, 2H), 7.50 (d, J = 8.0 Hz, 2H), 7.29 (m, 1H), 7.05 (m, 1H), 5.45 (t, J = 6.80 Hz, 1H), 2.86 (t, J = 7.20 Hz, 2H), 2.10 (m, 1H), 2.01 (m, 1H), 1.62 (q, J = 7.60 Hz, 2H), 1.48 (m, 1H), 1.39 (m, 1H), 0.95 (t, J = 7.60 Hz, 3H), 0.87 (t, J = 7.20 Hz, 3H) |

TABLE 1-continued

Characterisation of compounds by LCMS and $^1$H NMR

| Cpd No | Name | LCMS m/z = [M + H]+ | $^1$H NMR |
|---|---|---|---|
| 31 | 3-(1-(4-(4-chlorophenyl)thiazol-2-yl)-2-(dimethylamino)-2-oxoethoxy)-2,6-difluorobenzamide | 451.99 | $^1$H NMR (DMSO-d6) δ 8.30 (s, 1H), 8.17 (br s, 1H), 7.88 (d, J = 8.40 Hz, 2H), 7.88 (br s, 1H), 7.54 (d, J = 8.40 Hz, 2H), 7.20 (m, 1H), 7.08 (m, 1H), 6.84 (s, 1H), 3.25 (s, 3H), 2.91 (s, 3H) |
| 32 | 3-(1-(5-chloro-4-(4-(trifluoromethyl)phenyl)oxazol-2-yl)ethoxy)-2,6-difluorobenzamide | 446.95 | $^1$H NMR (DMSO-d6) δ 8.14 (br s, 1H), 8.07 (d, J = 8.40 Hz, 2H), 7.87 (d, J = 8.40 Hz, 2H), 7.84 (br s, 1H), 7.36 (m, 1H), 7.10 (m, 1H), 5.70 (q, J = 6.40 Hz, 1H), 1.74 (d, J = 6.40 Hz, 3H) |
| 33 | 3-(1-(3-(4-chlorophenyl)-1,2,4-thiadiazol-5-yl)ethoxy)-2,6-difluorobenzamide | 395.99 | $^1$H NMR (DMSO-d6) δ 8.23 (d, J = 8.40 Hz, 2H), 8.16 (br s, 1H), 7.88 (br s, 1H), 7.61 (d J = 8.40 Hz, 2H), 7.45 (m, 1H), 7.11 (m, 1H), 6.14 (q, J = 6.0 Hz, 1H), 1.76 (d, J = 6.0 Hz, 3H) |
| 34 | 3-(1-(4-(4-chlorophenyl)thiazol-2-yl)-2-(methylamino)-2-oxoethoxy)-2,6-difluorobenzamide | 438.03 | $^1$H NMR (DMSO-d6) δ and 8.60 (br d, J = 4.40 Hz, 1H), 8.26 (s, 1H), 8.15 (br s, 1H), 7.97 (d, J = 8.40 Hz, 2H), 7.87 (br s, 1H), 7.50 (d, J = 8.40 Hz, 2H), 7.25 (m, 1H), 7.10 (m, 1H), 6.16 (s, 1H), 2.70 (d, J = 4.80 Hz, 3H) |
| 35 | 3-(1-(5-chloro-2'-methoxy-[4,5'-bithiazol]-2-yl)ethoxy)-2,6-difluorobenzamide | 432.08 | $^1$H NMR (DMSO-d6) δ 8.13 (br s, 1H), 7.87 (br s, 1H), 7.80 (s, 1H), 7.37 (m, 1H), 7.09 (m, 1H), 5.83 (m, 1H), 4.08 (s, 3H), 1.69 (d, J = 6.40 Hz, 3H) |
| 36 | 2-(5-bromo-4-(4-chlorophenyl)oxazol-2-yl)-2-(3 carbamoyl-2,4-difluorophenoxy)ethyl acetate | 515 | $^1$H NMR (DMSO-d6) δ 8.15 (br s, 1H), 7.90 (m, 3H), 7.59 (d, J = 8.40 Hz, 2H), 7.38 (m, 1H), 7.11 (m, 1H), 5.83 (t, J = 4.0 Hz, 1H), 4.65 (m, 2H), 2.03 (s, 3H) |
| 37 | 2-(5-bromo-4-(4-(trifluoromethyl)phenyl)oxazol-2-yl)-2-(3-carbamoyl-2,4-difluorophenoxy)ethyl acetate | 549 | $^1$H NMR (DMSO-d6) δ 8.23 (br s, 1H), 8.11 (d, J = 8.0 Hz, 2H), 7.90 (m, 3H), 7.38 (m, 1H), 7.11 (m, 1H), 5.85 (t, J = 2.0 Hz, 1H), 4.66 (m, 2H), 2.04 (s, 3H) |
| 38 | 3-(1-(5-bromo-4-(4-(trifluoromethyl)phenyl)oxazol-2-yl)-2-hydroxyethoxy)-2,6-difluorobenzamide | 507 | $^1$H NMR (DMSO-d6) δ 8.13 (br s, 1H), 8.10 (d, J = 8.40 Hz, 2H), 7.89 (d, J = 8.40 Hz, 2H), 7.85 (br s, 1H), 7.34 (m, 1H), 7.07 (m, 1H), 5.50 (t, J = 5.60 Hz, 1H), 5.42 (t, J = 5.60 Hz, 1H), 4.01 (t, J = 5.60 Hz, 2H) |
| 38A | (S)-3-(1-(5-bromo-4-(4-(trifluoromethyl)phenyl)oxazol-2-yl)-2-hydroxyethoxy)-2,6-difluorobenzamide | 506.9 | $^1$H NMR (DMSO-d6) δ 8.14 (br s, 1H), 8.10 (d, J = 8.40 Hz, 2H), 7.87-7.89 (m, 3H), 7.32-7.38 (m, 1H), 7.08 (m, 1H), 5.51 (m, 1H), 5.44 (t, J = 6.0 Hz, 1H), 4.01 (t, J = 6.0 Hz, 2H) |
| 38B | (R)-3-(1-(5-bromo-4-(4-(trifluoromethyl)phenyl)oxazol-2-yl)-2-hydroxyethoxy)-2,6-difluorobenzamide | 507.23 | $^1$H NMR (DMSO-d6) δ 8.13 (br s, 1H), 8.10 (d, J = 8.0 Hz, 2H), 7.87 (d, J = 8.40 Hz, 2H), 7.84 (br s, 1H), 7.32-7.38 (m, 1H), 7.05-7.10 (m, 1H), 5.52 (t, J = 6.0 Hz, 1H), 5.42 (t, J = 6.0 Hz, 1H), 4.01 (t, J = 6.0 Hz, 2H) |
| 39 | 3-(1-(5-bromo-4-(4-chlorophenyl)oxazol-2-yl)-2-hydroxyethoxy)-2,6-difluorobenzamide | 473 | $^1$H NMR (DMSO-d6) δ 8.14 (br s, 1H), 7.89 (m, 3H), 7.59 (d, J = 8.80 Hz, 2H), 7.34 (m, 1H), 7.08 (m, 1H), 5.50 (t, J = 5.60 Hz, 1H), 5.43 (t, J = 6.0 Hz, 1H), 4.0 (t, J = 5.60 Hz, 2H) |
| 40 | 3-(2-amino-1-(4-(4-chlorophenyl)thiazol-2-yl)-2-oxoethoxy)-2,6-difluorobenzamide | 424.06 | $^1$H NMR (DMSO-d6) δ 8.27 (s, 1H), 8.15 (br s, 1H), 8.04 (br s, 1H), 7.98 (d, J = 8.40 Hz, 2H), 7.87 (br s, 1H), 7.77 (br s, 1H), 7.53 (d, J = 8.40 Hz, 2H), 7.25 (m, 1H), 7.11 (m, 1H), 6.14 (s, 1H) |

TABLE 1-continued

Characterisation of compounds by LCMS and $^1$H NMR

| Cpd No | Name | LCMS m/z = [M + H]+ | $^1$H NMR |
|---|---|---|---|
| 41 | 3-(1-(4-(4-chlorophenyl)thiazol-2-yl)-2-(4-methylpiperazin-1-yl)-2-oxoethoxy)-2,6-difluorobenzamide | 507.25 | $^1$H NMR (DMSO-d6) δ 8.31 (s, 1H), 8.18 (br s, 1H), 7.99 (d, J = 8.40 Hz, 2H), 7.88 (br s, 1H), 7.55 (d, J = 8.40 Hz, 2H), 7.20 (m, 1H), 7.11 (m, 1H), 6.90 (s, 1H), 3.74 (m, 2H), 3.51 (m, 2H), 2.25 (m, 4H), 2.15 (s, 3H) |
| 42 | 2-(3-carbamoyl-2,4-difluorophenoxy)-2-(5-chloro-4-(4-(trifluoromethyl)phenyl)oxazol-2-yl)ethyl acetate | 505.02 | $^1$H NMR (DMSO-d6) δ 8.15 (br s, 1H), 8.07 (d, J = 8.0 Hz, 2H), 7.90 (m, 3H), 7.39 (m, 1H), 7.09 (m, 1H), 5.84 (m, 1H), 4.66 (m, 2H), 2.04 (s, 3H) |
| 43 | 3-(1-(5-chloro-4-(5-(trifluoromethyl)pyridin-2-yl)oxazol-2-yl)ethoxy)-2,6-difluorobenzamide | 448.16 | $^1$H NMR (MeOH-d4) δ 8.92 (s, 1H), 8.20 (dd, J = 1.60 and 8.40 Hz, 1H), 8.13 (d, J = 8.40 Hz, 1H), 7.30 (m, 1H), 6.96 (m, 1H), 5.52 (q, J = 6.40 Hz, 1H), 1.83 (d, J = 6.40 Hz, 3H) |
| 44 | 3-(1-(5-chloro-4-(4-(trifluoromethyl)phenyl)oxazol-2-yl)-2-hydroxyethoxy)-2,6-difluorobenzamide | 462.93 | $^1$H NMR (DMSO-d6) δ 8.15 (br s, 1H), 8.05 (d, J = 8.40 Hz, 2H), 7.89 (m, 3H), 7.34 (m, 1H), 7.08 (m, 1H), 5.52 (t, J = 5.60 Hz, 1H), 5.44 (t, J = 6.0 Hz, 1H), 4.02 (t, J = 5.60 Hz, 2H) |
| 45 | 2-(3-carbamoyl-2,4-difluorophenoxy)-2-(5-chloro-4-(4-(trifluoromethyl)phenyl)oxazol-2-yl)ethyl methanesulfonate | 540.87 | $^1$H NMR (DMSO-d6) δ 8.17 (br s, 1H), 8.08 (d J = 8.40 Hz, 2H), 7.90 (m, 3H), 7.42 (m, 1H), 7.11 (m, 1H), 5.98 (t, J = 5.60 Hz, 1H), 4.84 (m, 2H), 3.29 (s, 3H) |
| 46 | 2-(3-carbamoyl-2,4-difluorophenoxy)-2-(5-chloro-4-(4-chlorophenyl)oxazol-2-yl)ethyl acetate | 470.97 | $^1$H NMR (DMSO-d6) δ 8.16 (br s, 1H), 7.88 (br s, 1H), 7.87 (d, J = 8.80 Hz, 2H), 7.59 (d, J = 8.80 Hz, 2H), 7.39 (m, 1H), 7.09 (m, 1H), 5.83 (m, 1H), 4.65 (m, 2H), 2.03 (s, 3H) |
| 47 | 3-(1-(5-chloro-4-(4-chlorophenyl)oxazol-2-yl)-2-hydroxyethoxy)-2,6-difluorobenzamide | 428.93 | $^1$H NMR (DMSO-d6) δ 8.14 (br s, 1H), 7.86 (m, 3H), 7.58 (d, J = 8.40 Hz, 2H), 7.34 (m, 1H), 7.08 (m, 1H), 5.50 (t, J = 5.60 Hz, 1H), 5.42 (t, J = 6.0 Hz, 1H), 4.0 (t, J = 5.60 Hz, 2H) |
| 48 | 2-(3-carbamoyl-2,4-difluorophenoxy)-2-(5-chloro-4-(4-chlorophenyl)oxazol-2-yl)ethyl methanesulfonate | 506.89 | $^1$H NMR (DMSO-d6) δ 8.17 (br s, 1H), 7.90 (br s, 1H), 7.87 (d, J = 8.40 Hz, 2H), 7.58 (d, J = 8.40 Hz, 2H), 7.40 (m, 1H), 7.11 (m, 1H), 5.96 (m, 1H), 4.84 (m, 2H), 3.29 (s, 3H) |
| 49 | 3-(1-(5-chloro-4-(4-chlorophenyl)oxazol-2-yl)-2-(methylamino)-2-oxoethoxy)-2,6-difluorobenzamide | 456.06 | $^1$H NMR (DMSO-d6) δ 8.57 (br d, J = 4.0 Hz, 1H), 8.14 (br s, 1H), 7.88 (br s, 1H), 7.85 (d, J = 8.40 Hz, 2H), 7.59 (d, J = 8.40 Hz, 2H), 7.36 (m, 1H), 7.12 (m, 1H), 6.09 (s, 1H), 2.73 (d. J = 4.0 Hz, 3H) |
| 50 | 3-(1-(5-chloro-4-(6-(trifluoromethyl)pyridin-3 yl)oxazol-2-yl)ethoxy)-2,6-difluorobenzamide | 447.99 | $^1$H NMR (DMSO-d6) δ and 9.19 (s, 1H), 8.47 (d, J = 8.0 Hz, 1H), 8.13 (br s, 1H), 8.04 (d, J = 8.40 Hz, 1H), 7.86 (br s, 1H), 7.40 (m, 1H), 7.10 (m, 1H), 5.70 (q, J = 6.40 Hz, 1H), 1.75 (d, J = 6.40 Hz, 3H) |
| 51 | 3-(1-(5-chloro-4-(4-(trifluoromethyl)phenyl)oxazol-2-yl)-2-(methylamino)-2-oxoethoxy)-2,6-difluorobenzamide | 490.16 | $^1$H NMR (DMSO-d6) δ 8.59 (br d, J = 5.20 Hz, 1H), 8.14 (br s, 1H), 8.06 (d, J = 8.0 Hz, 2H), 7.89 (m, 3H), 7.35 (m, 1H), 7.12 (m, 1H), 6.12 (s, 1H), 2.74 (d. J = 4.8 Hz, 3H) |
| 52 | 2-(3-carbamoyl-2,4-difluorophenoxy)-2-(5-chloro-4-(4-(trifluoromethyl)phenyl)oxazol-2-yl)ethyl carbamate | 506.06 | $^1$H NMR (DMSO-d6) δ 8.15 (br s, 1H, D$_2$O exchangeable), 8.07 (d, J = 8.40 Hz, 2H), 7.89 (m, 3H, 1H D$_2$O exchangeable), 7.40 (m, 1H), 7.09 (m, 1H), 6.70 (br s, 1H, D$_2$O exchangeable), 6.63 (br s, 1H, D$_2$O exchangeable), 5.78 (t, J = 5.20 Hz, 1H), 4.55 (m, 2H) |

TABLE 1-continued

Characterisation of compounds by LCMS and $^1$H NMR

| Cpd No | Name | LCMS m/z = [M + H]+ | $^1$H NMR |
|---|---|---|---|
| 53 | 2-(3-carbamoyl-2,4-difluorophenoxy)-2-(5-chloro-4-(4-chlorophenyl)oxazol-2-yl)acetic acid | 443.16 | $^1$H NMR (DMSO-d6) δ 8.13 (br s, 1H), 7.88 (d, J = 8.40 Hz, 2H), 7.79 (br s, 1H), 7.58 (d, J = 8.40 Hz, 2H), 7.14 (m, 1H), 7.01 (m, 1H), 5.38 (s, 1H) |
| 54 | 3-(1-(5-bromo-4-(5-(trifluoromethyl)pyridin-2-yl)oxazol-2-yl)ethoxy)-2,6-difluorobenzamide | 492.08 | $^1$H NMR (MeOH-d4) δ 8.92 (s, 1H), 8.18 (m, 2H), 7.30 (m, 1H), 6.98 (m, 1H), 5.54 (q, J = 6.80 Hz, 1H), 1.81 (d, J = 6.80 Hz, 3H) |
| 55 | 3-(1-(5-chloro-4-(2-(trifluoromethyl)pyrimidin-5-yl)oxazol-2-yl)ethoxy)-2,6-difluorobenzamide | 449.11 | $^1$H NMR (DMSO-d6) δ 9.42 (s, 2H), 8.15 (br s, 1H), 7.88 (br s, 1H), 7.41 (m, 1H), 7.11 (m, 1H), 5.75 (m, 1H), 1.75 (d, J = 6.80 Hz, 3H) |
| 56 | 2-(3-carbamoyl-2,4-difluorophenoxy)-2-(5-chloro-4-(4-(trifluoromethyl)phenyl)oxazol-2-yl)ethyl ethyl succinate | 591.1 | $^1$H NMR (MeOH-d4) δ 8.10 (d, J = 8.40 Hz, 2H), 7.78 (d, J = 8.40 Hz, 2H), 7.36 (m, 1H), 7.02 (m, 1H), 5.66 (t, J = 5.60 Hz, 1H), 4.75 (m, 2H), 4.07 (q, J = 7.20 Hz, 2H), 2.62 (m, 2H), 2.59 (m, 2H), 1.21 (t, J = 7.20 Hz, 3H) |
| 57 | 2-(5-bromo-4-(4-(trifluoromethyl)phenyl)oxazol-2-yl)-2-(3-carbamoyl-2,4-difluorophenoxy)ethyl 2-(dimethylamino)acetate | 592.12 | $^1$H NMR (DMSO-d6) δ 8.16 (br s, 1H), .11 (d, J = 8.0 Hz, 2H), 7.90 (m, 3H), 7.40 (m, 1H), 7.13 (m, 1H), 5.94 (m, 1H), 4.85 (d, J = 4.40 Hz, 2H), 4.25 (s, 2H), 2.81 (s, 6H) |
| 58 | 2-(3-carbamoyl-2,4-difluorophenoxy)-2-(5-chloro-4-(4-chlorophenyl)oxazol-2-yl)ethyl 2-((tert-butoxycarbonyl)(methyl)amino)acetate | 598.43 | $^1$H NMR (DMSO-d6) δ 8.14 (br s, 1H), 7.84-7.87 (m, 3H), 7.59 (d, J = 8.40 Hz, 2H), 7.39 (m, 1H), 7.11 (m, 1H), 5.84 (m, 1H), 4.72 (m, 2H), 4.25 (s, 2H), 3.35 (s, 3H), 1.27 (s, 9H) |
| 59 | 2-(3-carbamoyl-2,4-difluorophenoxy)-2-(5-chloro-4-(4-chlorophenyl)oxazol-2-yl)ethyl 2-(methylamino)acetate | 500.14 | $^1$H NMR (DMSO-d6) δ 9.08 (br s, 2H), 8.15 (br s, 1H), 7.85-7.89 (m, 3H), 7.60 (d, J = 8.40 Hz, 2H), 7.40 (m, 1H), 7.13 (m, 1H), 5.87 (t, J = 4.40 Hz, 1H), 5.59 (m, 1H), 4.84 (d, J = 4.80 Hz, 2H), 4.05 (s, 2H), 2.58 (s, 3H) |
| 60 | 2-(5-bromo-4-(4-(trifluoromethyl)phenyl)oxazol-2-yl)-2-(3-carbamoyl-2,4-difluorophenoxy)ethyl 2-(1,3-dioxoisoindolin-2-yl)acetate | 694.17 | $^1$H NMR (DMSO-d6) δ 8.13 (br s, 1H), 8.06 (d, J = 8.0 Hz, 2H), 7.80-7.88 (m, 7H), 7.35 (m, 1H), 7.10 (m, 1H), 5.86 (t, J = 5.60 Hz, 1H), 4.77 (d, J = 4.80 Hz, 2H), 4.47 (s, 2H) |
| 61 | 2-(5-bromo-4-(4-(trifluoromethyl)phenyl)oxazol-2-yl)-2-(3-carbamoyl-2,4-difluorophenoxy)ethyl 2-((tert-butoxycarbonyl)(methyl)amino)acetate | 678.13 | $^1$H NMR (DMSO-d6) δ 8.15 (br s, 1H), 8.10 (m, 2H), 7.87-7.89 (m, 3H), 7.38 (m, 1H), 7.11 (m, 1H), 5.87 (m, 1H), 4.74 (m, 2H), 3.99 (m, 2H), 3.33 (s, 3H), 1.27 (s, 9H) |
| 62 | 2-(5-bromo-4-(4-(trifluoromethyl)phenyl)oxazol-2-yl)-2-(3-carbamoyl-2,4-difluorophenoxy)ethyl 2-(methylamino)acetate | 578.13 | $^1$H NMR (DMSO-d6) δ 9.14 (br s, 2H), 8.16 (br s, 1H), 8.11 (d, J = 8.40 Hz, 2H), 7.88-7.94 (m, 3H), 7.40 (m, 1H), 7.13 (m, 1H), 5.91 (t, J = 5.20 Hz, 1H), 5.59 (m, 1H), 4.84 (d, J = 4.80 Hz, 2H), 4.04 (s, 2H), 2.57 (s, 3H) |
| 63 | 2-(5-allyl-4-(4-(trifluoromethyl)phenyl)oxazol-2-yl)-2-(3-carbamoyl-2,4-difluorophenoxy)ethyl acetate | 511.16 | $^1$H NMR (DMSO-d6) δ 8.14 (br s, 1H), 7.80-7.90 (m, 5H), 7.35 (m, 1H), 7.09 (m, 1H), 5.90-6.0 (m, 1H), 5.76 (m, 1H), 5.05-5.15 (m, 2H), 4.58-4.72 (m, 2H), 3.76 (d, J = 5.60 Hz, 2H), 2.05 (s, 3H) |
| 64 | 2-(5-bromo-4-(4-(trifluoromethyl)phenyl)oxazol-2-yl)-2-(3-carbamoyl-2,4-difluorophenoxy)ethyl 3-(1,3-dioxoisoindolin-2-yl)propanoate | 708.1 | $^1$H NMR (DMSO-d6) δ 8.13 (br s, 1H), 8.06 (d, J = 8.0 Hz, 2H), 7.86-7.88 (m, 3H), 7.78-7.83 (m, 4H), 7.33 (m, 1H), 7.09 (m, 1H), 5.82 (t, J = 5.20 Hz, 1H), 4.66 (d, J = 5.20 Hz, 2H), 3.78 (t, J = 7.20 Hz, 2H), 2.74 (t, J = 7.20 Hz, 2H) |

TABLE 1-continued

Characterisation of compounds by LCMS and $^1$H NMR

| Cpd No | Name | LCMS m/z = [M + H]+ | $^1$H NMR |
|---|---|---|---|
| 65 | 2-(3-carbamoyl-2,4-difluorophenoxy)-2-(5-propyl-4-(4-(trifluoromethyl)phenyl)oxazol-2-yl)ethyl acetate | 513.18 | $^1$H NMR (DMSO-d6) δ 8.14 (br s, 1H), 7.79-7.87 (m, 5H), 7.35 (m, 1H), 7.10 (m, 1H), 5.75-5.78 (m, 1H), 4.67-4.71 (m, 1H), 4.59-4.63 (m, 1H), 2.93 (t, J = 7.60 Hz, 2H), 2.03 (s, 3H), 1.64-1.69 (m, 2H), 0.89 (t, J = 7.20 Hz, 3H) |
| 66 | 3-(1-(5-allyl-4-(4-(trifluoromethyl)phenyl)oxazol-2-yl)-2-hydroxyethoxy)-2,6-difluorobenzamide | 469.38 | $^1$H NMR (DMSO-d6) δ 8.13 (br s, 1H), 7.79-7.85 (m, 5H), 7.33 (m, 1H), 7.06 (m, 1H), 5.94 (m, 1H), 5.45 (t, J = 6.0 Hz, 1H), 5.38 (br s, 1H), 5.04-5.16 (m, 2H), 4.00 (br s, 2H), 3.74 (d, J = 6.0 Hz, 2H) |
| 67 | 2,6-difluoro-3-(2-hydroxy-1-(5-propyl-4-(4-(trifluoromethyl)phenyl)oxazol-2-yl)ethoxy)benzamide | 471.15 | $^1$H NMR (DMSO-d6) δ 8.11 (br s, 1H), 7.85 (m, 3H), 7.80 (d, J = 8.4 Hz, 2H), 7.33 (m, 1H), 7.06 (m, 1H), 5.43 (t, J = 6.0 Hz, 1H), 5.36 (t, J = 5.6 Hz, 1H), 4.01 (m, 2H), 2.92 (t, J = 7.2 Hz, 2H), 1.67 (m, 2H), 0.89 (t, J = 7.20 Hz, 3H) |
| 68 | 2-(5-bromo-4-(4-(trifluoromethyl)phenyl)oxazol-2-yl)-2-(3-carbamoyl-2,4-difluorophenoxy)ethyl 2-(1H-pyrrol-1-yl)acetate | 614.01 | $^1$H NMR (DMSO-d6) δ 8.16 (br s, 1H), 8.09 (d, J = 8.0 Hz, 2H), 7.88-7.90 (m, 3H), 7.37 (m, 1H), 7.12 (m, 1H), 6.67 (m, 2H), 5.96 (m, 2H), 5.86 (t, J = 5.60 Hz, 1H), 4.91 (s, 2H), 4.75 (m, 2H) |
| 69 | 2-(5-bromo-4-(4-(trifluoromethyl)phenyl)oxazol-2-yl)-2-(3-carbamoyl-2,4-difluorophenoxy)ethyl 4-(1,3-dioxoisoindolin-2-yl)butanoate | 722.04 | $^1$H NMR (DMSO-d6 + D$_2$O) δ 8.05 (d, J = 8.0 Hz, 2H), 7.79-7.82 (m, 6H), 7.35 (m, 1H), 7.07 (m, 1H), 5.78 (t, J = 5.60 Hz, 1H), 4.61 (m, 2H), 3.52 (t, J = 6.80 Hz, 2H), 2.37 (t, J = 7.20 Hz, 2H), 1.79 (m, 2H) |
| 70 | allyl (2-(5-bromo-4-(4-(trifluoromethyl)phenyl)oxazol-2-yl)-2-(3-carbamoyl-2,4-difluorophenoxy)ethyl) succinate | 647.02 | $^1$H NMR (DMSO-d6) δ 8.14 (br s, 1H), 8.11 (d, J = 8.0 Hz, 2H), 7.87-7.89 (m, 3H), 7.39 (m, 1H), 7.11 (m, 1H), 5.87 (m, 2H), 5.18-5.28 (m, 2H), 4.68 (m, 2H), 4.49 (m, 2H), 2.59 (br s, 4H) |
| 71 | diallyl (2-(5-bromo-4-(4-(trifluoromethyl)phenyl)oxazol-2-yl)-2-(3-carbamoyl-2,4-difluorophenoxy)ethyl) phosphate | 667.31 | $^1$H NMR (DMSO-d6) δ 8.15 (br s, 1H), 8.10 (d, J = 8.40 Hz, 2H), 7.88-7.90 (m, 3H), 7.40 (m, 1H), 7.12 (m, 1H), 5.86-5.96 (m, 3H), 5.28 (m, 2H), 5.20 (m, 2H), 4.59 (m, 2H), 4.47-4.52 (m, 4H) |
| 72 | 3-(5-bromo-4-(4-(trifluoromethyl)phenyl)oxazol-2-yl)-3-(3-carbamoyl-2,4-difluorophenoxy)propyl acetate | 563.02 | $^1$H NMR (DMSO-d6) δ 8.15 (br s, 1H), 8.09 (d, J = 8.0 Hz, 2H), 7.87-7.89 (m, 3H), 7.34 (m, 1H), 7.10 (m, 1H), 5.67 (t, J = 6.0 Hz, 1H), 4.25 (m, 2H), 2.45 (m, 2H), 1.91 (s, 3H) |
| 73 | 3-(1-(5-bromo-4-(4-(trifluoromethyl)phenyl)oxazol-2-yl)-3-hydroxypropoxy)-2,6-difluorobenzamide | 521.02 | $^1$H NMR (DMSO-d6) δ 8.13 (br s, 1H), 8.10 (d, J = 8.40 Hz, 2H), 7.89 (d, J = 8.40 Hz, 2H), 7.85 (br s, 1H), 7.34 (m, 1H), 7.11 (m, 1H), 5.60 (t, J = 6.0 Hz, 1H), 4.76 (t, J = 5.20 Hz, 1H), 3.60 (m, 2H), 2.28 (m, 2H) |
| 74 | 4-(2-(5-bromo-4-(4-(trifluoromethyl)phenyl)oxazol-2-yl)-2-(3-carbamoyl-2,4-difluorophenoxy)ethoxy)-4-oxobutanoic acid | 607.2 | $^1$H NMR (DMSO-d6 + D$_2$O) δ 8.08 (d, J = 8.0 Hz, 2H), 7.86 (d, J = 8.40 Hz, 2H), 7.37-7.38 (m, 1H), 7.05-7.10 (m, 1H), 5.76 (t, J = 5.60 Hz, 1H), 4.63 (m, 2H), 3.25 (m, 1H), 3.0 (m, 2H), 2.41 (t, J = 6.40 Hz, 2H), 2.25 (m, 2H), 1.64 (m, 2H), 1.54 (m, 2H) |
| 75 | allyl (2-(5-bromo-4-(4-(trifluoromethyl)phenyl)oxazol-2-yl)-2-(3-carbamoyl-2,4-difluorophenoxy)ethyl) hydrogen phosphate | 625.12 | $^1$H NMR (DMSO-d6) δ 8.22 (br s, 1H), 8.11 (d, J = 8.0 Hz, 2H), 7.86 (d, J = 8.0 Hz, 2H), 7.82 (br s, 1H), 7.44 (m, 1H), 7.08 (m, 1H), 5.88 (m, 1H), 5.82 (t, J = 6.0 Hz, 1H), 5.18 (d, J = 17.60 Hz, 1H), 5.01 (d, J = 10.80 Hz, 1H), 4.18 (br s, 2H), 4.08 (br s, 2H) |

TABLE 1-continued

Characterisation of compounds by LCMS and $^1$H NMR

| Cpd No | Name | LCMS m/z = [M + H]+ | $^1$H NMR |
|---|---|---|---|
| 76 | 2-(5-bromo-4-(4-cyanophenyl)oxazol-2-yl)-2-(3-carbamoyl-2,4-difluorophenoxy)ethyl acetate | 506.07 | $^1$H NMR (DMSO-d6) δ 8.15 (br s, 1H), 8.05 (d, J = 8.40 Hz, 2H), 7.97 (d, J = 8.40 Hz, 2H), 7.88 (br s, 1H), 7.39 (m, 1H), 7.11 (m, 1H), 5.85 (t, J = 6.40 Hz, 1H), 4.65 (m, 2H), 2.03 (s, 3H) |
| 77 | 3-(5-bromo-4-(4-(trifluoromethyl)phenyl)oxazol-2-yl)-3-(3-carbamoyl-2,4-difluorophenoxy)propanoic acid | 535.09 | $^1$H NMR (DMSO-d6) δ 8.14 (br s, 1H), 8.09 (d, J = 8.40 Hz, 2H), 7.88 (d, J = 8.40 Hz, 2H), 7.85 (br s, 1H), 7.45 (m, 1H), 7.11 (m, 1H), 5.77 (t, J = 6.40 Hz, 1H), 3.16 (m, 1H), 3.04 (m, 1H) |
| 78 | 2-(5-bromo-4-(5-(trifluoromethyl)pyridin-2-yl)oxazol-2-yl)-2-(3-carbamoyl-2,4-difluorophenoxy)ethyl acetate | 550.1 | $^1$H NMR (DMSO-d6) δ and 9.06 (br s, 1H), 8.32 (d, J = 6.40 Hz, 1H), 8.15 (s, 1H), 8.10 (d, J = 8.80 Hz, 1H), 7.88 (br s, 1H), 7.42 (m, 1H), 7.13 (m, 1H), 5.85 (m, 1H), 4.65 (m, 2H), 2.04 (s, 3H) |
| 79 | 3-(1-(5-bromo-4-(5-(trifluoromethyl)pyridin-2-yl)oxazol-2-yl)-2-hydroxyethoxy)-2,6-difluorobenzamide | 508.01 | $^1$H NMR (MeOH-d4) δ 8.92 (s, 1H), 8.18 (m, 2H), 7.32 (m, 1H), 6.98 (m, 1H), 5.44 (t, J = 6.0 Hz, 1H), 4.17 (m, 2H) |
| 80 | 3-(1-(5-bromo-4-(4-cyanophenyl)oxazol-2-yl)-2-hydroxyethoxy)-2,6-difluorobenzamide | 464.05 | $^1$H NMR (DMSO-d6) δ 8.14 (br s, 1H), 8.06 (d, J = 8.0 Hz, 2H), 7.98 (d, J = 8.0 Hz, 2H), 7.86 (br s, 1H), 7.35 (m, 1H), 7.08 (m, 1H), 5.52 (t, J = 5.60 Hz, 1H), 5.43 (t, J = 5.60 Hz, 1H), 4.01 (t, J = 5.60 Hz, 2H) |
| 81 | 2-(5-bromo-4-(4-(trifluoromethyl)phenyl)oxazol-2-yl)-2-(3-carbamoyl-2,4-difluorophenoxy)ethyl dihydrogen phosphate | 584.96 | $^1$H NMR (DMSO-d6) δ 8.26 (br s, 1H, D$_2$O exchangeable), 8.11 (d, J = 8.0 Hz, 2H), 7.88 (d, J = 8.0 Hz, 2H), 7.83 (br s, 1H, D$_2$O exchangeable), 7.48 (m, 1H), 7.10 (m, 1H), 5.76 (m, 1H), 4.20 (m, 2H) |
| 82 | 2-(5-bromo-4-(4-(5-methyl-1,2,4-oxadiazol-3-yl)phenyl)oxazol-2-yl)-2-(3-carbamoyl-2,4-difluorophenoxy)ethyl acetate | 563.11 | $^1$H NMR (DMSO-d6) δ 8.16 (br s, 1H), 8.14 (d, J = 8.40 Hz, 2H), 8.06 (d, J = 8.40 Hz, 2H), 7.89 (br s, 1H), 7.39 (m, 1H), 7.12 (m, 1H), 5.85 (t, J = 6.40 Hz, 1H), 4.63-4.72 (m, 2H), 2.68 (s, 3H), 2.04 (s, 3H) |
| 83 | 3-(1-(5-bromo-4-(4-(5-methyl-1,2,4-oxadiazol-3-yl)phenyl)oxazol-2-yl)-2-hydroxyethoxy)-2,6-difluorobenzamide | 521.06 | $^1$H NMR (DMSO-d6) δ 8.15 (br s, 1H), 8.13 (d, J = 8.40 Hz, 2H), 8.08 (d, J = 8.40 Hz, 2H), 7.87 (br s, 1H), 7.34 (m, 1H), 7.11 (m, 1H), 5.52 (t, J = 5.60 Hz, 1H), 5.45 (t, J = 5.60 Hz, 2H), 4.03 (m, 2H), 2.68 (s, 3H) |
| 84 | ethyl 2-(2-(5-bromo-4-(4-(trifluoromethyl)phenyl)oxazol-2-yl)-2-(3-carbamoyl-2,4-difluorophenoxy)ethoxy)acetate | 593 | $^1$H NMR (DMSO-d6) δ 8.15 (br s, 1H), 8.10 (d, J = 8.40 Hz, 2H), 7.89 (m, 3H), 7.42 (m, 1H), 7.10 (m, 1H), 5.82 (t, J = 5.60 Hz, 1H), 4.28 (s, 2H), 4.18 (d, J = 5.60 Hz, 2H), 4.08 (m, 2H), 1.18 (t, J = 7.20 Hz, 3H) |
| 85 | 3-(1-(5-bromo-4-(4-(3-methyl-1,2,4-oxadiazol-5-yl)phenyl)oxazol-2-yl)-2-hydroxyethoxy)-2,6-difluorobenzamide | 521.17 | $^1$H NMR (DMSO-d6) δ 8.23 (d, J = 8.80 Hz, 2H), 8.15 (br s, 1H), 8.14 (d, J = 8.80 Hz, 2H), 7.90 (br s, 1H), 7.36 (m, 1H), 7.08 (m, 1H), 5.53 (t, J = 5.60 Hz, 1H), 5.45 (t, J = 5.60 Hz, 1H), 4.02 (m, 2H), 2.43 (s, 3H) |
| 86 | 2-(2-(5-bromo-4-(4-(trifluoromethyl)phenyl)oxazol-2-yl)-2-(3-carbamoyl-2,4-difluorophenoxy)ethoxy)acetic acid | 564.95 | $^1$H NMR (DMSO-d6) δ 8.17 (br s, 1H), 8.09 (d, J = 7.60 Hz, 2H), 7.88 (m, 3H), 7.43 (m, 1H), 7.10 (m, 1H), 5.83 (m, 1H), 4.14 (m, 2H), 3.83 (s, 2H) |
| 87 | 3-(1-(5-bromo-4-(4-(trifluoromethyl)phenyl)oxazol-2-yl)-3-(methylamino)-3-oxopropoxy)-2,6-difluorobenzamide | 548.08 | $^1$H NMR (DMSO-d6) δ 8.13 (br s, 2H), 8.09 (d, J = 8.0 Hz, 2H), 7.89 (d, J = 8.40 Hz, 2H), 7.85 (br s, 1H), 7.43 (m, 1H), 7.13 (m, 1H), 5.81 (m, 1H), 3.04 (m, 2H), 2.60 (d, J = 4.80 Hz, 3H) |

TABLE 1-continued

Characterisation of compounds by LCMS and $^1$H NMR

| Cpd No | Name | LCMS m/z = [M + H]+ | $^1$H NMR |
|---|---|---|---|
| 88 | 3-(1-(5-bromo-4-(4-(trifluoromethyl)phenyl)oxazol-2-yl)-3-(dimethylamino)-3-oxopropoxy)-2,6-difluorobenzamide | 562.06 | $^1$H NMR (DMSO-d6) δ 8.13 (br s, 1H), 8.09 (d, J = 8.0 Hz, 2H), 7.89 (d, J = 7.60 Hz, 2H), 7.85 (br s, 1H), 7.46 (m, 1H), 7.13 (m, 1H), 5.82 (m, 1H), 3.33 (m, 2H), 3.04 (s, 3H), 2.82 (s, 3H) |
| 89 | 4-(5-bromo-4-(4-(trifluoromethyl)phenyl)oxazol-2-yl)-4-(3-carbamoyl-2,4-difluorophenoxy)butyl acetate | 577.1 | $^1$H NMR (DMSO-d6) δ 8.14 (br s, 1H), 8.09 (d, J = 8.40 Hz, 2H), 7.89 (m, 3H), 7.35 (m, 1H), 7.11 (m, 1H), 5.62 (t, J = 6.0 Hz, 1H), 4.08 (t, J = 6.40 Hz, 2H), 2.10-2.25 (m, 2H), 1.99 (s, 3H), 1.70-1.88 (m, 2H) |
| 90 | 3-(1-(5-bromo-4-(4-(trifluoromethyl)phenyl)oxazol-2-yl)-4-hydroxybutoxy)-2,6-difluorobenzamide | 535.07 | $^1$H NMR (DMSO-d6) δ 8.13 (br s, 1H), 8.10 (d, J = 8.40 Hz, 2H), 7.88 (d, J = 8.40 Hz, 2H), 7.85 (br s, 1H), 7.35 (m, 1H), 7.10 (m, 1H), 5.59 (t, J = 6.40 Hz, 1H), 4.53 (t, J = 5.20 Hz, 1H), 3.47 (q, J = 5.60 Hz, 2H), 2.07-2.18 (m, 2H), 1.51-1.69 (m, 2H) |
| 91 | 4-(5-bromo-4-(4-(trifluoromethyl)phenyl)oxazol-2-yl)-4-(3-carbamoyl-2,4-difluorophenoxy)butanoic acid | 547 | $^1$H NMR (DMSO-d6) δ 8.16 (br s, 1H), 8.10 (d, J = 8.0 Hz, 2H), 7.88 (m, 3H), 7.37 (m, 1H), 7.10 (m, 1H), 5.61 (t, J = 6.40 Hz, 1H), 2.33 (m, 2H), 2.26 (m, 2H) |
| 92 | 3-(4-(2-acetylhydrazinyl)-1-(5-bromo-4-(4-(trifluoromethyl)phenyl)oxazol-2-yl)-4-oxobutoxy)-2,6-difluorobenzamide | 603.09 | $^1$H NMR (DMSO-d6) δ 9.78 (br s, 2H), 8.13 (br s, 1H), 8.10 (d, J = 8.40 Hz, 2H), 7.86-7.89 (m, 3H), 7.35 (m, 1H), 7.09 (m, 1H), 5.60 (t, J = 6.0 Hz, 1H), 2.41 (m, 2H), 2.35 (m, 2H), 1.84 (s, 3H) |
| 93 | 3-(1-(5-bromo-4-(4-(trifluoromethyl)phenyl)oxazol-2-yl)-4-(methylamino)-4-oxobutoxy)-2,6-difluorobenzamide | 562.08 | $^1$H NMR (DMSO-d6) δ 8.13 (br s, 1H, D$_2$O exchangeable), 8.10 (d, J = 8.0 Hz, 2H), 7.89 (d, J = 8.40 Hz, 2H), 7.85 (br s, 1H, D$_2$O exchangeable), 7.81 (m, 1H, D$_2$O exchangeable), 7.35 (m, 1H), 7.11 (m, 1H), 5.58 (m, 1H), 2.54 (d, J = 4.40 Hz, 3H), 2.32 (m, 4H) |
| 94 | 3-(1-(5-bromo-4-(4-(trifluoromethyl)phenyl)oxazol-2-yl)-4-(dimethylamino)-4-oxobutoxy)-2,6-difluorobenzamide | 576.1 | $^1$H NMR (DMSO-d6) δ 8.13 (br s, 1H, D$_2$O exchangeable), 8.10 (d, J = 8.0 Hz, 2H), 7.89 (d, J = 8.40 Hz, 2H), 7.85 (br s, 1H, D$_2$O exchangeable), 7.35 (m, 1H), 7.11 (m, 1H), 5.60 (t, J = 6.80 Hz, 1H), 2.93 (s, 3H), 2.79 (s, 3H), 2.54 (m, 2H), 2.34 (m, 2H) |
| 95 | 3-(3-amino-1-(5-bromo-4-(4-(trifluoromethyl)phenyl)oxazol-2-yl)propoxy)-2,6-difluorobenzamide | 520.12 | $^1$H NMR (DMSO-d6) δ 8.13 (br s, 1H), 8.10 (d, J = 8.40 Hz, 2H), 7.88-7.90 (m, 3H), 7.32 (m, 1H), 7.11 (m, 1H), 5.71 (t, J = 5.60 Hz, 1H), 2.99 (m, 2H), 2.38 (m, 2H) |
| 96 | 3-(3-amino-1-(5-bromo-4-(4-(trifluoromethyl)phenyl)oxazol-2-yl)-3-oxopropoxy)-2,6-difluorobenzamide | 534.04 | $^1$H NMR (DMSO-d6) δ 8.13 (br s, 1H), 8.09 (d, J = 8.0 Hz, 2H), 7.87-7.89 (m, 3H), 7.84 (br s, 1H), 7.65 (br s, 1H), 7.43 (m, 1H), 7.11 (m, 1H), 5.80 (m, 1H), 3.05 (m, 2H) |
| 97 | 3-(1-(5-bromo-4-(4-(trifluoromethyl)phenyl)oxazol-2-yl)-3-(5-methyl-1,3,4-oxadiazol-2-yl)propoxy)-2,6-difluorobenzamide | 587.05 | $^1$H NMR (DMSO-d6) δ 8.14 (br s, 1H), 8.08 (d, J = 8.0 Hz, 2H), 7.87-7.89 (m, 3H), 7.33 (m, 1H), 7.10 (m, 1H), 5.71 (t, J = 6.40 Hz, 1H), 3.11 (m, 2H), 2.56 (m, 2H), 2.40 (s, 3H) |
| 98 | 3-(1-(5-bromo-4-(4-(trifluoromethyl)phenyl)oxazol-2-yl)-3-(dimethylamino)propoxy)-2,6-difluorobenzamide | 548.12 | $^1$H NMR (DMSO-d6) δ 8.14 (br s, 1H, D$_2$O exchangeable), 8.10 (d, J = 8.0 Hz, 2H), 7.87-7.89 (m, 3H, 1H D$_2$O exchangeable), 7.32 (m, 1H), 7.09 (m, 1H), 5.56 (t, J = 6.40 Hz, 1H), 2.36 (m, 2H), 2.23 (m, 2H), 2.11 (s, 6H) |

TABLE 1-continued

Characterisation of compounds by LCMS and $^1$H NMR

| Cpd No | Name | LCMS m/z = [M + H]+ | $^1$H NMR |
|---|---|---|---|
| 99 | 3-((5-bromo-4-(4-chlorophenyl)oxazol-2-yl)(pyridin-3-yl)methoxy)-2,6-difluorobenzamide | 520.05 | $^1$H NMR (DMSO-d6) δ 8.82 (s, 1H), 8.64 (m, 1H), 8.14 (m, 1H), 8.03-8.05 (m, 1H), 7.81-7.86 (m, 3H), 7.58 (d, J = 8.80 Hz, 2H), 7.52 (m, 1H), 7.42 (m, 1H), 7.12 (m, 1H), 6.93 (s, 1H) |
| 100 | 3-(3-(2-acetylhydrazinyl)-1-(5-bromo-4-(trifluoromethyl)phenyl)oxazol-2-yl)-3-oxopropoxy)-2,6-difluorobenzamide | 590.94 | $^1$H NMR (DMSO-d6) δ 10.11 (br s, 1H), 9.87 (br s, 1H), 8.07-8.16 (m, 3H), 7.84-7.91 (m, 3H), 7.43 (m, 1H), 7.11 (m, 1H), 5.82 (t, J = 6.0 Hz, 1H), 3.08-3.20 (m, 2H), 1.83 (s, 3H) |
| 101 | 3-(4-amino-1-(5-bromo-4-(trifluoromethyl)phenyl)oxazol-2-yl)-4-oxobutoxy)-2,6-difluorobenzamide | 547.95 | $^1$H NMR (DMSO-d6) δ 8.15 (br s, 1H, D$_2$O exchangeable), 8.10 (d, J = 8.0 Hz, 2H), 7.87 (d, J = 8.40 Hz, 2H), 7.85 (br s, 1H, D$_2$O exchangeable), 7.37 (br s, 1H, D$_2$O exchangeable), 7.30 (m, 1H), 7.09 (m, 1H), 6.85 (br s, 1H, D$_2$O exchangeable), 5.57 (m, 1H), 2.31 (m, 4H) |
| 102 | 3-((1-(5-bromo-4-(trifluoromethyl)phenyl)oxazol-2-yl)allyl)oxy)-2,6-difluorobenzamide | 503.06 | $^1$H NMR (DMSO-d6) δ 8.11-8.13 (m, 3H), 7.87-7.89 (m, 3H), 7.30 (m, 1H), 7.09 (m, 1H), 6.89-6.95 (dt, J = 5.20 and 16.0 Hz respectively, 1H), 6.71 (d, J = 16.0 Hz, 1H), 4.95 (d, J = 4.80 Hz, 2H) |
| 103 | 3-(1-(5-bromo-4-(trifluoromethyl)phenyl)oxazol-2-yl)-2-methoxyethoxy)-2,6-difluorobenzamide | 520.94 | $^1$H NMR (DMSO-d6) δ 8.15 (br s, 1H), 8.09 (d, J = 8.0 Hz, 2H), 7.87-7.89 (m, 3H), 7.37 (m, 1H), 7.09 (m, 1H), 5.80 (t, J = 6.0 Hz, 1H), 4.0 (m, 2H), 3.36 (s, 3H) |
| 104 | 3-((1-(5-bromo-4-(4-chlorophenyl)oxazol-2-yl)but-3-en-1-yl)oxy)-2,6-difluorobenzamide | 482.9 | $^1$H NMR (DMSO-d6) δ 8.13 (br s, 1H), 7.89 (d, J = 8.80 Hz, 2H), 7.85 (br s, 1H), 7.56 (d, J = 8.40 Hz, 2H), 7.33 (m, 1H), 7.08 (m, 1H), 5.85 (m, 1H), 5.63 (t, J = 6.40 Hz, 1H), 5.12-5.23 (m, 2H), 2.88 (m, 2H) |
| 105 | 3-(1-(5-bromo-4-(trifluoromethyl)phenyl)oxazol-2-yl)-2-((tetrahydro-2H-pyran-2-yl)oxy)ethoxy)-2,6-difluorobenzamide | 590.89 | $^1$H NMR (DMSO-d6) δ 8.15 (br s, 1H), 8.10 (d, J = 8.40 Hz, 2H), 7.87-7.89 (m, 3H), 7.40 (m, 1H), 7.10 (m, 1H), 5.81 (m, 1H), 4.75 (m, 1H), 4.20 (m, 1H), 4.06 (m, 1H), 3.69 (t, J = 8.0 Hz, 1H), 3.45 (m, 1H), 1.58 (m, 2H), 1.45 (m, 4H) |
| 106 | 3-((1-(5-bromo-4-(trifluoromethyl)phenyl)oxazol-2-yl)but-3-en-1-yl)oxy)-2,6-difluorobenzamide | 516.9 | $^1$H NMR (DMSO-d6) δ 8.14 (br s, 1H), 8.09 (d, J = 8.40 Hz, 2H), 7.87-7.89 (m, 3H), 7.36 (m, 1H), 7.09 (m, 1H), 5.85 (m, 1H), 5.66 (t, J = 6.40 Hz, 1H), 5.12-5.24 (m, 2H), 2.90 (m, 2H) |
| 107 | 2-(5-bromo-4-(trifluoromethyl)phenyl)oxazol-2-yl)-2-(3-carbamoyl-2,4-difluorophenoxy)ethyl dimethylcarbamate | 578.01 | $^1$H NMR (DMSO-d6) δ 8.16 (br s, 1H), 8.10 (d, J = 8.0 Hz, 2H), 7.88-7.90 (m, 3H), 7.37 (m, 1H), 7.11 (m, 1H), 5.84 (t, J = 5.20 Hz, 1H), 4.60 (d, J = 5.20 Hz, 2H), 2.78-2.80 (m, 6H) |
| 108 | 2-(5-bromo-4-(3-methoxyphenyl)oxazol-2-yl)-2-(3-carbamoyl-2,4-difluorophenoxy)ethyl acetate | 510.97 | $^1$H NMR (DMSO-d6) δ 8.15 (br s, 1H), 7.87 (br s, 1H), 7.34-7.50 (m, 4H), 7.13 (m, 1H), 7.0 (m, 1H), 5.82 (m, 1H), 4.60-4.71 (m, 2H), 3.80 (s, 3H), 2.03 (s, 3H) |
| 109 | 3-(1-(5-bromo-4-(trifluoromethyl)phenyl)oxazol-2-yl)-3,4-dihydroxybutoxy)-2,6-difluorobenzamide (mixture of two diastereomeric pairs of enantiomers)[a] | 551.1 | $^1$H NMR (DMSO-d6) δ 8.14 (br s, 1H, D$_2$O exchangeable), 8.08-8.10 (m, 2H), 7.89 (d, J = 8.40 Hz, 2H), 7.85 (br s, 1H, D$_2$O exchangeable), 7.35 (m, 1H), 7.09 (m, 1H), 5.60 (m, 1H), 4.85 (m, 1H, D$_2$O exchangeable), 4.69 (m, 1H, br s, D$_2$O exchangeable), 3.50 (m, 1H), 3.28-3.41 (m, 2H), 2.34 (m, 1H), 1.92-2.16 (m, 1H) |

TABLE 1-continued

Characterisation of compounds by LCMS and $^1$H NMR

| Cpd No | Name | LCMS m/z = [M + H]+ | $^1$H NMR |
|---|---|---|---|
| 110 | 3-(1-(5-bromo-4-(4-hydroxyphenyl)oxazol-2-yl)-2-hydroxyethoxy)-2,6-difluorobenzamide | 455.04 | $^1$H NMR (DMSO-d6) δ 9.80 (s, 1H), 8.15 (br s, 1H), 7.86 (br s, 1H), 7.70 (d, J = 8.40 Hz, 2H), 7.35 (m, 1H), 7.10 (m, 1H), 6.85 (d, J = 8.40 Hz, 2H), 5.46 (t, J = 5.60 Hz, 1H), 5.41 (t, J = 5.60 Hz, 1H), 4.0 (m, 2H) |
| 111 | 2-(5-bromo-4-(4-methoxyphenyl)oxazol-2-yl)-2-(3-carbamoyl-2,4-difluorophenoxy)ethyl acetate | 510.97 | $^1$H NMR (DMSO-d6) δ 8.15 (br s, 1H), 7.87 (br s, 1H), 7.81 (d, J = 8.80 Hz, 2H), 7.35 (m, 1H), 7.11 (m, 1H), 7.05 (d, J = 8.80 Hz, 2H), 5.80 (m, 1H), 4.59-4.70 (m, 2H), 3.79 (s, 3H), 2.03 (s, 3H) |
| 112 | 3-(1-(5-bromo-4-(4-methoxyphenyl)oxazol-2-yl)-2-hydroxyethoxy)-2,6-difluorobenzamide | 468.99 | $^1$H NMR (DMSO-d6) δ 8.13 (br s, 1H), 7.84 (br s, 1H), 7.81 (d, J = 8.40 Hz, 2H), 7.35 (m, 1H), 7.04-7.09 (m, 3H), 5.47 (t, J = 5.60 Hz, 1H), 5.40 (t, J = 5.60 Hz, 1H), 4.0 (t, J = 5.60 Hz, 2H), 3.79 (s, 3H) |
| 113 | 2-(5-bromo-4-(4-(trifluoromethyl)phenyl)oxazol-2-yl)-2-(3-carbamoyl-2,4-difluorophenoxy)ethyl methylcarbamate | 564 | $^1$H NMR (DMSO-d6) δ 8.14 (br s, 1H), 8.10 (d, J = 8.0 Hz, 2H), 7.87-7.89 (m, 3H), 7.36 (m, 1H), 7.25 (m, 1H), 7.10 (m, 1H), 5.80 (t, J = 5.60 Hz, 1H), 4.59 (m, 2H), 2.54 (d, J = 4.40 Hz, 3H) |
| 114 | 3-(1-(5-bromo-4-(4-(trifluoromethyl)phenyl)oxazol-2-yl)-2-(1H-imidazol-1-yl)ethoxy)-2,6-difluorobenzamide | 557.1 | $^1$H NMR (DMSO-d6) δ 8.13 (br s, 1H, D$_2$O exchangeable), 8.09 9d, J = 8.0 Hz, 2H), 7.90 (d, J = 8.40 Hz, 2H), 7.87 (br s, 1H, D$_2$O exchangeable), 7.72 (s, 1H), 7.27 (s, 1H), 7.03-7.14 (m, 2H), 6.89 (s, 1H), 5.94 (t, J = 5.60 Hz, 1H), 4.77 (d, J = 4.80 Hz, 2H) |
| 115 | 2-(5-bromo-4-(4-(trifluoromethoxy)phenyl)oxazol-2-yl)-2-(3-carbamoyl-2,4-difluorophenoxy)ethyl acetate | 564.97 | $^1$H NMR (DMSO-d6) δ 8.15 (br s, 1H), 7.98 (d, J = 8.80 Hz, 2H), 7.88 (br s, 1H), 7.51 (d, J = 8.40 Hz, 2H), 7.35 (m, 1H), 7.11 (m, 1H), 5.83 (t, J = 6.40 Hz, 1H), 4.60-4.70 (m, 2H), 2.03 (s, 3H) |
| 116 | 3-(1-(5-bromo-4-(4-(trifluoromethoxy)phenyl)oxazol-2-yl)-2-hydroxyethoxy)-2,6-difluorobenzamide | 522.95 | $^1$H NMR (DMSO-d6) δ 8.15 (br s, 1H), 7.99 (d, J = 8.80 Hz, 2H), 7.87 (br s, 1H), 7.50 (d, J = 8.40 Hz, 2H), 7.35 (m, 1H), 7.10 (m, 1H), 5.51 (t, J = 6.0 Hz, 1H), 5.43 (t, J = 5.60 Hz, 1H), 4.0 (t, J = 5.60 Hz, 2H) |
| 117 | 3-(1-(5-bromo-4-(3-methoxyphenyl)oxazol-2-yl)-2-hydroxyethoxy)-2,6-difluorobenzamide | 468.94 | $^1$H NMR (DMSO-d6) δ 8.13 (br s, 1H), 7.85 (br s, 1H), 7.39-7.50 (m, 3H), 7.35 (m, 1H), 7.05-7.10 (m, 1H), 6.99-7.01 (m, 1H), 5.50 (t, J = 5.60 Hz, 1H), 5.41 (t, J = 5.60 Hz, 1H), 4.0 (m, 2H), 3.80 (s, 3H) |
| 118 | 3-(1-(5-bromo-4-(3-hydroxyphenyl)oxazol-2-yl)-2-hydroxyethoxy)-2,6-difluorobenzamide | 455 | $^1$H NMR (DMSO-d6) δ 9.66 (s, 1H), 8.14 (br s, 1H), 7.85 (br s, 1H), 7.25-7.52 (m, 4H), 7.10 (m, 1H), 6.80 (m, 1H), 5.50 (t, J = 5.60 Hz, 1H), 5.42 (t, J = 5.60 Hz, 1H), 4.01 (m, 2H) |
| 119 | diethyl 2-(2-(5-bromo-4-(4-(trifluoromethyl)phenyl)oxazol-2-yl)-2-(3-carbamoyl-2,4-difluorophenoxy)ethyl)malonate | 648.88 | $^1$H NMR (DMSO-d6) δ 8.13 (br s, 1H), 8.09 (d, J = 8.40 Hz, 2H), 7.86-7.89 (m, 3H), 7.29 (m, 1H), 7.10 (m, 1H), 5.65 (m, 1H), 4.03-4.13 (m, 4H), 3.84 (t, J = 6.80 Hz, 1H), 2.66 (m, 2H), 1.11-1.16 (m, 6H) |
| 120 | 3-(1-(5-bromo-4-(4-(trifluoromethyl)phenyl)oxazol-2-yl)-2-(5-methyl-1,3,4-oxadiazol-2-yl)ethoxy)-2,6-difluorobenzamide | 573.13 | $^1$H NMR (DMSO-d6) δ 8.13 (br s, 1H), 8.09 (d, J = 7.20 Hz, 2H), 7.90 (d, J = 8.40 Hz, 2H), 7.85 (br s, 1H), 7.40 (m, 1H), 7.11 (m, 1H), 6.0 (m, 1H), 3.81 (d, J = 4.40 Hz, 2H), 2.50 (s, 3H) |

TABLE 1-continued

Characterisation of compounds by LCMS and $^1$H NMR

| Cpd No | Name | LCMS m/z = [M + H]+ | $^1$H NMR |
|---|---|---|---|
| 121 | 2-(5-bromo-4-(1-(3-carbamoyl-2,4-difluorophenoxy)propyl)oxazol-2-yl)ethyl acetate | 446.98 | $^1$H NMR (DMSO-d6) δ 8.09 (br s, 1H), 7.83 (br s, 1H), 6.98-7.08 (m, 2H), 5.02 (t, J = 6.80 Hz, 1H), 4.31 (t, J = 6.40 Hz, 2H), 3.09 (t, J = 6.40 Hz, 2H), 1.89-2.09 (m, 2H), 1.94 (s, 3H), 0.87 (t, J = 7.20 Hz, 3H) |
| 122 | 3-(1-(5-bromo-2-(2-hydroxyethyl)oxazol-4-yl)propoxy)-2,6-difluorobenzamide | 404.91 | $^1$H NMR (DMSO-d6) δ 8.10 (br s, 1H), 7.83 (br s, 1H), 6.98-7.08 (m, 2H), 5.02 (t, J = 7.20 Hz, 1H), 4.85 (t, J = 5.20 Hz, 1H), 3.70 (q, J = 6.0 Hz, 2H), 2.87 (t, J = 6.40 Hz, 2H), 1.98-2.09 (m, 1H), 1.89-1.96 (m, 1H), 0.88 (t, J = 7.20 Hz, 3H) |
| 123 | 3-(1-(4-bromo-5-(4-(trifluoromethyl)phenyl)oxazol-2-yl)ethoxy)-2,6-difluorobenzamide | 490.95 | $^1$H NMR (DMSO-d6) δ 8.23 (br s, 1H), 8.05 (d, J = 8.40 Hz, 2H), 7.94 (d, J = 8.40 Hz, 2H), 7.87 (br s, 1H), 7.40 (m, 1H), 7.11 (m, 1H), 5.72 (m, 1H), 1.76 (d, J = 6.40 Hz, 3H) |
| 124 | 3-((1-(5-bromo-4-(4-(trifluoromethyl)phenyl)oxazol-2-yl)pent-4-en-1-yl)oxy)-2,6-difluorobenzamide | 531.15 | $^1$H NMR (DMSO-d6) δ 8.15 (br s, 1H), 8.07 (d, J = 8.40 Hz, 2H), 7.87 (m, 3H), 7.28-7.34 (m, 1H), 7.08 (m, 1H), 5.80-5.89 (m, 1H), 5.54 (t, J = 5.60 Hz, 1H), 4.98-5.06 (m, 2H), 2.19-2.26 (m, 4H) |
| 125 | ethyl 2-(3-carbamoyl-2,4-difluorophenoxy)-2-(2-(4-(trifluoromethyl)phenyl)thiazol-4-yl)acetate | 487.07 | $^1$H NMR (DMSO-d6) δ 8.15 (m, 3H), 8.08 (s, 1H), 7.88 (m, 3H), 7.28-7.35 (m, 1H), 7.09 (t, J = 8.40 Hz, 1H), 6.34 (s, 1H), 4.19-4.24 (m, 2H), 1.16 (t, J = 7.20 Hz, 3H) |
| 126 | 2,6-difluoro-3-(2-hydroxy-1-(2-(4-(trifluoromethyl)phenyl)thiazol-4-yl)ethoxy)benzamide | 444.97 | $^1$H NMR (DMSO-d6) δ 8.15 (m, 3H), 7.87 (d, J = 8.4 Hz, 2H), 7.84 (s, 2H), 7.25-7.30 (m, 1H), 7.00 (t, J = 9.2 Hz, 1H), 5.53 (t, J = 5.6 Hz, 1H), 5.23 (t, J = 6.0 Hz, 1H), 3.94 (m, 2H) |
| 127 | 2-(3-carbamoyl-2,4-difluorophenoxy)-2-(2-(4-(trifluoromethyl)phenyl)thiazol-4-yl)acetic acid | 458.97 | $^1$H NMR (DMSO-d6) δ 8.15 (d, J = 8.0 Hz, 2H), 8.13 (br s, 1H, D$_2$O exchangeable), 7.86 (d, J = 8.0 Hz, 2H), 7.85 (br s, 1H, D$_2$O exchangeable), 7.81 (s, 1H), 7.16 (m, 1H), 7.01 (m, 1H), 5.75 (s, 1H) |
| 128 | 3-((1-(5-bromo-4-(4-(trifluoromethyl)phenyl)oxazol-2-yl)-4,5-dihydroxypentyl)oxy)-2,6-difluorobenzamide (mixture of two diastereomeric pairs of enantiomers) | 565.32 | $^1$H NMR (DMSO-d6) δ 8.16 (br s, 1H), 8.10 (d, J = 8.40 Hz, 2H), 7.87-7.89 (m, 3H), 7.32 (m, 1H), 7.10 (m, 1H), 5.58 (m, 1H), 4.63 (m, 1H), 4.54 (t, J = 6.0 Hz, 1H), 3.46 (m, 1H), 3.22 (m, 2H), 2.08-2.23 (m, 2H), 1.43-1.70 (m, 2H) |
| 129 | ethyl 2-(3-carbamoyl-2,4-difluorophenoxy)-2-(2-(4-(trifluoromethyl)phenyl)oxazol-4-yl)acetate | 471.04 | $^1$H NMR (DMSO-d6) δ 8.55 (s, 1H), 8.20 (d, J = 8.40 Hz, 2H), 8.16 (br s, 1H), 7.93 (d, J = 8.0 Hz, 2H), 7.87 (br s, 1H), 7.33 (m, 1H), 7.09 (m, 1H), 6.23 (s, 1H), 4.23 (q, J = 7.20 Hz, 2H), 1.17 (t, J = 7.20 Hz, 3H) |
| 130 | 2-(5-bromo-2-(4-(trifluoromethyl)phenyl)thiazol-4-yl)-2-(3-carbamoyl-2,4-difluorophenoxy)ethyl acetate | 564.82 | $^1$H NMR (DMSO-d6) δ 8.15 (d, J = 8.40 Hz, 2H), 8.11 (br s, 1H), 7.91 (d, J = 8.40 Hz, 2H), 7.86 (br s, 1H), 7.12 (m, 1H), 7.06 (m, 1H), 5.65 (m, 1H), 4.77 (m, 1H), 4.50 (m, 1H), 2.03 (s, 3H) |
| 131 | 3-(1-(5-bromo-2-(4-(trifluoromethyl)phenyl)thiazol-4-yl)-2-hydroxyethoxy)-2,6-difluorobenzamide | 522.91 | $^1$H NMR (DMSO-d6) δ 8.13 (d, J = 8.40 Hz, 2H), 8.11 (br s, 1H), 7.90 (d, J = 8.40 Hz, 2H), 7.86 (br s, 1H), 7.12 (m, 1H), 7.03 (m, 1H), 5.41 (t, J = 6.40 Hz, 1H), 5.30 (t, J = 6.40 Hz, 1H), 4.05 (m, 1H), 3.91 (m, 1H) |

TABLE 1-continued

Characterisation of compounds by LCMS and $^1$H NMR

| Cpd No | Name | LCMS m/z = [M + H]+ | $^1$H NMR |
|---|---|---|---|
| 132 | 2-(3-carbamoyl-2,4-difluorophenoxy)-2-(2-(4-(trifluoromethyl)phenyl)oxazol-4-yl)acetic acid | 441.09 | $^1$H NMR (DMSO-d6) δ 8.29 (br s, 1H, D$_2$O exchangeable), 8.19 (s, 1H), 8.16 (d, J = 8.0 Hz, 2H), 7.91 (d, J = 8.0 Hz, 2H), 7.81 (br s, 1H, D$_2$O exchangeable), 7.15 (m, 1H), 7.01 (m, 1H), 5.42 (s, 1H) |
| 133 | 2-(2-(5-bromo-4-(trifluoromethyl)phenyl)oxazol-2-yl)-2-(3-carbamoyl-2,4-difluorophenoxy)ethyl)propane-1,3-diyl diacetate | 648.91 | $^1$H NMR (DMSO-d6) δ 8.15 (br s, 1H, D$_2$O exchangeable), 8.08 (d, J = 83.0 Hz, 2H), 7.87-7.89 (m, 3H, D$_2$O exchangeable 1H), 7.35 (m, 1H), 7.10 (m, 1H), 5.72 (m, 1H), 4.09 (s, 4H), 2.24 (m, 2H), 2.19 (m, 1H), 2.01 (s, 3H), 1.95 (s, 3H) |
| 134 | 2-(5-bromo-4-(trifluoromethyl)phenyl)oxazol-2-yl)-2-(3-carbamoyl-2,4-difluorophenoxy)ethyl (2-(dimethylamino)ethyl)carbamate | 620.94 | $^1$H NMR (DMSO-d6) δ 8.17 (br s, 1H), 8.10 (d, J = 8.0 Hz, 2H), 7.87-7.89 (m, 3H), 7.36 (m, 1H), 7.31 (m, 1H), 7.09 (m, 1H), 5.80 (t, J = 5.20 Hz, 1H), 4.59 (m, 2H), 3.02 (m, 2H), 2.18 (m, 2H), 2.06 (s, 6H) |
| 135 | 2-(5-bromo-4-(trifluoromethyl)phenyl)oxazol-2-yl)-2-(3-carbamoyl-2,4-difluorophenoxy)ethyl piperazine-1-carboxylate | 618.95 | $^1$H NMR (DMSO-d6) δ 8.91 (br s, 2H), 8.17 (br s, 1H), 8.09 (d, J = 8.0 Hz, 2H), 7.89-7.91 (m, 3H), 7.38 (m, 1H), 7.12 (m, 1H), 5.87 (t, J = 6.0 Hz, 1H), 4.63-4.71 (m, 2H), 3.58 (m, 4H), 3.06 (m, 4H) |
| 136 | 2,6-difluoro-3-(2-hydroxy-1-(2-(4-(trifluoromethyl)phenyl)oxazol-4-yl)ethoxy)benzamide | 428.98 | $^1$H NMR (DMSO-d6) δ and 8.34 (s, 1H), 8.18 (d, J = 8.0 Hz, 2H), 8.11 (br s, 1H), 7.91 (d, J = 8.0 Hz, 2H), 7.83 (br s, 1H), 7.33 (m, 1H), 7.02 (m, 1H), 5.37 (t, J = 5.60 Hz, 1H), 5.21 (t, J = 6.0 Hz, 1H), 3.93 (m, 2H) |
| 137 | 2-(5-bromo-2-(4-(trifluoromethyl)phenyl)oxazol-4-yl)-2-(3-carbamoyl-2,4-difluorophenoxy)ethyl acetate | 548.92 | $^1$H NMR (DMSO-d6) δ 8.18 (d, J = 8.0 Hz, 2H), 8.13 (br s, 1H, D$_2$O exchangeable), 7.93 (d, J = 8.0 Hz, 2H), 7.87 (br s, 1H, D$_2$O exchangeable), 7.19 (m, 1H), 7.05 (m 1H), 5.50 (t, J = 6.40 Hz, 1H), 4.64-4.69 (m, 1H), 4.45 (dd, J = 3.60 and 11.60 Hz respectively, 1H), 2.04 (s, 3H) |
| 138 | 3-(1-(5-bromo-2-(4-(trifluoromethyl)phenyl)oxazol-4-yl)-2-hydroxyethoxy)-2,6-difluorobenzamide | 506.89 | $^1$H NMR (DMSO-d6) δ 8.17 (d, J = 8.0 Hz, 2H), 8.11 (br s, 1H, D$_2$O exchangeable), 7.92 (d, J = 8.0 Hz, 2H), 7.84 (br s, 1H, D$_2$O exchangeable), 7.15 (m, 1H), 7.04 (m 1H), 5.23 (m, 2H, D$_2$O exchangeable 1H), 4.0 (m, 1H), 3.88 (m, 1H) |
| 139 | 3-(1-(5-bromo-4-(4-(trifluoromethyl)phenyl)oxazol-2-yl)-4-hydroxy-3-(hydroxymethyl)butoxy)-2,6-difluorobenzamide | 565.05 | $^1$H NMR (DMSO-d6) δ 8.17 (br s, 1H, D$_2$O exchangeable), 8.09 (d, J = 8.0 Hz, 2H), .89 (d, J = 8.40 Hz, 2H), 7.85 (br s, 1H, D$_2$O exchangeable), 7.35 (m, 1H), 7.11 (m, 1H), 5.69 (m, 1H), 4.59 (t, J = 4.80 Hz, 1H, D$_2$O exchangeable), 4.55 (t, J = 5.20 Hz, 1H, D$_2$O exchangeable), 3.42-3.47 (m, 4H), 2.01-2.19 (m, 2H), 1.72-1.75 (m, 1H) |
| 140 | ethyl 2-(((2-(5-bromo-4-(trifluoromethyl)phenyl)oxazol-2-yl)-2-(3-carbamoyl-2,4-difluorophenoxy)ethoxy)carbonyl)amino)acetate | 635.97 | $^1$H NMR (DMSO-d6) δ 8.15 (br s, 1H), 8.10 (d, J = 8.0 Hz, 2H), 7.85-7.89 (m, 3H), 7.82 (m, 1H), 7.40 (m, 1H), 7.10 (m, 1H), 5.82 (t, J = 5.60 Hz, 1H), 4.65 (m, 2H), 4.06 (q, J = 7.20 Hz, 2H), 3.72 (d, J = 6.0 Hz, 2H), 1.16 (t, J = 7.20 Hz, 3H) |

TABLE 1-continued

Characterisation of compounds by LCMS and $^1$H NMR

| Cpd No | Name | LCMS m/z = [M + H]+ | $^1$H NMR |
|---|---|---|---|
| 141 | methyl 3-(((2-(5-bromo-4-(4-(trifluoromethyl)phenyl)oxazol-2-yl)-2-(3-carbamoyl-2,4-difluorophenoxy)ethoxy)carbonyl)amino)propanoate | 636 | $^1$H NMR (DMSO-d6) δ 8.14 (br s, 1H), 8.10 (d, J = 8.0 Hz, 2H), 7.87-7.89 (m, 3H), 7.48 (t, J = 5.20 Hz, 1H), 7.37 (m, 1H), 7.11 (m, 1H), 5.80 (t, J = 4.80 Hz, 1H), 4.59 (m, 2H), 3.55 (s, 3H), 3.20 (m, 2H), 2.42 (t, J = 7.20 Hz, 2H) |
| 142 | 2-(((2-(5-bromo-4-(4-(trifluoromethyl)phenyl)oxazol-2-yl)-2-(3-carbamoyl-2,4-difluorophenoxy)ethoxy)carbonyl)amino)acetic acid | 608.17 | $^1$H NMR (DMSO-d6) δ 8.25 (br s, 1H, D$_2$O exchangeable), 8.11 (d, J = 8.0 Hz, 2H), 7.89 (d, J = 8.40 Hz, 2H), 7.85 (br s, 1H, D$_2$O exchangeable), 7.40 (m, 1H), 7.09 (m, 1H), 5.79 (t, J = 5.60 Hz, 1H), 4.56 (d, J = 4.56 Hz, 2H), 3.31 (m, 2H) |
| 143 | 3-(((2-(5-bromo-4-(4-(trifluoromethyl)phenyl)oxazol-2-yl)-2-(3-carbamoyl-2,4-difluorophenoxy)ethoxy)carbonyl)amino)propanoic acid | 622.31 | $^1$H NMR (DMSO-d6) δ 8.17 (br s, 1H), 8.10 (d, J = 8.40 Hz, 2H), 7.86-7.89 (m, 3H), 7.33-7.41 (m, 2H), 7.09 (m, 1H), 5.78 (t, J = 5.60 Hz, 1H), 4.59 (m, 2H), 3.16 (m, 2H), 2.34 (t, J = 5.20 Hz, 2H) |
| 144 | 2-(5-bromo-4-(4-(methylsulfonyl)phenyl)oxazol-2-yl)-2-(3-carbamoyl-2,4-difluorophenoxy)ethyl acetate | 558.95 | $^1$H NMR (DMSO-d6) δ 8.17 (br s, 1H), 8.13 (d, J = 8.40 Hz, 2H), 8.07 (d, J = 8.40 Hz, 2H), 7.90 (br s, 1H), 7.39 (m, 1H), 7.10 (m, 1H), 5.86 (m, 1H), 4.67 (m, 2H), 3.25 (s, 3H), 2.04 (s, 3H) |
| 145 | 3-(1-(5-bromo-4-(4-(methylsulfonyl)phenyl)oxazol-2-yl)-2-hydroxyethoxy)-2,6-difluorobenzamide | 516.93 | $^1$H NMR (DMSO-d6) δ 8.14 (br s, 1H), 8.13 (d, J = 8.40 Hz, 2H), 8.08 (d, J = 8.0 Hz, 2H), 7.86 (br s, 1H), 7.36 (m, 1H), 7.08 (m, 1H), 5.53 (t, J = 6.0 Hz, 1H), 5.44 (t, J = 6.0 Hz, 1H), 4.02 (t, J = 6.0 Hz, 2H), 3.25 (s, 3H) |
| 146 | 3-(1-(5-bromo-4-(4-(trifluoromethyl)phenyl)oxazol-2-yl)-3,4-dihydroxybutoxy)-2,6-difluorobenzamide (racemic mixture of diastereomer A)[a] | 551.08 | $^1$H NMR (DMSO-d6) δ 8.16 (br s, 1H), 8.10 (d, J = 8.0 Hz, 2H), 7.87-7.89 (m, 3H), 7.32 (m, 1H), 7.09 (m, 1H), 5.62 (m, 1H), 4.90 (d, J = 5.60 Hz, 1H), 4.68 (t, J = 5.60 Hz, 1H), .49 (m, 1H), 3.37 (m, 2H), 2.38 (m, 1H), 2.12 (m, 1H) |
| 147 | 3-(1-(5-bromo-4-(4-(trifluoromethyl)phenyl)oxazol-2-yl)-3,4-dihydroxybutoxy)-2,6-difluorobenzamide (racemic mixture of diastereomer B)[a] | 551.09 | $^1$H NMR (DMSO-d6) δ 8.15 (br s, 1H), 8.09 (d, J = 8.0 Hz, 2H), 7.86-7.88 (m, 3H), 7.32 (m, 1H), 7.09 (m, 1H), 5.62 (m, 1H), 4.89 (d, J = 5.60 Hz, 1H), 4.70 (t, J = 5.60 Hz, 1H), .74 (m, 1H), 3.41 (m, 2H), 2.40 (m, 1H), 1.95 (m, 1H) |
| 148 | 3-(1-(5-bromo-4-(4-(trifluoromethyl)phenyl)oxazol-2-yl)-3,4-dihydroxybutoxy)-2,6-difluorobenzamide (isomer I)[a] | 551.09 | $^1$H NMR (DMSO-d6) δ 8.16 (br s, 1H), 8.09 (d, J = 8.40 Hz, 2H), 7.86-7.88 (m, 3H), 7.36 (m, 1H), 7.09 (m, 1H), 5.62 (m, 1H), 4.89 (d, J = 5.20 Hz, 1H), 4.71 (t, J = 5.20 Hz, 1H), .74 (m, 1H), 3.41 (m, 2H), 2.40 (m, 1H), 1.94 (m, 1H) |
| 149 | 3-(1-(4-bromo-5-(4-(trifluoromethyl)phenyl)oxazol-2-yl)-2-hydroxyethoxy)-2,6-difluorobenzamide | 506.93 | $^1$H NMR (DMSO-d6) δ 8.16 (br s, 1H), 8.05 (d, J = 8.40 Hz, 2H), 7.94 (d, J = 8.80 Hz, 2H), 7.88 (br s, 1H), 7.37 (m, 1H), 7.11 (m, 1H), 5.54 (t, J = 6.0 Hz, 1H), 5.46 (t, J = 5.60 Hz, 1H), 4.03 (t, J = 6.0 Hz, 2H) |
| 150 | 3-(1-(5-bromo-4-(4-(trifluoromethyl)phenyl)oxazol-2-yl)-2-(2-hydroxyethoxy)ethoxy)-2,6-difluorobenzamide | 551.05 | $^1$H NMR (DMSO-d6) δ 8.14 (br s, 1H, D$_2$O exchangeable), 8.10 (d, J = 8.0 Hz, 2H), 7.87 (d, J = 8.40 Hz, 2H), 7.85 (br s, 1H, D$_2$O exchangeable), 7.40 (m, 1H), 7.11 (m, 1H), 5.76 (d, J = 5.60 Hz, 1H), 4.65 (t, J = 5.60 Hz, 1H, D$_2$O |

TABLE 1-continued

Characterisation of compounds by LCMS and $^1$H NMR

| Cpd No | Name | LCMS m/z = [M + H]+ | $^1$H NMR |
|---|---|---|---|
| | | | exchangeable), 4.10 (d, J = 5.60 Hz, 2H), 3.57 (t, J = 4.80 Hz, 2H), 3.48 (dd, J = 5.20 and 10.0 Hz respectively, 2H) |
| 151 | 2-(5-bromo-4-(4-(trifluoromethyl)phenyl)oxazol-2-yl)-2-(3-carbamoyl-2,4-difluorophenoxy)ethyl tert-butyl ethane-1,2-diyldicarbamate | 693.08 | $^1$H NMR (DMSO-d6) δ 8.14 (br s, 1H, D$_2$O exchangeable), 8.10 (d, J = 8.0 Hz, 2H), 7.89 (br s, 1H, D$_2$O exchangeable), 7.85 (d, J = 8.40 Hz, 2H), 7.34-7.40 (m, 2H), 7.10 (m, 1H), 6.77 (br s, 1H), 5.80 (t, J = 5.60 Hz, 1H), 4.60 (m, 2H), 2.97 (m, 4H), 1.35 (s, 9H) |
| 152 | 2-(5-bromo-4-(4-(trifluoromethyl)phenyl)oxazol-2-yl)-2-(3-carbamoyl-2,4-difluorophenoxy)ethyl (2-aminoethyl)carbamate | 593 | $^1$H NMR (DMSO-d6) δ 8.16 (br s, 1H, D$_2$O exchangeable), 8.10 (d, J = 8.0 Hz, 2H), 7.90 (br s, 1H, D$_2$O exchangeable), 7.87 (d, J = 8.0 Hz, 2H), 7.79 (br s, 2H, D$_2$O exchangeable), 7.55 (m, 1H, D$_2$O exchangeable), 7.38 (m, 1H), 7.11 (m, 1H), 5.84 (m, 1H), 4.62 (m, 2H), 3.20 (m, 2H), 2.83 (m, 2H) |
| 153 | tert-butyl (2-(((2-(5-bromo-4-(4-(trifluoromethyl)phenyl)oxazol-2-yl)-2-(3-carbamoyl-2,4-difluorophenoxy)ethoxy)carbonyl)amino)ethyl)(methyl)carbamate | 705.21 | $^1$H NMR (DMSO-d6) δ 8.15 (br s, 1H, D$_2$O exchangeable), 8.10 (d, J = 8.0 Hz, 2H), 7.89 (br s, 1H, D$_2$O exchangeable), 7.87 (d, J = 8.40 Hz, 2H), 7.46 (m, 1H, D$_2$O exchangeable), 7.36 (m, 1H), 7.10 (m, 1H), 5.80 (m, 1H), 4.58 (m, 2H), 3.16 (m, 2H), 3.04 (m, 2H), 2.79 (s, 3H), 1.33 (s, 9H) |
| 154 | 2-(5-bromo-4-(4-(trifluoromethyl)phenyl)oxazol-2-yl)-2-(3-carbamoyl-2,4-difluorophenoxy)ethyl (2-(methylamino)ethyl)carbamate | 607.07 | $^1$H NMR (DMSO-d6) δ 8.50 (br s, 1H, D$_2$O exchangeable), 8.16 (br s, 1H, D$_2$O exchangeable), 8.10 (d, J = 8.0 Hz, 2H), 7.90 (br s, 1H, D$_2$O exchangeable), 7.87 (d, J = 7.20 Hz, 2H), 7.60 (m, 1H, D$_2$O exchangeable), 7.37 (m, 1H), 7.11 (m, 1H), 5.84 (m, 1H), 4.63 (m, 2H), 3.25 (m, 2H), 2.92 (m, 2H), 2.53 (s, 3H) |
| 155 | 3-(1-(5-bromo-4-(4-(trifluoromethyl)phenyl)oxazol-2-yl)-2-(2-methoxyethoxy)ethoxy)-2,6-difluorobenzamide | 565 | $^1$H NMR (DMSO-d6) δ 8.15 (br s, 1H, D$_2$O exchangeable), 8.10 (d, J = 8.0 Hz, 2H), 7.87-7.89 (m, 3H), 7.40 (m, 1H), 7.09 (m, 1H), 5.77 (t, J = 5.60 Hz, 1H), 4.09 (d, J = 5.60 Hz, 2H), 3.65 (m, 2H), 3.43 (m, 2H), 3.20 (s, 3H) |
| 156 | 3-(1-(5-bromo-4-(4-(trifluoromethyl)phenyl)oxazol-2-yl)-3,4-dihydroxybutoxy)-2,6-difluorobenzamide (isomer II)$^{(a)}$ | 551.01 | $^1$H NMR (DMSO-d6) δ 8.15 (br s, 1H), 8.11 (d, J = 8.40 Hz, 2H), 7.87-7.89 (m, 3H), 7.31 (m, 1H), 7.09 (m, 1H), 5.62 (m, 1H), 4.87 (d, J = 4.80 Hz, 1H), 4.66 (t, J = 5.60 Hz, 1H), .50 (m, 1H), 3.37 (m, 2H), 2.40 (m, 1H), 2.15 (m, 1H) |
| 157 | 3-(1-(5-bromo-4-(4-(trifluoromethyl)phenyl)oxazol-2-yl)-3,4-dihydroxybutoxy)-2,6-difluorobenzamide (isomer III)$^{(a)}$ | 551.09 | $^1$H NMR (DMSO-d6) δ 8.15 (br s, 1H), 8.09 (d, J = 8.0 Hz, 2H), 7.86-7.88 (m, 3H), 7.34 (m, 1H), 7.09 (m, 1H), 5.62 (m, 1H), 4.88 (m, 1H), 4.70 (m, 1H), .73 (m, 1H), 3.41 (m, 2H), 2.37 (m, 1H), 1.94 (m, 1H) |
| 158 | 2-(5-bromo-4-(4-(trifluoromethyl)phenyl)oxazol-2-yl)-2-(3-carbamoyl-2-fluorophenoxy)ethyl acetate | 531.02 | $^1$H NMR (DMSO-d6) δ 8.10 (d, J = 8.0 Hz, 2H), 7.90 (d, J = 8.40 Hz, 2H), 7.79 (br s, 1H), 7.67 (br s, 1H), 7.41 (m, 1H), 7.24 (m, 1H), 7.18 (m, 1H), 5.93 (t, J = 6.0 Hz, 1H), 4.63-4.72 (m, 2H), 2.03 (s, 3H) |

TABLE 1-continued

Characterisation of compounds by LCMS and $^1$H NMR

| Cpd No | Name | LCMS m/z = [M + H]+ | $^1$H NMR |
|---|---|---|---|
| 159 | 3-(1-(5-bromo-4-(4-(trifluoromethyl)phenyl)oxazol-2-yl)-2-hydroxyethoxy)-2-fluorobenzamide | 489.07 | $^1$H NMR (DMSO-d6) δ 8.10 (d, J = 8.40 Hz, 2H), 7.89 (d, J = 8.40 Hz, 2H), 7.78 (br s, 1H), 7.66 (br s, 1H), 7.37 (m, 1H), 7.13-7.21 (m, 2H), 5.60 (t, J = 6.0 Hz, 1H), 5.45 (t, J = 6.0 Hz, 1H), 4.02 (t, J = 5.60 Hz, 2H) |
| 160 | 2-(5-bromo-4-(4-(trifluoromethyl)phenyl)oxazol-2-yl)-2-(3-carbamoyl-2,4-difluorophenoxy)ethyl morpholine-4-carboxylate | 619.98 | $^1$H NMR (DMSO-d6) δ 8.16 (br s, 1H), 8.10 (d, J = 8.40 Hz, 2H), 7.88-7.90 (m, 3H), 7.37 (m, 1H), 7.11 (m, 1H), 5.86 (t, J = 5.20 Hz, 1H), 4.65 (d, J = 5.20 Hz, 2H), 3.50 (m, 4H), 3.30 (m, 4H) |
| 161 | 2-(5-bromo-4-(4-(trifluoromethyl)phenyl)oxazol-2-yl)-2-(3-carbamoyl-2,4-difluorophenoxy)ethyl (2-(pyrrolidin-1-yl)ethyl)carbamate | 647.09 | $^1$H NMR (DMSO-d6) δ 8.15 (br s, 1H, D$_2$O exchangeable), 8.10 (d, J = 7.20 Hz, 2H), 7.88-7.90 (m, 3H, D$_2$O exchangeable 1H), 7.37 (m, 2H, D$_2$O exchangeable 1H), 7.12 (m, 1H), 5.82 (m, 1H), 4.61 (m, 2H), 3.11 (m, 2H), 2.50 (m, 6H), 1.68 (m, 4H) |
| 162 | 2-(5-bromo-4-(4-(trifluoromethyl)phenyl)oxazol-2-yl)-2-(3-carbamoyl-2,4-difluorophenoxy)ethyl (2-(1H-imidazol-4-yl)ethyl)carbamate | 644.02 | $^1$H NMR (DMSO-d6) δ 14.25 (br s, 1H), 8.90 (br s, 1H), 8.16 (br s, 1H), 8.09 (d, J = 8.0 Hz, 2H), 7.87-7.89 (m, 3H), 7.57 (m, 1H), 7.32-7.39 (m, 2H), 7.10 (m, 1H), 5.80 (t, J = 5.60 Hz, 1H), 4.59 (m, 2H), 3.26 (m, 2H), 2.75 (t, J = 6.40 Hz, 2H) |
| 163 | 2-(5-bromo-4-(4-(trifluoromethyl)phenyl)oxazol-2-yl)-2-(3-carbamoyl-2,4-difluorophenoxy)ethyl (2-hydroxyethyl)carbamate | 593.99 | $^1$H NMR (DMSO-d6) δ 8.14 (br s, 1H), 8.10 (d, J = 8.40 Hz, 2H), 7.87-7.89 (m, 3H), 7.31-7.41 (m, 2H), 7.10 (m, 1H), 5.80 (t, J = 5.60 Hz, 1H), 4.54-4.62 (m, 3H), 3.36 (m, 2H), 3.0 (m, 2H) |
| 164 | 2-(5-bromo-4-(4-(trifluoromethyl)phenyl)oxazol-2-yl)-2-(3-carbamoyl-2,4-difluorophenoxy)ethyl (2-methoxyethyl)carbamate | 608.02 | $^1$H NMR (DMSO-d6) δ 8.14 (br s, 1H), 8.10 (d, J = 8.0 Hz, 2H), 7.87-7.89 (m, 3H), 7.34-7.44 (m, 2H), 7.10 (m, 1H), 5.80 (t, J = 6.0 Hz, 1H), 4.54-4.62 (m, 2H), 3.28 (t, J = 5.60 Hz, 2H), 3.17 (s, 3H), 3.11 (m, 2H) |
| 165 | 2-(5-bromo-4-(4-(trifluoromethyl)phenyl)oazol-2-yl)-2-(3-carbamoyl-2,4-difluorophenoxy)ethyl (pyridin-2-ylmethyl)carbamate | 640.97 | $^1$H NMR (DMSO-d6) δ 8.46 (m, 1H), 8.15 (br s, 1H), 8.10 (d, J = 8.40 Hz, 2H), 8.01 (m, 1H), 7.87-7.89 (m, 3H), 7.67 (m, 1H), 7.40 (m, 1H), 7.20-7.23 (m, 2H), 7.10 (m, 1H), 5.83 (t, J = 5.20 Hz, 1H), 4.60-4.70 (m, 2H), 4.25 (d, J = 6.0 Hz, 2H) |
| 166 | 2-(5-bromo-4-(4-(trifluoromethyl)phenyl)oxazol-2-yl)-2-(3-carbamoyl-2,4-difluorophenoxy)ethyl (pyridin-3-ylmethyl)carbamate | 640.98 | $^1$H NMR (DMSO-d6) δ 8.41-8.44 (m, 2H), 8.15 (br s, 1H), 8.09 (d, J = 8.0 Hz, 2H), 8.01 (t, J = 6.0 Hz, 1H), 7.87-7.89 (m, 3H), 7.61 (d, J = 8.0 Hz, 1H), 7.37 (m, 1H), 7.27-7.30 (m, 1H), 7.10 (m, 1H), 5.83 (t, J = 5.60 Hz, 1H), 4.59-4.69 (m, 2H), 4.25 (d, J = 6.0 Hz, 2H) |
| 167 | 2-(5-bromo-4-(4-(trifluoromethyl)phenyl)oxazol-2-yl)-2-(3-carbamoyl-2,4-difluorophenoxy)ethyl (pyridin-4-ylmethyl)carbamate | 640.97 | $^1$H NMR (DMSO-d6) δ 8.43 (m, 2H), 8.16 (br s, 1H), 8.10 (d, J = 8.0 Hz, 2H), 8.05 (t, J = 6.0 Hz, 1H), 7.88-7.90 (m, 3H), 7.37 (m, 1H), 7.18 (d, J = 5.60 Hz, 2H), 7.10 (m, 1H), 5.84 (t, J = 5.60 Hz, 1H), 4.60-4.70 (m, 2H), 4.21 (d, J = 6.0 Hz, 2H) |
| 168 | 3-(1-(5-bromo-4-(4-(trifluoromethyl)phenyl)oxazol-2-yl)-2-(2-morpholinoethoxy)ethoxy)-2,6-difluorobenzamide | 620.03 | $^1$H NMR (DMSO-d6) δ 8.14 (br s, 1H), 8.09 (d, J = 8.0 Hz, 2H), 7.87-7.90 (m, 3H), 7.38 (m, 1H), 7.09 (m, 1H), 5.80 (t, J = 6.0 Hz, 1H), 4.06 (d, J = 6.40 Hz, 2H), 3.65 (t, J = 5.60 Hz, 2H), 3.45 (t, J = 4.40 Hz, 4H), 2.43 (t, J = 5.60 Hz, 2H), 2.31 (m, 4H) |

TABLE 1-continued

Characterisation of compounds by LCMS and ¹H NMR

| Cpd No | Name | LCMS m/z = [M + H]+ | ¹H NMR |
|---|---|---|---|
| 169 | 2-(5-bromo-4-(4-(trifluoromethyl)phenyl)oxazol-2-yl)-2-(3-carbamoyl-2,4-difluorophenoxy)ethyl 3-(methylsulfonyl)-2-oxoimidazolidine-1-carboxylate | 697.07 | ¹H NMR (DMSO-d6) δ 8.15 (br s, 1H), 8.11 (d, J = 8.0 Hz, 2H), 7.88-7.90 (m, 3H), 7.42 (m, 1H), 7.12 (m, 1H), 5.90 (t, J = 5.20 Hz, 1H), 4.80 (d, J = 4.80 Hz, 2H), 3.75 (m, 4H), 3.30 (s, 3H) |
| 170 | 2-(5-bromo-4-(4-(trifluoromethyl)phenyl)oxazol-2-yl)-2-(3-carbamoyl-2,4-difluorophenoxy)ethyl pyridin-3-ylcarbamate | 626.99 | ¹H NMR (DMSO-d6) δ 10.10 (br s, 1H), 8.61 (br s, 1H), 8.20 (m, 1H), 8.15 (br s, 1H), 8.09 (d, J = 8.0 Hz, 2H), 7.85-7.87 (m, 4H), 7.42 (m, 1H), 7.31 (m, 1H), 7.12 (m, 1H), 5.94 (m, 1H), 4.77 (m, 2H) |
| 171 | 2-(5-bromo-4-(4-(trifluoromethyl)phenyl)oxazol-2-yl)-2-(3-carbamoyl-2,4-difluorophenoxy)ethyl (2-(3-methyl-1,2,4-oxadiazol-5-yl)ethyl)carbamate | 660.06 | ¹H NMR (DMSO-d6) δ 8.08-8.14 (m, 3H), 7.88 (m, 3H), 7.62 (m, 1H), 7.37 (m, 1H), 7.10 (m, 1H), 5.80 (m, 1H), 4.59 (m, 2H), 3.32 (m, 2H), 2.99 (m, 2H), 2.27 (s, 3H) |
| 172 | 2-(5-bromo-4-(4-(trifluoromethyl)phenyl)oxazol-2-yl)-2-(3-carbamoyl-2,4-difluorophenoxy)ethyl ((5-methyl-1,3,4-oxadiazol-2-yl)methyl)carbamate | 646.08 | ¹H NMR (DMSO-d6) δ 8.19-8.19 (m, 2H), 8.10 (d, J = 8.40 Hz, 2H), 7.87-7.89 (m, 3H), 7.40 (m, 1H), 7.10 (m, 1H), 5.83 (t, J = 5.60 Hz, 1H), 4.61-4.68 (m, 2H), 4.38 (m, 2H), 2.44 (s, 3H) |
| 173 | 2-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide | 656.9 | ¹H NMR (DMSO-d6) δ 8.33 (d, J = 7.20 Hz, 1H), 8.16 (br s, 1H), 8.10 (d, J = 8.0 Hz, 2H), 8.01 (t, J = 6.0 Hz, 1H), 7.87-7.90 (m, 3H), 7.22-7.42 (m, 4H), 7.11 (m, 1H), 5.86 (t, J = 6.0 Hz, 1H), 4.66 (m, 2H), 4.27 (d, J = 6.0 Hz, 2H) |
| 174 | 3-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide | 656.8 | ¹H NMR (DMSO-d6) δ 8.16 (br s, 1H), 8.04-8.08 (m, 5H), 7.89 (m, 3H), 7.29-7.36 (m, 2H), 7.18 (m, 1H), 7.09 (m, 1H), 5.83 (m, 1H), 4.65 (m, 2H), 4.16 (d, J = 6.40 Hz, 2H) |
| 175 | 4-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide | 656.9 | ¹H NMR (DMSO-d6) δ 8.16 (br s, 1H), 8.04-8.11 (m, 5H), 7.89 (m, 3H), 7.39 (m, 1H), 7.20 (d, J = 6.80 Hz, 2H), 7.10 (m, 1H), 5.83 (t, J = 5.60 Hz, 1H), 4.65 (m, 2H), 4.16 (d, J = 6.0 Hz, 2H) |
| 176 | 2-(5-bromo-4-(4-(trifluoromethyl)phenyl)oxazol-2-yl)-2-(3-carbamoyl-2,4-difluorophenoxy)ethyl pyridin-4-ylcarbamate | 626.9 | ¹H NMR (DMSO-d6) δ 10.35 (br s, 1H), 8.40 (d, J = 8.40 Hz, 2H), 8.16 (br s, 1H), 8.09 (d, J = 8.0 Hz, 2H), 7.85-7.95 (m, 3H), 7.38-7.44 (m, 3H), 7.10 (m, 1H), 5.96 (t, J = 5.20 Hz, 1H), 4.75-4.84 (m, 2H) |
| 177 | 2-(5-bromo-4-(4-(trifluoromethyl)phenyl)oxazol-2-yl)-2-(3-carbamoyl-2,4-difluorophenoxy)ethyl 1H-tetrazol-5-ylcarbamate | 616 | ¹H NMR (DMSO-d6) δ 11.48 (br s, 1H), 8.15 (br s, 1H), 8.09 (d, J = 8.0 Hz, 2H), 7.86-7.88 (m, 3H), 7.40 (m, 1H), 7.11 (m, 1H), 5.92 (t, J = 5.60 Hz, 1H), 4.81-4.89 (m, 2H) |
| 178 | 2-(5-bromo-4-(4-(trifluoromethyl)phenyl)oxazol-2-yl)-2-(3-carbamoyl-2,4-difluorophenoxy)ethyl 4-methylpiperazine-1-carboxylate | 633.11 | ¹H NMR (DMSO-d6) δ 8.14 (br s, 1H), 8.10 (d, J = 8.0 Hz, 2H), 7.88-7.90 (m, 3H), 7.36 (m, 1H), 7.10 (m, 1H), 5.86 (t, J = 5.20 Hz, 1H), 4.64 (d, J = 5.20 Hz, 2H), 3.30 (m, 4H), 2.19 (m, 4H), 2.10 (s, 3H) |
| 179 | 2-(5-bromo-4-(4-(trifluoromethyl)phenyl)oxazol-2-yl)-2-(3-carbamoyl-2,4-difluorophenoxy)ethyl ((3-methyl-1,2,4-oxadiazol-5-yl)methyl)carbamate | 645.9 | ¹H NMR (DMSO-d6) δ 8.26 (t, J = 6.0 Hz, 1H), 8.16 (br s, 1H), 8.10 (d, J = 8.0 Hz, 2H), 7.87-7.89 (m, 3H), 7.38 (m, 1H), 7.10 (m, 1H), 5.85 (t, J = 5.20 Hz, 1H), 4.65 (m, 2H), 4.45 (d, J = 6.0 Hz, 2H), 2.29 (s, 3H) |
| 180 | ethyl 2-(3-carbamoyl-2,4-difluorophenoxy)-2-(4-(tetrahydro-2H-pyran-4-yl)oxazol-2-yl)acetate | 411.11 | ¹H NMR (CDCl₃) δ 7.42 (s, 1H), 7.17 (m, 1H), 6.87 (m 1H), 5.99 (br s, 1H), 5.86 (br s, 1H), 5.71 (s, 1H), 4.33 (m, 2H), 4.03 (m, 2H), |

TABLE 1-continued

Characterisation of compounds by LCMS and $^1$H NMR

| Cpd No | Name | LCMS m/z = [M + H]+ | $^1$H NMR |
|---|---|---|---|
| | | | 3.50 (m, 2H), 2.80 (m, 1H), 1.93 (m, 2H), 1.70 (m, 2H), 1.30 (t, J = 7.20 Hz, 3H) |
| 181 | (R)-4-(2-(5-bromo-4-(4-(trifluoromethyl)phenyl)oxazol-2-yl)-2-(3-carbamoyl-2,4-difluorophenoxy)ethoxy)-4-oxobutanoic acid | 605.16 | $^1$H NMR (DMSO-d6 + D$_2$O) δ 8.09 (d, J = 8.0 Hz, 2H), 7.86 (d, J = 8.40 Hz, 2H), 7.37-7.42 (m, 1H), 7.06-7.10 (m, 1H), 5.77 (t, J = 5.60 Hz, 1H), 4.61 (m, 2H), 3.22 (t, J = 5.60 Hz, 1H), 3.0 (m, 2H), 2.39 (t, J = 6.80 Hz, 2H), 2.12 (t, J = 7.20 Hz, 2H), 1.68 (m, 2H), 1.55 (m, 2H) |
| 182 | 2,6-difluoro-3-(2-hydroxy-1-(4-(tetrahydro-2H-pyran-4-yl)oxazol-2-yl)ethoxy)benzamide | 369.13 | $^1$H NMR (DMSO-d6) δ 8.13 (br s, 1H), 7.87 (s, 1H), 7.84 (br s, 1H), 7.25 (m, 1H), 7.05 (m 1H), 5.38 (t, J = 6.40 Hz, 1H), 5.31 (m, 1H), 3.95 (m, 2H), 3.86 (m, 2H), 3.40 (m, 2H), 2.70 (m, 1H), 1.80 (m, 2H), 1.52 (m, 2H) |
| 183 | (R)-2,6-difluoro-3-(1-(4-(4-(trifluoromethyl)phenyl)oxazol-2-yl)ethoxy)benzamide | 413.03 | $^1$H NMR (DMSO-d6) δ 8.83 (s, 1H), 8.14 (br s, 1H), 7.99 (d, J = 8.0 Hz, 2H), 7.86 (br s, 1H), 7.81 (d, J = 8.0 Hz, 2H), 7.33 (m, 1H), 7.10 (m, 1H), 5.74 (q, J = 6.40 Hz, 1H), 1.75 (d, J = 6.40 Hz, 3H) |
| 184 | (R)-3-(1-(5-bromo-4-(4-(trifluoromethyl)phenyl)oxazol-2-yl)ethoxy)-2,6-difluorobenzamide | 490.92 | $^1$H NMR (DMSO-d6) δ 8.14 (br s, 1H), 8.10 (d, J = 8.40 Hz, 2H), 7.89 (d, J = 8.40 Hz, 2H), 7.86 (br s, 1H), 7.38 (m, 1H), 7.10 (m, 1H), 5.71 (q, J = 6.40 Hz, 1H), 1.74 (d, J = 6.40 Hz, 3H) |
| 185 | 2-(5-bromo-4-(4-(trifluoromethyl)phenyl)oxazol-2-yl)-2-(3-carbamoyl-2,4-difluorophenoxy)ethyl methyl(pyridin-3-ylmethyl)carbamate | 654.99 | $^1$H NMR (DMSO-d6) δ 8.36-8.46 (2H, split signal), 8.16 (br s, 1H), 8.01-8.11 (2H, split signal), 7.86-7.90 (m, 3H), 7.32-7.40 (m, 1H), 7.04-7.15 (m, 3H), 5.90 (m, 1H), 4.65-4.71 (2H, split signal), 4.37-4.44 (m, 2H), 2.83 (3H, split signal) |
| 186 | 2-(5-bromo-4-(4-(trifluoromethyl)phenyl)oxazol-2-yl)-2-(3-carbamoyl-2,4-difluorophenoxy)ethyl methyl(pyridin-4-ylmethyl)carbamate | 655.07 | $^1$H NMR (DMSO-d6) δ 8.37-8.46 (2H, split signal), 8.16 (br s, 1H), 8.01-8.11 (2H, split signal), 7.88-7.90 (m, 3H), 7.30-7.39 (m, 1H), 7.06-7.14 (m, 3H), 5.90 (m, 1H), 4.66-4.72 (2H, split signal), 4.41-4.69 (m, 2H), 2.83 (3H, split signal) |
| 187 | 3-(1-(5-bromo-4-(tetrahydro-2H-pyran-4-yl)oxazol-2-yl)-2-hydroxyethoxy)-2,6-difluorobenzamide | 446.97 | $^1$H NMR (DMSO-d6) δ and 8.13 (br s, 1H, D$_2$O exchangeable), 7.84 (br s, 1H, D$_2$O exchangeable), 7.29 (m, 1H), 7.07 (m 1H), 5.35 (m, 2H, D$_2$O exchangeable 1H), 3.86-3.94 (m, 4H), 3.39 (m, 2H), 2.75 (m, 1H), 1.70 (m, 2H), 1.59 (m, 2H) |
| 188 | 2,6-difluoro-3-((3-methyl-1,2,4-oxadiazol-5-yl)(4-(4-(trifluoromethyl)phenyl)oxazol-2-yl)methoxy)benzamide | 481.12 | $^1$H NMR (DMSO-d6) δ 9.01 (s, 1H), 8.18 (br s, 1H), 7.97 (d, J = 8.0 Hz, 2H), 7.92 (br s, 1H), 7.84 (d, J = 8.40 Hz, 2H), 7.54 (s, 1H), 7.46 (m, 1H), 7.15 (m, 1H), 2.41 (s, 3H) |
| 189 | 3-(1-(5-bromo-4-(4-(trifluoromethyl)phenyl)oxazol-2-yl)-2,3-dihydroxypropoxy)-2,6-difluorobenzamide | 537.04 | $^1$H NMR (DMSO-d6) δ 8.16 (br s, 1H, D$_2$O exchangeable), 8.11 (d, J = 8.0 Hz, 2H), 7.87-7.89 (m, 3H, D$_2$O exchangeable 1H), 7.26 (m, 1H), 7.07 (m, 1H), 5.50 (m, 1H, D$_2$O exchangeable), 5.37 (d, J = 7.20 Hz, 1H), 4.88 (t, J = 5.60 Hz, 1H, D$_2$O exchangeable), 4.11 (m, 1H), 3.64 (m, 1H), 3.50 (m, 1H) |
| 190 | 2-(5-bromo-4-(4-(trifluoromethyl)phenyl)oxazol-2-yl)-2-(3-carbamoyl-2,4-difluorophenoxy)ethyl (2-(2- | 658.06 | $^1$H NMR (DMSO-d6) δ 8.19 (br s, 1H), 8.08-8.10 (m, 2H), 7.88-7.90 (m, 3H), 7.59 (m, 1H), 7.36 (m, 1H), 7.09-7.13 (m, 2H), 6.87 (s, |

TABLE 1-continued

Characterisation of compounds by LCMS and ¹H NMR

| Cpd No | Name | LCMS m/z = [M + H]+ | ¹H NMR |
|---|---|---|---|
| | methyl-1H-imidazol-1-yl)ethyl)carbamate | | 1H), 5.80 (t, J = 5.60 Hz, 1H), 4.59 (m, 2H), 3.94 (t, J = 5.60 Hz, 2H), 3.38 (m, 2H), 2.26 (s, 3H) |
| 191 | 2-(5-bromo-4-(4-(trifluoromethyl)phenyl)oxazol-2-yl)-2-(3-carbamoyl-2,4-difluorophenoxy)ethyl methyl(pyridin-2-ylmethyl)carbamate | 654.98 | ¹H NMR (DMSO-d6) δ 8.43 (br s, 1H), 7.68-8.05 (m, 7H), 7.03-7.32 (m, 4H), 5.76 (br s, 1H), 4.65 (br s, 2H), 4.46 (br s, 2H), 2.86 (s, 3H) |
| 192 | 2-(5-bromo-4-(4-(trifluoromethyl)phenyl)oxazol-2-yl)-2-(3-carbamoyl-2,4-difluorophenoxy)ethyl methyl(pyrazin-2-ylmethyl)carbamate | 655.99 | ¹H NMR (333K, DMSO-d6) δ 8.47 (br s, 3H), 8.04 (br s, 2H), 7.95 (s, 1H), 7.85 (d, J = 8.40 Hz, 2H), 7.67 (s, 1H), 7.31 (br s, 1H), 7.03 (m, 1H), 5.75 (br s, 1H), 4.64 (br s, 2H), 4.54 (s, 2H), 2.88 (s, 3H) |
| 193 | 2-(5-bromo-4-(4-(trifluoromethyl)phenyl)oxazol-2-yl)-2-(3-carbamoyl-2,4-difluorophenoxy)ethyl ((1-methyl-1H-pyrazol-3-yl)methyl)carbamate | 643.97 | ¹H NMR (333K, DMSO-d6) δ 8.13 (br s, 1H), 8.10 (d, J = 8.0 Hz, 2H), 7.87-7.89 (m, 3H), 7.77 (t, J = 5.60 Hz, 1H), 7.50 (s, 1H), 7.37 (m, 1H), 7.08 (m, 1H), 6.02 (s, 1H), 5.81 (m, 1H), 4.61 (m, 2H), 4.09 (d, J = 5.60 Hz, 2H), 3.73 (s, 3H) |
| 194 | 2-(5-bromo-4-(4-(trifluoromethyl)phenyl)oxazol-2-yl)-2-(3-carbamoyl-2,4-difluorophenoxy)ethyl ((1-methyl-1H-pyrazol-5-yl)methyl)carbamate | 643.92 | ¹H NMR (DMSO-d6) δ 8.15 (br s, 1H), 8.09 (d, J = 8.0 Hz, 2H), 7.95 (t, J = 6.0 Hz, 1H), 7.87-7.89 (m, 3H), 7.37 (m, 1H), 7.21 (s, 1H), 7.09 (m, 1H), 6.03 (s, 1H), 5.82 (t, J = 5.60 Hz, 1H), 4.64 (m, 2H), 4.20 (d, J = 6.0 Hz, 2H), 3.71 (s, 3H) |
| 195 | 2-(5-bromo-4-(4-(trifluoromethyl)phenyl)oxazol-2-yl)-2-(3-carbamoyl-2,4-difluorophenoxy)ethyl ((1-methyl-1H-imidazol-5-yl)methyl)carbamate | 643.93 | ¹H NMR (DMSO-d6) δ 8.17 (br s, 1H), 8.09 (d, J = 8.0 Hz, 2H), 7.87-7.89 (m, 3H), 7.83 (t, J = 5.60 Hz, 1H), 7.49 (s, 1H), 7.36 (m, 1H), 7.08 (m, 1H), 6.71 (s, 1H), 5.81 (t, J = 5.60 Hz, 1H), 4.64 (m, 2H), 4.16 (d, J = 5.60 Hz, 2H), 3.52 (s, 3H) |
| 196 | 2-(5-bromo-4-(4-(trifluoromethyl)phenyl)oxazol-2-yl)-2-(3-carbamoyl-2,4-difluorophenoxy)ethyl ((2-methoxypyridin-3-yl)methyl)carbamate | 670.93 | ¹H NMR (DMSO-d6) δ 8.16 (br s, 1H), 8.10 (d, J = 8.40 Hz, 2H), 8.02 (m, 1H), 7.87-7.89 (m, 4H), 7.32-7.43 (m, 2H), 7.12 (m, 1H), 6.87 (m, 1H), 5.83 (t, J = 5.60 Hz, 1H), 4.59-4.69 (m, 2H), 4.11 (d, J = 5.60 Hz, 2H), 3.85 (s, 3H) |
| 197 | 2-(5-bromo-4-(4-(trifluoromethyl)phenyl)oxazol-2-yl)-2-(3-carbamoyl-2,4-difluorophenoxy)ethyl methyl(pyrimidin-4-ylmethyl)carbamate | 656.06 | ¹H NMR (DMSO-d6) δ 8.95-9.12 (1H, split signal), 8.53-8.69 (1H split signal), 8.0-8.17 (m, 3H), 7.86-7.90 (m, 3H), 7.23-7.29 (m, 2H), 7.03-7.14 (m, 1H), 5.75-5.89 (m, 1H), 4.69 (m, 1H), 4.60 (m, 1H), 4.48-4.51 (m, 2H), 2.92 (3H, split signal) |
| 198 | 2-(5-bromo-4-(4-(trifluoromethyl)phenyl)oxazol-2-yl)-2-(3-carbamoyl-2,4-difluorophenoxy)ethyl ((1-methyl-1H-pyrazol-4-yl)methyl)carbamate | 644.05 | ¹H NMR (DMSO-d6) δ 8.13 (br s, 1H), 809 (d, J = 8.40 Hz, 2H), 7.87-7.89 (m, 3H), 7.70 (t, J = 6.0 Hz, 1H), 7.48 (s, 1H), 7.36 (m, 1H), 7.25 (s, 1H), 7.08 (m, 1H), 5.80 (m, 1H), 4.60 (m, 2H), 3.99 (d, J = 6.0 Hz, 2H), 3.74 (s, 3H) |
| 199 | 2-(5-bromo-4-(4-(trifluoromethyl)phenyl)oxazol-2-yl)-2-(3-carbamoyl-2,4-difluorophenoxy)ethyl ((6-methylpyridin-2-yl)methyl)carbamate | 654.96 | ¹H NMR (DMSO-d6) δ 8.16 (br s, 1H, D₂O exchangeable), 8.10 (d, J = 8.0 Hz, 2H), 8.0 (m, 1H, D₂O exchangeable), 7.87-7.89 (m, 3H, D₂O exchangeable 1H), 7.56 (m, 1H), 7.38 (m, 1H), 6.93-7.12 (m, 3H), 5.83 (t, J = −5.20 Hz, 1H), 4.65 (m, 2H), 4.20 (d, J = 6.0 Hz, 2H), 2.40 (s, 3H) |
| 200 | 2-(5-bromo-4-(4-(trifluoromethyl)phenyl)oxazol-2-yl)-2-(3-carbamoyl-2,4-difluorophenoxy)ethyl ((2- | 654.95 | ¹H NMR (DMSO-d6) δ 8.29 (d, J = 7.20 Hz, 1H), 8.15 (br s, 1H, D₂O exchangeable), 8.10 (d, J = 8.40 Hz, 2H), 8.02 (t, J = 6.0 Hz, |

TABLE 1-continued

Characterisation of compounds by LCMS and $^1$H NMR

| Cpd No | Name | LCMS m/z = [M + H]+ | $^1$H NMR |
|---|---|---|---|
| | methylpyridin-4-yl)methyl)carbamate | | 1H, D$_2$O exchangeable), 7.87-7.89 (m, 3H, D$_2$O exchangeable 1H), 7.39 (m, 1H), 6.91-7.12 (m, 3H), 5.83 (t, J = −5.20 Hz, 1H), 4.65 (m, 2H), 4.16 (d, J = 6.0 Hz, 2H), 2.39 (s, 3H) |
| 201 | 2-(5-bromo-4-(4-(trifluoromethyl)phenyl)oxazol-2-yl)-2-(3-carbamoyl-2,4-difluorophenoxy)ethyl ((1-methyl-1H-imidazol-2-yl)methyl)carbamate | 644.06 | $^1$H NMR (DMSO-d6) δ 8.16 (br s, 1H), 8.09 (d, J = 8.0 Hz, 2H), 7.87-7.89 (m, 4H), 7.38 (m, 1H), 7.09 (m, 1H), 7.02 (s, 1H), 6.74 (s, 1H), 5.81 (t, J = 5.60 Hz, 1H), 4.63 (m, 2H), 4.23 (d, J = 6.0 Hz, 2H), 3.55 (s, 3H) |
| 202 | 2-(5-bromo-4-(4-(trifluoromethyl)phenyl)oxazol-2-yl)-2-(3-carbamoyl-2,4-difluorophenoxy)ethyl ((1-methyl-1H-pyrrol-2-yl)methyl)carbamate | 641.16 | $^1$H NMR (DMSO-d6) δ 8.14 (br s, 1H), 8.10 (d, J = 8.40 Hz, 2H), 7.87-7.89 (m, 3H), 7.73 (t, J = 5.60 Hz, 1H), 7.37 (m, 1H), 7.08 (m, 1H), 6.59 (s, 1H), 5.78-5.84 (m, 3H), 4.62 (m, 2H), 4.13 (d, J = 5.60 Hz, 2H), 3.48 (s, 3H) |
| 203 | 2-(5-bromo-4-(4-(trifluoromethyl)phenyl)oxazol-2-yl)-2-(3-carbamoyl-2,4-difluorophenoxy)ethyl ((1-methyl-1H-imidazol-4-yl)methyl)carbamate | 644.08 | $^1$H NMR (DMSO-d6) δ 8.16 (br s, 1H), 8.10 (d, J = 8.0 Hz, 2H), 7.87-7.89 (m, 3H), 7.69 (t, J = 5.60 Hz, 1H), 7.44 (s, 1H), 7.38 (m, 1H), 7.09 (m, 1H), 6.82 (s, 1H), 5.79 (t, J = 5.60 Hz, 1H), 4.60 (m, 2H), 4.02 (d, J = 5.60 Hz, 2H), 3.54 (s, 3H) |
| 204 | 2-(5-bromo-4-(4-(trifluoromethyl)phenyl)oxazol-2-yl)-2-(3-carbamoyl-2,4-difluorophenoxy)ethyl ((1,3-dimethyl-1H-pyrazol-4-yl)methyl)carbamate | 658.07 | $^1$H NMR (DMSO-d6) δ 8.13 (br s, 1H), 8.09 (d, J = 8.0 Hz, 2H), 7.87-7.89 (m, 3H), 7.63 (m, 1H), 7.35 (m, 2H), 7.09 (m, 1H), 5.79 (t, J = 6.0 Hz, 1H), 4.60 (m, 2H), 3.93 (d, J = 5.60 Hz, 2H), 3.65 (s, 3H), 2.08 (s, 3H) |
| 205 | 2-(5-bromo-4-(4-(trifluoromethyl)phenyl)oxazol-2-yl)-2-(3-carbamoyl-2,4-difluorophenoxy)ethyl ((1,5-dimethyl-1H-pyrazol-4-yl)methyl)carbamate | 658.06 | $^1$H NMR (DMSO-d6) δ 8.15 (br s, 1H), 8.09 (d, J = 8.0 Hz, 2H), 7.87-7.89 (m, 3H), 7.65 (t, J = 5.60 Hz, 1H), 7.35 (m, 1H), 7.16 (s, 1H), 7.07 (m, 1H), 5.79 (t, J = 5.60 Hz, 1H), 4.60 (m, 2H), 3.93 (d, J = 5.60 Hz, 2H), 3.63 (s, 3H), 2.14 (s, 3H) |
| 206 | 2-(5-bromo-4-(4-(trifluoromethyl)phenyl)oxazol-2-yl)-2-(3-carbamoyl-2,4-difluorophenoxy)ethyl ((4-(2-methoxyethyl)-4H-1,2,4-triazol-3-yl)methyl)carbamate | 689.04 | $^1$H NMR (DMSO-d6) δ 8.36 (s, 1H), 8.15 (br s, 1H, D$_2$O exchangeable), 8.08 (d, J = 8.0 Hz, 2H), 8.03 (t, J = 5.60 Hz, 1H, D$_2$O exchangeable), 7.87 (d, J = 8.40 Hz, 2H), 7.85 (br s, 1H, D$_2$O exchangeable), 7.40 (m, 1H), 7.11 (m, 1H), 5.81 (t, J = 5.20 Hz, 1H), 4.63 (m, 2H), 4.35 (d, J = 5.60 Hz, 2H), 4.14 (t, J = 5.20 Hz, 2H), 3.52 (t, J = 5.20 Hz, 2H), 3.19 (s, 3H) |
| 207 | 2-(5-bromo-4-(4-(trifluoromethyl)phenyl)oxazol-2-yl)-2-(3-carbamoyl-2,4-difluorophenoxy)ethyl ((1-(2-methoxyethyl)-1H-imidazol-5-yl)methyl)carbamate | 688.09 | $^1$H NMR (DMSO-d6) δ 8.17 (br s, 1H), 8.09 (d, J = 8.40 Hz, 2H), 7.87-7.89 (m, 3H), 7.80 (t, J = 5.60 Hz, 1H), 7.50 (s, 1H), 7.37 (m, 1H), 7.08 (m, 1H), 6.69 (s, 1H), 5.81 (t, J = 5.20 Hz, 1H), 4.62 (m, 2H), 4.18 (d, J = 5.60 Hz, 2H), 4.05 (t, J = 5.20 Hz, 2H), 3.49 (t, J = 5.20 Hz, 2H), 3.18 (s, 3H) |
| 208 | 2-(5-bromo-4-(4-(trifluoromethyl)phenyl)oxazol-2-yl)-2-(3-carbamoyl-2,4-difluorophenoxy)ethyl ((6-methoxypyridin-3-yl)methyl)carbamate | 671.02 | $^1$H NMR (DMSO-d6) δ 8.15 (br s, 1H), 8.08 (d, J = 8.40 Hz, 2H), 8.0 (s, 1H), 7.93 (t, J = 5.60 Hz, 1H), 7.87-7.89 (m, 3H), 7.51 (m, 1H), 7.35 (m, 1H), 7.08 (m, 1H), 6.71 (d, J = 8.40 Hz, 1H), 5.83 (t, J = 5.20 Hz, 1H), 4.63 (m, 2H), 4.10 (d, J = 6.40 Hz, 2H), 3.79 (s, 3H) |

TABLE 1-continued

Characterisation of compounds by LCMS and $^1$H NMR

| Cpd No | Name | LCMS m/z = [M + H]+ | $^1$H NMR |
|---|---|---|---|
| 209 | 2-(5-bromo-4-(4-(trifluoromethyl)phenyl)oxazol-2-yl)-2-(3-carbamoyl-2,4-difluorophenoxy)ethyl ((2-methoxypyridin-4-yl)methyl)carbamate | 671.06 | $^1$H NMR (DMSO-d6) δ 8.15 (br s, 1H), 8.10 (d, J = 8.40 Hz, 2H), 8.03 (m, 2H), 7.87-7.89 (m, 3H), 7.37 (m, 1H), 7.10 (m, 1H), 6.80 (d, J = 5.20 Hz, 1H), 6.61 (s, 1H), 5.84 (t, J = 6.40 Hz, 1H), 4.66 (m, 2H), 4.16 (d, J = 6.0 Hz, 2H), 3.79 (s, 3H) |
| 210 | 2-(5-bromo-4-(4-(trifluoromethyl)phenyl)oxazol-2-yl)-2-(3-carbamoyl-2,4-difluorophenoxy)ethyl ((1-methyl-1H-benzo[d]imidazol-2-yl)methyl)carbamate | 694.1 | $^1$H NMR (DMSO-d6) δ 8.16 (br s, 1H), 8.06-8.08 (m, 3H), 7.85-7.88 (m, 3H), 7.55 (d, J = 8.0 Hz, 1H), 7.48 (d, J = 8.0 Hz, 1H), 7.39 (m, 1H), 7.14-7.23 (m, 2H), 7.08 (m, 1H), 5.80 (m, 1H), 4.64 (m, 2H), 4.49 (d, J = 5.60 Hz, 2H), 3.73 (s, 3H) |
| 211 | 2-(5-bromo-4-(4-(trifluoromethyl)phenyl)oxazol-2-yl)-2-(3-carbamoyl-2,4-difluorophenoxy)ethyl ((1,5-dimethyl-1H-pyrrol-2-yl)methyl)carbamate | 657.13 | $^1$H NMR (DMSO-d6) δ 8.14 (br s, 1H, D$_2$O exchangeable), 8.10 (d, J = 8.40 Hz, 2H), 7.87-7.89 (m, 3H, D$_2$O exchangeable 1H), 7.68 (t, J = 5.60 Hz, 1H, D$_2$O exchangeable), 7.37 (m, 1H), 7.08 (m, 1H), 5.80 (t, J = 5.60 Hz, 1H), 5.73 (m, 1H), 5.60 (m, 1H), 4.56-4.66 (m, 2H), 4.10 (d, J = 5.20 Hz, 2H), 3.30 (s, 3H), 2.07 (s, 3H) |
| 212 | 2-(5-bromo-4-(4-(trifluoromethyl)phenyl)oxazol-2-yl)-2-(3-carbamoyl-2,4-difluorophenoxy)ethyl ((1,3-dimethyl-1H-pyrazol-5-yl)methyl)carbamate | 658.09 | $^1$H NMR (DMSO-d6) δ 8.15 (br s, 1H), 8.09 (d, J = 8.40 Hz, 2H), 7.87-7.93 (m, 4H), 7.37 (m, 1H), 7.09 (m, 1H), 5.82 (m, 1H), 4.58-4.68 (m, 2H), 4.15 (d, J = 5.60 Hz, 2H), 3.62 (s, 3H), 2.06 (s, 3H) |
| 213 | 2-(5-bromo-4-(4-(trifluoromethyl)phenyl)oxazol-2-yl)-2-(3-carbamoyl-2,4-difluorophenoxy)ethyl ((1,5-dimethyl-1H-pyrazol-3-yl)methyl)carbamate | 658.08 | $^1$H NMR (DMSO-d6) δ 8.14 (br s, 1H), 8.10 (d, J = 8.40 Hz, 2H), 7.87-7.89 (m, 3H), 7.75 (m, 1H), 7.37 (m, 1H), 7.09 (m, 1H), 5.80 (m, 2H), 4.57-4.65 (m, 2H), 4.01 (d, J = 6.40 Hz, 2H), 3.60 (s, 3H), 2.12 (s, 3H) |
| 214 | 2-(5-bromo-4-(4-(trifluoromethyl)phenyl)oxazol-2-yl)-2-(3-carbamoyl-2,4-difluorophenoxy)ethyl ((6-methylpyridin-3-yl)methyl)carbamate | 655.03 | $^1$H NMR (DMSO-d6) δ 8.28 (s, 1H), 8.17 (br s, 1H), 8.09 (d, J = 8.40 Hz, 2H), 7.96 (t, J = 6.0 Hz, 1H), 7.87-7.89 (m, 3H), 7.47 (dd, J = 2.0 and 8.0 Hz respectively, 1H), 7.37 (m, 1H), 7.10 (m, 2H), 5.82 (t, J = 5.60 Hz, 1H), 4.57-4.69 (m, 2H), 4.14 (d, J = 5.60 Hz, 2H), 2.39 (s, 3H) |
| 215 | 2-(5-bromo-4-(4-(trifluoromethyl)phenyl)oxazol-2-yl)-2-(3-carbamoyl-2,4-difluorophenoxy)ethyl ((2-methylpyridin-3-yl)methyl)carbamate | 655.01 | $^1$H NMR (DMSO-d6) δ 8.28 (m, 1H), 8.15 (br s, 1H), 8.09 (d, J = 8.0 Hz, 2H), 7.96 (t, J = 5.60 Hz, 1H), 7.87-7.89 (m, 3H), 7.46 (d, J = 7.60 Hz, 1H), 7.38 (m, 1H), 7.09 (m, 2H), 5.83 (t, J = 5.20 Hz, 1H), 4.59-4.70 (m, 2H), 4.18 (d, J = 5.60 Hz, 2H), 2.41 (s, 3H) |
| 216 | 2-(5-bromo-4-(4-(trifluoromethyl)phenyl)oxazol-2-yl)-2-(3-carbamoyl-2,4-difluorophenoxy)ethyl ((3-methylpyridin-4-yl)methyl)carbamate | 655.02 | $^1$H NMR (DMSO-d6) δ 8.28 (s, 1H), 8.25 (m, 1H), 8.16 (br s, 1H), 8.10 (d, J = 8.0 Hz, 2H), 8.0 (t, J = 5.60 Hz, 1H), 7.88-7.90 (m, 3H), 7.37 (m, 1H), 7.05-7.12 (m, 2H), 5.84 (t, J = 5.20 Hz, 1H), 4.60-4.72 (m, 2H), 4.17 (d, J = 5.60 Hz, 2H), 2.20 (s, 3H) |
| 217 | 2-(5-bromo-4-(4-(trifluoromethyl)phenyl)oxazol-2-yl)-2-(3-carbamoyl-2,4-difluorophenoxy)ethyl (2-(2-oxopyridin-1(2H)-yl)ethyl)carbamate | 671.08 | $^1$H NMR (DMSO-d6) δ 8.16 (br s, 1H), 8.10 (d, J = 8.40 Hz, 2H), 7.90 (m, 3H), 7.34-7.52 (m, 4H), 7.11 (m, 1H), 6.35 (d, J = 5.60 Hz, 1H), 6.09 (t, J = 6.40 Hz, 1H), 5.78 (t, J = 5.60 Hz, 1H), 4.57 (m, 2H), 3.88 (t, J = 6.0 Hz, 2H), 3.25 (m, 2H) |

TABLE 1-continued

Characterisation of compounds by LCMS and ¹H NMR

| Cpd No | Name | LCMS m/z = [M + H]+ | ¹H NMR |
|---|---|---|---|
| 218 | 2,6-difluoro-3-((5-methyl-1,3,4-oxadiazol-2-yl)(4-(4-(trifluoromethyl)phenyl)oxazol-2-yl)methoxy)benzamide | 481.1 | ¹H NMR (DMSO-d6) δ 9.0 (s, 1H), 8.17 (br s, 1H), 8.0 (d, J = 8.0 Hz, 2H), 7.90 (br s, 1H), 7.83 (d, J = 8.80 Hz, 2H), 7.48 (m, 1H), 7.36 (s, 1H), 7.14 (m, 1H), 2.58 (s, 3H) |
| 219 | 3-(5-bromo-4-(4-(trifluoromethyl)phenyl)oxazol-2-yl)-3-(3-carbamoyl-2,4-difluorophenoxy)propane-1,2-diyl diacetate | 621.28 | ¹H NMR (MeOH-d4) δ 8.14 (d, J = 8.40 Hz, 2H), 7.78 (d, J = 8.0 Hz, 2H), 7.30 (m, 1H), 6.98 (m, 1H), 5.64 (m, 2H), 4.71 (m, 1H), 4.44 (m, 1H), 2.03 (s, 3H), 2.0 (s, 3H) |
| 220 | 2,6-difluoro-3-(2-hydroxy-1-(4-(6-(methylamino)pyridin-3-yl)oxazol-2-yl)ethoxy)benzamide | 391 | ¹H NMR (DMSO-d6) δ 8.40 (s, 1H), 8.37 (d, J = 2.0 Hz, 1H), 8.13 (br s, 1H, D₂O exchangeable), 7.84 (br s, 1H, D₂O exchangeable), 7.70 (dd, J = 2.40 and 8.80 Hz respectively, 1H), 7.30 (m, 1H), 7.07 (m, 1H), 6.69 (m, 1H, D₂O exchangeable), 6.49 (d, J = 8.80 Hz, 1H), 5.47 (t, J = 6.0 Hz, 1H), 5.35 (t, J = 6.0 Hz, 1H, D₂O exchangeable), 3.93-4.04 (m, 2H), 2.78 (s, 3H) |
| 221 | 3-(1-(5-bromo-4-propyloxazol-2-yl)-2-hydroxyethoxy)-2,6-difluorobenzamide | 404.9 | ¹H NMR (DMSO-d6) δ 8.12 (br s, 1H), 7.84 (br s, 1H), 7.25 (m, 1H), 7.06 (m, 1H), 5.36 (m, 2H), 3.95 (m, 2H), 2.35 (m, 2H), 1.56 (m, 2H), 0.84 (t, J = 7.20 Hz, 3H) |
| 222 | 3-(1-(4-(4-chloro-3-fluorophenyl)oxazol-2-yl)-2-hydroxyethoxy)-2,6-difluorobenzamide | 413.1 | ¹H NMR (DMSO-d6) δ 8.76 (s, 1H), 8.13 (br s, 1H), 7.84 (br s, 1H), 7.76-7.79 (m, 1H), 7.62-7.66 (m, 2H), 7.31 (m, 1H), 7.05 (m, 1H), 5.50 (t, J = 6.0 Hz, 1H), 5.38 (t, J = 6.0 Hz, 1H), 3.97-4.04 (m, 2H) |
| 223 | 2,6-difluoro-3-(1-(4-(2-fluorophenyl)oxazol-2-yl)-2-hydroxyethoxy)benzamide | 379.15 | ¹H NMR (DMSO-d6) δ 8.49 (d, J = 4.0 Hz, 1H), 8.14 (br s, 1H), 7.95 (m, 1H), 7.86 (br s, 1H), 7.28-7.43 (m, 4H), 7.06 (m, 1H), 5.53 (t, J = 6.0 Hz, 1H), 5.40 (t, J = 6.0 Hz, 1H), 4.0-4.05 (m, 2H) |
| 224 | 3-(1-(5-bromo-4-(6-(methylamino)pyridin-3-yl)oxazol-2-yl)-2-hydroxyethoxy)-2,6-difluorobenzamide | 469.05 | ¹H NMR (DMSO-d6) δ 8.48 (d, J = 2.0 Hz, 1H), 8.14 (br s, 1H), 7.86 (br s, 1H), 7.80 (dd, J = 2.40 and 8.80 Hz respectively, 1H), 7.35 (m, 1H), 7.08 (m, 1H), 6.86 (m, 1H), 6.54 (d, J = 8.80 Hz, 1H), 5.46 (t, J = 6.0 Hz, 1H), 5.40 (t, J = 5.60 Hz, 1H), 3.98 (t, J = 6.0 Hz, 2H), 2.78 (d, J = 4.80 Hz, 3H) |
| 225 | 3-(1-(5-bromo-4-(4-chloro-3-fluorophenyl)oxazol-2-yl)-2-hydroxyethoxy)-2,6-difluorobenzamide | 490.96 | ¹H NMR (DMSO-d6) δ 8.14 (br s, 1H), 7.86 (br s, 1H), 7.81 (m, 1H), 7.75 (m, 2H), 7.35 (m, 1H), 7.08 (m, 1H), 5.50 (t, J = 6.0 Hz, 1H), 5.42 (t, J = 6.0 Hz, 1H), 4.0 (t, J = 6.0 Hz, 2H) |
| 226 | 3-(1-(4-(2,4-difluorophenyl)oxazol-2-yl)-2-hydroxyethoxy)-2,6-difluorobenzamide | 397.14 | ¹H NMR (DMSO-d6) δ 8.48 (d, J = 8.0 Hz, 1H), 8.14 (br s, 1H, D₂O exchangeable), 7.94-8.00 (m, 1H), 7.85 (br s, 1H, D₂O exchangeable), 7.38-7.44 (m, 1H), 7.27-7.33 (m, 1H), 7.19-7.23 (m, 1H), 7.06 (t, J = 8.80 Hz, 1H), 5.52-5.53 (t, J = 6.40 Hz, 1H), 5.38-5.41 (t, J = 5.60 Hz, 1H, D₂O exchangeable), 3.93-4.06 (m, 2H) |
| 227 | 3-(1-(4-(4-chloro-2-methoxyphenyl)oxazol-2-yl)-2-hydroxyethoxy)-2,6-difluorobenzamide | 425.2 | ¹H NMR (DMSO-d6) δ 8.44 (s, 1H), 8.12 (b rs, 1H), 7.92 (d, J = 8.40 Hz, 1H), 7.84 (br s, 1H), 7.26-7.31 (m, 1H), 7.20 (s, 1H), 7.10 (d, J = 8.40 Hz, 1H), 7.05 (m, 1H), 5.50 (t, J = 5.60 Hz, 1H), 5.36 (t, J = 5.60 Hz, 1H), 4.00-4.32 (m, 2H), 3.94 (s, 3H) |

TABLE 1-continued

Characterisation of compounds by LCMS and $^1$H NMR

| Cpd No | Name | LCMS m/z = [M + H]+ | $^1$H NMR |
|---|---|---|---|
| 228 | 2,6-difluoro-3-(1-(4-(2-fluoro-4-methoxyphenyl)oxazol-2-yl)-2-hydroxyethoxy)benzamide | 409.19 | $^1$H NMR (DMSO-d6) δ 8.35 (d, J = 3.60 Hz, 1H), 8.14 (br s, 1H), 7.82-7.86 (m, 2H), 7.27-7.33 (m, 1H), 7.03-7.08 (m, 1H), 6.98-6.99 (d, J = 2.0 and 8.40 Hz respectively, 1H), 6.88-6.91 (dd, J = 2.0 and 8.40 Hz respectively, 1H), 5.50 (t, J = 5.60 Hz, 1H), 5.38 (t, J = 5.60 Hz, 1H), 3.99-4.04 (m, 2H), 3.80 (s, 3H) |
| 229 | 3-(1-(5-bromo-4-(2-fluorophenyl)oxazol-2-yl)-2-hydroxyethoxy)-2,6-difluorobenzamide | 457.14 | $^1$H NMR (DMSO-d6) δ 8.14 (br s, 1H), 7.86 (br s, 1H), 7.50-7.60 (m, 2H), 7.31-7.37 (m, 3H), 7.09 (m, 1H), 5.51 (t, J = 6.0 Hz, 1H), 5.43 (t, J = 6.0 Hz, 1H), 4.0 (t, J = 6.0 Hz, 2H) |
| 230 | 3-(1-(5-bromo-4-(6-methoxypyridin-3-yl)oxazol-2-yl)-2-hydroxyethoxy)-2,6-difluorobenzamide | 470.08 | $^1$H NMR (DMSO-d6) δ 8.64 (m, 1H), 8.14 (br s, 1H), 8.10 (dd, J = 2.40 and 8.40 Hz respectively, 1H), 7.85 (br s, 1H), 7.34 (m, 1H), 7.08 (m, 1H), 6.97 (d, J = 8.80 Hz, 1H), 5.50 (t, J = 6.0 Hz, 1H), 5.41 (t, J = 6.0 Hz, 1H), 4.0 (t, J = 6.0 Hz, 2H), 3.89 (s, 3H) |
| 231 | 3-(1-(5-bromo-4-(6-methylpyridin-3-yl)oxazol-2-yl)-2-hydroxyethoxy)-2,6-difluorobenzamide | 454.06 | $^1$H NMR (DMSO-d6) δ 8.91 (s, 1H), 8.13 (br s, 1H), 8.09 (m, 1H), 7.85 (br s, 1H), 7.40 (d, J = 8.40 Hz, 1H), 7.34 (m, 1H), 7.08 (m, 1H), 5.51 (t, J = 6.0 Hz, 1H), 5.42 (m, 1H), 4.0 (t, J = 6.0 Hz, 2H), 2.50 (s, 3 H, merged with DMSO signal) |
| 232 | 3-(1-(5-bromo-4-(5-bromo-4-chloro-2-methoxyphenyl)oxazol-2-yl)-2-hydroxyethoxy)-2,6-difluorobenzamide | 580.92 | $^1$H NMR (DMSO-d6) δ 8.15 (br s, 1H), 7.87 (br s, 1H), 7.69 (s, 1H), 7.44 (s, 1H), 7.35 (m, 1H), 7.09 (m, 1H), 5.48 (t, J = 6.0 Hz, 1H), 5.42 (t, J = 6.0 Hz, 1H), 3.98 (t, J = 5.60 Hz, 2H), 3.84 (s, 3H) |
| 233 | 3-(1-(5-bromo-4-(2,4-difluorophenyl)oxazol-2-yl)-2-hydroxyethoxy)-2,6-difluorobenzamide | 475.01 | $^1$H NMR (DMSO-d6) δ 8.14 (br s, 1H), 7.86 (br s, 1H), 7.64 (m, 1H), 7.43 (m, 1H), 7.35 (m, 1H), 7.24 (m, 1H), 7.08 (m, 1H), 5.50 (m, 1H), 5.42 (t, J = 5.60 Hz, 1H), 4.0 (t, J = 5.60 Hz, 2H) |
| 233A | (S)-3-(1-(5-bromo-4-(2,4-difluorophenyl)oxazol-2-yl)-2-hydroxyethoxy)-2,6-difluorobenzamide | 474.94 | $^1$H NMR (DMSO-d6) δ 8.15 (br s, 1H), 7.86 (br s, 1H), 7.63 (m, 1H), 7.41 (m, 1H), 7.34 (m, 1H), 7.24 (m, 1H), 7.08 (m, 1H), 5.50 (t, J = 6.0 Hz, 1H), 5.43 (br s, 1H), 4.0 (m, 2H) |
| 233B | (R)-3-(1-(5-bromo-4-(2,4-difluorophenyl)oxazol-2-yl)-2-hydroxyethoxy)-2,6-difluorobenzamide | 474.97 | $^1$H NMR (DMSO-d6) δ 8.14 (br s, 1H), 7.86 (br s, 1H), 7.63 (m, 1H), 7.41 (m, 1H), 7.34 (m, 1H), 7.24 (m, 1H), 7.08 (m, 1H), 5.50 (t, J = 5.60 Hz, 1H), 5.42 (br s, 1H), 4.01 (m, 2H) |
| 234 | 3-(1-(5-bromo-4-(2-fluoro-4-methoxyphenyl)oxazol-2-yl)-2-hydroxyethoxy)-2,6-difluorobenzamide | 487.13 | $^1$H NMR (DMSO-d6) δ 8.14 (br s, 1H), 7.86 (br s, 1H), 7.47 (m, 1H), 7.35 (m, 1H), 7.08 (m, 1H), 6.90-6.98 (m, 2H), 5.48 (t, J = 5.60 Hz, 1H), 5.42 (t, J = 5.60 Hz, 1H), 3.99 (t, J = 5.60 Hz, 2H), 3.81 (s, 3H) |
| 235 | 3-(1-(5-bromo-4-(4-chloro-2-fluorophenyl)oxazol-2-yl)-2-hydroxyethoxy)-2,6-difluorobenzamide | 490.96 | $^1$H NMR (DMSO-d6) δ 8.13 (br s, 1H), 7.85 (br s, 1H), 7.62 (m, 2H), 7.42 (m, 1H), 7.35 (m, 1H), 7.08 (m, 1H), 5.50 (t, J = 5.60 Hz, 1H), 5.42 (t, J = 5.60 Hz, 1H), 4.0 (t, J = 5.60 Hz, 2H) |
| 236 | 3-(1-(5-bromo-4-(5-cyanothiophen-2-yl)oxazol-2-yl)-2-hydroxyethoxy)-2,6-difluorobenzamide | 470.04 | $^1$H NMR (MeOH-d4) δ 7.77 (d, J = 4.0 Hz, 1H), 7.68 (d, J = 4.0 Hz, 1H), 7.29 (m, 1H), 6.96 (m, 1H), 5.40 (t, J = 6.0 Hz, 1H), 4.09-4.19 (m, 2H) |

TABLE 1-continued

Characterisation of compounds by LCMS and $^1$H NMR

| Cpd No | Name | LCMS m/z = [M + H]+ | $^1$H NMR |
|---|---|---|---|
| 237 | 3-(1-(5-bromo-4-(5-bromothiophen-2-yl)oxazol-2-yl)-2-hydroxyethoxy)-2,6-difluorobenzamide | 522.98 | $^1$H NMR (DMSO-d6) δ 8.13 (br s, 1H, D$_2$O exchangeable), 7.85 (br s, 1H, D$_2$O exchangeable), 7.37 (d, J = 4.0 Hz, 1H), 7.28-7.33 (m, 2H), 7.05-7.09 (m, 1H), 5.48 (t, J = 5.60 Hz, 1H), 5.41 (br s, 1H, D$_2$O exchangeable), 3.96-4.01 (m, 2H) |
| 238 | 3-(1-(5-bromo-4-(5-methoxypyridin-2-yl)oxazol-2-yl)-2-hydroxyethoxy)-2,6-difluorobenzamide | 470.13 | $^1$H NMR (DMSO-d6) δ 8.38 (br s, 1H), 8.13 (br s, 1H), 7.84 (d, J = 8.80 Hz, 2H), 7.48 (m, 1H), 7.33 (m, 1H), 7.07 (m, 1H), 5.48 (t, J = 6.0 Hz, 1H), 5.41 (m, 1H), 3.99 (m, 2H), 3.87 (s, 3H) |
| 239 | 3-(1-(5-bromo-4-(4-chloro-2-methylphenyl)oxazol-2-yl)-2-hydroxyethoxy)-2,6-difluorobenzamide | 487.06 | $^1$H NMR (DMSO-d6) δ 8.13 (br s, 1H), 7.85 (br s, 1H), 7.43 (s, 1H), 7.30-7.35 (m, 3H), 7.08 (m, 1H), 5.47 (t, J = 6.0 Hz, 1H), 5.41 (t, J = 6.0 Hz, 1H), 4.0 (t, J = 6.0 Hz, 2H), 2.21 (s, 3H) |
| 240 | 3-(1-(5-bromo-4-(4,5-dimethylthiazol-2-yl)oxazol-2-yl)-2-hydroxyethoxy)-2,6-difluorobenzamide | 474.04 | $^1$H NMR (DMSO-d6) δ 8.13 (br s, 1H), 7.84 (br s, 1H), 7.32 (m, 1H), 7.07 (m, 1H), 5.47 (t, J = 6.0 Hz, 1H), 5.41 (t, J = 6.0 HZ, 1H), 3.98 (t, J = 6.0 Hz, 2H), 2.38 (s, 3H), 2.31 (s, 3H) |
| 241 | 3-(1-(5-bromo-4-(6-chloropyridin-3-yl)oxazol-2-yl)-2-hydroxyethoxy)-2,6-difluorobenzamide | 474.04 | $^1$H NMR (DMSO-d6) δ 8.86 (m, 1H), 8.27 (dd, J = 2.40 and 8.40 Hz, 1H), 8.13 (br s, 1H), 7.85 (br s, 1H), 7.68 (d, J = 8.40 Hz, 1H), 7.36 (m, 1H), 7.07 (m, 1H), 5.52 (t, J = 6.0 Hz, 1H), 5.42 (t, J = 6.0 Hz, 1H), 4.01 (t, J = 6.0 Hz, 2H) |
| 242 | 3-(1-(5-bromo-4-(4-(2-methoxyethoxy)phenyl)oxazol-2-yl)-2-hydroxyethoxy)-2,6-difluorobenzamide | 513.12 | $^1$H NMR (DMSO-d6) δ 8.14 (br s, 1H), 7.86 (br s, 1H), 7.80 (d, J = 8.40 Hz, 2H), 7.33 (m, 1H), 7.07 (m, 3H), 5.48 (t, J = 5.60 Hz, 1H), 5.41 (t, J = 5.60 Hz, 1H), 4.13 (m, 2H), 3.99 (t, J = 6.0 Hz, 2H), 3.66 (m, 2H), 3.30 (s, 3H) |
| 243 | 3-(1-(5-bromo-4-(thiophen-2-yl)oxazol-2-yl)-2-hydroxyethoxy)-2,6-difluorobenzamide | 445.04 | $^1$H NMR (MeOH-d4) δ 7.60 (d, J = 3.20 Hz, 1H), 7.48 (d, J = 4.80 Hz, 1H), 7.26-7.32 (m, 1H), 7.11-7.13 (m, 1H), 6.96 (t, J = 8.80 Hz, 1H), 5.38 (t, J = 6.0 Hz, 1H), 4.08-4.18 (m, 2H) |
| 244 | 3-(1-(5-bromo-4-(5-methylthiophen-2-yl)oxazol-2-yl)-2-hydroxyethoxy)-2,6-difluorobenzamide | 459.06 | $^1$H NMR (DMSO-d6) δ 8.13 (br s, 1H), 7.85 (br s, 1H), 7.28-7.34 (m, 2H), 7.07 (m, 1H), 6.86 (m, 1H), 5.46 (t, J = 6.0 Hz, 1H), 5.40 (m, 1H), 3.98 (m, 2H), 2.47 (s, 3H) |
| 245 | 3-(1-(5-bromo-4-(2,4-dimethylthiazol-5-yl)oxazol-2-yl)-2-hydroxyethoxy)-2,6-difluorobenzamide | 474.07 | $^1$H NMR (DMSO-d6) δ 8.12 (br s, 1H), 7.84 (br s, 1H), 7.33 (m, 1H), 7.08 (m, 1H), 5.48 (t, J = 6.0 Hz, 1H), 5.40 (t, J = 6.0 Hz, 1H), 3.99 (t, J = 6.0 Hz, 2H), 2.63 (s, 3H), 2.42 (s, 3H) |
| 246 | methyl 4-(5-bromo-2-(1-(3-carbamoyl-2,4-difluorophenoxy)-2-hydroxyethyl)oxazol-4-yl)benzoate | 497.11 | $^1$H NMR (DMSO-d6) δ 8.14 (br s, 1H), 8.09 (d, J = 8.40 Hz, 2H), 8.04 (d, J = 8.40 Hz, 2H), 7.86 (br s, 1H), 7.31-7.37 (m, 1H), 7.05-7.10 (m, 1H), 5.52 (t, J = 6.0 Hz, 1H), 5.43 (t, J = 6.0 Hz, 1H), 4.01 (t, J = 6.0 Hz, 2H), 3.87 (s, 3H) |
| 247B | (R)-3-(1-(5-bromo-4-(thiazol-5-yl)oxazol-2-yl)-2-hydroxyethoxy)-2,6-difluorobenzamide | 446.35 | $^1$H NMR (DMSO-d6) δ 9.20 (s, 1H), 8.30 (s, 1H), 8.15 (br s, 1H), 7.87 (br s, 1H), 7.33 (m, 1H), 7.08 (m, 1H), 5.50 (t, J = 6.0 Hz, 1H), 5.43 (t, J = 6.0 Hz, 1H), 3.98 (t, J = 5.60 Hz, 2H) |
| 248 | 3-(1-(5-bromo-4-(3,4-difluorophenyl)oxazol-2-yl)-2-hydroxyethoxy)-2,6-difluorobenzamide | 475.07 | $^1$H NMR (DMSO-d6) δ 8.15 (br s, 1H), 7.86 (m, 2H), 7.72 (m, 1H), 7.60 (m, 1H), 7.34 (m, 1H), 7.08 (m, 1H), 5.43-5.50 (m, 2H), 4.0 (m, 2H) |

TABLE 1-continued

Characterisation of compounds by LCMS and $^1$H NMR

| Cpd No | Name | LCMS m/z = [M + H]+ | $^1$H NMR |
|---|---|---|---|
| 249B | (R)-3-(1-(5-bromo-4-(6-cyanopyridin-3-yl)oxazol-2-yl)-2-hydroxyethoxy)-2,6-difluorobenzamide | 464.99 | $^1$H NMR (DMSO-d6) δ 9.20 (d, J = 1.20 Hz, 1H), 8.45 (dd, J = 2.0 and 8.40 Hz respectively, 1H), 8.18 (d, J = 8.40 Hz, 1H), 8.14 (br s, 1H), 7.87 (br s, 1H), 7.35 (m, 1H), 7.08 (m, 1H), 5.55 (t, J = 6.0 Hz, 1H), 5.44 (t, J = 6.0 Hz, 1H), 4.01 (t, J = 6.0 Hz, 2H) |
| 250B | (R)-3-(1-(5-bromo-4-(5-chlorothiophen-2-yl)oxazol-2-yl)-2-hydroxyethoxy)-2,6-difluorobenzamide | 478.98 | $^1$H NMR (DMSO-d6) δ 8.17 (br s, 1H), 7.85 (br s, 1H), 7.40 (d, J = 4.0 Hz, 1H), 7.32 (m, 1H), 7.22 (d, J = 4.0 Hz, 1H), 7.07 (m, 1H), 5.48 (t, J = 6.0 Hz, 1H), 5.42 (t, J = 6.0 Hz, 1H), 3.97 (t, J = 6.0 Hz, 2H) |
| 251 | 4-(5-bromo-2-(1-(3-carbamoyl-2,4-difluorophenoxy)-2-hydroxyethyl)oxazol-4-yl)benzoic acid | 483.17 | $^1$H NMR (DMSO-d6) δ 13.10 (br s, 1H), 8.15 (br s, 1H), 7.99-8.06 (m, 4H), 7.86 (br s, 1H), 7.35 (m, 1H), 7.08 (m, 1H), 5.52 (t, J = 5.60 Hz, 1H), 5.43 (t, J = 5.60 Hz, 1H), 4.01 (t, J = 6.0 Hz, 2H) |
| 252 | 4-(5-bromo-2-(1-(3-carbamoyl-2,4-difluorophenoxy)-2-hydroxyethyl)oxazol-4-yl)-N,N-dimethylbenzamide | 510.04 | $^1$H NMR (DMSO-d6) δ 8.15 (br s, 1H), 7.93 (m, 2H), 7.86 (br s, 1H), 7.53 (m, 2H), 7.33 (m, 1H), 7.08 (m, 1H), 5.51 (m, 1H), 5.43 (m, 1H), 4.01 (m, 2H), 2.98 (s, 3H), 2.92 (s, 3H) |
| 253B | (R)-3-(1-(5-bromo-4-(2,3-dihydrobenzofuran-5-yl)oxazol-2-yl)-2-hydroxyethoxy)-2,6-difluorobenzamide | 481.11 | $^1$H NMR (DMSO-d6) δ 8.22 (br s, 1H), 7.97 (br s, 1H), 7.79 (s, 1H), 7.62 (m, 1H), 7.32 (m, 1H), 7.08 (m, 1H), 6.88 (m, 1H), 5.41-5.55 (m, 2H), 4.57 (m, 2H), 3.99 (m, 2H), 3.23 (m, 2H) |
| 254B | (R)-3-(1-(4-(benzofuran-5-yl)-5-bromooxazol-2-yl)-2-hydroxyethoxy)-2,6-difluorobenzamide | 479.01 | $^1$H NMR (DMSO-d6) δ 8.15 (br s, 2H), 8.06 (d, J = 1.60 Hz, 1H), 7.82-7.86 (m, 2H), 7.71 (d, J = 8.80 Hz, 1H), 7.36 (m, 1H), 7.06-7.11 (m, 2H), 5.51 (t, J = 6.0 Hz, 1H), 5.43 (t, J = 5.60 Hz, 1H), 4.02 (t, J = 6.0 Hz, 2H) |
| 255B | (R)-3-(1-(5-bromo-4-(4-(morpholine-4-carbonyl)phenyl)oxazol-2-yl)-2-hydroxyethoxy)-2,6-difluorobenzamide | 552.2 | $^1$H NMR (DMSO-d6) δ 8.14 (br s, 1H), 7.95 (d, J = 8.0 Hz, 2H), 7.85 (br s, 1H), 7.55 (d, J = 7.60 Hz, 2H), 7.35 (m, 1H), 7.08 (m, 1H), 5.51 (t, J = 6.0 Hz, 1H), 5.46 (br s, 1H), 4.01 (m, 2H), 3.50-3.70 (br s, 8H) |
| 256 | 3-(1-(5-bromo-4-(3-bromo-4-(pyrrolidin-1-yl)phenyl)oxazol-2-yl)-2-hydroxyethoxy)-2,6-difluorobenzamide | 586.04 | $^1$H NMR (DMSO-d6) δ 8.14 (br s, 1H), 7.95 (s, 1H), 7.86 (br s, 1H), 7.73 (m, 1H), 7.32 (m, 1H), 7.02-7.10 (m, 2H), 5.47 (m, 1H), 5.41 (m, 1H), 3.98 (m, 2H), 3.38 (m, 4H), 1.88 (m, 4H) |
| 257B | (R)-3-(1-(5-bromo-4-(2-methoxypyrimidin-5-yl)oxazol-2-yl)-2-hydroxyethoxy)-2,6-difluorobenzamide | 471.16 | $^1$H NMR (DMSO-d6) δ 8.99 (s, 2H), 8.14 (br s, 1H), 7.86 (br s, 1H), 7.35 (m, 1H), 7.10 (m, 1H), 5.52 (t, J = 5.60 Hz, 1H), 5.43 (t, J = 5.60 Hz, 1H), 4.0 (m, 2H), 3.97 (s, 3H) |
| 258 | 3-(1-(2-(4-chlorophenyl)thiazol-4-yl)-2-hydroxyethoxy)-2,6-difluorobenzamide | 411.12 | $^1$H NMR (DMSO-d6) δ 8.11 (br s, 1H), 7.95 (d, J = 8.40 Hz, 2H), 7.82 (br s, 1H), 7.74 (s, 1H), 7.57 (d, J = 8.0 Hz, 2H), 7.25 (m, 1H), 7.0 (m, 1H), 5.50 (t, J = 5.60 Hz, 1H), 5.20 (t, J = 5.60 Hz, 1H), 3.93 (m, 2H) |
| 259 | 2,6-difluoro-3-(2-hydroxy-1-(4-(4-methoxyphenyl)thiazol-2-yl)ethoxy)benzamide | 407.16 | $^1$H NMR (DMSO-d6) δ 8.14 (br s, 1H), 7.96 (s, 1H), 7.86-7.88 (m, 3H), 7.32 (m, 1H), 6.98-7.06 (m, 3H), 5.72 (m, 1H), 5.40 (m, 1H), 3.93-3.98 (m, 2H), 3.79 (s, 3H) |

TABLE 1-continued

Characterisation of compounds by LCMS and $^1$H NMR

| Cpd No | Name | LCMS m/z = [M + H]+ | $^1$H NMR |
|---|---|---|---|
| 260 | 2,6-difluoro-3-(2-hydroxy-1-(4-(5-methoxypyridin-2-yl)thiazol-2-yl)ethoxy)benzamide | 408.17 | $^1$H NMR (DMSO-d6) δ 8.33 (d, J = 2.80 Hz, 1H), 8.15 (br s, 1H), 8.09 (s, 1H), 8.0 (d, J = 8.80 Hz, 1H), 7.86 (br s, 1H), 7.48 (dd, J = 2.80 and 8.80 Hz, 1H), 7.35 (m, 1H), 7.06 (m, 1H), 5.73 (t, J = 5.60 Hz, 1H), 5.42 (t, J = 5.60 Hz, 1H), 3.93-4.04 (m, 2H), 3.86 (s, 3H) |
| 261 | 2,6-difluoro-3-(2-hydroxy-1-(4-(5-methoxypyrazin-2-yl)thiazol-2-yl)ethoxy)benzamide | 409.21 | $^1$H NMR (DMSO-d6) δ 8.78 (s, 1H), 8.37 (s, 1H), 8.17 (s, 1H), 8.15 (br s, 1H), 7.86 (br s, 1H), 7.35 (m, 1H), 7.05 (m, 1H), 5.76 (t, J = 4.80 Hz, 1H), 5.43 (t, J = 5.60 Hz, 1H), 4.0 (m, 2H), 3.96 (s, 3H) |
| 262 | 2,6-difluoro-3-(2-hydroxy-1-(4-(4-methoxyphenethyl)thiazol-2-yl)ethoxy)benzamide | 435.2 | $^1$H NMR (DMSO-d6) δ 8.14 (br s, 1H), 7.85 (br s, 1H), 7.23-7.29 (m, 2H), 7.09 (d, J = 8.40 Hz, 2H), 7.01 (m, 1H), 6.81 (d, J = 8.80 Hz, 2H), 5.64 (m, 1H), 5.36 (t, J = 5.60 Hz, 1H), 3.85-3.91 (m, 2H), 3.70 (s, 3H), 2.86-2.94 (m, 4H) |
| 263 | 4-(2-(5-bromo-4-(2,4-difluorophenyl)oxazol-2-yl)-2-(3 carbamoyl-2,4-difluorophenoxy)ethoxy)-4-oxobutanoic acid | 573.1 | $^1$H NMR (DMSO-d6 + D$_2$O) δ 7.62-7.66 (m, 1H), 7.35-7.41 (m, 2H), 7.19-7.24 (m, 1H), 7.06-7.14 (m, 1H), 5.74 (t, J = 5.60 Hz, 1H), 4.61 (m, 2H), 3.24 (t, J = 6.0 Hz, 1H), 3.0 (m, 2H), 2.39 (t, J = 6.80 Hz, 2H), 2.20 (t, J = 6.80 Hz, 2H), 1.65 (m, 2H), 1.55 (m, 2H) |
| 264 | 2,6-difluoro-3-(2-hydroxy-1-(4-(6-methylpyridin-3-yl)thiazol-2-yl)ethoxy)benzamide | 392.24 | $^1$H NMR (DMSO-d6) δ 9.01 (s, 1H), 8.22 (s, 1H), 8.16 (m, 2H), 7.86 (br s, 1H), 7.32-7.38 (m, 2H), 7.04 (m, 1H), 5.75 (m, 1H), 5.42 (m, 1H, D$_2$O exchangeable), 3.92-4.03 (m, 2H), 2.45 (s, 3H) |
| 265B | (R)-3-(1-(5-bromo-4-(2,4-difluorophenyl)oxazol-2-yl)-2-(2-hydroxyethoxy)ethoxy)-2,6-difluorobenzamide | 519.12 | $^1$H NMR (MeOH-d4) δ 7.58-7.64 (m, 1H), 7.31-7.37 (m, 1H), 7.07-7.13 (m, 2H), 6.97 (m, 1H), 5.57 (t, J = 6.0 Hz, 1H), 4.15 (m, 2H), 3.65-3.69 (m, 4H) |
| 266B | (R)-3-(1-(6-chlorothiazolo[5,4-b]pyridin-2-yl)-2-hydroxyethoxy)-2,6-difluorobenzamide | 386.1 | $^1$H NMR (DMSO-d6) δ 8.71 (s, 1H), 8.67 (s, 1H), 8.16 (br s, 1H), 7.88 (br s, 1H), 7.36 (m, 1H), 7.05 (m, 1H), 5.83 (m, 1H), 5.49 (t, J = 5.20 Hz, 1H), 4.02 (m, 2H) |
| 267 | 2-(1-(3-carbamoyl-2,4-difluorophenoxy)-2-hydroxyethyl)-4-(4-chlorophenyl)thiazole 3-oxide | 427.04 | $^1$H NMR (DMSO-d6) δ 8.26 (s, 1H), 8.15 (br s, 1H), 8.06 (d, J = 8.80 Hz, 2H), 7.86 (br s, 1H), 7.55 (d, J = 8.80 Hz, 2H), 7.38 (m, 1H), 7.09 (m, 1H), 5.89 (t, J = 4.0 Hz, 1H), 5.58 (t, J = 5.60 Hz, 1H), 4.0 (m, 1H), 3.90 (m, 1H) |
| 268A | (S)-2,6-difluoro-3-(1-(4-(4-methoxyphenyl)oxazol-2-yl)ethoxy)benzamide | 374.9 | $^1$H NMR (acetone-d6) δ 8.27 (s, 1H), 7.74 (d, J = 8.8 Hz, 2H), 7.43 (br s, 1H), 7.30 (td, J = 9.2, 5.3 Hz, 1H), 7.13 (br s, 1H), 6.98 (d, J = 8.8 Hz, 2H), 6.95 (td, J = 8.9, 1.9 Hz, 1H), 5.57 (q, J = 6.6 Hz, 1H), 3.83 (s, 3H), 1.80 (d, J = 6.6 Hz, 3H). |
| 268B | (R)-2,6-difluoro-3-(1-(4-(4-methoxyphenyl)oxazol-2-yl)ethoxy)benzamide | 375.0 | $^1$H NMR (acetone-d6) δ 8.26 (s, 1H), 7.74 (d, J = 8.9 Hz, 2H), 7.43 (br s, 1H), 7.30 (td, J = 9.2, 5.3 Hz, 1H), 7.14 (br s, 1H), 6.98 (d, J = 8.8 Hz, 2H), 6.95 (td, J = 9.0, 1.8 Hz, 1H), 5.57 (q, J = 6.6 Hz, 1H), 3.82 (s, 3H), 1.80 (d, J = 6.6 Hz, 3H). |

TABLE 1-continued

Characterisation of compounds by LCMS and $^1$H NMR

| Cpd No | Name | LCMS m/z = [M + H]+ | $^1$H NMR |
|---|---|---|---|
| 269 | 3-(1-(5-cyclopropyl-4-(4-(trifluoromethyl)phenyl)oxazol-2-yl)-2-hydroxyethoxy)-2,6-difluorobenzamide | 468.94 | $^1$H NMR (CDCl$_3$) δ 7.90 (d, J = 8.3 Hz, 2H), 7.70 (d, J = 8.3 Hz, 2H), 7.22 (td, J = 9.0, 5.2 Hz, 1H), 6.89 (td, J = 9.1, 1.8 Hz, 1H), 6.12 (d, J = 10.2 Hz, 2H), 5.25 (dd, J = 6.2, 4.7 Hz, 1H), 4.28 (dt, J = 11.8, 5.8 Hz, 1H), 4.23-4.08 (m, 1H), 2.95 (dt, J = 23.0, 11.5 Hz, 1H), 2.19-2.08 (m, 1H), 1.18-1.09 (m, 2H), 1.00-0.91 (m, 2H). |
| 270 | 2-fluoro-3-(2-hydroxy-1-(5-(methylthio)-4-(4-(trifluoromethyl)phenyl)oxazol-2-yl)ethoxy)-6-(methylthio)benzamide | 502.9 | $^1$H NMR (CDCl$_3$) δ 8.16 (d, J = 8.4 Hz, 2H), 7.71 (d, J = 8.4 Hz, 2H), 7.19 (dd, J = 9.1, 4.7 Hz, 1H), 7.08 (t, J = 8.6 Hz, 1H), 5.94 (s, 1H), 5.80 (s, 1H), 5.34 (dd, J = 7.1, 4.0 Hz, 1H), 4.43-4.27 (m, 1H), 4.25-4.11 (m, 1H), 3.30-3.21 (m, 1H), 2.54 (s, 3H), 2.51 (s, 3H). |
| 271 | 2,6-difluoro-3-(2-hydroxy-1-(5-(methylthio)-4-(4-(trifluoromethyl)phenyl)oxazol-2-yl)ethoxy)benzamide | 474.91 | $^1$H NMR (CDCl$_3$) δ 8.13 (d, J = 8.1 Hz, 2H), 7.70 (d, J = 8.2 Hz, 2H), 7.25 (dd, J = 9.0, 5.2 Hz, 1H), 6.91 (td, J = 9.1, 1.7 Hz, 1H), 6.07 (s, 2H), 5.31 (dd, J = 6.1, 4.6 Hz, 1H), 4.41-4.28 (m, 1H), 4.28-4.15 (m, 1H), 2.90-2.77 (m, 1H), 2.50 (s, 3H). |
| 272B | (R)-2,6-difluoro-3-(2-hydroxy-1-(4-(4-(trifluoromethyl)phenyl)oxazol-2-yl)ethoxy)benzamide | 429.1 | $^1$H NMR (acetone-d6) δ 8.59 (s, 1H), 8.04 (dd, J = 8.7, 0.7 Hz, 2H), 7.77 (dd, J = 8.7, 0.6 Hz, 2H), 7.44 (br s, 1H), 7.35 (td, J = 9.2, 5.2 Hz, 1H), 7.14 (br s, 1H), 6.96 (ddd, J = 9.2, 8.7, 2.1 Hz, 1H), 5.51 (dd, J = 6.5, 5.6 Hz, 1H), 4.62-4.48 (m, 1H), 4.28-4.16 (m, 2H). |
| 273B | (R)-3-(1-(5-bromo-4-(4-(difluoromethoxy)phenyl)oxazol-2-yl)-2-hydroxyethoxy)-2,6-difluorobenzamide | 504.9 | $^1$H NMR (acetone-d6) δ 8.02 (d, J = 9.0 Hz, 2H), 7.44 (br s, 1H), 7.37 (td, J = 9.2, 5.2 Hz, 1H), 7.31 (d, J = 9.0 Hz, 2H), 7.14 (br s, 1H), 7.07 (t, J = 74.0 Hz, 1H), 6.98 (ddd, J = 9.2, 8.8, 2.1 Hz, 1H), 5.47 (t, J = 6.1 Hz, 1H), 4.57 (br t, J = 5.6 Hz, 1H), 4.27-4.15 (m, 2H). |
| 274B | (R)-3-(1-(4-(4-(difluoromethoxy)phenyl)oxazol-2-yl)-2-hydroxyethoxy)-2,6-difluorobenzamide | 427.0 | $^1$H NMR (acetone-d6) δ 8.42 (s, 1H), 7.87 (d, J = 8.7 Hz, 2H), 7.46 (br s, 1H), 7.33 (td, J = 9.2, 5.2 Hz, 1H), 7.24 (d, J = 8.6 Hz, 2H), 7.16 (br s, 1H), 7.03 (t, J = 74.2 Hz, 1H), 6.95 (td, J = 8.9, 2.0 Hz, 1H), 5.61-5.39 (m, 1H), 4.54 (br s, 1H), 4.27-4.13 (m, 2H). |
| 275B | (R)-3-(1-(5-bromo-4-ethyloxazol-2-yl)-2-hydroxyethoxy)-2,6-difluorobenzamide | 391.0 | $^1$H NMR (acetone-d6) δ 7.44 (br s, 1H), 7.29 (td, J = 9.2, 5.2 Hz, 1H), 7.13 (br s, 1H), 6.96 (ddd, J = 9.2, 8.7, 2.1 Hz, 1H), 5.35 (dd, J = 6.4, 5.8 Hz, 1H), 4.53-4.42 (m, 1H), 4.24-4.04 (m, 2H), 2.44 (q, J = 7.6 Hz, 2H), 1.15 (t, J = 7.6 Hz, 3H). |
| 276 | benzyl (2-(3-carbamoyl-2,4-difluorophenoxy)-2-(4-(4-(trifluoromethyl)phenyl)oxazol-2-yl)ethyl)carbamate | 562.01 | $^1$H NMR (CDCl$_3$) δ 7.99 (s, 1H), 7.84 (d, J = 8.2 Hz, 2H), 7.68 (d, J = 8.2 Hz, 2H), 7.37-7.33 (m, 5H), 7.25-7.19 (m, 1H), 6.87 (t, J = 8.5 Hz, 1H), 6.00 (bs, 1H), 5.96 (bs, 1H), 5.46 (t, J = 5.6 Hz, 1H), 5.39 (t, J = 5.9 Hz, 1H), 5.13, (s, 2H), 4.07-3.95 (m, 2H). |
| 277 | 3-(1-(5-butyl-4-(4-(trifluoromethyl)phenyl)oxazol-2-yl)-2-hydroxyethoxy)-2,6-difluorobenzamide | 485 | $^1$H NMR (CDCl$_3$) δ 7.76 (d, J = 8.2 Hz, 2H), 7.70 (d, J = 8.3 Hz, 2H), 7.27-7.21 (m, 1H), 6.90 (td, J = 9.1, 2.0 Hz, 1H), 5.98 (s, 1H), 5.87 (s, 1H), 5.30 (dd, J = 6.4, 4.6 Hz, 1H), 4.41-4.25 (m, 1H), |

TABLE 1-continued

Characterisation of compounds by LCMS and $^1$H NMR

| Cpd No | Name | LCMS m/z = [M + H]+ | $^1$H NMR |
|---|---|---|---|
| | | | 4.25-4.16 (m, 1H), 2.96-2.83 (m, 2H), 2.74 (dd, J = 8.4, 5.5 Hz, 1H), 1.77-1.64 (m, 2H), 1.45-1.33 (m, 2H), 0.95 (t, J = 7.3 Hz, 3H). |
| 278B | (R)-2,6-difluoro-3-(1-(4-(4-fluorophenyl)oxazol-2-yl)-2-hydroxyethoxy)benzamide | 379.0 | $^1$H NMR (acetone-d6) δ 8.39 (s, 1H), 7.86 (dd, J = 8.9, 5.4 Hz, 2H), 7.44 (br s, 1H), 7.33 (td, J = 9.2, 5.2 Hz, 1H), 7.20 (t, J = 8.9 Hz, 2H), 7.13 (br s, 1H), 6.96 (td, J = 9.0, 2.1 Hz, 1H), 5.48 (dd, J = 6.5, 5.6 Hz, 1H), 4.58-4.46 (m, 1H), 4.20 (qd, J = 11.6, 6.1 Hz, 2H). |
| 279B | (R)-3-(1-(5-bromo-4-(4-fluorophenyl)oxazol-2-yl)-2-hydroxyethoxy)-2,6-difluorobenzamide | 456.9 | $^1$H NMR (acetone-d6) δ 8.04-7.98 (m, 2H), 7.44 (br s, 1H), 7.37 (td, J = 9.2, 5.2 Hz, 1H), 7.30-7.23 (m, 2H), 7.14 (br s, 1H), 6.98 (td, J = 9.0, 2.0 Hz, 1H), 5.47 (t, J = 6.1 Hz, 1H), 4.60-4.53 (m, 1H), 4.26-4.15 (m, 2H). |
| 280 | benzyl (2-(5-bromo-4-(trifluoromethyl)phenyl)oxazol-2-yl)-2-(3-carbamoyl-2,4-difluorophenoxy)ethyl)carbamate | 656.77/ 658.72 | $^1$H NMR (CDCl$_3$) δ 8.07 (d, J = 8.2 Hz, 2H), 7.71 (d, J = 8.2 Hz, 2H), 7.37-7.34 (m, 5H), 7.25-7.20 (m, 1H), 6.88 (t, J = 8.6 Hz, 1H), 6.25 (bs, 1H), 6.07 (bs, 1H), 5.49 (t, J = 6.2 Hz, 1H), 5.36 (t, J = 5.9 Hz, 1H), 5.12, (dd, J = 15.3 and 12.2 Hz, 2H), 4.04-3.88 (m, 2H). |
| 281 | 3-(2-amino-1-(4-(4-trifluoromethyl)phenyl)oxazol-2-yl)ethoxy)-2,6-difluorobenzamide | 428 | $^1$H NMR (CH3CN + D$_2$O) δ 8.39 (s, 1H), 7.97 (d, J = 8.4 Hz, 2H), 7.77 (d, J = 8.4 Hz, 2H), 7.41 (td, J = 9.2 and 5.2 Hz, 1H), 7.00 (td, J = 9.1 and 2.0 Hz, 1H), 5.83 (dd, J = 7.5 and 4.3 Hz, 1H), 3.81-3.72 (m, 2H). |
| 282 | 3-(2-acetamido-1-(4-(4-trifluoromethyl)phenyl)oxazol-2-yl)ethoxy)-2,6-difluorobenzamide | 469.99 | $^1$H NMR (CDCl$_3$) δ 8.03 (s, 1H), 7.84 (d, J = 8.1 Hz, 2H), 7.67 (d, J = 8.1 Hz, 2H), 7.23 (td, J = 9.1 and 5.2 Hz, 1H), 6.87 (td, J = 9.1 and 2.0 Hz, 1H), 6.37 (t, J = 5.9 Hz, 1H), 6.25 (bs, 2H), 5.39 (dd, J = 6.9 and 5.0 Hz, 1H), 4.15-4.08 (m, 1H), 3.93-3.86, (m, 1H), 2.04 (s, 3H). |
| 283 | 3-(2-acetamido-1-(5-bromo-4-(trifluoromethyl)phenyl)oxazol-2-yl)ethoxy)-2,6-difluorobenzamide | 547.81/ 549.87 | $^1$H NMR (CDCl$_3$) δ 8.09 (d, J = 8.2 Hz, 2H), 7.71 (d, J = 8.2 Hz, 2H), 7.30-7.24 (m, 1H), 6.90 (td, J = 9.1 and 2.0 Hz, 1H), 6.27 (t, J = 5.9 Hz, 1H), 6.17 (bs, 2H), 5.36 (dd, J = 6.9 and 5.0 Hz, 1H), 4.13-4.06 (m, 1H), 3.93-3.86, (m, 1H), 2.05 (s, 3H). |
| 284 | 2,6-difluoro-3-(2-(methylsulfonamido)-1-(4-(4-trifluoromethyl)phenyl)oxazol-2-yl)ethoxy)benzamide | 505.99 | $^1$H NMR (CD$_3$CN) δ 8.35 (s, 1H), 7.96 (d, J = 8.2 Hz, 2H), 7.77 (d, J = 8.2 Hz, 2H), 7.29 (td, J = 9.1 and 5.2 Hz, 1H), 6.97 (td, J = 9.1 and 2.0 Hz, 1H), 6.71 (bs, 1H), 6.46 (bs, 1H), 5.78 (bs, 1H), 5.50 (t, J = 6.1 Hz, 1H), 3.84, (d, J = 5.9 Hz, 2H), 2.99 (s, 3H). |
| 285 | 3-(1-(5-bromo-4-(trifluoromethyl)phenyl)oxazol-2-yl)-2-(methylsulfonamido)ethoxy)-2,6-difluorobenzamide | 583.83/ 585.78 | $^1$H NMR (CD$_3$CN) δ 8.15 (d, J = 8.2 Hz, 2H), 7.81 (d, J = 8.2 Hz, 2H), 7.31 (td, J = 9.1 and 5.2 Hz, 1H), 6.98 (td, J = 9.1 and 2.0 Hz, 1H), 6.71 (bs, 1H), 6.46 (bs, 1H), 5.77 (t, J = 6.1 Hz, 1H), 5.47 (t, J = 6.1 Hz, 1H), 3.82, (t, J = 6.3 Hz, 2H), 2.99 (s, 3H). |
| 286 | 3-(2-(3-ethylureido)-1-(4-(4-trifluoromethyl)phenyl)oxazol-2-yl)ethoxy)-2,6-difluorobenzamide | 498.94 | $^1$H NMR (acetone-d6) δ 8.61 (s, 1H), 8.06 (d, J = 8.1 Hz, 2H), 7.78 (d, J = 8.1 Hz, 2H), 7.51 (bs, 1H), 7.43 (td, J = 9.1 and 5.2 Hz, 1H), 7.19 (bs, 1H), 6.99 (td J = 9.1 and 2.0 Hz, 1H), 5.97 (bt, J = 5.9 Hz, |

TABLE 1-continued

Characterisation of compounds by LCMS and $^1$H NMR

| Cpd No | Name | LCMS m/z = [M + H]+ | $^1$H NMR |
|---|---|---|---|
| | | | 1H), 5.66 (bt, J = 6.4 Hz, 1H), 5.57 (t, J = 6.4 Hz, 1H), 3.92-3.88, (m, 2H), 3.18-3.11 (m, 2H), 1.04 (t, J = 7.2 Hz, 3H). |
| 287 | methyl (2-(3-carbamoyl-2,4-difluorophenoxy)-2-(4-(4-(trifluoromethyl)phenyl)oxazol-2-yl)ethyl)carbamate | 485.92 | $^1$H NMR (CD$_3$CN) δ 8.34 (s, 1H), 7.96 (d, J = 8.1 Hz, 2H), 7.76 (d, J = 8.1 Hz, 2H), 7.26 (td, J = 9.1 and 5.2 Hz, 1H), 6.95 (td, J = 9.1 and 2.0 Hz, 1H), 6.71 (bs, 1H), 6.45 (bs, 1H), 6.00 (bs, 1H), 5.46 (t, J = 6.2 Hz, 1H), 3.84 (t, J = 6.2 Hz, 2H), 3.61 (s, 3H). |
| 288 | methyl (2-(5-bromo-4-(4-(trifluoromethyl)phenyl)oxazol-2-yl)-2-(3-carbamoyl-2,4-difluorophenoxy)ethyl)carbamate | 563.71/ 565.78 | $^1$H NMR (CD$_3$CN) δ 8.14 (d, J = 8.2 Hz, 2H), 7.81 (d, J = 8.2 Hz, 2H), 7.28 (td, J = 9.2 and 5.3 Hz, 1H), 6.96 (td, J = 9.1 and 2.0 Hz, 1H), 6.71 (bs, 1H), 6.46 (bs, 1H), 6.00 (bs, 1H), 5.43 (t, J = 6.1 Hz, 1H), 3.82 (t, J = 6.2 Hz, 2H), 3.61 (s, 3H). |
| 289 | 3-(2-benzamido-1-(4-(4-(trifluoromethyl)phenyl)oxazol-2-yl)ethoxy)-2,6-difluorobenzamide | 532.02 | $^1$H NMR (CD$_3$CN) δ 8.35 (s, 1H), 7.95 (d, J = 8.1 Hz, 2H), 7.80-7.75 (m, 4H), 7.58-7.54 (m, 1H), 7.50-7.45 (m, 3H), 7.30 (td, J = 9.1 and 5.2 Hz, 1H), 6.94 (td, J = 9.1 and 2.0 Hz, 1H), 6.68 (bs, 1H), 6.42 (bs, 1H), 5.64 (t, J = 6.3 Hz, 1H), 4.12 (t, J = 6.0 Hz, 2H). |
| 290 | 3-(2-amino-1-(5-bromo-4-(4-(trifluoromethyl)phenyl)oxazol-2-yl)ethoxy)-2,6-difluorobenzamide | 505.91/ 507.94 | $^1$H NMR (DMSO-d6) δ 8.34 (bs, 3H), 8.15 (s, 1H), 8.11 (d, J = 8.2 Hz, 2H), 7.92-7.89 (m, 3H), 7.46 (td, J = 9.1 and 5.3 Hz, 1H), 7.17 (td, J = 9.1 and 1.8 Hz, 1H), 5.81-5.77 (m, 1H), 3.65-3.63 (m, 2H). |
| 291 | 3-(1-(5-bromo-4-(4-(trifluoromethyl)phenyl)oxazol-2-yl)-2-(3-ethylureido)ethoxy)-2,6-difluorobenzamide | 576.91/ 578.86 | $^1$H NMR (acetone-d6) δ 8.21 (d, J = 8.2 Hz, 2H), 7.86 (d, J = 8.2 Hz, 2H), 7.50 (bs, 1H), 7.45 (td, J = 9.1 and 5.2 Hz, 1H), 7.18 (bs, 1H), 7.00 (td, J = 9.1 and 2.0 Hz, 1H), 5.98 (bt, J = 5.9 Hz, 1H), 5.64 (bt, J = 5.2 Hz, 1H), 5.56 (t, J = 6.3 Hz, 1H), 3.90, (t, J = 6.2 Hz, 2H), 3.16-3.12 (m, 2H), 1.03 (t, J = 7.2 Hz, 3H). |
| 292 | 3-(2-benzamido-1-(5-bromo-4-(4-(trifluoromethyl)phenyl)oxazol-2-yl)ethoxy)-2,6-difluorobenzamide | 609.89/ 611.87 | $^1$H NMR (CDCl$_3$) δ 8.08 (d, J = 8.2 Hz, 2H), 7.81-7.78 (m, 2H), 7.72 (d, J = 8.2 Hz, 2H), 7.56-7.52 (m, 1H), 7.48-7.44 (m, 2H), 7.35-7.27 (m, 1H), 6.99 (bt, J = 6.0 Hz, 1H), 6.90 (td, J = 9.1 and 2.0 Hz, 1H), 6.11 (bs, 1H), 6.08 (bs, 1H), 5.51 (dd, J = 6.6 and 5.1 Hz, 1H), 4.35-4.28 (m, 1H), 4.15-4.08 (m, 1H). |
| 293 | N-(2-(3-carbamoyl-2,4-difluorophenoxy)-2-(4-(4-(trifluoromethyl)phenyl)oxazol-2-yl)ethyl)nicotinamide | 533.12 | $^1$H NMR (DMSO-d6) δ 9.30 (bt, J = 5.3 Hz, 1H), 9.05 (s, 1H), 8.89 (s, 1H), 8.80 (dd, J = 5.0 and 1.4 Hz, 1H), 8.36 (d, J = 8.0 Hz, 1H), 8.13 (s, 1H), 7.99 (d, J = 8.1 Hz, 2H), 7.85 (s, 1H), 7.81 (d, J = 8.1 Hz, 2H), 7.69 (dd, J = 7.7 and 5.0 Hz, 1H), 7.32 (td, J = 9.3 and 5.3 Hz, 1H), 7.07 (td, J = 9.1 and 1.8 Hz, 1H), 5.72 (t, J = 6.1 Hz, 1H), 4.08-4.00 (m, 2H). |
| 294 | N-(2-(3-carbamoyl-2,4-difluorophenoxy)-2-(4-(4-(trifluoromethyl)phenyl)oxazol-2-yl)ethyl)picolinamide | 532.96 | $^1$H NMR (DMSO-d6) δ 9.19 (bt, J = 5.9 Hz, 1H), 8.88 (s, 1H), 8.68-8.65 (m, 1H), 8.12 (bs, 1H), 8.13-7.97 (m, 2H), 7.99 (d, J = 8.6 Hz, 2H), 7.84 (bs, 1H), 7.80 (d, J = 8.6 Hz, 2H), 7.64-7.60 (m, 1H), 7.32 (td, J = 9.2 and 5.3 Hz, 1H), 7.07 (td, J = 9.2 and 1.6 Hz, 1H), 5.79 (t, J = 6.1 Hz, 1H), 4.13-4.00 (m, 2H). |

TABLE 1-continued

Characterisation of compounds by LCMS and $^1$H NMR

| Cpd No | Name | LCMS m/z = [M + H]+ | $^1$H NMR |
|---|---|---|---|
| 295 | N-(2-(5-bromo-4-(4-(trifluoromethyl)phenyl)oxazol-2-yl)-2-(3-carbamoyl-2,4-difluorophenoxy)ethyl)nicotinamide | 610.99/ 612.94 | $^1$H NMR (DMSO-d6) δ 9.23 (bt, J = 5.6 Hz, 1H), 9.02 (d, J = 2.1 Hz, 1H), 8.78 (dd, J = 5.0 and 1.6 Hz, 1H), 8.29 (dt, J = 8.1 and 1.8 Hz, 1H), 8.14 (bs, 1H), 8.09 (d, J = 8.2 Hz, 2H), 7.88 (d, J = 8.2 Hz, 2H), 7.88-7.85 (m, 1H), 7.64 (dd, J = 8.0 and 5.0 Hz, 1H), 7.36 (td, J = 9.2 and 5.3 Hz, 1H), 7.09 (td, J = 9.2 and 1.8 Hz, 1H), 5.69 (t, J = 6.1 Hz, 1H), 4.91-3.95 (m, 2H). |
| 296 | N-(2-(5-bromo-4-(4-(trifluoromethyl)phenyl)oxazol-2-yl)-2-(3-carbamoyl-2,4-difluorophenoxy)ethyl)picolinamide | 610.93/ 612.92 | $^1$H NMR (DMSO-d6) δ 9.21 (bt, J = 6.1 Hz, 1H), 8.68-8.64 (m, 1H), 8.13 (bs, 1H), 8.08 (d, J = 8.3 Hz, 2H), 8.06-7.98 (m, 2H), 7.87 (d, J = 8.3 Hz, 2H), 7.87-7.84 (m, 1H), 7.65-7.60 (m, 1H), 7.36 (td J = 9.2 and 5.2 Hz, 1H), 7.08 (td, J = 9.2 and 1.8 Hz, 1H), 5.74 (t, J = 6.2 Hz, 1H), 4.12-4.00 (m, 2H). |
| 297 | 3-((1R,2R)-1-(5-bromo-4-(4-(difluoromethoxy)phenyl)oxazol-2-yl)-2-hydroxypropoxy)-2,6-difluorobenzamide | 520.9 | $^1$H NMR (acetone-d6) δ 8.02 (d, J = 9.0 Hz, 2H), 7.45 (br s, 1H), 7.34-7.25 (m, 3H), 7.15 (br s, 1H), 7.06 (t, J = 74.0 Hz, 1H), 6.99-6.90 (m, 1H), 5.14 (d, J = 7.0 Hz, 1H), 4.54 (br s, 1H), 4.47-4.39 (m, 1H), 1.47 (d, J = 6.2 Hz, 3H). |
| 298 | 3-(1-(5-bromo-4-(4-(trifluoromethyl)phenyl)oxazol-2-yl)-2-(2-(pyridin-3-yl)acetamido)ethoxy)-2,6-difluorobenzamide | 625.04/ 626.95 | $^1$H NMR (DMSO-d6 + D$_2$O) δ 8.76 (bt, J = 5.7 Hz, 2H), 8.29 (d, J = 7.8 Hz, 1H), 8.07 (d, J = 8.3 Hz, 2H), 7.88 (d, J = 8.3 Hz, 2H), 7.89-7.86 (m, 1H), 7.31 (td, J = 9.1 and 5.3 Hz, 1H), 7.07 (td, J = 9.1 and 1.5 Hz, 1H), 5.53 (t, J = 6.1 Hz, 1H), 3.85-3.80 (m, 2H), 3.74 (s, 2H). |
| 299 | (R)-3-(1-(5-bromo-4-(4-(trifluoromethyl)phenyl)oxazol-2-yl)ethoxy)-2-fluorobenzamide | 472.89/ 474.87 | $^1$H NMR (CDCl$_3$) δ 7.94 (d, J = 8.1 Hz, 2H), 7.61 (ddd, J = 8.2, 6.7, 1.7 Hz, 1H), 7.57 (d, J = 8.2 Hz, 2H), 7.17 (td, J = 8.1, 1.7 Hz, 1H), 7.03 (td, J = 8.1, 1.3 Hz, 1H), 6.49 (s, 1H), 5.71 (s, 1H), 5.31 (q, J = 6.6 Hz, 1H), 1.75 (d, J = 6.6 Hz, 3H). |
| 300 | 3-((1R,2S)-1-(5-bromo-4-(4-(difluoromethoxy)phenyl)oxazol-2-yl)-2-hydroxypropoxy)-2,6-difluorobenzamide | 520.9 | $^1$H NMR (acetone-d6) δ 8.02 (d, J = 8.9 Hz, 2H), 7.44 (br s, 1H), 7.36-7.27 (m, 3H), 7.15 (br s, 1H), 7.07 (t, J = 74.0 Hz, 1H), 6.95 (td, J = 9.0, 2.0 Hz, 1H), 5.25 (d, J = 6.4 Hz, 1H), 4.64 (br s, 1H), 4.48-4.40 (m, 1H), 1.29 (d, J = 6.4 Hz, 3H). |
| 301 | 3-(1-(5-bromo-4-(4-(trifluoromethyl)phenyl)oxazol-2-yl)-2-(2-(2-methoxyethoxy)acetamido)ethoxy)-2,6-difluorobenzamide | 621.85/ 623.86 | $^1$H NMR (CDCl$_3$) δ 8.10 (d, J = 8.2 Hz, 2H), 7.71 (d, J = 8.2 Hz, 2H), 7.65 (bt, J = 6.0 Hz, 1H), 7.31-7.25 (m, 1H), 6.90 (td, J = 9.1 and 2.0 Hz, 1H), 6.22 (bs, 1H), 6.16 (bs, 1H), 5.41 (dd, J = 6.9 and 5.4 Hz, 1H), 4.15-4.07 (m, 1H), 4.02 (s, 2H), 4.02-3.94 (m, 1H), 3.68-3.65 (m, 2H), 3.54-3.51 (m, 2H), 3.35 (s, 3H). |
| 302 | 4-((2-(5-bromo-4-(4-(trifluoromethyl)phenyl)oxazol-2-yl)-2-(3-carbamoyl-2,4-difluorophenoxy)ethyl)amino)-4-oxobutanoic acid | 605.88/ 607.86 | $^1$H NMR (CD$_3$CN) δ 8.15 (d, J = 8.3 Hz, 2H), 7.81 (d, J = 8.3 Hz, 2H), 7.31 (td, J = 9.2 and 5.3 Hz, 1H), 7.00-6.94 (m, 2H), 6.76 (bs, 1H), 6.49 (bs, 1H), 5.44 (t, J = 6.1 Hz, 1H), 3.92-3.87 (m, 2H), 2.55-2.51 (m, 2H), 2.48-2.43 (m, 2H). |

TABLE 1-continued

Characterisation of compounds by LCMS and ¹H NMR

| Cpd No | Name | LCMS m/z = [M + H]+ | ¹H NMR |
|---|---|---|---|
| 303B | (R)-3-(1-(5-ethyl-4-(4-methoxyphenyl)oxazol-2-yl)-2-hydroxyethoxy)-2,6-difluorobenzamide | 419.0 | ¹H NMR (CDCl₃) δ 7.51 (d, J = 8.9 Hz, 2H), 7.22 (td, J = 9.1, 5.3 Hz, 1H), 6.95 (d, J = 8.9 Hz, 2H), 6.86 (td, J = 9.1, 2.0 Hz, 1H), 6.02 (br s, 1H), 5.93 (br s, 1H), 5.24 (dd, J = 6.4, 4.6 Hz, 1H), 4.34-4.21 (m, 1H), 4.21-4.10 (m, 1H), 3.84 (s, 3H), 2.95-2.89 (m, 1H), 2.86 (q, J = 7.5 Hz, 2H), 1.27 (t, J = 7.5 Hz, 3H). |
| 304B | (R)-2,6-difluoro-3-(2-hydroxy-1-(5-(methoxymethyl)-4-(4-methoxyphenyl)oxazol-2-yl)ethoxy)benzamide | 434.6 | ¹H NMR (CDCl₃) δ 7.61 (d, J = 8.9 Hz, 2H), 7.26-7.19 (m, 1H), 6.97 (d, J = 8.9 Hz, 2H), 6.86 (td, J = 9.1, 2.0 Hz, 1H), 6.08 (bs, 1H), 5.90 (bs, 1H), 5.28 (dd, J = 6.4, 4.6 Hz, 1H), 4.54 (s, 2H), 4.34-4.24 (m, 1H), 4.19 (dd, J = 10.5, 6.1 Hz, 1H), 3.85 (s, 3H), 3.39 (s, 3H), 2.89-2.78 (m, 1H). |
| 305 | 2,6-difluoro-3-(2-hydroxy-1-(2-(4-methoxyphenyl)-5-vinyloxazol-4-yl)ethoxy)benzamide | 417 | ¹H NMR (CD₃CN) δ 8.02 (d, J = 9.0 Hz, 2H), 7.13 (td, J = 9.0 and 5.3 Hz, 1H), 7.08 (d, J = 9.0 Hz, 2H), 6.90 (td, J = 9.0 and 2.0 Hz, 1H), 6.76 (dd, J = 17.4 and 11.4 Hz, 1H), 6.68 (bs, 1H), 6.43 (bs, 1H), 5.85 (dd, J = 17.4 and 1.3 Hz, 1H), 5.40-5.33 (m, 2H), 4.12-4.05 (m, 1H), 4.00-3.89 (m, 1H), 3.89 (s, 3H), 3.32 (dd, J = 7.0 and 6.0 Hz, 1H). |
| 306 | 3-(1-(5-ethyl-2-(4-methoxyphenyl)oxazol-4-yl)-2-hydroxyethoxy)-2,6-difluorobenzamide | 419.02 | ¹H NMR (DMSO-d6) δ 8.10 (bs, 1H), 7.87 (d, J = 9.0 Hz, 2H), 7.82 (bs, 1H), 7.18 (td, J = 9.1 and 5.4 Hz, 1H), 7.07 (d, J = 9.0 Hz, 2H), 7.02 (td, J = 9.1 and 1.8 Hz, 1H), 5.30 (dd, J = 6.7 and 5.2 Hz, 1H), 5.13 (t, J = 5.8 Hz, 1H), 4.00-3.93 (m, 1H), 3.86-3.81 (m, 1H), 3.84 (s, 3H), 2.75 (q, J = 7.5 Hz, 2H), 1.13 (t, J = 7.5 Hz, 3H). |
| 307B | (R)-2,6-difluoro-3-(2-hydroxy-1-(3-(4-methoxyphenyl)-1,2,4-oxadiazol-5-yl)ethoxy)benzamide | 391.9 | ¹H NMR (acetone-d6) δ 8.00 (d, J = 8.8 Hz, 2H), 7.50 (br. s., 1H), 7.35 (td, J = 9.2, 5.1 Hz, 1H), 7.21 (br. s., 1H), 7.09 (d, J = 8.8 Hz, 2H), 6.98 (td, J = 8.8, 1.6 Hz, 1H), 5.72 (t, J = 5.5 Hz, 1H), 4.27 (d, J = 5.8 Hz, 2H), 3.88 (s, 3H). |
| 308 | 4-((2-(5-bromo-4-(trifluoromethyl)phenyl)oxazol-2-yl)-2-(3-carbamoyl-2,4-difluorophenoxy)ethyl)carbamoyl)benzoic acid | 653.91/ 655.86 | ¹H NMR (DMSO-d6) δ 9.03 (bt, J = 5.6 Hz, 1H), 8.15 (s, 1H), 8.10 (d, J = 8.1 Hz, 2H), 8.00 (d, J = 8.4 Hz, 2H), 7.90-7.84 (m, 5H), 7.37 (td, J = 9.2 and 5.3 Hz, 1H), 7.09 (td, J = 9.2 and 1.8 Hz, 1H), 5.69 (t, J = 6.3 Hz, 1H), 4.08-3.93 (m, 2H). |

[a] Refer to Representative Example 11 in which 3-(1-(5-bromo-4-(4-(trifluoromethyl)-phenyl)oxazol-2-yl)-3,4-dihydroxybutoxy)-2,6-difluorobenzamide was obtained as a mixture of two diastereomeric pairs of enantiomers (compound 109) noting that these two racemates, viz. (R,S)/(S,R)-3-(1-(5-bromo-4-(4-(trifluoromethyl)phenyl)oxazol-2-yl)-3,4-dihydroxybutoxy)-2,6-difluorobenzamide and (S,S)/(R,R)-3-(1-(5-bromo-4-(4-(trifluoromethyl) phenyl)oxazol-2-yl)-3,4-dihydroxybutoxy)-2,6-difluorobenzamide (compounds 146 and 147) were isolated from each other by reverse-phase HPLC (C18) and three of the four individual enantiomers were also successfully isolated from the original mixture by means of preparative chiral HPLC (compounds 148, 156 and 159) however the stereochemical assignment of the enantiomers was not determined Example of Chiral HPLC Method for the Separation of Enantiomers The chiral HPLC conditions used to separate a representative compound of the invention, Compound 38, are as follows:
Preparative Method:
   Column: CHIRALPAK® AD-H, (250×30) mm, 5 μm
   Mobile phase: n-Hexane:EtOH:MeOH (80:10:10 v/v/v)
   Flow rate: 40 ml/min
   Detection: UV 265 nm
   Temperature: 25° C.
   Diluent: Mobile phase
   Feed Conc.: 9.0 mg/ml
   Inj Volume: 7 ml (on column: 63 mg)
Analytical Method:
   Column: CHIRALPAK® IA (250×4.6) mm, 5 μm
   Mobile phase: n-Hexane:EtOH (80:20 v/v)
   Flow rate: 1.0 ml/min
   Detection: DAD 265 nm
   Temperature: 25° C.

Isomer-A (Compound 38A): 9.20 min (Isomeric purity 99.30%)

Isomer-B (Compound 38B): 9.90 min (Isomeric purity 99.60%) was determined to be the active enantiomer based on biological data with absolute configuration as follows:

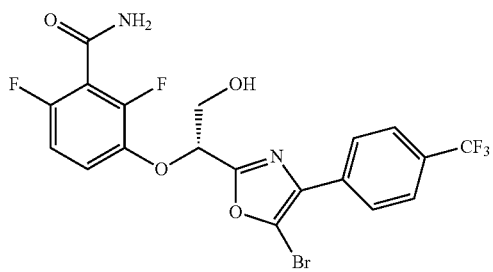 [SMILES: NC(=O)c1c(F)ccc(O[C@H](CO)c2nc(-c3ccc(C(F)(F)F)cc3)c(Br)o2)c1F]

Turbidimetric Assay: Determination of Solubility

The solubility of the compounds may be measured using a turbidimetric method as follows. A series of doubling dilutions of compounds is prepared in neat dimethyl sulfoxide (DMSO). 5 µl samples are diluted twenty-fold into 95 µl volumes of 100 mM citrate buffer (pH 4), phosphate buffered saline (PBS, pH 7.4) or carbonate-bicarbonate buffer (pH 9) in microtitre assay plates and allowed to reach equilibrium at room temperature for 24 hours. The absorbance within each well of the plate is read spectrophotometrically at a wavelength of 620 nm. A precipitate forms when the maximum aqueous solubility level is reached. The value quoted is the highest concentration where the compound was in solution i.e. where no measurable precipitate was present. Solubility ranges may be expressed as L="Low" solubility <12.5 µg/mL; M="Moderate" solubility ≥12.5 µg/mL to <400 µg/mL; H="High" solubility ≥400 µg/mL to <800 µg/mL; and VH="Very High" solubility≥800 µg/mL. ND=not determined.

Biological Data

The in vivo and in vitro biological activity of the compounds may be determined using the following protocols.

Bacterial Assay:

Determination of Antibacterial Activity

Compounds are tested for antimicrobial activity by susceptibility testing in liquid or on solid media. Minimum inhibitory concentrations (MICs) for compounds against each strain are determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition.* Document M7-A7. CLSI, Wayne, Pa., 2006; Clinical Laboratories and Standards Institute). The bacterial strains tested include *S. aureus* (*Staphylococcus aureus* (Isolate ID ATCC 29213)) and an FtsZ mutant of this isolate (FtsZ-G196A *Staphylococcus aureus* (Isolate ID GG/190723/sa/1.2)). Compound MICs were determined to be in the following activity ranges "A" activity≤0.25 µg/mL; "B" activity>0.25 µg/mL-1.0 µg/mL; "C" activity>1.0 µg/mL-16 µg/mL; "D" activity>16 µg/mL and ND=not determined. The antibacterial activity range of selected compounds against *S. aureus* is shown in Table 2. The bracketed entries indicate entantiomer(s) and their activity.

TABLE 2

Minimum inhibitory concentrations (MICs) against *S. aureus* (ATCC29213)

| Compound No. | S. aureus MIC (µg/mL) Activity Range | Compound No. | S. aureus MIC (µg/mL) Activity Range | Compound No. | S. aureus MIC (µg/mL) Activity Range |
|---|---|---|---|---|---|
| 1 | A | 2 | C | 3 | A |
| 4 | C | 5 (5A/5B) | B (C/B) | 6 | C |
| 7 | B | 8 | C | 9 | B |
| 10 | D | 11 | A | 12 | D |
| 13 | B | 14 | A | 15 | B |
| 16 | B | 17 | B | 18 | C |
| 19 | B | 20 | A | 21 | A |
| 22 | C | 23 | C | 24 | C |
| 25 | B | 26 | B | 27 | A |
| 28 | C | 29 | C | 30 | C |
| 31 | C | 32 | B | 33 | A |
| 34 | A | 35 | A | 36 | B |
| 37 | B | 38 (38A/38B) | A (C/A) | 39 | A |
| 40 | C | 41 | C | 42 | B |
| 43 | C | 44 | B | 45 | C |
| 46 | B | 47 | B | 48 | C |
| 49 | C | 50 | C | 51 | C |
| 52 | B | 53 | D | 54 | B |
| 55 | C | 56 | B | 57 | B |
| 58 | C | 59 | B | 60 | B |
| 61 | B | 62 | B | 63 | C |
| 64 | A | 65 | C | 66 | C |
| 67 | C | 68 | A | 69 | B |
| 70 | B | 71 | B | 72 | C |
| 73 | B | 74 | C | 75 | D |
| 76 | C | 77 | D | 78 | D |
| 79 | C | 80 | C | 81 | B |
| 82 | C | 83 | C | 84 | B |
| 85 | C | 86 | D | 87 | B |
| 88 | C | 89 | B | 90 | B |
| 91 | C | 92 | C | 93 | B |
| 94 | A | 95 | D | 96 | C |
| 97 | C | 98 | C | 99 | C |
| 100 | C | 101 | B | 102 | C |
| 103 | B | 104 | C | 105 | B |
| 106 | C | 107 | A | 108 | D |
| 109 | B | 110 | D | 111 | C |
| 112 | C | 113 | B | 114 | C |
| 115 | A | 116 | A | 117 | D |
| 118 | D | 119 | D | 120 | C |
| 121 | D | 122 | D | 123 | C |
| 124 | C | 125 | B | 126 | C |
| 127 | D | 128 | B | 129 | C |
| 130 | D | 131 | D | 132 | D |
| 133 | D | 134 | C | 135 | C |
| 136 | C | 137 | D | 138 | C |
| 139 | C | 140 | B | 141 | A |
| 142 | D | 143 | C | 144 | D |
| 145 | D | 146 | B | 147 | B |
| 148 | C | 149 | C | 150 | B |
| 151 | A | 152 | C | 153 | B |
| 154 | C | 155 | B | 156 | C |
| 157 | B | 158 | A | 159 | A |
| 160 | A | 161 | C | 162 | C |
| 163 | B | 164 | B | 165 | B |
| 166 | A | 167 | A | 168 | C |
| 169 | C | 170 | B | 171 | B |
| 172 | B | 173 | B | 174 | D |
| 175 | C | 176 | B | 177 | D |
| 178 | B | 179 | A | 180 | D |
| 181 | C | 182 | D | 183 | C |
| 184 | A | 185 | B | 186 | B |
| 187 | D | 188 | D | 189 | C |
| 190 | C | 191 | C | 192 | B |
| 193 | A | 194 | A | 195 | C |
| 196 | A | 197 | B | 198 | B |
| 199 | B | 200 | B | 201 | B |
| 202 | B | 203 | B | 204 | B |
| 205 | B | 206 | C | 207 | C |
| 208 | B | 209 | B | 210 | B |

TABLE 2-continued

Minimum inhibitory concentrations (MICs) against S. aureus (ATCC29213)

| Compound No. | S. aureus MIC (µg/mL) Activity Range | Compound No. | S. aureus MIC (µg/mL) Activity Range | Compound No. | S. aureus MIC (µg/mL) Activity Range |
|---|---|---|---|---|---|
| 211 | B | 212 | B | 213 | B |
| 214 | B | 215 | B | 216 | B |
| 217 | B | 218 | D | 219 | D |
| 220 | D | 221 | C | 222 | D |
| 223 | D | 224 | D | 225 | B |
| 226 | D | 227 | D | 228 | D |
| 229 | D | 230 | C | 231 | D |
| 232 | C | 233 (233A/233B) | A (D/A) | 234 | B |
| 235 | A | 236 | B | 237 | B |
| 238 | D | 239 | A | 240 | D |
| 241 | C | 242 | C | 243 | C |
| 244 | C | 245 | D | 246 | C |
| 247B | D | 248 | C | 249B | C |
| 250B | A | 251 | D | 252 | D |
| 253B | C | 254B | C | 255B | D |
| 256 | C | 257B | D | 258 | C |
| 259 | C | 260 | C | 261 | C |
| 262 | C | 263 | C | 264 | D |
| 265B | C | 266B | C | 267 | D |
| 268A/268B | D/C | 269 | C | 270 | D |
| 271 | B | 272B | C | 273B | A |
| 274B | C | 275B | D | 276 | C |
| 277 | C | 278B | D | 279B | B |
| 280 | B | 281 | D | 282 | D |
| 283 | C | 284 | D | 285 | C |
| 286 | D | 287 | D | 288 | B |
| 289 | C | 290 | C | 291 | A |
| 292 | A | 293 | D | 294 | D |
| 295 | B | 296 | A | 297 | A |
| 298 | C | 299 | C | 300 | A |
| 301 | C | 302 | C | 303 | D |
| 304B | C | 305B | C | 306 | C |
| 307 | C | 308B | C | 309 | C |

Selected compounds were also tested against a panel of target strains and their MICs are shown in Table 3 against the gold standard Linezolid. The selected compounds demonstrated comparatively better activity against all staphylococcal species tested including methicillin (MRSA) and multidrug (MDRSA) resistant S. aureus. The activity of the compounds observed against S. aureus was also shown to be maintained within a narrow range across the staphylococcal panel tested.

TABLE 3

Antibacterial activity of Linezolid and compounds 38B and 233 against a panel of staphylococcal pathogenic species

| | MIC (µg/mL) | | |
|---|---|---|---|
| Organism | Linezolid | Compound 38B | Compound 233 |
| *Staphylococcus aureus* ATCC 29213 | 2 | 0.125 | 0.25 |
| *S. aureus* ATCC 19636 (Smith) | 2 | 0.125 | 0.25 |
| *S. aureus* ATCC 43300 (MRSA) | 2 | 0.125 | 0.5 |
| *S. aureus* ATCC BAA-44 (MDRSA) | 1 | 0.125 | 0.25 |
| *S. epidermidis* ATCC 12228 | 1 | 0.125 | 0.5 |
| *S. haemolyticus* ATCC 29970 | 1 | 0.125 | 0.5 |
| *S. hominis* ATCC 27844 | 1 | 0.125 | 0.5 |
| *S. lugdunensis* ATCC 43809 | 1 | 0.25 | 0.5 |
| *S. saprophyticus* ATCC 43809 | 2 | 0.06 | 0.5 |
| *S. warneri* ATCC 49454 | 2 | 0.25 | 0.5 |

As previously described, a subclass of the compounds described herein having a bromo-substituted oxazole, shows particularly useful antibacterial activity against the *S. aureus* FtsZ G196A mutant. The comparative activity of selected compounds having a bromo-substituted oxazole against their corresponding non-brominated analogues is shown in Table 4.

TABLE 4

Comparative antibacterial activity of compounds against the FtsZ G196A mutant strain.

| Compound No. | Oxazole | MIC (µg/mL) FtsZ G196A mutant strain |
|---|---|---|
| 5B | Bromo-substituted | 16 |
| 268B | Unsubstituted analogue of Compound 5B | >256 |
| 184 | Bromo-substituted | 0.5 |
| 183 | Unsubstituted analogue of Compound 184 | >256 |
| 288 | Bromo-substituted | 16 |
| 287 | Unsubstituted analogue of Compound 288 | >256 |
| 292 | Bromo-substituted | 1 |
| 289 | Unsubstituted analogue of Compound 292 | >256 |

The antibacterial activity of racemates and individual enantiomers of selected compounds was also determined against the ATCC 29213 type strain of *S. aureus*. The MICs for each compound are shown in Table 5. Generally, the antibacterial activity of the R enantiomer is within a doubling dilution of the activity of the racemic mixture which is in contrast to the considerably lower activity shown by the S enantiomer.

TABLE 5

Minimum inhibitory concentration (MIC) of Compounds 5, 38 and 233 (racemate and enantiomers) against S. aureus (ATCC29213) and FtsZ G196A mutant strain.

| Compound No. | Chirality | MIC (µg/mL) S. aureus (ATCC29213) | MIC (µg/mL) G196A mutant strain |
|---|---|---|---|
| 5 | Racemic mixture | 1 | 32 |
| 5A | S-enantiomer | 16 | >256 |
| 5B | R-enantiomer | 0.5 | 16 |
| 38 | Racemic mixture | 0.25 | 4 |
| 38A | S-enantiomer | 16 | 64 |
| 38B | R-enantiomer | 0.125 | 2 |
| 233 | Racemic mixture (83:17/R:S) | 0.25 | 8 |
| 233A | S-enantiomer | 32 | >256 |
| 233B | R-enantiomer | 0.25 | 8 |

Pharmacokinetic Assays: Determination of PK Profile

The pharmacokinetic profiles of selected comparator compounds A-N in Table 6 and compounds of the invention were determined by measuring the compound concentration in plasma by LC/MS/MS following a single intravenous or peroral administration of the compounds at a dose of 3 mg/kg. The concentrations described are the mean plasma concentrations at each time point from three animals. Intravenous dose formulation was administered as a single bolus dose through the tail vein. Oral dose formulation was administered to animals by an oral gavage needle. In both cases the dose volume was 5.0 mL/kg. Blood was collected from anesthetized mice through a capillary guided into the retro-orbital plexus. The collected blood was centrifuged to obtain plasma and the compounds extracted into methanol prior to determining the compound concentration by LC/MS/MS. The results are shown graphically in FIG. 1 and for the AUC and CL parameters in Table 6.

TABLE 6

Pharmacokinetic parameters following 3 mg/kg IV dosing in mice for selected comparator compounds A to N against representative compounds of Formula (I)

| Compound | Name | AUC (μg · hr/mL) | CL (mL/min/kg) |
|---|---|---|---|
| A | 3-((3-(4-chlorophenyl)-1,2,4-oxadiazol-5-yl)methoxy)-2,6-difluorobenzamide | 0.9 | 52 |
| B | 2,6-difluoro-3-((6-phenylthiazolo[5,4-b]pyridin-2-yl)methylphenylthiazolo[5,4-b]pyridin-2-yl)methoxy)benzamide | 0.5 | 91 |
| C | 2,6-difluoro-3-((4-(6-methylpyridin-3-yl)thiazol-2-yl)methoxy)benzamide | 0.4 | 130 |
| D | 3-((5-(6-(dimethylamino)pyridin-3-yl)-4-(4-methoxyphenyl)thiazol-2-yl)methoxy)-2,6-difluorobenzamide | 0.9 | 55 |
| E | 3-((6-ethoxythiazolo[5,4-b]pyridin-2-yl)methylethoxythiazolo[5,4-b]pyridin-2-yl)methoxy)-2,6-difluorobenzamide | 0.2 | 203 |
| F | 3-((4-(6-chloropyridin-3-yl)thiazol-2-yl)methoxy)-2,6-difluorobenzamide | 0.4 | 139 |
| G | 2,6-difluoro-3-((4-(5-methoxypyrazin-2-yl)thiazol-2-yl)methoxy)benzamide | 0.6 | 82 |
| H | 3-((4-(2-chloropyrimidin-5-yl)thiazol-2-yl)methoxy)-2,6-difluorobenzamide | 0.3 | 173 |
| I | 3-((5-ethyl-4-(4-methoxyphenyl)oxazol-2-yl)methoxy)-2,6-difluorobenzamide | 0.2 | 319 |
| J | 2,6-difluoro-3-((2'-methoxy-4,5'-bithiazol-2-yl)methoxy)benzamide | 0.3 | 180 |
| K | 3-(4-chlorophenyl)-5-propyloxazol-2-yl)methoxy)-2,6-difluorobenzamide | 0.4 | 137 |
| L | 2,6-difluoro-3-((4-(2-(3-methyl-1,2,4-oxadiazol-5-yl)ethyl)thiazol-2-yl)methoxy)benzamide | 0.8 | 59 |
| M | 2,6-difluoro-3-((4-(3-hydroxyphenyl)-5-propyloxazol-2-yl)methoxy)benzamide | 0.1 | 369 |
| N | 3-((5-allyl-4-(3-hydroxyphenyl)oxazol-2-yl)methoxy)-2,6-difluorobenzamide | 0.2 | 270 |
| 16 | 3-(1-(5-bromo-4-(trifluoromethoxy)phenyl)oxazol-2-yl)ethoxy)-2,6-difluorobenzamide | 1.4 | 36 |
| 21 | 3-(1-(5-chloro-4-(trifluoromethoxy)phenyl)oxazol-2-yl)ethoxy)-2,6-difluorobenzamide | 1.6 | 31 |
| 27 | 3-(1-(5-bromo-4-(trifluoromethyl)phenyl)oxazol-2-yl)ethoxy)-2,6-difluorobenzamide | 2.2 | 22 |
| 38 | 3-(1-(5-bromo-4-(trifluoromethyl)phenyl)oxazol-2-yl)-2-hydroxyethoxy)-2,6-difluorobenzamide | 6.7 | 7 |
| 38A | (S)-3-(1-(5-bromo-4-(trifluoromethyl)phenyl)oxazol-2-yl)-2-hydroxyethoxy)-2,6-difluorobenzamide | 7.8 | 6 |
| 38B | (R)-3-(1-(5-bromo-4-(trifluoromethyl)phenyl)oxazol-2-yl)-2-hydroxyethoxy)-2,6-difluorobenzamide | 4.0 | 12 |
| 181 | (R)-4-(2-(5-bromo-4-(trifluoromethyl)phenyl)oxazol-2-yl)-2-(3-carbamoyl-2,4-difluorophenoxy)ethoxy)-4-oxobutanoic acid | 3.0 | 16 |
| 233 | 3-(1-(5-bromo-4-(2,4-difluorophenyl)oxazol-2-yl)-2-hydroxyethoxy)-2,6-difluorobenzamide | 2.3 | 18 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The invention claimed is:

1. A compound of Formula (I):

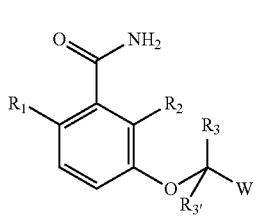

(I)

or a salt, racemate, diastereoisomer, enantiomer, hydrate, solvate, N-oxide, or prodrug thereof wherein W is a substituted $C_{6-10}$-membered monocyclic or fused bicyclic aryl group or an optionally substituted 5-6-membered monocyclic heteroaryl or a 9-membered fused bicyclic heteroaryl group;

$R_1$ and $R_2$ are each independently selected from halo or H;

$R_3$ is selected from the group consisting of $C_t$alkyl-$R_4$, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;

t is an integer selected from 0, 1, 2 and 3;

$R_{3'}$ is H;

$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, (C=O)$R_6$, O(C=O)$R_6$, C(=O)$OR_6$, N($R_6$)$_2$, $NR_6$C(=O)$R_5$, C(=O)N($R_6$)$_2$, $NR_6$C(=O)$OR_5$, OC(=O)N($R_6$)$_2$, C(=O)NH—NHC(=O)$R_5$, NHC(=O)NH$C_{1-6}$alkyl, NHS(O)$_x$$R_5$, S(O)$_x$$R_5$, OS(O)$_x$$R_5$, OP(=O)(O$R_6$)$_2$ and P(=O)(O$R_6$)$_2$ wherein each $C_{2-6}$alkenyl, $C_{2-6}$alkynyl, $C_{6-10}$aryl, $C_{1-6}$alkylaryl, 4-10 membered heterocyclyl and $C_{1-6}$alkylheterocycly may be further optionally substituted with one or more substituents independently selected from the group consisting of $C_{1-3}$alkyl, $C_{2-3}$alkenyl, $C_{1-3}$alkoxyl, $OR_7$, oxo, (C=O)$R_7$, O(C=O)$R_7$, C(=O)$R_7$, N($R_7$)$_2$, $NR_7$C(=O)$R_7$, C(=O)N($R_7$)$_2$, $NR_7$C(=O)$OR_7$, OC(=O)N($R_7$)$_2$, C(=O)NH—HNC(=O)$R_7$, S(O)$_x$$R_7$, OS(O)$_x$$R_7$, OP(=O)(O$R_7$)$_2$ and P(=O)(O$R_7$)$_2$ wherein each $R_7$ is independently selected from H, $C_{1-3}$alkyl and $C_{2-3}$alkenyl;

each $R_5$ is selected from $C_1$ alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H, $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl; and wherein each $R_5$ and $R_6$ independently may be optionally substituted with one or more substituents independently selected from the group consisting of $C_{1-3}$alkyl, $C_{2-3}$alkenyl, $C_{1-3}$alkoxyl, $OR_7$, oxo, (C=O)$R_7$, O(C=O)$R_7$, C(=O)$OR_7$, N($R_7$)$_2$, $NR_7$C(=O)$R_7$, C(=O)N($R_7$)$_2$, $NR_7$C(=O)$OR_7$, OC(=O)N($R_7$)$_2$, C(=O)NH—NHC(=O)$R_7$, S(O)$_x$$R_7$, OS(O)$_x$$R_7$, OP(=O)(O$R_7$)$_2$ and P(=O)(O$R_7$)$_2$ wherein each $R_7$ is independently selected from H, $C_{1-3}$alkyl and $C_{2-3}$alkenyl; and x is 0 or an integer from 1 to 2.

2. A compound according to claim 1 wherein W is an optionally substituted 5-6-membered monocyclic heteroaryl or a 9-membered fused bicyclic heteroaryl group.

3. A compound of Formula (Ia):

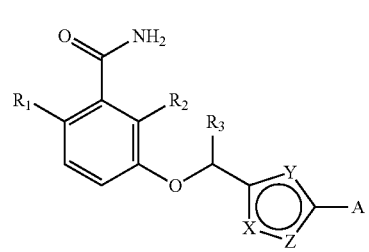

(Ia)

or a salt, racemate, diastereoisomer, enantiomer, hydrate, solvate, N-oxide, or prodrug thereof wherein X and Y are each independently a heteroatom selected from O, N and S or a carbon atom having an optional substituent;

Z is a heteroatom selected from O, N and S or is C—B;

A is selected from H, halo, optionally substituted $C_{6-10}$aryl, optionally substituted 4-10 membered heterocyclyl or A together with B and the carbon atoms to which they are respectively attached join to form an optionally substituted 6-membered fused ring system;

B is selected from H, halo, optionally substituted $C_{1-6}$alkyl, optionally substituted $C_{2-6}$alkenyl, optionally substituted $C_{2-6}$alkynyl or B together with A and the carbon atoms to which they are respectively attached join to form an optionally substituted 6-membered fused ring system;

$R_1$ and $R_2$ are each independently selected from halo or H;

$R_3$ is selected from the group consisting of $C_t$alkyl-$R_4$, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;

t is an integer selected from 0, 1, 2 or 3;

$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, (C=O)$R_6$, O(C=O)$R_6$, C(=O)$OR_6$, N($R_6$)$_2$, $NR_6$C(=O)$R_5$, C(=O)N($R_6$)$_2$, $NR_6$C(=O)$OR_5$, OC(=O)N($R_6$)$_2$, C(=O)NH—NHC(=O)$R_5$, NHC(=O)NH$C_{1-6}$alkyl, NHS(O)$_x$$R_5$, S(O)$_x$$R_5$, OS(O)$_x$$R_5$, OP(=O)(O$R_6$)$_2$ and P(=O)(O$R_6$)$_2$ wherein each $C_{2-6}$alkenyl, $C_{2-6}$alkynyl, $C_{6-10}$aryl, $C_{1-6}$alkylaryl, 4-10 membered heterocyclyl, and $C_{1-6}$alkylheterocyclyl may be further optionally substituted with one or more substituents independently selected from the group consisting of $C_{1-3}$alkyl, $C_{2-3}$alkenyl, $C_{1-3}$alkoxyl, $OR_7$, oxo, (C=O)$R_7$, O(C=O)$R_7$, C(=O)$R_7$, N($R_7$)$_2$, $NR_7$C(=O)$R_7$, C(=O)N($R_7$)$_2$, $NR_7$C(=O)$OR_7$, OC(=O)N($R_7$)$_2$, C(=O)NH—HNC(=O)$R_7$, S(O)$_x$$R_7$, OS(O)$_x$$R_7$, OP(=O)(OR$_7$)$_2$ and P(=O)(OR$_7$)$_2$ wherein each R$_7$ is independently selected from H and C$_{1-3}$alkyl;

each R$_5$ is optionally substituted and is selected from C$_{1-6}$alkyl, C$_{2-6}$alkenyl, C$_{2-6}$alkynyl, C$_{6-10}$aryl, C$_{1-6}$alkylaryl, 4-10 membered heterocyclyl and C$_{1-6}$alkylheterocyclyl;

each R$_6$ is independently selected from H or is optionally substituted C$_{1-6}$alkyl, C$_{2-6}$alkenyl, C$_{2-6}$alkynyl, C$_{6-10}$aryl, C$_{1-6}$alkylaryl, 4-10 membered heterocyclyl and C$_{1-6}$alkylheterocyclyl;

wherein each R$_5$ and R$_6$ independently may be further optionally substituted with one or more optional substituents independently selected from the group consisting of C$_{1-3}$alkyl, C$_{2-3}$alkenyl, C$_{1-3}$alkoxyl, OR$_7$, oxo, (C=O)R$_7$, O(C=O)R$_7$, C(=O)OR$_7$, N(R$_7$)$_2$, NR$_7$C(=O)R$_7$, C(=O)N(R$_7$)$_2$, NR$_7$C(=O)OR$_7$, OC(=O)N(R$_7$)$_2$, C(=O)NH—NHC(=O)R$_7$, S(O)$_x$R$_7$, OS(O)$_x$R$_7$, OP(=O)(OR$_7$)$_2$ and P(=O)(OR$_7$)$_2$ wherein each R$_7$ is independently selected from H and C$_{1-3}$alkyl;

and x is 0 or an integer from 1 to 2.

4. A compound according to claim 3 wherein A is an optionally substituted C$_6$aryl or an optionally substituted 5-6 membered heteroaryl containing one, two, three or four heteroatoms independently selected from O, N and S.

5. A compound according to claim 1 wherein R$_3$ is selected from C$_t$alkyl-R$_4$, and C$_{2-6}$alkenyl where each alkyl and alkenyl group may be optionally substituted with one or more R$_4$ groups and t is an integer selected from 1, 2 and 3.

6. A compound according to claim 1 wherein R$_3$ is C$_t$alkyl-R$_4$ and t is 1, 2 or 3.

7. A compound according to claim 1 wherein R$_4$ is selected from OR$_6$, (C=O)R$_6$, O(C=O)R$_6$, C(=O)OR$_6$, N(R$_6$)$_2$, NR$_6$C(=O)R$_5$, C(=O)N(R$_6$)$_2$, NR$_6$C(=O)OR$_5$, OC(=O)N(R$_6$)$_2$, C(=O)NH—NHC(=O)R$_5$, NHC(=O)NHC$_{1-6}$alkyl, NHS(O)$_x$R$_5$, S(O)$_x$R$_5$, OS(O)$_x$R$_5$, OP(=O)(OR$_6$)$_2$ and P(=O)(OR$_6$)$_2$ where R$_5$ and R$_6$ are as defined in claim 1.

8. A compound according to claim 1 in the form of a racemate, a single enantiomer or mixtures thereof.

9. A compound of general Formula (II):

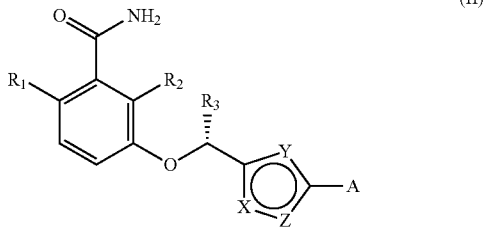

(II)

or a salt, diastereoisomer, hydrate, solvate, N-oxide, or prodrug thereof wherein X and Y are each independently a heteroatom selected from O, N and S or a carbon atom having an optional substituent;

Z is a heteroatom selected from O, N and S or is C—B;

A is selected from H, halo, optionally substituted C$_{6-10}$aryl, optionally substituted 4-10 membered heterocyclyl or A together with B and the carbon atoms to which they are respectively attached join to form an optionally substituted 6-membered fused ring system;

B is selected from H, halo, optionally substituted C$_{1-6}$alkyl, optionally substituted C$_{2-6}$alkenyl, optionally substituted C$_{2-6}$alkynyl or B together with A and the carbon atoms to which they are respectively attached join to form an optionally substituted 6-membered fused ring system;

R$_1$ and R$_2$ are each independently selected from halo or H;

R$_3$ is selected from the group consisting of C$_t$alkyl-R$_4$, C$_{2-6}$alkenyl, C$_{2-6}$alkynyl, C$_{3-7}$cycloalkyl, C$_6$aryl, and 5-6 membered heterocyclyl wherein each alkyl, alkenyl, alkynyl, cycloalkyl, aryl or heterocyclyl may be optionally substituted with one or more R$_4$ or R$_5$ groups;

t is an integer selected from 0, 1, 2 or 3;

R$_4$ is selected from the group consisting of C$_{2-6}$alkenyl, C$_{2-6}$alkynyl, C$_{6-10}$aryl, C$_{1-6}$alkylaryl, 4-10 membered heterocyclyl, C$_{1-6}$alkylheterocyclyl, OR$_6$, (C=O)R$_6$, O(C=O)R$_6$, C(=O)OR$_6$, N(R$_6$)$_2$, NR$_6$C(=O)R$_5$, C(=O)N(R$_6$)$_2$, NR$_6$C(=O)OR$_5$, OC(=O)N(R$_6$)$_2$, C(=O)NH—NHC(=O)R$_5$, NHC(=O)NHC$_{1-6}$alkyl, NHS(O)$_x$R$_5$, S(O)$_x$R$_5$, OS(O)$_x$R$_5$, OP(=O)(OR$_6$)$_2$ and P(=O)(OR$_6$)$_2$ wherein each C$_{2-6}$alkenyl, C$_{2-6}$alkynyl, C$_{6-10}$aryl, C$_{1-6}$alkylaryl, 4-10 membered heterocyclyl and C$_{1-6}$alkylheterocycly may be further optionally substituted with one or more substituents independently selected from the group consisting of C$_{1-3}$alkyl, C$_{2-3}$alkenyl, C$_{1-3}$alkoxyl, OR$_7$, oxo, (C=O)R$_7$, O(C=O)R$_7$, C(=O)OR$_7$, N(R$_7$)$_2$, NR$_7$C(=O)R$_7$, C(=O)N(R$_7$)$_2$, NR$_7$C(=O)OR$_7$, OC(=O)N(R$_7$)$_2$, C(=O)NH—HNC(=O)R$_7$, S(O)$_x$R$_7$, OS(O)$_x$R$_7$, OP(=O)(OR$_7$)$_2$ and P(=O)(OR$_7$)$_2$ wherein each R$_7$ is independently selected from H, C$_{1-3}$alkyl and C$_{2-3}$alkenyl;

each R$_5$ is optionally substituted and is selected from C$_{1-6}$alkyl, C$_{2-6}$alkenyl, C$_{2-6}$alkynyl, C$_{6-10}$aryl, C$_{1-6}$alkylaryl, 4-10 membered heterocyclyl and C$_{1-6}$alkylheterocyclyl;

each R$_6$ is independently selected from H or is optionally substituted C$_{1-6}$alkyl, C$_{2-6}$alkenyl, C$_{2-6}$alkynyl, C$_{6-10}$aryl, C$_{1-6}$alkylaryl, 4-10 membered heterocyclyl and C$_{1-6}$alkylheterocyclyl;

wherein each R$_5$ and R$_6$ independently may be further optionally substituted with one or more optional substituents independently selected from the group consisting of C$_{1-3}$alkyl, C$_{2-3}$alkenyl, C$_{1-3}$alkoxyl, OR$_7$, oxo, (C=O)R$_7$, O(C=O)R$_7$, C(=O)OR$_7$, N(R$_7$)$_2$, NR$_7$C(=O)R$_7$, C(=O)N(R$_7$)$_2$, NR$_7$C(=O)OR$_7$, OC(=O)N(R$_7$)$_2$, C(=O)NH—NHC(=O)R$_7$, S(O)$_x$R$_7$, OS(O)$_x$R$_7$, OP(=O)(OR$_7$)$_2$ and P(=O)(OR$_7$)$_2$ wherein each R$_7$ is independently selected from H and C$_{1-3}$alkyl; and x is 0 or an integer from 1 to 2.

10. A compound selected from the group consisting of:
ethyl 2-(3-carbamoyl-2,4-difluorophenoxy)-2-(4-(4-chlorophenyl)oxazol-2-yl)acetate;
3-(1-(4-(4-chlorophenyl)oxazol-2-yl)-2-hydroxyethoxy)-2,6-difluorobenzamide;
ethyl 2-(3-carbamoyl-2,4-difluorophenoxy)-2-(4-(4-chlorophenyl)thiazol-2-yl)acetate;
2-(3-carbamoyl-2,4-difluorophenoxy)-2-(4-(4-chlorophenyl)oxazol-2-yl)acetic acid;
3-(1-(4-(4-chlorophenyl)thiazol-2-yl)-2-hydroxyethoxy)-2,6-difluorobenzamide;
3-(1-(4-(4-chlorophenyl)thiazol-2-yl)-2-(dimethylamino)-2-oxoethoxy)-2,6-difluorobenzamide;
3-(1-(4-(4-chlorophenyl)thiazol-2-yl)-2-(methylamino)-2-oxoethoxy)-2,6-difluorobenzamide;

2-(5-bromo-4-(4-chlorophenyl)oxazol-2-yl)-2-(3-carbamoyl-2,4-difluorophenoxy)ethyl acetate;
2-(5-bromo-4-(4-(trifluoromethyl)phenyl)oxazol-2-yl)-2-(3-carbamoyl-2,4-difluorophenoxy)ethyl acetate;
3-(1-(5-bromo-4-(4-(trifluoromethyl)phenyl)oxazol-2-yl)-2-hydroxyethoxy)-2,6-difluorobenzamide;
(S)-3-(1-(5-bromo-4-(4-(trifluoromethyl)phenyl)oxazol-2-yl)-2-hydroxyethoxy)-2,6-difluorobenzamide;
(R)-3-(1-(5-bromo-4-(4-(trifluoromethyl)phenyl)oxazol-2-yl)-2-hydroxyethoxy)-2,6-difluorobenzamide;
3-(1-(5-bromo-4-(4-chlorophenyl)oxazol-2-yl)-2-hydroxyethoxy)-2,6-difluorobenzamide;
3-(2-amino-1-(4-(4-chlorophenyl)thiazol-2-yl)-2-oxoethoxy)-2,6-difluorobenzamide;
3-(1-(4-(4-chlorophenyl)thiazol-2-yl)-2-(4-methylpiperazin-1-yl)-2-oxoethoxy)-2,6-difluorobenzamide;
2-(3-carbamoyl-2,4-difluorophenoxy)-2-(5-chloro-4-(4-(trifluoromethyl)phenyl)oxazol-2-yl)ethyl acetate;
3-(1-(5-chloro-4-(4-(trifluoromethyl)phenyl)oxazol-2-yl)-2-hydroxyethoxy)-2,6-difluorobenzamide;
2-(3-carbamoyl-2,4-difluorophenoxy)-2-(5-chloro-4-(4-(trifluoromethyl)phenyl)oxazol-2-yl)ethyl methanesulfonate;
2-(3-carbamoyl-2,4-difluorophenoxy)-2-(5-chloro-4-(4-chlorophenyl)oxazol-2-yl)ethyl acetate;
3-(1-(5-chloro-4-(4-chlorophenyl)oxazol-2-yl)-2-hydroxyethoxy)-2,6-difluorobenzamide;
2-(3-carbamoyl-2,4-difluorophenoxy)-2-(5-chloro-4-(4-chlorophenyl)oxazol-2-yl)ethyl methanesulfonate;
3-(1-(5-chloro-4-(4-chlorophenyl)oxazol-2-yl)-2-(methylamino)-2-oxoethoxy)-2,6-difluorobenzamide;
3-(1-(5-chloro-4-(4-(trifluoromethyl)phenyl)oxazol-2-yl)-2-(methylamino)-2-oxoethoxy)-2,6-difluorobenzamide;
2-(3-carbamoyl-2,4-difluorophenoxy)-2-(5-chloro-4-(4-(trifluoromethyl)phenyl)oxazol-2-yl)ethyl carbamate;
2-(3-carbamoyl-2,4-difluorophenoxy)-2-(5-chloro-4-(4-chlorophenyl)oxazol-2-yl)acetic acid;
2-(3-carbamoyl-2,4-difluorophenoxy)-2-(5-chloro-4-(4-(trifluoromethyl)phenyl)oxazol-2-yl)ethyl ethyl succinate;
2-(5-bromo-4-(4-(trifluoromethyl)phenyl)oxazol-2-yl)-2-(3-carbamoyl-2,4-difluorophenoxy)ethyl 2-(dimethylamino)acetate;
2-(3-carbamoyl-2,4-difluorophenoxy)-2-(5-chloro-4-(4-chlorophenyl)oxazol-2-yl)ethyl 2-((tert-butoxycarbonyl)(methyl)amino)acetate;
2-(3-carbamoyl-2,4-difluorophenoxy)-2-(5-chloro-4-(4-chlorophenyl)oxazol-2-yl)ethyl 2-(methylamino)acetate;
2-(5-bromo-4-(4-(trifluoromethyl)phenyl)oxazol-2-yl)-2-(3-carbamoyl-2,4-difluorophenoxy)ethyl 2-(1,3-dioxoisoindolin-2-yl)acetate;
2-(5-bromo-4-(4-(trifluoromethyl)phenyl)oxazol-2-yl)-2-(3-carbamoyl-2,4-difluorophenoxy)ethyl 2-((tert-butoxycarbonyl)(methyl)amino)acetate;
2-(5-bromo-4-(4-(trifluoromethyl)phenyl)oxazol-2-yl)-2-(3-carbamoyl-2,4-difluorophenoxy)ethyl 2-(methylamino)acetate;
2-(5-allyl-4-(4-(trifluoromethyl)phenyl)oxazol-2-yl)-2-(3-carbamoyl-2,4-difluorophenoxy)ethyl acetate;
2-(5-bromo-4-(4-(trifluoromethyl)phenyl)oxazol-2-yl)-2-(3-carbamoyl-2,4-difluorophenoxy)ethyl 3-(1,3-dioxoisoindolin-2-yl)propanoate;
2-(3-carbamoyl-2,4-difluorophenoxy)-2-(5-propyl-4-(4-(trifluoromethyl)phenyl)oxazol-2-yl)ethyl acetate;
3-(1-(5-allyl-4-(4-(trifluoromethyl)phenyl)oxazol-2-yl)-2-hydroxyethoxy)-2,6-difluorobenzamide;
2,6-difluoro-3-(2-hydroxy-1-(5-propyl-4-(4-(trifluoromethyl)phenyl)oxazol-2-yl)ethoxy)benzamide;
2-(5-bromo-4-(4-(trifluoromethyl)phenyl)oxazol-2-yl)-2-(3-carbamoyl-2,4-difluorophenoxy)ethyl 2-(1H-pyrrol-1-yl)acetate;
2-(5-bromo-4-(4-(trifluoromethyl)phenyl)oxazol-2-yl)-2-(3-carbamoyl-2,4-difluorophenoxy)ethyl 4-(1,3-dioxoisoindolin-2-yl)butanoate;
allyl (2-(5-bromo-4-(4-(trifluoromethyl)phenyl)oxazol-2-yl)-2-(3-carbamoyl-2,4-difluorophenoxy)ethyl) succinate;
diallyl (2-(5-bromo-4-(4-(trifluoromethyl)phenyl)oxazol-2-yl)-2-(3-carbamoyl-2,4-difluorophenoxy)ethyl) phosphate;
3-(5-bromo-4-(4-(trifluoromethyl)phenyl)oxazol-2-yl)-3-(3-carbamoyl-2,4-difluorophenoxy)propyl acetate;
3-(1-(5-bromo-4-(4-(trifluoromethyl)phenyl)oxazol-2-yl)-3-hydroxypropoxy)-2,6-difluorobenzamide;
4-(2-(5-bromo-4-(4-(trifluoromethyl)phenyl)oxazol-2-yl)-2-(3-carbamoyl-2,4-difluorophenoxy)ethoxy)-4-oxobutanoic acid;
allyl (2-(5-bromo-4-(4-(trifluoromethyl)phenyl)oxazol-2-yl)-2-(3-carbamoyl-2,4-difluorophenoxy)ethyl) hydrogen phosphate;
2-(5-bromo-4-(4-cyanophenyl)oxazol-2-yl)-2-(3-carbamoyl-2,4-difluorophenoxy)ethyl acetate;
3-(5-bromo-4-(4-(trifluoromethyl)phenyl)oxazol-2-yl)-3-(3-carbamoyl-2,4-difluorophenoxy)propanoic acid;
2-(5-bromo-4-(5-(trifluoromethyl)pyridin-2-yl)oxazol-2-yl)-2-(3-carbamoyl-2,4-difluorophenoxy)ethyl acetate;
3-(1-(5-bromo-4-(5-(trifluoromethyl)pyridin-2-yl)oxazol-2-yl)-2-hydroxyethoxy)-2,6-difluorobenzamide;
3-(1-(5-bromo-4-(4-cyanophenyl)oxazol-2-yl)-2-hydroxyethoxy)-2,6-difluorobenzamide;
2-(5-bromo-4-(4-(trifluoromethyl)phenyl)oxazol-2-yl)-2-(3-carbamoyl-2,4-difluorophenoxy)ethyl dihydrogen phosphate;
2-(5-bromo-4-(4-(5-methyl-1,2,4-oxadiazol-3-yl)phenyl)oxazol-2-yl)-2-(3-carbamoyl-2,4-difluorophenoxy)ethyl acetate;
3-(1-(5-bromo-4-(4-(5-methyl-1,2,4-oxadiazol-3-yl)phenyl)oxazol-2-yl)-2-hydroxyethoxy)-2,6-difluorobenzamide;
ethyl 2-(2-(5-bromo-4-(4-(trifluoromethyl)phenyl)oxazol-2-yl)-2-(3-carbamoyl-2,4-difluorophenoxy)ethoxy)acetate;
3-(1-(5-bromo-4-(4-(3-methyl-1,2,4-oxadiazol-5-yl)phenyl)oxazol-2-yl)-2-hydroxyethoxy)-2,6-difluorobenzamide;
2-(2-(5-bromo-4-(4-(trifluoromethyl)phenyl)oxazol-2-yl)-2-(3-carbamoyl-2,4-difluorophenoxy)ethoxy)acetic acid;
3-(1-(5-bromo-4-(4-(trifluoromethyl)phenyl)oxazol-2-yl)-3-(methylamino)-3-oxopropoxy)-2,6-difluorobenzamide;
3-(1-(5-bromo-4-(4-(trifluoromethyl)phenyl)oxazol-2-yl)-3-(dimethylamino)-3-oxopropoxy)-2,6-difluorobenzamide;
4-(5-bromo-4-(4-(trifluoromethyl)phenyl)oxazol-2-yl)-4-(3-carbamoyl-2,4-difluorophenoxy)butyl acetate;
3-(1-(5-bromo-4-(4-(trifluoromethyl)phenyl)oxazol-2-yl)-4-hydroxybutoxy)-2,6-difluorobenzamide;
4-(5-bromo-4-(4-(trifluoromethyl)phenyl)oxazol-2-yl)-4-(3-carbamoyl-2,4-difluorophenoxy)butanoic acid;

3-(4-(2-acetylhydrazinyl)-1-(5-bromo-4-(4-(trifluoromethyl)phenyl)oxazol-2-yl)-4-oxobutoxy)-2,6-difluorobenzamide;
3-(1-(5-bromo-4-(4-(trifluoromethyl)phenyl)oxazol-2-yl)-4-(methylamino)-4-oxobutoxy)-2,6-difluorobenzamide;
3-(1-(5-bromo-4-(4-(trifluoromethyl)phenyl)oxazol-2-yl)-4-(dimethylamino)-4-oxobutoxy)-2,6-difluorobenzamide;
3-(3-amino-1-(5-bromo-4-(4-(trifluoromethyl)phenyl)oxazol-2-yl)propoxy)-2,6-difluorobenzamide;
3-(3-amino-1-(5-bromo-4-(4-(trifluoromethyl)phenyl)oxazol-2-yl)-3-oxopropoxy)-2,6-difluorobenzamide;
3-(1-(5-bromo-4-(4-(trifluoromethyl)phenyl)oxazol-2-yl)-3-(5-methyl-1,3,4-oxadiazol-2-yl)propoxy)-2,6-difluorobenzamide;
3-(1-(5-bromo-4-(4-(trifluoromethyl)phenyl)oxazol-2-yl)-3-(dimethylamino)propoxy)-2,6-difluorobenzamide;
3-((5-bromo-4-(4-chlorophenyl)oxazol-2-yl)(pyridin-3-yl)methoxy)-2,6-difluorobenzamide;
3-(3-(2-acetylhydrazinyl)-1-(5-bromo-4-(4-(trifluoromethyl)phenyl)oxazol-2-yl)-3-oxopropoxy)-2,6-difluorobenzamide;
3-(4-amino-1-(5-bromo-4-(4-(trifluoromethyl)phenyl)oxazol-2-yl)-4-oxobutoxy)-2,6-difluorobenzamide;
3-((1-(5-bromo-4-(4-(trifluoromethyl)phenyl)oxazol-2-yl)allyl)oxy)-2,6-difluorobenzamide;
3-(1-(5-bromo-4-(4-(trifluoromethyl)phenyl)oxazol-2-yl)-2-methoxyethoxy)-2,6-difluorobenzamide;
3-((1-(5-bromo-4-(4-chlorophenyl)oxazol-2-yl)but-3-en-1-yl)oxy)-2,6-difluorobenzamide;
3-(1-(5-bromo-4-(4-(trifluoromethyl)phenyl)oxazol-2-yl)-2-((tetrahydro-2H-pyran-2-yl)oxy)ethoxy)-2,6-difluorobenzamide;
3-((1-(5-bromo-4-(4-(trifluoromethyl)phenyl)oxazol-2-yl)but-3-en-1-yl)oxy)-2,6-difluorobenzamide;
2-(5-bromo-4-(4-(trifluoromethyl)phenyl)oxazol-2-yl)-2-(3-carbamoyl-2,4-difluorophenoxy)ethyl dimethylcarbamate;
2-(5-bromo-4-(3-methoxyphenyl)oxazol-2-yl)-2-(3-carbamoyl-2,4-difluorophenoxy)ethyl acetate;
3-(1-(5-bromo-4-(4-(trifluoromethyl)phenyl)oxazol-2-yl)-3,4-dihydroxybutoxy)-2,6-difluorobenzamide;
(R,S)-3-(1-(5-bromo-4-(4-(trifluoromethyl)phenyl)oxazol-2-yl)-3,4-dihydroxybutoxy)-2,6-difluorobenzamide;
(S,R)-3-(1-(5-bromo-4-(4-(trifluoromethyl)phenyl)oxazol-2-yl)-3,4-dihydroxybutoxy)-2,6-difluorobenzamide;
(S,S)-3-(1-(5-bromo-4-(4-(trifluoromethyl)phenyl)oxazol-2-yl)-3,4-dihydroxybutoxy)-2,6-difluorobenzamide;
(R,R)-3-(1-(5-bromo-4-(4-(trifluoromethyl)phenyl)oxazol-2-yl)-3,4-dihydroxybutoxy)-2,6-difluorobenzamide;
3-(1-(5-bromo-4-(4-hydroxyphenyl)oxazol-2-yl)-2-hydroxyethoxy)-2,6-difluorobenzamide;
2-(5-bromo-4-(4-methoxyphenyl)oxazol-2-yl)-2-(3-carbamoyl-2,4-difluorophenoxy)ethyl acetate;
3-(1-(5-bromo-4-(4-methoxyphenyl)oxazol-2-yl)-2-hydroxyethoxy)-2,6-difluorobenzamide;
2-(5-bromo-4-(4-(trifluoromethyl)phenyl)oxazol-2-yl)-2-(3-carbamoyl-2,4-difluorophenoxy)ethyl methylcarbamate;
3-(1-(5-bromo-4-(4-(trifluoromethyl)phenyl)oxazol-2-yl)-2-(1H-imidazol-1-yl)ethoxy)-2,6-difluorobenzamide;
2-(5-bromo-4-(4-(trifluoromethoxy)phenyl)oxazol-2-yl)-2-(3-carbamoyl-2,4-difluorophenoxy)ethyl acetate;
3-(1-(5-bromo-4-(4-(trifluoromethoxy)phenyl)oxazol-2-yl)-2-hydroxyethoxy)-2,6-difluorobenzamide;
3-(1-(5-bromo-4-(3-methoxyphenyl)oxazol-2-yl)-2-hydroxyethoxy)-2,6-difluorobenzamide;
3-(1-(5-bromo-4-(3-hydroxyphenyl)oxazol-2-yl)-2-hydroxyethoxy)-2,6-difluorobenzamide;
diethyl 2-(2-(5-bromo-4-(4-(trifluoromethyl)phenyl)oxazol-2-yl)-2-(3-carbamoyl-2,4-difluorophenoxy)ethyl)malonate;
3-(1-(5-bromo-4-(4-(trifluoromethyl)phenyl)oxazol-2-yl)-2-(5-methyl-1,3,4-oxadiazol-2-yl)ethoxy)-2,6-difluorobenzamide;
2-(5-bromo-4-(1-(3-carbamoyl-2,4-difluorophenoxy)propyl)oxazol-2-yl)ethyl acetate;
3-((1-(5-bromo-4-(4-(trifluoromethyl)phenyl)oxazol-2-yl)pent-4-en-1-yl)oxy)-2,6-difluorobenzamide;
ethyl 2-(3-carbamoyl-2,4-difluorophenoxy)-2-(2-(4-(trifluoromethyl)phenyl)thiazol-4-yl)acetate;
2,6-difluoro-3-(2-hydroxy-1-(2-(4-(trifluoromethyl)phenyl)thiazol-4-yl)ethoxy)benzamide;
2-(3-carbamoyl-2,4-difluorophenoxy)-2-(2-(4-(trifluoromethyl)phenyl)thiazol-4-yl)acetic acid;
3-((1-(5-bromo-4-(4-(trifluoromethyl)phenyl)oxazol-2-yl)-4,5-dihydroxypentyl)oxy)-2,6-difluorobenzamide;
ethyl 2-(3-carbamoyl-2,4-difluorophenoxy)-2-(2-(4-(trifluoromethyl)phenyl)oxazol-4-yl)acetate;
2-(5-bromo-2-(4-(trifluoromethyl)phenyl)thiazol-4-yl)-2-(3-carbamoyl-2,4-difluorophenoxy)ethyl acetate;
3-(1-(5-bromo-2-(4-(trifluoromethyl)phenyl)thiazol-4-yl)-2-hydroxyethoxy)-2,6-difluorobenzamide;
2-(3-carbamoyl-2,4-difluorophenoxy)-2-(2-(4-(trifluoromethyl)phenyl)oxazol-4-yl)acetic acid;
2-(2-(5-bromo-4-(4-(trifluoromethyl)phenyl)oxazol-2-yl)-2-(3-carbamoyl-2,4-difluorophenoxy)ethyl)propane-1,3-diyl diacetate;
2-(5-bromo-4-(4-(trifluoromethyl)phenyl)oxazol-2-yl)-2-(3-carbamoyl-2,4-difluorophenoxy)ethyl (2-(dimethylamino)ethyl)carbamate;
2-(5-bromo-4-(4-(trifluoromethyl)phenyl)oxazol-2-yl)-2-(3-carbamoyl-2,4-difluorophenoxy)ethyl piperazine-1-carboxylate;
2,6-difluoro-3-(2-hydroxy-1-(2-(4-(trifluoromethyl)phenyl)oxazol-4-yl)ethoxy)benzamide;
2-(5-bromo-2-(4-(trifluoromethyl)phenyl)oxazol-4-yl)-2-(3-carbamoyl-2,4-difluorophenoxy)ethyl acetate;
3-(1-(5-bromo-2-(4-(trifluoromethyl)phenyl)oxazol-4-yl)-2-hydroxyethoxy)-2,6-difluorobenzamide;
3-(1-(5-bromo-4-(4-(trifluoromethyl)phenyl)oxazol-2-yl)-4-hydroxy-3-(hydroxymethyl)butoxy)-2,6-difluorobenzamide;
ethyl 2-(((2-(5-bromo-4-(4-(trifluoromethyl)phenyl)oxazol-2-yl)-2-(3-carbamoyl-2,4-difluorophenoxy)ethoxy)carbonyl)amino)acetate;
methyl 3-(((2-(5-bromo-4-(4-(trifluoromethyl)phenyl)oxazol-2-yl)-2-(3-carbamoyl-2,4-difluorophenoxy)ethoxy)carbonyl)amino)propanoate;
2-(((2-(5-bromo-4-(4-(trifluoromethyl)phenyl)oxazol-2-yl)-2-(3-carbamoyl-2,4-difluorophenoxy)ethoxy)carbonyl)amino)acetic acid;
3-(((2-(5-bromo-4-(4-(trifluoromethyl)phenyl)oxazol-2-yl)-2-(3-carbamoyl-2,4-difluorophenoxy)ethoxy)carbonyl)amino)propanoic acid;

2-(5-bromo-4-(4-(methylsulfonyl)phenyl)oxazol-2-yl)-2-(3-carbamoyl-2,4-difluorophenoxy)ethyl acetate;
3-(1-(5-bromo-4-(4-(methylsulfonyl)phenyl)oxazol-2-yl)-2-hydroxyethoxy)-2,6-difluorobenzamide;
3-(1-(4-bromo-5-(4-(trifluoromethyl)phenyl)oxazol-2-yl)-2-hydroxyethoxy)-2,6-difluorobenzamide;
3-(1-(5-bromo-4-(4-(trifluoromethyl)phenyl)oxazol-2-yl)-2-(2-hydroxyethoxy)ethoxy)-2,6-difluorobenzamide;
2-(5-bromo-4-(4-(trifluoromethyl)phenyl)oxazol-2-yl)-2-(3-carbamoyl-2,4-difluorophenoxy)ethyl tert-butyl ethane-1,2-diyldicarbamate;
2-(5-bromo-4-(4-(trifluoromethyl)phenyl)oxazol-2-yl)-2-(3-carbamoyl-2,4-difluorophenoxy)ethyl (2-aminoethyl)carbamate;
tert-butyl (2-(((2-(5-bromo-4-(4-(trifluoromethyl)phenyl)oxazol-2-yl)-2-(3-carbamoyl-2,4-difluorophenoxy)ethoxy)carbonyl)amino)ethyl)(methyl)carbamate;
2-(5-bromo-4-(4-(trifluoromethyl)phenyl)oxazol-2-yl)-2-(3-carbamoyl-2,4-difluorophenoxy)ethyl (2-(methylamino)ethyl)carbamate;
3-(1-(5-bromo-4-(4-(trifluoromethyl)phenyl)oxazol-2-yl)-2-(2-methoxyethoxy)ethoxy)-2,6-difluorobenzamide;
2-(5-bromo-4-(4-(trifluoromethyl)phenyl)oxazol-2-yl)-2-(3-carbamoyl-2-fluorophenoxy)ethyl acetate;
3-(1-(5-bromo-4-(4-(trifluoromethyl)phenyl)oxazol-2-yl)-2-hydroxyethoxy)-2-fluorobenzamide;
2-(5-bromo-4-(4-(trifluoromethyl)phenyl)oxazol-2-yl)-2-(3-carbamoyl-2,4-difluorophenoxy)ethyl morpholine-4-carboxylate;
2-(5-bromo-4-(4-(trifluoromethyl)phenyl)oxazol-2-yl)-2-(3-carbamoyl-2,4-difluorophenoxy)ethyl (2-(pyrrolidin-1-yl)ethyl)carbamate;
2-(5-bromo-4-(4-(trifluoromethyl)phenyl)oxazol-2-yl)-2-(3-carbamoyl-2,4-difluorophenoxy)ethyl (2-(1H-imidazol-4-yl)ethyl)carbamate;
2-(5-bromo-4-(4-(trifluoromethyl)phenyl)oxazol-2-yl)-2-(3-carbamoyl-2,4-difluorophenoxy)ethyl (2-hydroxyethyl)carbamate;
2-(5-bromo-4-(4-(trifluoromethyl)phenyl)oxazol-2-yl)-2-(3-carbamoyl-2,4-difluorophenoxy)ethyl (2-methoxyethyl)carbamate;
2-(5-bromo-4-(4-(trifluoromethyl)phenyl)oxazol-2-yl)-2-(3-carbamoyl-2,4-difluorophenoxy)ethyl (pyridin-2-ylmethyl)carbamate;
2-(5-bromo-4-(4-(trifluoromethyl)phenyl)oxazol-2-yl)-2-(3-carbamoyl-2,4-difluorophenoxy)ethyl (pyridin-3-ylmethyl)carbamate;
2-(5-bromo-4-(4-(trifluoromethyl)phenyl)oxazol-2-yl)-2-(3-carbamoyl-2,4-difluorophenoxy)ethyl (pyridin-4-ylmethyl)carbamate;
3-(1-(5-bromo-4-(4-(trifluoromethyl)phenyl)oxazol-2-yl)-2-(2-morpholinoethoxy)ethoxy)-2,6-difluorobenzamide;
2-(5-bromo-4-(4-(trifluoromethyl)phenyl)oxazol-2-yl)-2-(3-carbamoyl-2,4-difluorophenoxy)ethyl 3-(methylsulfonyl)-2-oxoimidazolidine-1-carboxylate;
2-(5-bromo-4-(4-(trifluoromethyl)phenyl)oxazol-2-yl)-2-(3-carbamoyl-2,4-difluorophenoxy)ethyl pyridin-3-ylcarbamate;
2-(5-bromo-4-(4-(trifluoromethyl)phenyl)oxazol-2-yl)-2-(3-carbamoyl-2,4-difluorophenoxy)ethyl (2-(3-methyl-1,2,4-oxadiazol-5-yl)ethyl)carbamate;
2-(5-bromo-4-(4-(trifluoromethyl)phenyl)oxazol-2-yl)-2-(3-carbamoyl-2,4-difluorophenoxy)ethyl ((5-methyl-1,3,4-oxadiazol-2-yl)methyl)carbamate;
2-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide;
3-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide;
4-((((2-(5-bromo-4-(4-(trifluoromethyl)phenyl)oxazol-2-yl)-2-(3-carbamoyl-2,4-difluorophenoxy)ethoxy)carbonyl)amino)methyl)pyridine 1-oxide;
2-(5-bromo-4-(4-(trifluoromethyl)phenyl)oxazol-2-yl)-2-(3-carbamoyl-2,4-difluorophenoxy)ethyl pyridin-4-ylcarbamate;
2-(5-bromo-4-(4-(trifluoromethyl)phenyl)oxazol-2-yl)-2-(3-carbamoyl-2,4-difluorophenoxy)ethyl 1H-tetrazol-5-ylcarbamate;
2-(5-bromo-4-(4-(trifluoromethyl)phenyl)oxazol-2-yl)-2-(3-carbamoyl-2,4-difluorophenoxy)ethyl 4-methylpiperazine-1-carboxylate;
2-(5-bromo-4-(4-(trifluoromethyl)phenyl)oxazol-2-yl)-2-(3-carbamoyl-2,4-difluorophenoxy)ethyl ((3-methyl-1,2,4-oxadiazol-5-yl)methyl)carbamate;
ethyl 2-(3-carbamoyl-2,4-difluorophenoxy)-2-(4-(tetrahydro-2H-pyran-4-yl)oxazol-2-yl)acetate;
(R)-4-(2-(5-bromo-4-(4-(trifluoromethyl)phenyl)oxazol-2-yl)-2-(3-carbamoyl-2,4-difluorophenoxy)ethoxy)-4-oxobutanoic acid;
2,6-difluoro-3-(2-hydroxy-1-(4-(tetrahydro-2H-pyran-4-yl)oxazol-2-yl)ethoxy)benzamide;
2-(5-bromo-4-(4-(trifluoromethyl)phenyl)oxazol-2-yl)-2-(3-carbamoyl-2,4-difluorophenoxy)ethyl methyl(pyridin-3-ylmethyl)carbamate;
2-(5-bromo-4-(4-(trifluoromethyl)phenyl)oxazol-2-yl)-2-(3-carbamoyl-2,4-difluorophenoxy)ethyl methyl(pyridin-4-ylmethyl)carbamate;
3-(1-(5-bromo-4-(tetrahydro-2H-pyran-4-yl)oxazol-2-yl)-2-hydroxyethoxy)-2,6-difluorobenzamide;
2,6-difluoro-3-((3-methyl-1,2,4-oxadiazol-5-yl)(4-(4-(trifluoromethyl)phenyl)oxazol-2-yl)methoxy)benzamide;
3-(1-(5-bromo-4-(4-(trifluoromethyl)phenyl)oxazol-2-yl)-2,3-dihydroxypropoxy)-2,6-difluorobenzamide;
2-(5-bromo-4-(4-(trifluoromethyl)phenyl)oxazol-2-yl)-2-(3-carbamoyl-2,4-difluorophenoxy)ethyl (2-(2-methyl-1H-imidazol-1-yl)ethyl)carbamate;
2-(5-bromo-4-(4-(trifluoromethyl)phenyl)oxazol-2-yl)-2-(3-carbamoyl-2,4-difluorophenoxy)ethyl methyl(pyridin-2-ylmethyl)carbamate;
2-(5-bromo-4-(4-(trifluoromethyl)phenyl)oxazol-2-yl)-2-(3-carbamoyl-2,4-difluorophenoxy)ethyl methyl(pyrazin-2-ylmethyl)carbamate;
2-(5-bromo-4-(4-(trifluoromethyl)phenyl)oxazol-2-yl)-2-(3-carbamoyl-2,4-difluorophenoxy)ethyl ((1-methyl-1H-pyrazol-3-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-pyrazol-5-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-imidazol-5-yl)methyl)carbamate;
2-(5-bromo-4-(4-(trifluoromethyl)phenyl)oxazol-2-yl)-2-(3-carbamoyl-2,4-difluorophenoxy)ethyl ((2-methoxypyridin-3-yl)methyl)carbamate;
2-(5-bromo-4-(4-(trifluoromethyl)phenyl)oxazol-2-yl)-2-(3-carbamoyl-2,4-difluorophenoxy)ethyl methyl(pyrimidin-4-ylmethyl)carbamate;
2-(5-bromo-4-(4-(trifluoromethyl)phenyl)oxazol-2-yl)-2-(3-carbamoyl-2,4-difluorophenoxy)ethyl ((1-methyl-1H-pyrazol-4-yl)methyl)carbamate;

2-(5-bromo-4-(4-(trifluoromethyl)phenyl)oxazol-2-yl)-2-(3-carbamoyl-2,4-difluorophenoxy)ethyl ((6-methylpyridin-2-yl)methyl)carbamate;
2-(5-bromo-4-(4-(trifluoromethyl)phenyl)oxazol-2-yl)-2-(3-carbamoyl-2,4-difluorophenoxy)ethyl ((2-methylpyridin-4-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-imidazol-2-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-pyrrol-2-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-imidazol-4-yl)methyl)carbamate;
2-(5-bromo-4-(4-(trifluoromethyl)phenyl)oxazol-2-yl)-2-(3-carbamoyl-2,4-difluorophenoxy)ethyl ((1,3-dimethyl-1H-pyrazol-4-yl)methyl)carbamate;
2-(5-bromo-4-(4-(trifluoromethyl)phenyl)oxazol-2-yl)-2-(3-carbamoyl-2,4-difluorophenoxy)ethyl ((1,5-dimethyl-1H-pyrazol-4-yl)methyl)carbamate;
2-(5-bromo-4-(4-(trifluoromethyl)phenyl)oxazol-2-yl)-2-(3-carbamoyl-2,4-difluorophenoxy)ethyl ((4-(2-methoxyethyl)-4H-1,2,4-triazol-3-yl)methyl)carbamate;
2-(5-bromo-4-(4-(trifluoromethyl)phenyl)oxazol-2-yl)-2-(3-carbamoyl-2,4-difluorophenoxy)ethyl ((1-(2-methoxyethyl)-1H-imidazol-5-yl)methyl)carbamate;
2-(5-bromo-4-(4-(trifluoromethyl)phenyl)oxazol-2-yl)-2-(3-carbamoyl-2,4-difluorophenoxy)ethyl ((6-methoxypyridin-3-yl)methyl)carbamate;
2-(5-bromo-4-(4-(trifluoromethyl)phenyl)oxazol-2-yl)-2-(3-carbamoyl-2,4-difluorophenoxy)ethyl ((2-methoxypyridin-4-yl)methyl)carbamate;
2-(5-bromo-4-(4-(trifluoromethyl)phenyl)oxazol-2-yl)-2-(3-carbamoyl-2,4-difluorophenoxy)ethyl ((1-methyl-1H-benzo[d]imidazol-2-yl)methyl)carbamate;
2-(5-bromo-4-(4-(trifluoromethyl)phenyl)oxazol-2-yl)-2-(3-carbamoyl-2,4-difluorophenoxy)ethyl ((1,5-dimethyl-1H-pyrrol-2-yl)methyl)carbamate;
2-(5-bromo-4-(4-(trifluoromethyl)phenyl)oxazol-2-yl)-2-(3-carbamoyl-2,4-difluorophenoxy)ethyl ((1,3-dimethyl-1H-pyrazol-5-yl)methyl)carbamate;
2-(5-bromo-4-(4-(trifluoromethyl)phenyl)oxazol-2-yl)-2-(3-carbamoyl-2,4-difluorophenoxy)ethyl ((1,5-dimethyl-1H-pyrazol-3-yl)methyl)carbamate;
2-(5-bromo-4-(4-(trifluoromethyl)phenyl)oxazol-2-yl)-2-(3-carbamoyl-2,4-difluorophenoxy)ethyl ((6-methylpyridin-3-yl)methyl)carbamate;
2-(5-bromo-4-(4-(trifluoromethyl)phenyl)oxazol-2-yl)-2-(3-carbamoyl-2,4-difluorophenoxy)ethyl ((2-methylpyridin-3-yl)methyl)carbamate;
2-(5-bromo-4-(4-(trifluoromethyl)phenyl)oxazol-2-yl)-2-(3-carbamoyl-2,4-difluorophenoxy)ethyl ((3-methylpyridin-4-yl)methyl)carbamate;
2-(5-bromo-4-(4-(trifluoromethyl)phenyl)oxazol-2-yl)-2-(3-carbamoyl-2,4-difluorophenoxy)ethyl (2-(2-oxopyridin-1(2H)-yl)ethyl)carbamate;
2,6-difluoro-3-((5-methyl-1,3,4-oxadiazol-2-yl)(4-(4-(trifluoromethyl)phenyl)oxazol-2-yl)methoxy)benzamide;
3-(5-bromo-4-(4-(trifluoromethyl)phenyl)oxazol-2-yl)-3-(3-carbamoyl-2,4-difluorophenoxy)propane-1,2-diyl diacetate;
2,6-difluoro-3-(2-hydroxy-1-(4-(6-(methylamino)pyridin-3-yl)oxazol-2-yl)ethoxy)benzamide;
3-(1-(5-bromo-4-propyloxazol-2-yl)-2-hydroxyethoxy)-2,6-difluorobenzamide;
3-(1-(4-(4-chloro-3-fluorophenyl)oxazol-2-yl)-2-hydroxyethoxy)-2,6-difluorobenzamide;
2,6-difluoro-3-(1-(4-(2-fluorophenyl)oxazol-2-yl)-2-hydroxyethoxy)benzamide;
3-(1-(5-bromo-4-(6-(methylamino)pyridin-3-yl)oxazol-2-yl)-2-hydroxyethoxy)-2,6-difluorobenzamide;
3-(1-(5-bromo-4-(4-chloro-3-fluorophenyl)oxazol-2-yl)-2-hydroxyethoxy)-2,6-difluorobenzamide;
3-(1-(4-(2,4-difluorophenyl)oxazol-2-yl)-2-hydroxyethoxy)-2,6-difluorobenzamide;
3-(1-(4-(4-chloro-2-methoxyphenyl)oxazol-2-yl)-2-hydroxyethoxy)-2,6-difluorobenzamide;
2,6-difluoro-3-(1-(4-(2-fluoro-4-methoxyphenyl)oxazol-2-yl)-2-hydroxyethoxy)benzamide;
3-(1-(5-bromo-4-(2-fluorophenyl)oxazol-2-yl)-2-hydroxyethoxy)-2,6-difluorobenzamide;
3-(1-(5-bromo-4-(6-methoxypyridin-3-yl)oxazol-2-yl)-2-hydroxyethoxy)-2,6-difluorobenzamide;
3-(1-(5-bromo-4-(6-methylpyridin-3-yl)oxazol-2-yl)-2-hydroxyethoxy)-2,6-difluorobenzamide;
3-(1-(5-bromo-4-(5-bromo-4-chloro-2-methoxyphenyl)oxazol-2-yl)-2-hydroxyethoxy)-2,6-difluorobenzamide;
3-(1-(5-bromo-4-(2,4-difluorophenyl)oxazol-2-yl)-2-hydroxyethoxy)-2,6-difluorobenzamide;
(S)-3-(1-(5-bromo-4-(2,4-difluorophenyl)oxazol-2-yl)-2-hydroxyethoxy)-2,6-difluorobenzamide;
(R)-3-(1-(5-bromo-4-(2,4-difluorophenyl)oxazol-2-yl)-2-hydroxyethoxy)-2,6-difluorobenzamide;
3-(1-(5-bromo-4-(2-fluoro-4-methoxyphenyl)oxazol-2-yl)-2-hydroxyethoxy)-2,6-difluorobenzamide;
3-(1-(5-bromo-4-(4-chloro-2-fluorophenyl)oxazol-2-yl)-2-hydroxyethoxy)-2,6-difluorobenzamide;
3-(1-(5-bromo-4-(5-cyanothiophen-2-yl)oxazol-2-yl)-2-hydroxyethoxy)-2,6-difluorobenzamide;
3-(1-(5-bromo-4-(5-bromothiophen-2-yl)oxazol-2-yl)-2-hydroxyethoxy)-2,6-difluorobenzamide;
3-(1-(5-bromo-4-(5-methoxypyridin-2-yl)oxazol-2-yl)-2-hydroxyethoxy)-2,6-difluorobenzamide;
3-(1-(5-bromo-4-(4-chloro-2-methylphenyl)oxazol-2-yl)-2-hydroxyethoxy)-2,6-difluorobenzamide;
3-(1-(5-bromo-4-(4,5-dimethylthiazol-2-yl)oxazol-2-yl)-2-hydroxyethoxy)-2,6-difluorobenzamide;
3-(1-(5-bromo-4-(6-chloropyridin-3-yl)oxazol-2-yl)-2-hydroxyethoxy)-2,6-difluorobenzamide;
3-(1-(5-bromo-4-(4-(2-methoxyethoxy)phenyl)oxazol-2-yl)-2-hydroxyethoxy)-2,6-difluorobenzamide;
3-(1-(5-bromo-4-(thiophen-2-yl)oxazol-2-yl)-2-hydroxyethoxy)-2,6-difluorobenzamide;
3-(1-(5-bromo-4-(5-methylthiophen-2-yl)oxazol-2-yl)-2-hydroxyethoxy)-2,6-difluorobenzamide;
3-(1-(5-bromo-4-(2,4-dimethylthiazol-5-yl)oxazol-2-yl)-2-hydroxyethoxy)-2,6-difluorobenzamide;
methyl 4-(5-bromo-2-(1-(3-carbamoyl-2,4-difluorophenoxy)-2-hydroxyethyl)oxazol-4-yl)benzoate;
(R)-3-(1-(5-bromo-4-(thiazol-5-yl)oxazol-2-yl)-2-hydroxyethoxy)-2,6-difluorobenzamide;
3-(1-(5-bromo-4-(3,4-difluorophenyl)oxazol-2-yl)-2-hydroxyethoxy)-2,6-difluorobenzamide;
(R)-3-(1-(5-bromo-4-(6-cyanopyridin-3-yl)oxazol-2-yl)-2-hydroxyethoxy)-2,6-difluorobenzamide;
(R)-3-(1-(5-bromo-4-(5-chlorothiophen-2-yl)oxazol-2-yl)-2-hydroxyethoxy)-2,6-difluorobenzamide;
4-(5-bromo-2-(1-(3-carbamoyl-2,4-difluorophenoxy)-2-hydroxyethyl)oxazol-4-yl)benzoic acid;
4-(5-bromo-2-(1-(3-carbamoyl-2,4-difluorophenoxy)-2-hydroxyethyl)oxazol-4-yl)-N,N-dimethylbenzamide;

(R)-3-(1-(5-bromo-4-(2,3-dihydrobenzofuran-5-yl)ox-azol-2-yl)-2-hydroxyethoxy)-2,6-difluorobenzamide;
(R)-3-(1-(4-(benzofuran-5-yl)-5-bromooxazol-2-yl)-2-hydroxyethoxy)-2,6-difluorobenzamide;
(R)-3-(1-(5-bromo-4-(4-(morpholine-4-carbonyl)phenyl)oxazol-2-yl)-2-hydroxyethoxy)-2,6-difluorobenzamide;
3-(1-(5-bromo-4-(3-bromo-4-(pyrrolidin-1-yl)phenyl)oxazol-2-yl)-2-hydroxyethoxy)-2,6-difluorobenzamide;
(R)-3-(1-(5-bromo-4-(2-methoxypyrimidin-5-yl)oxazol-2-yl)-2-hydroxyethoxy)-2,6-difluorobenzamide;
3-(1-(2-(4-chlorophenyl)thiazol-4-yl)-2-hydroxyethoxy)-2,6-difluorobenzamide;
2,6-difluoro-3-(2-hydroxy-1-(4-(4-methoxyphenyl)thiazol-2-yl)ethoxy)benzamide;
2,6-difluoro-3-(2-hydroxy-1-(4-(5-methoxypyridin-2-yl)thiazol-2-yl)ethoxy)benzamide;
2,6-difluoro-3-(2-hydroxy-1-(4-(5-methoxypyrazin-2-yl)thiazol-2-yl)ethoxy)benzamide;
2,6-difluoro-3-(2-hydroxy-1-(4-(4-methoxyphenethyl)thiazol-2-yl)ethoxy)benzamide;
4-(2-(5-bromo-4-(2,4-difluorophenyl)oxazol-2-yl)-2-(3-carbamoyl-2,4-difluorophenoxy)ethoxy)-4-oxobutanoic acid;
2,6-difluoro-3-(2-hydroxy-1-(4-(6-methylpyridin-3-yl)thiazol-2-yl)ethoxy)benzamide;
(R)-3-(1-(5-bromo-4-(2,4-difluorophenyl)oxazol-2-yl)-2-(2-hydroxyethoxy)ethoxy)-2,6-difluorobenzamide;
(R)-3-(1-(6-chlorothiazolo[5,4-b]pyridin-2-yl)-2-hydroxyethoxy)-2,6-difluorobenzamide;
2-(1-(3-carbamoyl-2,4-difluorophenoxy)-2-hydroxyethyl)-4-(4-chlorophenyl)thiazole 3-oxide;
3-(1-(5-cyclopropyl-4-(4-(trifluoromethyl)phenyl)oxazol-2-yl)-2-hydroxyethoxy)-2,6-difluorobenzamide;
2-fluoro-3-(2-hydroxy-1-(5-(methylthio)-4-(4-(trifluoromethyl)phenyl)oxazol-2-yl)ethoxy)-6-(methylthio)benzamide;
2,6-difluoro-3-(2-hydroxy-1-(5-(methylthio)-4-(4-(trifluoromethyl)phenyl)oxazol-2-yl)ethoxy)benzamide;
(R)-2,6-difluoro-3-(2-hydroxy-1-(4-(4-(trifluoromethyl)phenyl)oxazol-2-yl)ethoxy)benzamide;
(R)-3-(1-(5-bromo-4-(4-(difluoromethoxy)phenyl)oxazol-2-yl)-2-hydroxyethoxy)-2,6-difluorobenzamide;
(R)-3-(1-(4-(4-(difluoromethoxy)phenyl)oxazol-2-yl)-2-hydroxyethoxy)-2,6-difluorobenzamide;
(R)-3-(1-(5-bromo-4-ethyloxazol-2-yl)-2-hydroxyethoxy)-2,6-difluorobenzamide;
benzyl (2-(3-carbamoyl-2,4-difluorophenoxy)-2-(4-(4-(trifluoromethyl)phenyl)oxazol-2-yl)ethyl)carbamate;
3-(1-(5-butyl-4-(4-(trifluoromethyl)phenyl)oxazol-2-yl)-2-hydroxyethoxy)-2,6-difluorobenzamide;
(R)-2,6-difluoro-3-(1-(4-(4-fluorophenyl)oxazol-2-yl)-2-hydroxyethoxy)benzamide;
(R)-3-(1-(5-bromo-4-(4-fluorophenyl)oxazol-2-yl)-2-hydroxyethoxy)-2,6-difluorobenzamide;
benzyl (2-(5-bromo-4-(4-(trifluoromethyl)phenyl)oxazol-2-yl)-2-(3-carbamoyl-2,4-difluorophenoxy)ethyl)carbamate;
3-(2-amino-1-(4-(4-(trifluoromethyl)phenyl)oxazol-2-yl)ethoxy)-2,6-difluorobenzamide;
3-(2-acetamido-1-(4-(4-(trifluoromethyl)phenyl)oxazol-2-yl)ethoxy)-2,6-difluorobenzamide;
3-(2-acetamido-1-(5-bromo-4-(4-(trifluoromethyl)phenyl)oxazol-2-yl)ethoxy)-2,6-difluorobenzamide;
2,6-difluoro-3-(2-(methylsulfonamido)-1-(4-(4-(trifluoromethyl)phenyl)oxazol-2-yl)ethoxy)benzamide;
3-(1-(5-bromo-4-(4-(trifluoromethyl)phenyl)oxazol-2-yl)-2-(methylsulfonamido)ethoxy)-2,6-difluorobenzamide;
3-(2-(3-ethylureido)-1-(4-(4-(trifluoromethyl)phenyl)oxazol-2-yl)ethoxy)-2,6-difluorobenzamide;
methyl (2-(3-carbamoyl-2,4-difluorophenoxy)-2-(4-(4-(trifluoromethyl)phenyl)oxazol-2-yl)ethyl)carbamate;
methyl (2-(5-bromo-4-(4-(trifluoromethyl)phenyl)oxazol-2-yl)-2-(3-carbamoyl-2,4-difluorophenoxy)ethyl)carbamate;
3-(2-benzamido-1-(4-(4-(trifluoromethyl)phenyl)oxazol-2-yl)ethoxy)-2,6-difluorobenzamide;
3-(2-amino-1-(5-bromo-4-(4-(trifluoromethyl)phenyl)oxazol-2-yl)ethoxy)-2,6-difluorobenzamide;
3-(1-(5-bromo-4-(4-(trifluoromethyl)phenyl)oxazol-2-yl)-2-(3-ethylureido)ethoxy)-2,6-difluorobenzamide;
3-(2-benzamido-1-(5-bromo-4-(4-(trifluoromethyl)phenyl)oxazol-2-yl)ethoxy)-2,6-difluorobenzamide;
N-(2-(3-carbamoyl-2,4-difluorophenoxy)-2-(4-(4-(trifluoromethyl)phenyl)oxazol-2-yl)ethyl)nicotinamide;
N-(2-(3-carbamoyl-2,4-difluorophenoxy)-2-(4-(4-(trifluoromethyl)phenyl)oxazol-2-yl)ethyl)picolinamide;
N-(2-(5-bromo-4-(4-(trifluoromethyl)phenyl)oxazol-2-yl)-2-(3-carbamoyl-2,4-difluorophenoxy)ethyl)nicotinamide;
N-(2-(5-bromo-4-(4-(trifluoromethyl)phenyl)oxazol-2-yl)-2-(3-carbamoyl-2,4-difluorophenoxy)ethyl)picolinamide;
3-((1R,2R)-1-(5-bromo-4-(4-(difluoromethoxy)phenyl)oxazol-2-yl)-2-hydroxypropoxy)-2,6-difluorobenzamide;
3-(1-(5-bromo-4-(4-(trifluoromethyl)phenyl)oxazol-2-yl)-2-(2-(pyridin-3-yl)acetamido)ethoxy)-2,6-difluorobenzamide;
3-((1R,2S)-1-(5-bromo-4-(4-(difluoromethoxy)phenyl)oxazol-2-yl)-2-hydroxypropoxy)-2,6-difluorobenzamide;
3-(1-(5-bromo-4-(4-(trifluoromethyl)phenyl)oxazol-2-yl)-2-(2-(2-methoxyethoxy)acetamido)ethoxy)-2,6-difluorobenzamide;
4-((2-(5-bromo-4-(4-(trifluoromethyl)phenyl)oxazol-2-yl)-2-(3-carbamoyl-2,4-difluorophenoxy)ethyl)amino)-4-oxobutanoic acid;
(R)-3-(1-(5-ethyl-4-(4-methoxyphenyl)oxazol-2-yl)-2-hydroxyethoxy)-2,6-difluorobenzamide;
(R)-2,6-difluoro-3-(2-hydroxy-1-(5-(methoxymethyl)-4-(4-methoxyphenyl)oxazol-2-yl)ethoxy)benzamide;
2,6-difluoro-3-(2-hydroxy-1-(2-(4-methoxyphenyl)-5-vinyloxazol-4-yl)ethoxy)benzamide;
3-(1-(5-ethyl-2-(4-methoxyphenyl)oxazol-4-yl)-2-hydroxyethoxy)-2,6-difluorobenzamide;
(R)-2,6-difluoro-3-(2-hydroxy-1-(3-(4-methoxyphenyl)-1,2,4-oxadiazol-5-yl)ethoxy)benzamide; and
4-((2-(5-bromo-4-(4-(trifluoromethyl)phenyl)oxazol-2-yl)-2-(3-carbamoyl-2,4-difluorophenoxy)ethyl)carbamoyl)benzoic acid;
or a salt, racemate, diastereoisomer, enantiomer, hydrate, solvate, N-oxide, or prodrug thereof.

11. A method of treating a bacterial infection in a subject comprising administering an effective amount of a compound of Formula (I):

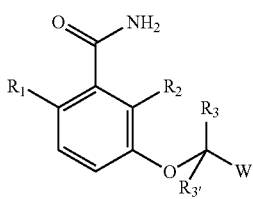

or a pharmaceutically acceptable salt, racemate, diastereoisomer, enantiomer, hydrate, solvate, N-oxide or prodrug thereof wherein:

W is a substituted $C_{6-10}$-membered monocyclic or fused bicyclic aryl group or an optionally substituted 5-6-membered monocyclic heteroaryl or a 9-membered fused bicyclic heteroaryl group;

$R_1$ and $R_2$ are each independently selected from halo or H;

$R_3$ is selected from the group consisting of $C_t$alkyl-$R_4$, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;

t is an integer selected from 0, 1, 2 and 3;

$R_{3'}$ is H;

$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$, $OC(=O)N(R_6)_2$, $C(=O)NH$—$NHC(=O)R_5$, $NHC(=O)NHC_{1-6}$alkyl, $NHS(O)_xR_5$, $S(O)_xR_5$, $OS(O)_xR_5$, $OP(=O)(OR_6)_2$ and $P(=O)(OR_6)_2$ wherein each $C_{2-6}$alkenyl, $C_{6-10}$aryl, $C_{1-6}$alkylaryl, 4-10 membered heterocyclyl and $C_{1-6}$alkylheterocycly may be further optionally substituted with one or more substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)NH$—$HNC(=O)R_7$, $S(O)_xR_7$, $OS(O)_xR_7$, $OP(=O)(OR$ and $P(=O)(OR_2)_2$ wherein each $R_7$ is independently selected from H, $C_{1-3}$alkyl and $C_{2-3}$alkenyl;

each $R_5$ is optionally substituted and is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H, or optionally substituted $C_{1-6}$alkyl, $C_{2-6}$alkynyl, $C_{6-10}$aryl, $C_{1-6}$alkylaryl, 4-10 membered heterocyclyl and $C_{1-6}$alkylheterocyclyl;

wherein each $R_5$ and $R_6$ independently may be further optionally substituted with one or more optional substituents independently selected from the group consisting of $C_{1-3}$alkyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_2)_2$, $NR_7C(=O)OR_7$, $OC(=O)N(R_2)_2$, $C(=O)NH$—$NHC(=O)R_7$, $S(O)_xR_7$, $OS(O)_xR_2$, $OP(=O)(OR_7)_2$ and $P(=O)(OR_7)_2$ wherein each $R_7$ is independently selected from H, $C_{1-3}$alkyl and $C_{2-3}$alkenyl; and x is 0 or an integer from 1 to 2 to the subject.

12. A method according to claim 11 wherein the compound is administered in combination with another antibacterial agent.

13. A method according to claim 11 wherein the administration is intravenous administration, oral administration or a combination thereof.

14. A compound as defined in claim 1 or a pharmaceutically acceptable salt, racemate, diastereoisomer, enantiomer, hydrate, solvate, N-oxide-or prodrug thereof for treating a bacterial infection.

15. A composition comprising a compound as defined in claim 1 or a salt, racemate, diastereoisomer, enantiomer, hydrate, solvate, N-oxide or prodrug thereof.

16. The composition according to claim 15 which is a pharmaceutical composition adapted for intravenous administration or oral administration.

17. A method of disinfecting a living or non-living substrate which is the subject of a bacterial infestation, the method comprising applying a compound as defined in claim 1 or a salt, racemate, diastereoisomer, enantiomer, hydrate, solvate, or N-oxide thereof to the substrate.

18. A process for preparing a compound as defined in claim 1 or a salt, racemate, diastereoisomer, enantiomer, hydrate, solvate, N-oxide, or prodrug thereof comprising the step of coupling a compound of Formula (III) with a compound of general formula LG-C($R_3$)($R_3'$)—W:

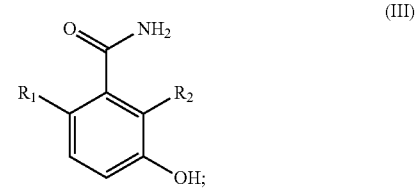

wherein W, $R_1$, $R_2$, $R_3$ and are $R_3'$ are defined according to claim 1 and LG is a leaving group.

19. A process according to claim 18 wherein the compound of general formula LG-C($R_3$)($R_3'$)—W is of Formula (IV)

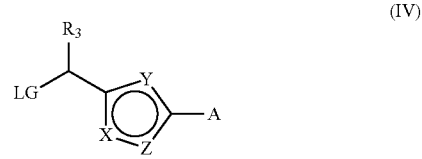

wherein

X and Y are each independently a heteroatom selected from O, N and S or a carbon atom having an optional substituent;

Z is a heteroatom selected from O, N and S or is C—B;

A is selected from H, halo, optionally substituted $C_{6-10}$aryl, optionally substituted 4-10 membered heterocyclyl or A together with B and the carbon atoms to which they are respectively attached join to form an optionally substituted 6-membered fused ring system;

B is selected from H, halo, optionally substituted $C_{1-6}$alkyl, optionally substituted $C_{2-6}$alkenyl, optionally substituted $C_{2-6}$alkynyl or B together with A and the carbon atoms to which they are respectively attached join to form an optionally substituted 6-membered fused ring system;

$R_1$ and $R_2$ are each independently selected from halo or H;

$R_3$ is selected from the group consisting of $C_t$alkyl-$R_4$, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;

t is an integer selected from 0, 1, 2 or 3;

$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$, $OC(=O)N(R_6)_2$, $C(=O)NH-NHC(=O)R_5$, $NHC(=O)NHC_{1-6}$alkyl, $NHS(O)_xR_5$, $S(O)_xR_5$, $OS(O)_xR_5$, $OP(=O)(OR_6)_2$, and $P(=O)(OR_6)_2$ wherein each $C_{2-6}$alkenyl, $C_{2-6}$alkynyl, $C_{6-10}$aryl, $C_{1-6}$alkylaryl, 4-10 membered heterocyclyl and $C_{1-6}$alkylheterocycly may be further optionally substituted with one or more substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)NH-HNC(=O)R_7$, $S(O)_xR_7$, $OS(O)_xR_7$, $OP(=O)(OR_7)_2$ and $P(=O)(OR_7)_2$ wherein each $R_7$ is independently selected from H, $C_{1-3}$alkyl and $C_{2-3}$alkenyl;

each $R_5$ is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl; and wherein each $R_5$ and $R_6$ independently may be optionally substituted with one or more substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)NH-NHC(=O)R_5$, $S(O)_xR_7$, $OS(O)_xR_7$, $OP(=O)(OR_7)_2$ and $P(=O)(OR_7)_2$ wherein each $R_7$ is independently selected from H and $C_{1-3}$alkyl;

x is 0 or an integer from 1 to 2; and

LG is a leaving group.

20. A compound of Formula (I):

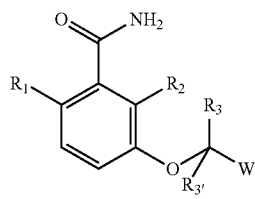

(I)

or a salt, racemate, diastereoisomer, enantiomer, hydrate, solvate, N-oxide, or prodrug thereof wherein W is a 9-10 membered fused bicyclic heteroaryl group;

$R_1$ and $R_2$ are each independently halo;

$R_3$ is selected from the group consisting of $C_t$alkyl-$R_4$, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;

t is an integer selected from 0, 1, 2 and 3;

$R_{3'}$ is H;

$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$, $OC(=O)N(R_6)_2$, $C(=O)NH-NHC(=O)R_5$, $NHC(=O)NHC_{1-6}$alkyl, $NHS(O)_xR_5$, $S(O)_xR_5$, $OS(O)_xR_5$, $OP(=O)(OR_6)_2$ and $P(=O)(OR_6)_2$ wherein each $C_{2-6}$alkenyl, $C_{2-6}$alkynyl, $C_{6-10}$aryl, $C_{1-6}$alkylaryl, 4-10 membered heterocyclyl and $C_{1-6}$alkylheterocycly may be further optionally substituted with one or more substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)NH-HNC(=O)R_7$, $S(O)_xR_7$, $OS(O)_xR_7$, $OP(=O)(OR_7)_2$ and $P(=O)(OR_7)_2$ wherein each $R_7$ is independently selected from H, $C_{1-3}$alkyl and $C_{2-3}$alkenyl;

each $R_5$ is optionally substituted and is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

each $R_6$ is independently selected from H or optionally substituted $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl;

wherein each $R_5$ and $R_6$ independently may be further optionally substituted with one or more optional substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)OR_7$, $N(R_7)_2$, $NR_7C(=O)R_7$, $C(=O)N(R_7)_2$, $NR_7C(=O)OR_7$, $OC(=O)N(R_7)_2$, $C(=O)NH-NHC(=O)R_7$, $S(O)_xR_7$, $OS(O)_xR_7$, $OP(=O)(OR_7)_2$ and $P(=O)(OR_7)_2$ wherein each $R_7$ is independently selected from H, $C_{1-3}$alkyl and $C_{2-3}$alkenyl; and x is 0 or an integer from 1 to 2.

21. A compound selected from the group consisting of:

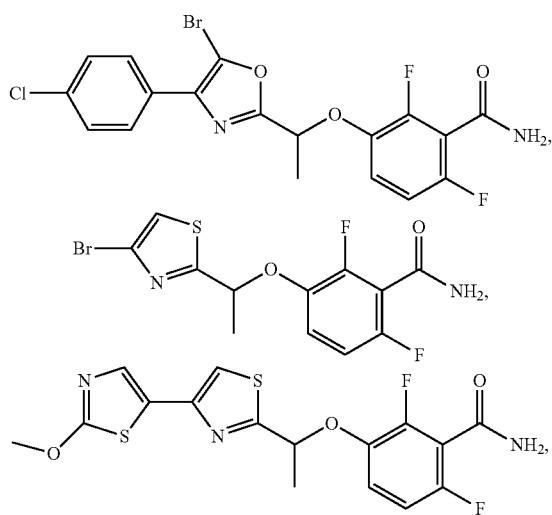

159
-continued
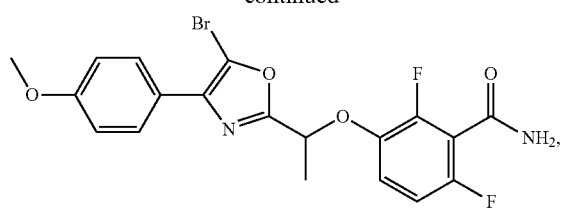
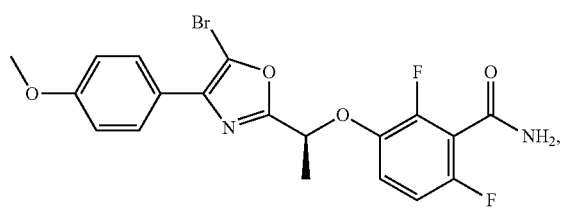
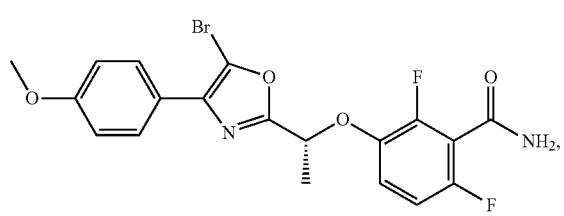
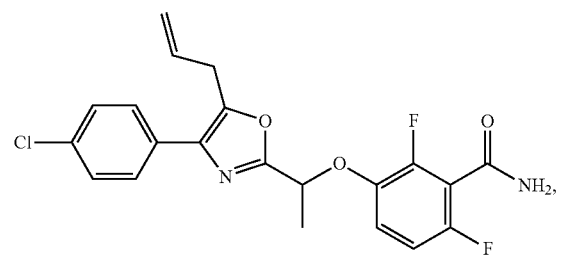
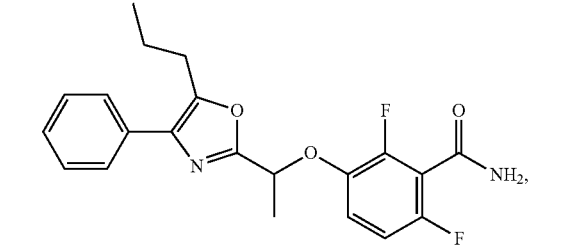
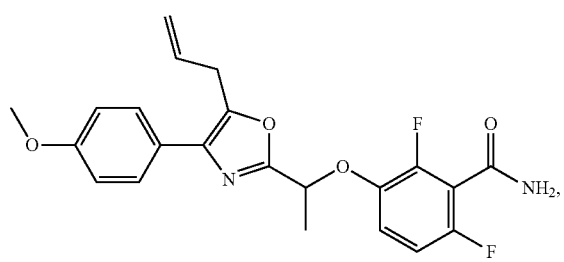
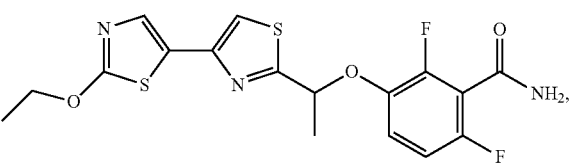
160
-continued
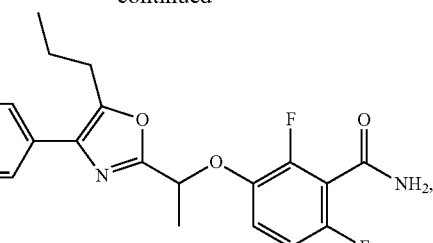
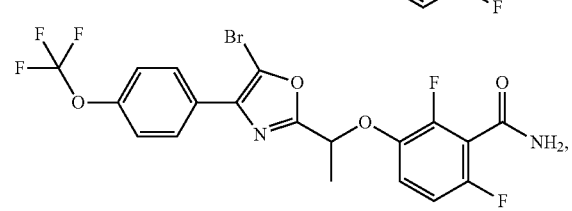
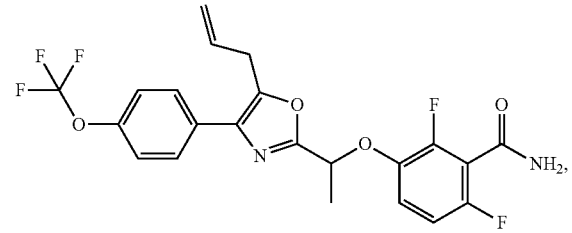
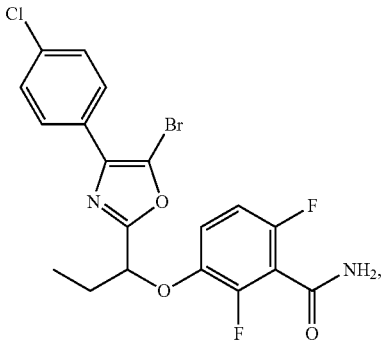
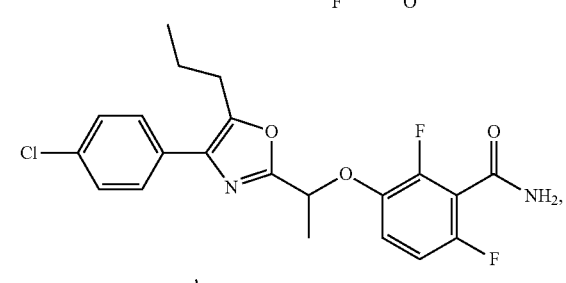
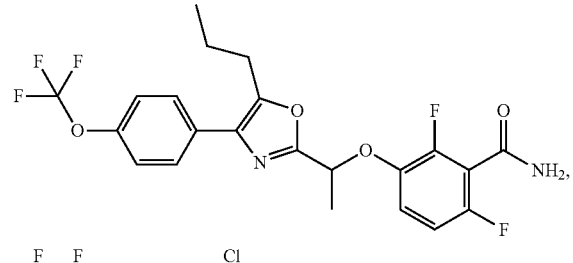
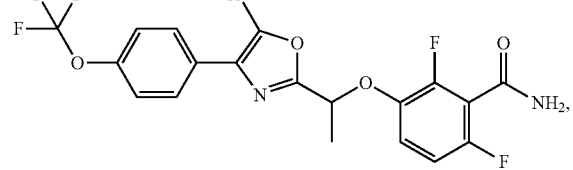

161
-continued
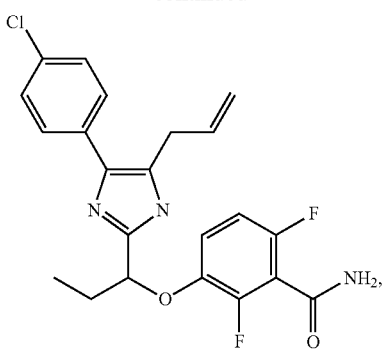
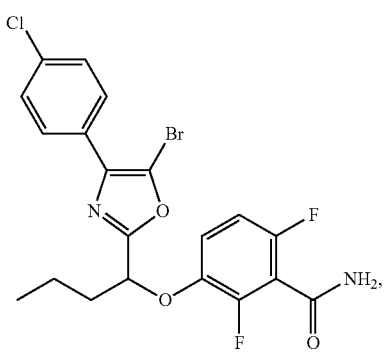
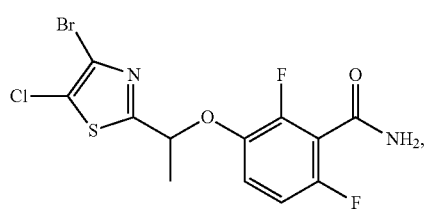
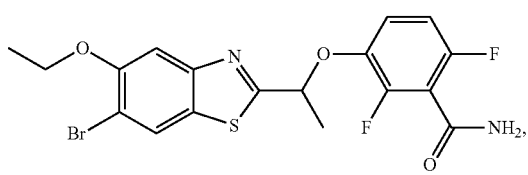
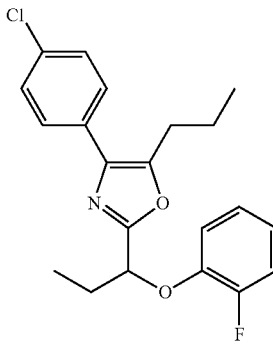
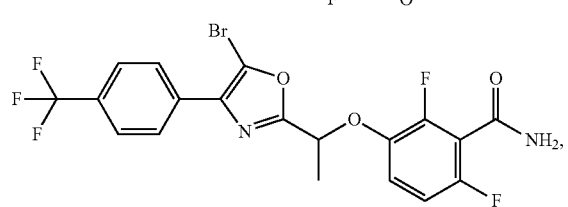
162
-continued
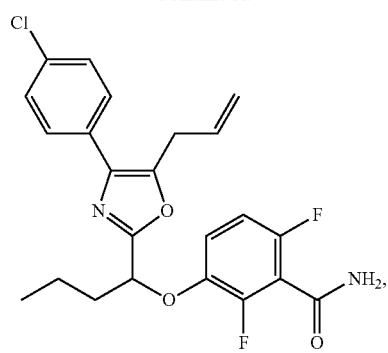
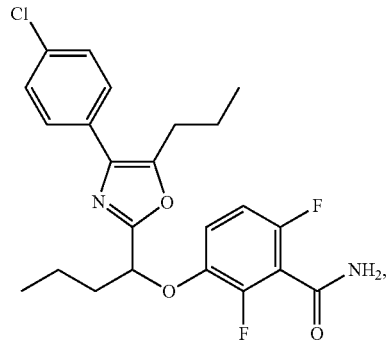
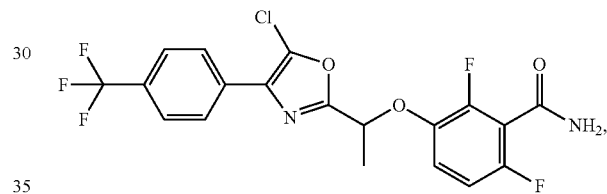
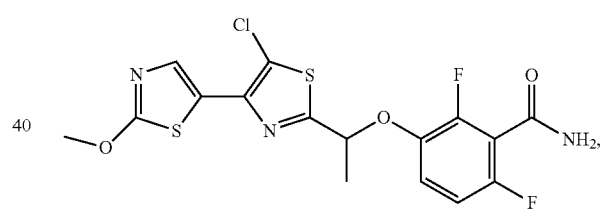
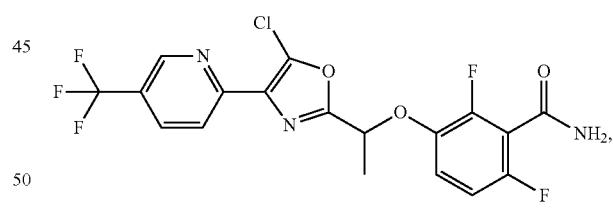
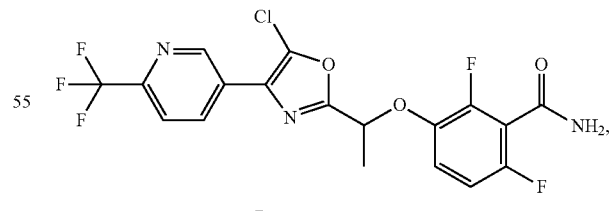
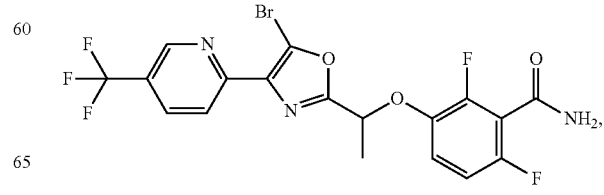

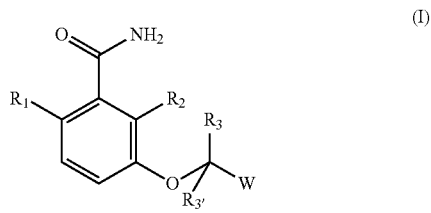

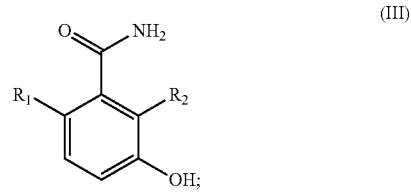

or a salt, racemate, diastereoisomer, enantiomer, hydrate, solvate, N-oxide, or prodrug thereof.

22. A composition comprising a compound as defined in claim 21 or a salt, racemate, diastereoisomer, enantiomer, hydrate, solvate, N-oxide or prodrug thereof.

23. A method of treating a bacterial infection in a subject comprising administering an effective amount of a compound as defined in claim 21 or a pharmaceutically acceptable salt, racemate, diastereoisomer, enantiomer, hydrate, solvate, N-oxide or prodrug thereof to the subject.

24. The compound of claim 1 wherein each $R_5$ is selected from $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl; each $R_6$ is independently selected from H, $C_{1-6}$alkyl, $C_{2-6}$alkenyl, $C_{2-6}$alkynyl, $C_{6-10}$aryl, $C_{1-6}$alkylaryl, 4-10 membered heterocyclyl and $C_{1-6}$alkylheterocyclyl and each $R_5$ and $R_6$ independently may be optionally substituted with one or more substituents independently selected from the group consisting of $C_{1-3}$alkyl, $C_{2-3}$alkenyl, $C_{1-3}$alkoxyl, $OR_7$, oxo, $(C=O)R_7$, $O(C=O)R_7$, $C(=O)$ $OR_7$, $NR_7C(=O)R_7$, $C(=O)N(R_7)_2$, $NR_7C(=O)OR_7$, $OC(=O)N(R_7)_2$, $C(=O)NH-NHC(=O)R_7$, $S(O)_xR_7$, $OS(O)_xR_7$, $OP(=O)(OR_7)_2$ and $P(=O)(OR_7)_2$ wherein each $R_7$ is independently selected from H, $C_{1-3}$alkyl and $C_{2-3}$alkenyl.

25. A composition comprising a compound as defined in claim 3 or a salt, racemate, diastereoisomer, enantiomer, hydrate, solvate, N-oxide or prodrug thereof.

26. A method of treating a bacterial infection in a subject comprising administering an effective amount of a compound as defined in claim 3 or a pharmaceutically acceptable salt, racemate, diastereoisomer, enantiomer, hydrate, solvate, N-oxide or prodrug thereof to the subject.

27. A composition comprising a compound as defined in claim 10 or a salt, racemate, diastereoisomer, enantiomer, hydrate, solvate, N-oxide or prodrug thereof.

28. A method of treating a bacterial infection in a subject comprising administering an effective amount of a compound as defined in claim 10 or a pharmaceutically acceptable salt, racemate, diastereoisomer, enantiomer, hydrate, solvate, N-oxide or prodrug thereof to the subject.

29. A process for preparing a compound of Formula (I):

or a salt, racemate, diastereoisomer, enantiomer, hydrate, solvate, N-oxide, or prodrug thereof comprising the step of coupling a compound of Formula (III) with a compound of general formula LG-C($R_3$)($R_3$')—W:

wherein
W is a substituted $C_{6-10}$-membered monocyclic or fused bicyclic aryl group or an optionally substituted 5-6-membered monocyclic heteroaryl or a 9-membered fused bicyclic heteroaryl group;
$R_1$ and $R_2$ are each independently selected from halo or H;
$R_3$ is selected from the group consisting of $C_t$alkyl-$R_4$, $C_{2-6}$alkenyl, $C_{2-6}$alkynyl, $C_{3-7}$cycloalkyl, $C_6$aryl, and 5-6 membered heterocyclyl wherein each alkyl, alkenyl, alkynyl, cycloalkyl, aryl or heterocyclyl may be optionally substituted with one or more $R_4$ or $R_5$ groups;
t is an integer selected from 0, 1, 2 and 3;
$R_3$' is H;
$R_4$ is selected from the group consisting of $C_{2-6}$alkenyl, $C_{2-6}$alkynyl, $C_{6-10}$aryl, $C_{1-6}$alkylaryl, 4-10 membered heterocyclyl, $C_{1-6}$alkylheterocyclyl, $OR_6$, $(C=O)R_6$, $O(C=O)R_6$, $C(=O)OR_6$, $N(R_6)_2$, $NR_6C(=O)R_5$, $C(=O)N(R_6)_2$, $NR_6C(=O)OR_5$, $OC(=O)N(R_6)_2$, C(=O)NH—NHC(=O)R₅, NHC(=O)NHC₁₋₆alkyl, NHS(O)ₓR₅, S(O)ₓR₅, OS(O)ₓR₅, OP(=O)(OR₆)₂ and P(=O)(OR₆)₂ wherein each C₂₋₆alkenyl, C₂₋₆alkynyl, C₆₋₁₀aryl, C₁₋₆alkylaryl, 4-10 membered heterocyclyl and C₁₋₆alkylheterocycly may be further optionally substituted with one or more substituents independently selected from the group consisting of C₁₋₃alkyl, C₂₋₃alkenyl, C₁₋₃alkoxyl, OR₇, oxo, (C=O)R₇, O(C=O)R₇, C(=O)OR₇, N(R₇)₂, NR₇C(=O)R₇, C(=O)N(R₇)₂, NR₇C(=O)OR₇, OC(=O)N(R₇)₂, C(=O)NH—HNC(=O)R₇, S(O)ₓR₇, OS(O)ₓR₇, OP(=O)(OR₇)₂ and P(=O)(OR₇)₂ wherein each R₇ is independently selected from H, C₁₋₃alkyl and C₂₋₃alkenyl;

each R₅ is optionally substituted and is selected from C₁₋₆alkyl, C₂₋₆alkenyl, C₂₋₆alkynyl, C₆₋₁₀aryl, C₁₋₆alkylaryl, 4-10 membered heterocyclyl and C₁₋₆alkylheterocyclyl;

each R₆ is independently selected from H or optionally substituted C₁₋₆alkyl, C₂₋₆alkenyl, C₂₋₆alkynyl, C₆₋₁₀aryl, C₁₋₆alkylaryl, 4-10 membered heterocyclyl and C₁₋₆alkylheterocyclyl;

wherein each R₅ and R₆ independently may be further optionally substituted with one or more optional substituents independently selected from the group consisting of C₁₋₃alkyl, C₂₋₃alkenyl, C₁₋₃alkoxyl, OR₇, oxo, (C=O)R₇, O(C=O)R₇, C(=O)OR₇, N(R₇)₂, NR₇C(=O)R₇, C(=O)N(R₇)₂, NR₇C(=O)OR₇, OC(=O)N(R₇)₂, C(=O)NH—NHC(=O)R₇, S(O)ₓR₇, OS(O)ₓR₇, OP(=O)(OR₇)₂ and P(=O)(OR₇)₂ wherein each R₇ is independently selected from H, C₁₋₃alkyl and C₂₋₃alkenyl;

x is 0 or an integer from 1 to 2;

and LG is a leaving group.

30. A process according to claim 29 wherein the compound of general formula LG-C(R₃)(R₃')—W is of Formula (IV)

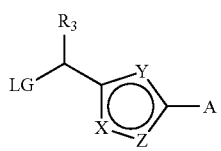

(IV)

wherein

X and Y are each independently a heteroatom selected from O, N and S or a carbon atom having an optional substituent;

Z is a heteroatom selected from O, N and S or is C—B;

A is selected from H, halo, optionally substituted C₆₋₁₀aryl, optionally substituted 4-10 membered heterocyclyl or A together with B and the carbon atoms to which they are respectively attached join to form an optionally substituted 6-membered fused ring system;

B is selected from H, halo, optionally substituted C₁₋₆alkyl, optionally substituted C₂₋₆alkenyl, optionally substituted C₂₋₆alkynyl or B together with A and the carbon atoms to which they are respectively attached join to form an optionally substituted 6-membered fused ring system;

R₁ and R₂ are each independently selected from halo or H;

R₃ is selected from the group consisting of Cₜalkyl-R₄, C₂₋₆alkenyl, C₂₋₆alkynyl, C₃₋₇cycloalkyl, C₆aryl, and 5-6 membered heterocyclyl wherein each alkyl, alkenyl, alkynyl, cycloalkyl, aryl or heterocyclyl may be optionally substituted with one or more R₄ or R₅ groups;

t is an integer selected from 0, 1, 2 or 3;

R₄ is selected from the group consisting of C₂₋₆alkenyl, C₂₋₆alkynyl, C₆₋₁₀aryl, C₁₋₆alkylaryl, 4-10 membered heterocyclyl, C₁₋₆alkylheterocyclyl, OR₆, (C=O)R₆, O(C=O)R₆, C(=O)OR₆, N(R₆)₂, NR₆C(=O)R₅, C(=O)N(R₆)₂, NR₆C(=O)OR₅, OC(=O)N(R₆)₂, C(=O)NH—NHC(=O)R₅, NHC(=O)NHC₁₋₆alkyl, NHS(O)ₓR₅, S(O)ₓR₅, OS(O)ₓR₅, OP(=O)(OR₆)₂, and P(=O)(OR₆)₂ wherein each C₂₋₆alkenyl, C₂₋₆alkynyl, C₆₋₁₀aryl, C₁₋₆alkylaryl, 4-10 membered heterocyclyl and C₁₋₆alkylheterocycly may be further optionally substituted with one or more substituents independently selected from the group consisting of C₁₋₃alkyl, C₂₋₃alkenyl, C₁₋₃alkoxyl, OR₇, oxo, (C=O)R₇, O(C=O)R₇, C(=O)OR₇, N(R₇)₂, NR₇C(=O)R₇, C(=O)N(R₇)₂, NR₇C(=O)OR₇, OC(=O)N(R₇)₂, C(=O)NH—HNC(=O)R₇, S(O)ₓR₇, OS(O)ₓR₇, OP(=O)(OR₇)₂ and P(=O)(OR₇)₂ wherein each R₇ is independently selected from H, C₁₋₃alkyl and C₂₋₃alkenyl;

each R₅ is optionally substituted and is selected from C₁₋₆alkyl, C₂₋₆alkenyl, C₂₋₆alkynyl, C₆₋₁₀aryl, C₁₋₆alkylaryl, 4-10 membered heterocyclyl and C₁₋₆alkylheterocyclyl;

each R₆ is independently selected from H or is optionally substituted C₁₋₆alkyl, C₂₋₆alkenyl, C₂₋₆alkynyl, C₆₋₁₀aryl, C₁₋₆alkylaryl, 4-10 membered heterocyclyl and C₁₋₆alkylheterocyclyl;

wherein each R₅ and R₆ independently may be further optionally substituted with one or more optional substituents independently selected from the group consisting of C₁₋₃alkyl, C₂₋₃alkenyl, C₁₋₃alkoxyl, OR₇, oxo, (C=O)R₇, O(C=O)R₇, C(=O)OR₇, N(R₇)₂, NR₇C(=O)R₇, C(=O)N(R₇)₂, NR₇C(=O)OR₇, OC(=O)N(R₇)₂, C(=O)NH—NHC(=O)R₅, S(O)ₓR₇, OS(O)ₓR₇, OP(=O)(OR₇)₂ and P(=O)(OR₇)₂ wherein each R₇ is independently selected from H and C₁₋₃alkyl;

x is 0 or an integer from 1 to 2; and

LG is a leaving group.

* * * * *

UNITED STATES PATENT AND TRADEMARK OFFICE
CERTIFICATE OF CORRECTION

PATENT NO.       : 9,511,073 B2
APPLICATION NO.  : 14/112735
DATED            : December 6, 2016
INVENTOR(S)      : David John Haydon et al.

It is certified that error appears in the above-identified patent and that said Letters Patent is hereby corrected as shown below:

In the Claims

Column 141, Line 59, Claim 1, please delete "$C_1$ alkyl" and insert -- $C_{1-6}$ alkyl --;

Column 142, Line 4, Claim 1, please delete "$OS(O)R_7$" and insert -- $OS(O)_xR_7$ --;

Column 155, Line 21, Claim 11, please delete "$C_talkyl-R_4$," and insert -- $C_talkyl-R_4$, $C_{2-6}alkenyl$, --;

Column 155, Line 35, Claim 11, please delete "$C_{2-6}alkenyl$," and insert -- $C_{2-6}alkenyl$, $C_{2-6}alkynyl$, --;

Column 155, Line 44, Claim 11, please delete "$P(=O)(OR_2)_2$" and insert -- $P(=O)(OR_7)_2$ --;

Column 155, Line 53, Claim 11, please delete "$C_{1-6}alkyl$," and insert -- $C_{1-6}alkyl$, $C_{2-6}alkenyl$, --;

Column 155, Line 58, Claim 11, please delete "$C_{1-3}alkyl$," and insert -- $C_{1-3}alkyl$, $C_{2-3}alkenyl$, --;

Column 155, Line 61, Claim 11, please delete "$C(=O)N(R_2)_2$" and insert -- $C(=O)N(R_7)_2$ --;

Column 155, Line 61, Claim 11, please delete "$OC(=O)N(R_2)_2$" and insert -- $OC(=O)N(R_7)_2$ --;

Column 155, Line 62, Claim 11, please delete "$OS(O)_xR_2$" and insert -- $OS(O)_xR_7$ --;

Signed and Sealed this
Twenty-second Day of May, 2018

Andrei Iancu
*Director of the United States Patent and Trademark Office*

CERTIFICATE OF CORRECTION (continued)
U.S. Pat. No. 9,511,073 B2

Column 161, Lines 1-15, Claim 21, please delete the following compound:

" 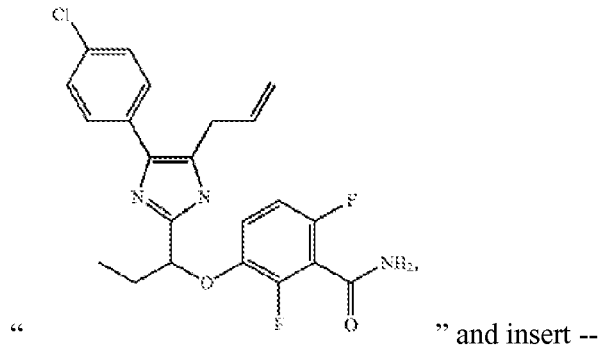 " and insert -- 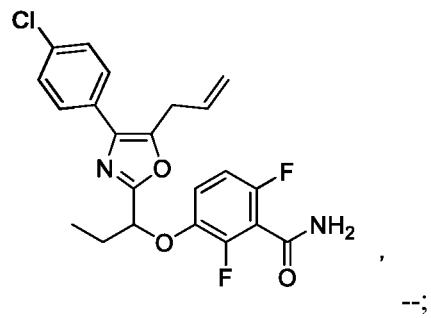 --;

Column 161, Lines 40-46, Claim 21, please delete the following compound:

" 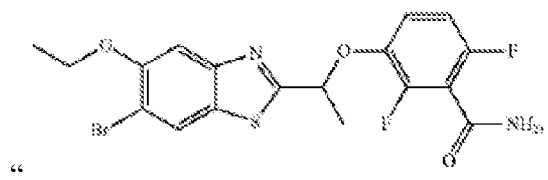 " and insert -- 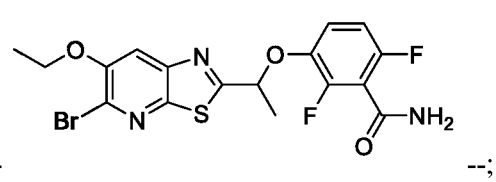 --;

Column 165, Line 17, Claim 29, please delete "$C_{6-10}$ aryl," and insert -- -$C_{6-10}$ aryl, -- therefor.